(12) United States Patent
Cheng et al.

(10) Patent No.: US 11,648,210 B2
(45) Date of Patent: *May 16, 2023

(54) COMPOSITIONS AND METHODS FOR ORGAN SPECIFIC DELIVERY OF NUCLEIC ACIDS

(71) Applicant: The Board of Regents of The University of Texas System, Austin, TX (US)

(72) Inventors: Qiang Cheng, Dallas, TX (US); Tuo Wei, Dallas, TX (US); Daniel J. Siegwart, Dallas, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/929,704

(22) Filed: Sep. 4, 2022

(65) Prior Publication Data

US 2023/0026843 A1 Jan. 26, 2023

Related U.S. Application Data

(63) Continuation of application No. 17/711,911, filed on Apr. 1, 2022, now Pat. No. 11,510,880, which is a continuation of application No. 17/572,615, filed on Jan. 10, 2022, which is a continuation of application No. 17/473,863, filed on Sep. 13, 2021, now Pat. No. 11,304,911, which is a continuation of application No. 17/191,895, filed on Mar. 4, 2021, now Pat. No. 11,229,609, which is a continuation of application No. PCT/US2019/049565, filed on Sep. 4, 2019.

(60) Provisional application No. 62/726,741, filed on Sep. 4, 2018.

(51) Int. Cl.

| C07H 21/02 | (2006.01) |
| C07H 21/04 | (2006.01) |
| A61K 9/51 | (2006.01) |
| A61K 48/00 | (2006.01) |
| C12N 9/22 | (2006.01) |
| C12N 15/11 | (2006.01) |
| C12N 15/113 | (2010.01) |

(52) U.S. Cl.
CPC ........ *A61K 9/5123* (2013.01); *A61K 48/0033* (2013.01); *C12N 9/22* (2013.01); *C12N 15/11* (2013.01); *C12N 15/111* (2013.01); *C12N 15/113* (2013.01); *C12N 2310/11* (2013.01); *C12N 2310/14* (2013.01); *C12N 2310/20* (2017.05); *C12N 2320/32* (2013.01)

(58) Field of Classification Search
CPC .............. C12N 15/113; C12N 2310/14; C12N 2310/11
See application file for complete search history.

(56) References Cited

U.S. PATENT DOCUMENTS

| 5,820,873 A | 10/1998 | Choi et al. |
| 7,314,956 B2 | 1/2008 | Li et al. |
| 7,404,969 B2 | 7/2008 | Chen et al. |
| 8,017,804 B2 | 9/2011 | Keil et al. |
| 8,058,069 B2 | 11/2011 | Yaworski et al. |
| 8,450,298 B2 | 5/2013 | Mahon et al. |
| 9,326,939 B2 | 5/2016 | Paulson et al. |
| 9,562,086 B2 | 2/2017 | Upton |
| 2004/0236015 A1 | 11/2004 | Kozlowski et al. |
| 2005/0008689 A1 | 1/2005 | Semple et al. |
| 2006/0008910 A1 | 1/2006 | MacLachlan et al. |
| 2007/0298006 A1 | 12/2007 | Tomalia et al. |
| 2008/0242626 A1 | 10/2008 | Zugates et al. |
| 2009/0221684 A1 | 9/2009 | Grinstaff et al. |
| 2010/0178267 A1 | 7/2010 | Puerta et al. |
| 2011/0009641 A1 | 1/2011 | Anderson et al. |
| 2013/0195967 A1 | 8/2013 | Guild et al. |
| 2014/0371293 A1 | 12/2014 | Brown et al. |
| 2015/0110859 A1 | 4/2015 | Heartlein et al. |
| 2015/0272886 A1 | 10/2015 | Chen et al. |
| 2016/0158354 A1 | 6/2016 | DeRosa et al. |
| 2016/0220681 A1 | 8/2016 | Siegwart et al. |
| 2016/0317647 A1 | 11/2016 | Ciaramella et al. |
| 2017/0121279 A1 | 5/2017 | Siegwart et al. |
| 2017/0240501 A1 | 8/2017 | DeRosa et al. |
| 2017/0326254 A1 | 11/2017 | Chen et al. |

FOREIGN PATENT DOCUMENTS

| CN | 101591428 | 5/2011 |
| CN | 103999853 | 8/2014 |
| EP | 3757570 | 12/2020 |
| JP | 2014-103108 | 6/2014 |
| JP | 2014-529328 | 11/2014 |

(Continued)

OTHER PUBLICATIONS

Adams et al., "Trial design and rationale for APOLLO, a Phase 3, placebo-controlled study of patisiran in patients with hereditary ATTR amyloidosis with polyneuropathy," *BMC Neurol*, 17(1):181, 2017.

Akinc et al., "A combinatorial library of lipid-like materials for delivery of RNAi therapeutics," *Nat. Biotechnol.*, 26:561-569, 2008.

(Continued)

*Primary Examiner* — Amy H Bowman
(74) *Attorney, Agent, or Firm* — Parker Highlander PLLC

(57) ABSTRACT

The present disclosure provides compositions which shown preferential targeting or delivery of a nucleic acid composition to a particular organ. In some embodiments, the composition comprises a steroid or sterol, an ionizable cationic lipid, a phospholipid, a PEG lipid, and a permanently cationic lipid which may be used to deliver a nucleic acid.

30 Claims, 39 Drawing Sheets

Specification includes a Sequence Listing.

(56) References Cited

FOREIGN PATENT DOCUMENTS

| | | |
|---|---|---|
| JP | 2015-519346 | 7/2015 |
| JP | 2019-515016 | 6/2019 |
| WO | WO 2006-138380 | 12/2006 |
| WO | WO 2010-129687 | 11/2010 |
| WO | WO 2010-141069 | 12/2010 |
| WO | WO 2012-090223 | 7/2012 |
| WO | WO 2012-170930 | 12/2012 |
| WO | WO 2012-170952 | 12/2012 |
| WO | WO 2013/177415 | 11/2013 |
| WO | WO 2013-177419 | 11/2013 |
| WO | WO 2014-026283 | 2/2014 |
| WO | WO 2014-105985 | 7/2014 |
| WO | WO 2014-106208 | 7/2014 |
| WO | WO 2014-144196 | 9/2014 |
| WO | WO 2015-148247 | 10/2015 |
| WO | WO 2015-191693 | 12/2015 |
| WO | WO 2016-010840 | 1/2016 |
| WO | WO 2016-094342 | 6/2016 |
| WO | WO 2016-118725 | 7/2016 |
| WO | WO 2017-048789 | 3/2017 |
| WO | WO 2017-053713 | 3/2017 |
| WO | WO 2017-173054 | 10/2017 |
| WO | WO 2017-201091 | 11/2017 |
| WO | WO 2017-201350 | 11/2017 |
| WO | WO 2018-029586 | 2/2018 |
| WO | WO 2018-078053 | 5/2018 |
| WO | WO 2019-246203 | 12/2019 |
| WO | WO 2020-051220 | 3/2020 |
| WO | WO 2020-051223 | 3/2020 |

OTHER PUBLICATIONS

Amoasii et al., "Gene editing restores dystrophin expression in a canine model of Duchenne muscular dystrophy," *Science*, 362:86-91, 2018.
Bartsch et al., "Massive and selective delivery of lipid-coated cationic lipoplexes of oligonucleotides targeted in vivo to hepatic endothelial cells," *Pharmaceutical Research*, 19(5):676-680, 2002.
Blasco et al., "Simple and rapid in vivo generation of chromosomal rearrangements using CRISPR/Cas9 technology," *Cell Rep.*, 9:1219-1227, 2014.
Bosman et al., "About dendrimers: Structure, physical properties, and applications," *Chem. Rev.*, 99:1665-1688, 1999.
Boyerinas et al., "The role of let-7 in cell differentiation and cancer," *Endocr.-Relat. Cancer*, 17:F19-F36, 2010.
Bryantsev et al., "pKa calculations of aliphatic amines, diamines, and aminoamides via density functional theory with a Poisson-Boltzmann continuum solvent model," *J. Phys. Chem. A.*, 111:4422-4430, 2007.
Carlmark et al., "New methodologies in the construction of dendritic materials," *Chem. Soc. Rev.*, 38:352-362, 2009.
Chatani et al., "Facile and Efficient Synthesis of Dendrimers and One-Pot Preparation of Dendritic-Linear Polymer Conjugates via a Single Chemistry: Utilization of Kinetically Selective Thiol-Michael Addition Reactions," *Macromolecules*, 47:4894-4900, 2014.
Cheng and Lee, "The role of helper lipids in lipid nanoparticles (LNPs) designed for oligonucleotide delivery," *Adv Drug Deliv Rev.*, 99(Pt A):129-137, 2016.
Cheng et al., "Dendrimer-Based Lipid Nanoparticles Deliver Therapeutic FAH mRNA to Normalize Liver Function and Extend Survival in a Mouse Model of Hepatorenal Tyrosinemia Type I," *Adv Mater.*, 30(52):e1805308, 2018.
Cheng et al., "Selective organ targeting (SORT) nanoparticles for tissue-specific mRNA delivery and CRISPR-Cas gene editing," *Nature Nanotechnology*, 15:313-320, 2020.
Chew et al., "A multifunctional AAV-CRISPR-Cas9 and its host response," *Nature methods*, 13:868, 2016.
Coelho et al., "Safety and efficacy of RNAi therapy for transthyretin amyloidosis," *New Engl J Med.*, 369(9):819-829, 2013.
Cong et al., "Multiplex genome engineering using CRISPR/Cas systems," *Science*, 339:819-823, 2013.
Dahlman et al., "In vivo endothelial siRNA delivery using polymeric nanoparticles with low molecular weight," *Nat Nanotechnol*, 9(8):648-655, 2014.
DeRosa et al., "Therapeutic efficacy in a hemophilia B model using a biosynthetic mRNA liver depot system," *Gene Ther.*, 23(10):699-707, 2016.
Dong et al., "Lipopeptide nanoparticles for potent and selective siRNA delivery in rodents and nonhuman primates," *Proc. Natl. Acad. Sci. USA*, 111(11):3955-3960, 2014.
Dong et al., "Poly(glycoamidoamine) Brushes Formulated Nanomaterials for Systemic siRNA and mRNA Delivery in Vivo," *Nano Lett.*, 16:842-848, 2016.
Doudna & Charpentier, "Genome editing. The new frontier of genome engineering with CRISPR-Cas9," *Science*, 346:1258096, 2014.
Duncan and Izzo, "Dendrimer biocompatibility and toxicity," *Adv. Drug Deliv. Rev.*, 57:2215-2237, 2005.
Extended European Search Report issued in European Application No. 16847193.6, dated Feb. 19, 2019.
Extended European Search Report issued in European Application No. 19857774.4, dated Jun. 7, 2022.
Fenton et al., "Bioinspired Alkenyl Amino Alcohol Ionizable Lipid Materials for Highly Potent In Vivo mRNA Delivery," *Adv. Mater.*, 28:2939-2943, 2016.
Fenton et al., "Synthesis and biological evaluation of ionizable lipid materials for the in vivo delivery of messenger RNA to B lymphocytes," *Adv. Mater.*, 29:1606944, 2017.
Finn et al., "A Single Administration of CRISPR/Cas9 Lipid Nanoparticles Achieves Robust and Persistent In Vivo Genome Editing," *Cell Rep.*, 22:2227-2235, 2018.
Franc and Kakkar, ""Click" methodologies: efficient, simple and greener routes to design dendrimers," *Chem. Soc. Rev.*, 39:1536-1544, 2010.
Gilleron et al., "Image-based analysis of lipid nanoparticle-mediated siRNA delivery, intracellular trafficking and endosomal escape," *Nat Biotechnol*, 31(7):638-646, 2013.
Gillies and Fréchet, "Designing macromolecules for therapeutic applications: Polyester dendrimer-poly(ethylene oxide) "bow-tie" hybrids with tunable molecular weight and architecture," *J. Am. Chem. Soc.*, 124:14137-14146, 2002.
Grayson and Fréchet, "Convergent dendrons and dendrimers: From synthesis to applications," *Chem. Rev.*, 101:3819-3868, 2001.
Grompe et al., "Pharmacological correction of neonatal lethal hepatic dysfunction in a murine model of hereditary tyrosinaemia type I," *Nat Genet.*, 10(4):453-460, 1995.
Gustafson et al., "Nanoparticle Uptake: The Phagocyte Problem," *Nano Today*, 10:487-510, 2015.
Hafez et al., "On the mechanism whereby cationic lipids promote intracellular delivery of polynucleic acids," *Gene Ther.*, 8:1188-1196, 2001.
Hajj & Whitehead, "Tools for translation: non-viral materials for therapeutic mRNA delivery," *Nat. Rev. Mater.*, 2:17056, 2017.
Hao et al., "Rapid Synthesis of a Lipocationic Polyester Library via Ring-Opening Polymerization of Functional Valerolactones for Efficacious siRNA Delivery," *Journal of the American Chemical Society*, 137(29):9206-9209, 2015.
Harvie et al., "Characterization of lipid DNA interactions. I. Destabilization of bound lipids and DNA dissociation," *Biophys J.*, 75(2):1040-1051, 1998.
Hendel et al., "Chemically modified guide RNAs enhance CRISPR-Cas genome editing in human primary cells," *Nat. Biotechnol.*, 33:985-989, 2015.
Hoyle et al., "Thiol-click chemistry: a multifaceted toolbox for small molecule and polymer synthesis," *Chem. Soc. Rev.*, 39:1355-1387, 2010.
Jarzębińska et al., "A Single Methylene Group in Oligoalkylamine-Based Cationic Polymers and Lipids Promotes Enhanced mRNA Delivery," *Angew. Chem. Int. Ed.*, 55:9591-9595, 2016.
Jayaraman et al., "Maximizing the potency of siRNA lipid nanoparticles for hepatic gene silencing in vivo," *Angew. Chem. Int. Ed.*, 51:8529-8533, 2012.

(56) References Cited

OTHER PUBLICATIONS

Jiang et al., "A non-viral CRISPR/Cas9 delivery system for therapeutically targeting HBV DNA and pcsk9 in vivo," Cell Research, 27:440-443, 2017.
Jinek et al., "A programmable dual-RNA-guided DNA endonuclease in adaptive bacterial immunity," Science, 337:816-821, 2012.
Kaczmarek et al., "Polymer-Lipid Nanoparticles for Systemic Delivery of mRNA to the Lungs," Angew. Chem. Int. Ed., 55:13808-13812, 2016.
Kanasty et al., "Delivery materials for siRNA therapeutics," Nat. Mater., 12:967-977, 2013.
Kang et al., "Tat-conjugated PAMAM dendrimers as delivery agents for antisense and siRNA oligonucleotides," Pharm. Res., 22:2099-2106, 2005.
Kauffman et al., "Optimization of Lipid Nanoparticle Formulations for mRNA Delivery in Vivo with Fractional Factorial and Definitive Screening Designs," Nano Lett., 15(11):7300-7306, 2015.
Khan et al., "Ionizable amphiphilic dendrimer-based nanomaterials with alkyl-chain-substituted amines for tunable siRNA delivery to the liver endothelium in vivo," Angew. Chem. Int. Ed., 53:14397-14401, 2014.
Killops et al., "Robust, efficient, and orthogonal synthesis of dendrimers via thiol-ene "click" chemistry," J. Am. Chem. Soc., 130:5062-5064, 2008.
Kormann et al., "Expression of therapeutic proteins after delivery of chemically modified mRNA in mice," Nat. Biotechnol., 29:154-157, 2011.
Lee et al., "Designing dendrimers for biological applications," Nat. Biotechnol., 23:1517-1526, 2005.
Leung et al., "Lipid nanoparticles containing siRNA synthesized by microfluidic mixing exhibit an electron-dense nanostructured core," J. Phys. Chem. C Nanomater Interaces, 116:18440-18450, 2012.
Li and Szoka, "Lipid-based nanoparticles for nucleic acid delivery," Pharm Res., 24(3):438-449, 2007.
Li et al., "A biomimetic lipid library for gene delivery through thiol-yne click chemistry," Biomaterials, 33(32):8160-8166, 2012.
Li et al., "An Orthogonal Array Optimization of Lipid-like Nanoparticles for mRNA Delivery in Vivo," Nano Lett., 15:8099-8107, 2015.
Li et al., "Effects of local structural transformation of lipid-like compounds on delivery of messenger RNA," Sci. Rep., 6:22137, 2016.
Love et al., "Lipid-like materials for low-dose, in vivo gene silencing," Proc Natl Acad Sci U S A, 107(5):1864-1869, 2010.
Lowe, "RNA vaccines and their lipids," In the Pipeline, https://blogs.sciencemag.org/pipeline/archives/2021/01/11/rna-vaccines-and-their-lipids, accessed Aug. 19, 2021, originally published Jan. 11, 2021.
Lu et al., "Toxicity of cationic lipids and cationic polymers in gene delivery," J. Controlled Release, 114:100-109, 2006.
Ma et al., "Facile synthesis of polyester dendrimers from sequential click coupling of asymmetrical monomers," J. Am. Chem. Soc., 131(41):14795-14803, 2009.
Maddalo et al., "In vivo engineering of oncogenic chromosomal rearrangements with the CRISPR/Cas9 system," Nature, 516:423-427, 2014.
Mali et al., "RNA-guided human genome engineering via Cas9," Science, 339:823-826, 2013.
Miller et al., "Non-viral CRISPR/Cas gene editing in vitro and in vivo enabled by synthetic nanoparticle co-delivery of Vas9 mRNA and sgRNA," Angewandte Chemie, 56(4):1059-1063, 2016.
Murat and Grest, "Molecular dynamics study of dendrimer molecules in solvents of varying quality," Macromolecules, 29:1278-1285, 1996.
Nelson et al., "Balancing cationic and hydrophobic content of PEGylated siRNA polyplexes enhances endosome escape, stability, blood circulation time, and bioactivity in vivo," ACS Nano, 7:8870-8880, 2013.
Office Action issued in British Application No. 2104769.1, dated Jun. 1, 2021.
Office Action issued in British Application No. 2104777.4, dated Jun. 1, 2021.
Office Action issued in British Application No. GB2100678.8, dated Jun. 11, 2021.
Office Action issued in British Application No. GB2104777.4, dated Mar. 2, 2022.
Office Action issued in British Application No. GB2111272.7, dated Mar. 2, 2022.
Office Action issued in Japanese Application No. 2018-513463, dated Sep. 7, 2020.
Office Action issued in Japanese Application No. 2021-536681, dated Nov. 9, 2022.
Office Action issued in U.S. Appl. No. 17/124,462, dated Apr. 22, 2021.
Office Action issued in U.S. Appl. No. 17/124,462, dated Jul. 12, 2021.
Office Action issued in U.S. Appl. No. 17/124,462, dated Nov. 15, 2021.
Office Action issued in U.S. Appl. No. 17/124,462, dated Jun. 22, 2022.
Office Action issued in U.S. Appl. No. 17/191,895, dated Jun. 16, 2021.
Office Action issued in U.S. Appl. No. 17/191,975, dated Aug. 25, 2021.
Office Action issued in U.S. Appl. No. 17/191,975, dated Feb. 11, 2022.
Office Action issued in U.S. Appl. No. 17/191,975, dated Nov. 1, 2021.
Office Action issued in U.S. Appl. No. 17/572,615, dated Mar. 24, 2022.
Office Action issued in U.S. Appl. No. 17/572,615, dated May 5, 2022.
Pankowicz et al., "Reprogramming metabolic pathways in vivo with CRISPR/Cas9 genome editing to treat hereditary tyrosinaemia," Nat Commun., 7:12642, 2016.
Pardi et al., "Expression kinetics of nucleoside-modified mRNA delivered in lipid nanoparticles to mice by various routes," J.Controlled Release, 217:345-351, 2015.
Patel et al., "Boosting Intracellular Delivery of Lipid Nanoparticle-Encapsulated mRNA," Nano Lett, 17:5711-5718, 2017.
PCT International Preliminary Report on Patentability issued in International Application No. PCT/US2019/049552, dated Mar. 18, 2021.
PCT International Preliminary Report on Patentability issued in International Application No. PCT/US2019/049565, dated Mar. 18, 2021.
PCT International Search Report and Written Opinion issued in International Application No. PCT/US2019/037904, dated Oct. 2, 2019.
PCT International Search Report and Written Opinion issued in International Application No. PCT/US2016/051648, dated Feb. 7, 2017.
PCT International Search Report and Written Opinion issued in International Application No. PCT/US2019/049552, dated Dec. 30, 2019.
PCT International Search Report and Written Opinion issued in International Application No. PCT/US2019/049565, dated Feb. 7, 2020.
Percec et al., "Self-assembly of Janus dendrimers into uniform dendrimersomes and other complex architectures," Science, 328:1009-1014, 2010.
Petsch et al., "Protective efficacy of in vitro synthesized, specific mRNA vaccines against influenza A virus infection," Nat. Biotechnol, 30:1210-1216, 2012.
Ramaswamy et al., "Systemic delivery of factor IX messenger RNA for protein replacement therapy," Proc. Natl. Acad. Sci. U.S.A., 114:E1941-E1950, 2017.
Regnaud, "Design and synthesis of dendrimers by combination of 'click' chemistry and A3-coupling," Thesis, McGill University, pp. 1-67, 2013.
Richner et al., "Modified mRNA Vaccines Protect against Zika Virus Infection," Cell, 169:176, 2017.

(56) References Cited

OTHER PUBLICATIONS

Sahay et al., "Efficiency of siRNA delivery by lipid nanoparticles is limited by endocytic recycling," *Nat. Biotechnol.*, 31(7):653-658, 2013.
Sahin et al., "mRNA-based therapeutics—developing a new class of drugs," *Nat. Rev. Drug Discovery*, 13:759-780, 2014.
Sander & Joung, "CRISPR-Cas systems for editing, regulating and targeting genomes," Nat. Biotechnol., 32:347-355, 2014.
Schaffert et al., "Solid-phase synthesis of sequence-defined T-, i-, and U-shape polymers for pDNA and siRNA delivery," *Angew. Chem. Int. Ed.*, 50:8986-8989, 2011.
Semple et al., "Rational design of cationic lipids for siRNA delivery," *Nat. Biotechnol.*, 28:172-176, 2010.
Shobaki et al., "Mixing lipids to manipulate the ionization status of lipid nanoparticles for specific tissue targeting," *International Journal of Nanomedicine*, 13:8395-8410, 2018.
Siegwart et al., "Combinatorial synthesis of chemically diverse core-shell nanoparticles for intracellular delivery," *Proc. Natl. Acad. Sci. U.S.A.*, 108:12996-13001, 2011.
Staahl et al., "Efficient genome editing in the mouse brain by local delivery of engineered Cas9 ribonucleoprotein complexes," *Nat. Biotechnol.*, 35:431-434, 2017.
Stiriba et al., "Dendritic polymers in biomedical applications: From potential to clinical use in diagnostics and therapy," *Angew. Chem. Int. Ed.*, 41:1329-1334, 2002.
Sun et al., "Self-assembled DNA nanoclews for the efficient delivery of CRISPR-Cas9 for genome editing," *Angew. Chem. Int. Ed.*, 54:12029-12033, 2015.
Sundaram et al., "Reversibly switchable polymer with cationic/zwitterionic/anionic behavior through synergistic protonation and deprotonation," *Chem. Sci.*, 5:200-205, 2014.
Tabebordbar et al., "In vivo gene editing in dystrophic mouse muscle and muscle stem cells," Science, 351:407-411, 2016.
Taratula et al., "Surface-engineered targeted PPI dendrimer for efficient intracellular and intramoral siRNA delivery," *J. Control. Release*, 140:284-293, 2009.
Tousignant et al., "Comprehensive analysis of the acute toxicities induced by systemic administration of cationic lipid:plasmid DNA complexes in mice," *Hum. Gene Ther.*, 11:2493-2513, 2000.
Uchida et al., "Modulated protonation of side chain aminoethylene repeats in N-substituted polyaspartamides promotes mRNA transfection," *J. Am. Chern. Soc.*, 136:12396-12405, 2014.
Wang et al., "Cas9-mediated allelic exchange repairs compound heterozygous recessive mutations in mice," Nat. Biotechnol., 36(9):839-842, 2018.
Wang et al., "CRISPR/Cas9-Based Genome Editing for Disease Modeling and Therapy: Challenges and Opportunities for Nonviral Delivery," *Chem. Rev.*, 117:9874-9906, 2017.
Whitehead et al., "Degradable lipid nanoparticles with predictable in vivo siRNA delivery activity," *Nat. Commun.*, 5:4277, 2014.
Wilhelm et al., "Analysis of nanoparticle delivery to tumours," Nat. Rev. Mater., 1:16014, 2016.
Wittrup et al., "Visualizing lipid-formulated siRNA release from endosomes and target gene knockdown," *Nat Biotechnol.*, 33:870-876, 2015.

Wood, "Traumatic brain injury induces transmissible tau pathology," *Nat. Rev. Neurol.*, 14:570-571, 2018.
Wu et al., "Dendrimers in medicine: Therapeutic concepts and pharmaceutical challenges," *Bioconjugate Chem.*, 26(7):1198-1211, 2015.
Wu et al., "Efficiency and fidelity in a click-chemistry route to triazole dendrimers by the copper(I)-catalyzed ligation of azides and alkynes," *Angew. Chem. Int. Ed.*, 43:3928-3932, 2004.
Wu et al., "RNAi therapies: drugging the undruggable," *Sci. Transl. Med.*, 6:240-247, 2014.
Xu et al., "Fluorescent water-soluble perylenediimide-cored cationic dendrimers: synthesis, optical properties, and cell uptake," *Chem. Commun.*, 49:3646-3648, 2013.
Xue et al., "CRISPR-mediated direct mutation of cancer genes in the mouse liver," Nature, 514:380-384, 2014.
Yan et al., "Functional polyesters enable selective siRNA delivery to lung cancer over matched normal cells," *Proc. Natl. Acad. Sci.*, 113:E5702-E5710, 2016.
Yan et al., "Systemic mRNA Delivery to the Lungs by Functional Polyester-based Carriers," *Biomacromolecules*, 18:4307-4315, 2017.
Yin et al., "Genome editing with Cas9 in adult mice corrects a disease mutation and phenotype," *Nat Biotechnol.*, 32:551-553, 2014.
Yin et al., "Structure-guided chemical modification of guide RNA enables potent non-viral in vivo genome editing," Nat. Biotechnol., 35:1179-1187, 2017.
Yin et al., "Therapeutic genome editing by combined viral and non-viral delivery of CRISPR system components in vivo," *Nat. Biotechnol.*, 34:328-333, 2016.
Yu et al., "An amphiphilic dendrimer for effective delivery of small interfering RNA and gene silencing in vitro and in vivo," *Angewandte Chem. Int. Ed.*, 51:8478-8484, 2012.
Zelphati and Szoca, "Intracellular distribution and mechanism of delivery of oligonucleotides mediated by cationic lipids," *Pharm Res.*, 13:1367-1372, 1996.
Zhang et al., "Biodegradable amino-ester nanomaterials for Cas9 mRNA delivery in vitro and in vivo," *ACS Appl Mater Interfaces*, 9(30):25481-25487, 2017.
Zhang et al., "Knockdown of Anillin Actin Binding Protein Blocks Cytokinesis in Hepatocytes and Reduces Liver Tumor Development in Mice Without Affecting Regeneration," *Gastroenterology*, 154(5):1421-1434, 2018.
Zhang et al., "The Polyploid State Plays a Tumor-Suppressive Role in the Liver," *Dev. Cell*, 44(4):447-459, 2018.
Zhou et al., "Balancing biocompatibility, internalization and pharmacokinetics of polycations/siRNA by structuring the weak negative charged ternary complexes with hyaluronic acid," *Journal of Biomedical Nanotechnology*, 13:1533-1544, 2017.
Zhou et al., "Modular degradable dendrimers enable small RNAs to extend survival in an aggressive liver cancer model," *Proc. Natl. Acad. Sci. USA*, 113(3):520-525, 2016.
Zhou et al., "PAMAM dendrimers for efficient siRNA delivery and potent gene silencing," *Chem. Commun.*, 22:2362-2364, 2006.
Zuris et al., "Cationic lipid-mediated delivery of proteins enables efficient protein-based genome editing in vitro and in vivo," Nat. Biotechnol., 33:73-80, 2015.

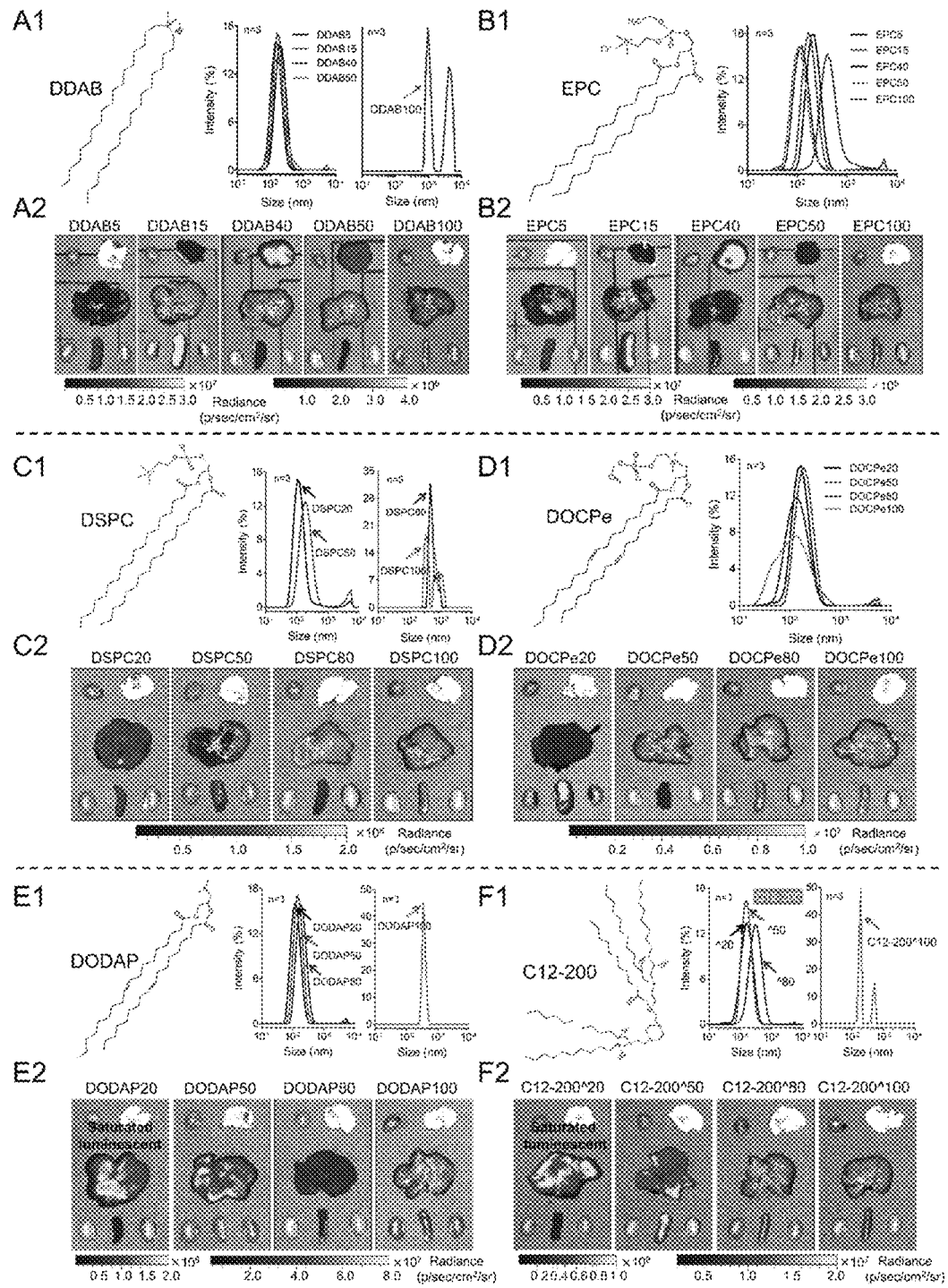
FIGS. 2A1-2F2

A
| Name | Molar Ratios | | | | | Molar Percentage (%) | | | | | Total Lipids/mRNA (wt/wt) | Size (nm) | PDI | Zeta-Potential (mV) |
|---|---|---|---|---|---|---|---|---|---|---|---|---|---|---|
| | 5A2-SC8 | DOPE | Chol | DMG-PEG | DOTAP | 5A2-SC8 | DOPE | Chol | DMG-PEG | DOTAP | | | | |
| 0% (mDLNP) | 15 | 15 | 30 | 3 | 0 | 23.81 | 23.81 | 47.62 | 4.76 | 0 | 40 | 93.2 | 0.14 | -3.58 |
| 5% | 15 | 15 | 30 | 3 | 3.315 | 22.62 | 22.62 | 45.24 | 4.52 | 5 | 40 | 156.3 | 0.16 | -3.86 |
| 10% | 15 | 15 | 30 | 3 | 7 | 21.43 | 21.43 | 42.86 | 4.29 | 10 | 40 | 152.8 | 0.10 | -2.28 |
| 15% | 15 | 15 | 30 | 3 | 11.13 | 20.24 | 20.24 | 40.47 | 4.05 | 15 | 40 | 123.0 | 0.11 | -2.28 |
| 20% | 15 | 15 | 30 | 3 | 15.75 | 19.05 | 19.05 | 38.10 | 3.81 | 20 | 40 | 113.0 | 0.18 | -2.44 |
| 25% | 15 | 15 | 30 | 3 | 21 | 17.86 | 17.86 | 35.71 | 3.57 | 25 | 40 | 108.8 | 0.21 | -2.07 |
| 30% | 15 | 15 | 30 | 3 | 27 | 16.67 | 16.67 | 33.33 | 3.33 | 30 | 40 | 101.6 | 0.18 | -2.07 |
| 35% | 15 | 15 | 30 | 3 | 33.83 | 15.48 | 15.48 | 30.95 | 3.10 | 35 | 40 | 104.0 | 0.23 | -2.03 |
| 40% | 15 | 15 | 30 | 3 | 42 | 14.29 | 14.29 | 28.57 | 2.86 | 40 | 40 | 108.0 | 0.27 | -1.46 |
| 45% | 15 | 15 | 30 | 3 | 51.54 | 13.10 | 13.10 | 26.19 | 2.62 | 45 | 40 | 115.1 | 0.19 | -0.74 |
| 50% | 15 | 15 | 30 | 3 | 63 | 11.90 | 11.90 | 23.81 | 2.38 | 50 | 40 | 113.1 | 0.22 | -0.52 |
| 55% | 15 | 15 | 30 | 3 | 77 | 10.71 | 10.71 | 21.43 | 2.14 | 55 | 40 | 108.3 | 0.19 | 0.13 |
| 60% | 15 | 15 | 30 | 3 | 94.5 | 9.52 | 9.52 | 19.05 | 1.90 | 60 | 40 | 113.5 | 0.19 | -0.94 |
| 65% | 15 | 15 | 30 | 3 | 117 | 8.33 | 8.33 | 16.67 | 1.67 | 65 | 40 | 125.3 | 0.16 | 5.13 |
| 70% | 15 | 15 | 30 | 3 | 147 | 7.14 | 7.14 | 14.29 | 1.43 | 70 | 40 | 115.8 | 0.17 | 3.11 |
| 75% | 15 | 15 | 30 | 3 | 188.95 | 5.95 | 5.95 | 11.91 | 1.19 | 75 | 40 | 117.7 | 0.20 | 6.50 |
| 80% | 15 | 15 | 30 | 3 | 252 | 4.76 | 4.76 | 9.52 | 0.95 | 80 | 40 | 129.7 | 0.15 | 6.86 |
| 85% | 15 | 15 | 30 | 3 | 357 | 3.57 | 3.57 | 7.14 | 0.71 | 85 | 40 | 119.1 | 0.19 | 14.87 |
| 90% | 15 | 15 | 30 | 3 | 567 | 2.38 | 2.38 | 4.76 | 0.48 | 90 | 40 | 137.6 | 0.21 | 15.97 |
| 95% | 15 | 15 | 30 | 3 | 1198 | 1.19 | 1.19 | 2.38 | 0.24 | 95 | 40 | 124.5 | 0.22 | 14.50 |
| 100% | 0 | 0 | 0 | 0 | 100 | 0 | 0 | 0 | 0 | 100 | 40 | 118.2 | 0.20 | 26.50 |
| Name | 5A2-SC8 | DOPE | Chol | DMG-PEG | 18PA | 5A2-SC8 | DOPE | Chol | DMG-PEG | 18PA | Total Lipids/mRNA (wt/wt) | Size (nm) | PDI | Zeta-Potential (mV) |
|---|---|---|---|---|---|---|---|---|---|---|---|---|---|---|
| 5% | 15 | 15 | 30 | 3 | 3.315 | 22.62 | 22.62 | 45.24 | 4.52 | 5 | 40 | 95.2 | 0.13 | -1.88 |
| 10% | 15 | 15 | 30 | 3 | 7 | 21.43 | 21.43 | 42.86 | 4.29 | 10 | 40 | 102.7 | 0.13 | -1.55 |
| 20% | 15 | 15 | 30 | 3 | 15.75 | 19.05 | 19.05 | 38.10 | 3.81 | 20 | 40 | 116.6 | 0.07 | -1.74 |
| 30% | 15 | 15 | 30 | 3 | 27 | 16.67 | 16.67 | 33.33 | 3.33 | 30 | 40 | 142.1 | 0.13 | -2.11 |
| 40% | 15 | 15 | 30 | 3 | 42 | 14.29 | 14.29 | 28.57 | 2.86 | 40 | 40 | 165.2 | 0.14 | -5.57 |
| 50% | 15 | 15 | 30 | 3 | 63 | 11.90 | 11.90 | 23.81 | 2.38 | 50 | 40 | 142.4 | 0.16 | -3.07 |
| 60% | 15 | 15 | 30 | 3 | 94.5 | 9.52 | 9.52 | 19.05 | 1.90 | 60 | 40 | 141.0 | 0.11 | -4.60 |
| 100% | 0 | 0 | 0 | 0 | 100 | 0 | 0 | 0 | 0 | 100 | 40 | 73.3 | 0.53 | -38.87 |
B
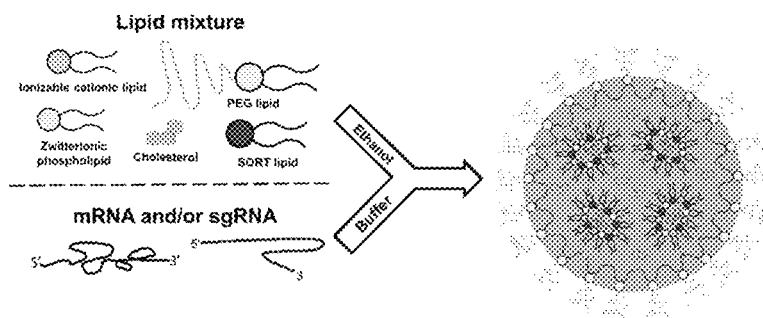
C
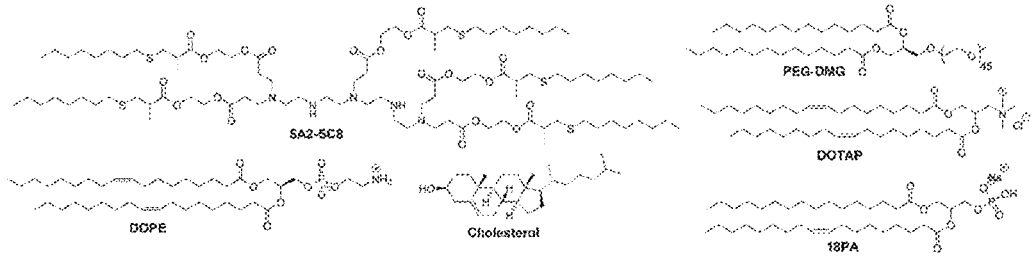
FIGS. 20A-20C

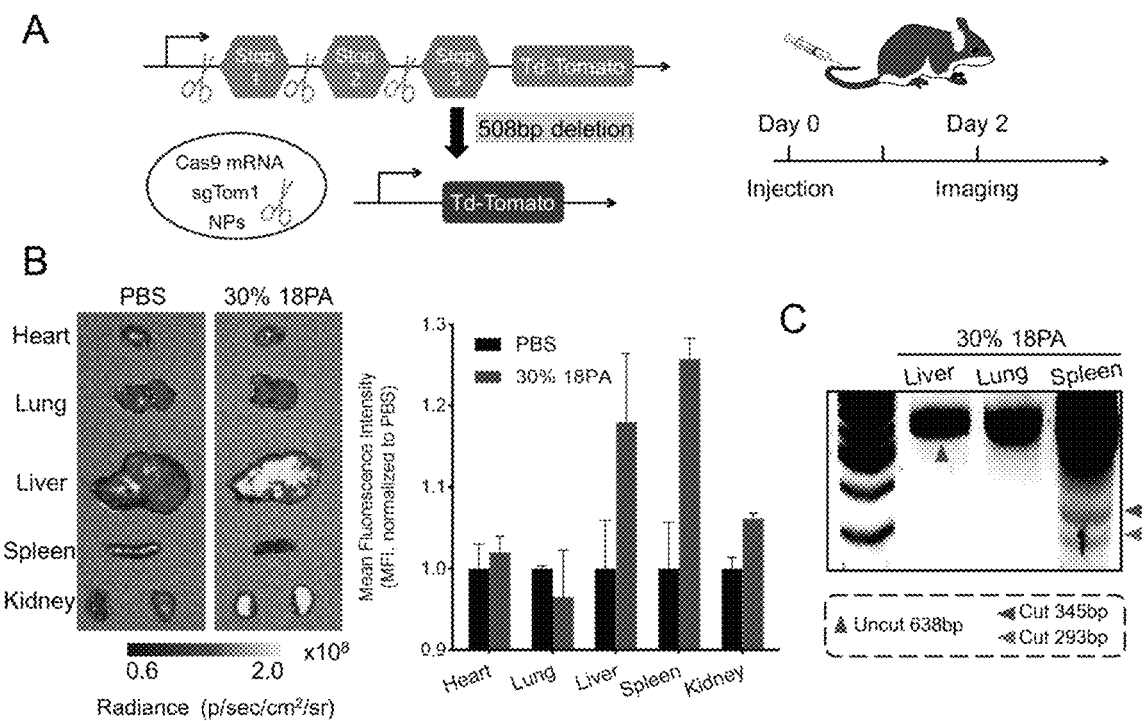
FIGS. 33A-C
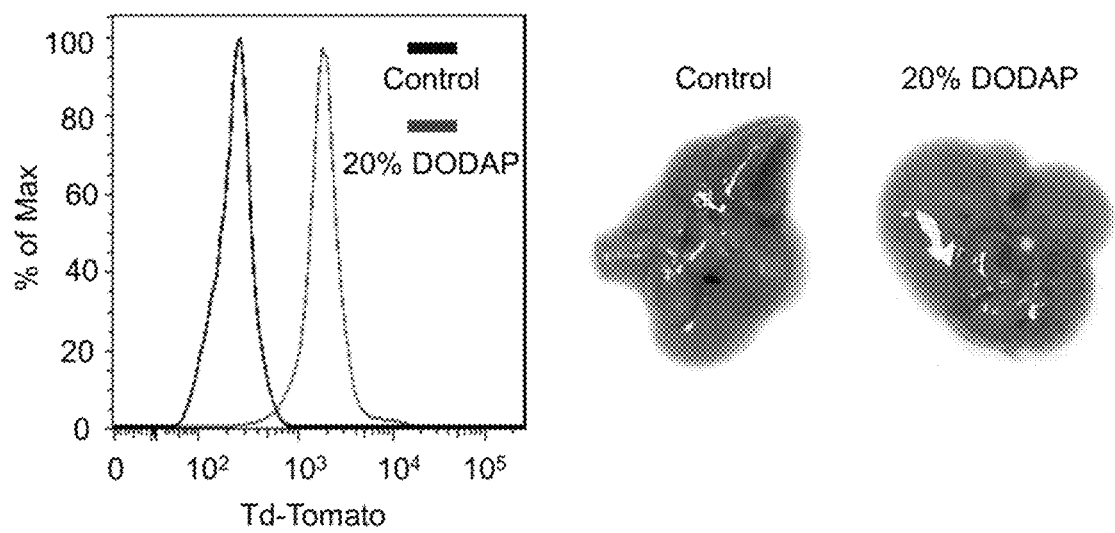
FIG. 34

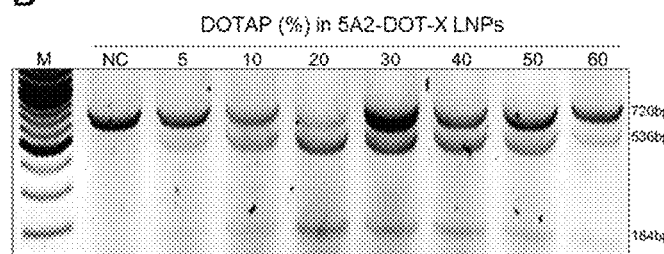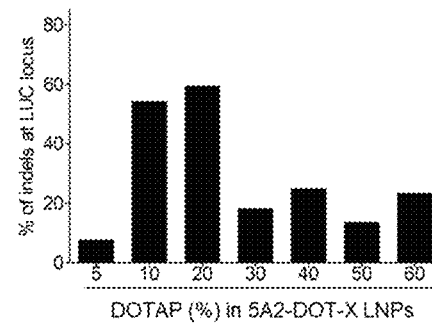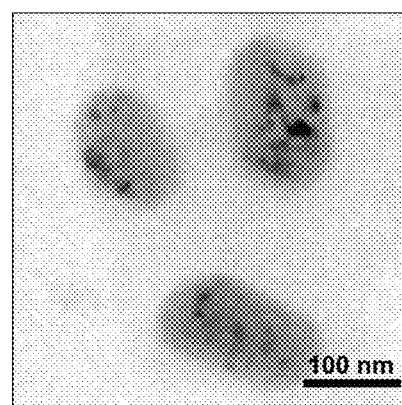
FIGS. 41A-41C
FIG. 42 ular biology. More particularly, it concerns tissue

```
                          SEQUENCE LISTING

Sequence total quantity: 62
SEQ ID NO: 1            moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 1
aagtaaaacc tctacaaatg                                                  20

SEQ ID NO: 2            moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 2
agatcgttag cagaaacaaa                                                  20

SEQ ID NO: 3            moltype = DNA   length = 45
FEATURE                 Location/Qualifiers
misc_feature            1..45
                        note = Synthetic oligonucleotide
source                  1..45
                        mol_type = other DNA
                        organism = synthetic construct
SEQUENCE: 3
atatatggat ccgccaccat ggccccaaag aagaagcgga aggtc                      45

SEQ ID NO: 4            moltype = DNA   length = 74
FEATURE                 Location/Qualifiers
misc_feature            1..74
                        note = Synthetic oligonucleotide
source                  1..74
                        mol_type = other DNA
                        organism = synthetic construct
SEQUENCE: 4
atatatgaat tcttactttt tctttttgc ctggccggcc ttttcgtggc cgccggcctt        60
ttgtcgcctc ccag                                                        74

SEQ ID NO: 5            moltype = DNA   length = 24
FEATURE                 Location/Qualifiers
misc_feature            1..24
                        note = Synthetic oligonucleotide
source                  1..24
                        mol_type = other DNA
                        organism = synthetic construct
SEQUENCE: 5
ctgagcgaca tcctgagagt gaac                                             24

SEQ ID NO: 6            moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 6
agcaggtcct ctctgttcag                                                  20

SEQ ID NO: 7            moltype = DNA   length = 24
FEATURE                 Location/Qualifiers
misc_feature            1..24
                        note = Synthetic oligonucleotide
source                  1..24
                        mol_type = other DNA
                        organism = synthetic construct
SEQUENCE: 7
gacggcttcg ccaacagaaa cttc                                             24
```

```
SEQ ID NO: 8              moltype = DNA  length = 21
FEATURE                   Location/Qualifiers
misc_feature              1..21
                          note = Synthetic oligonucleotide
source                    1..21
                          mol_type = other DNA
                          organism = synthetic construct
SEQUENCE: 8
tttgatgccc tcttcgatcc g                                            21

SEQ ID NO: 9              moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 9
gggagatcgt gtgggataag                                              20

SEQ ID NO: 10             moltype = DNA  length = 20
FEATURE                   Location/Qualifiers
misc_feature              1..20
                          note = Synthetic oligonucleotide
source                    1..20
                          mol_type = other DNA
                          organism = synthetic construct
SEQUENCE: 10
acttcttagg gtcccagtcc                                              20

SEQ ID NO: 11             moltype = DNA  length = 21
FEATURE                   Location/Qualifiers
misc_feature              1..21
                          note = Synthetic oligonucleotide
source                    1..21
                          mol_type = other DNA
                          organism = synthetic construct
SEQUENCE: 11
aagagagtga tcctggccga c                                            21

SEQ ID NO: 12             moltype = DNA  length = 75
FEATURE                   Location/Qualifiers
misc_feature              1..75
                          note = Synthetic oligonucleotide
source                    1..75
                          mol_type = other DNA
                          organism = synthetic construct
SEQUENCE: 12
atatatggat ccgccaccat gcccaagaag aagaggaagg tggccaatta ctgaccgtac  60
accaaaattt gcctg                                                   75

SEQ ID NO: 13             moltype = DNA  length = 32
FEATURE                   Location/Qualifiers
misc_feature              1..32
                          note = Synthetic oligonucleotide
source                    1..32
                          mol_type = other DNA
                          organism = synthetic construct
SEQUENCE: 13
atatatgaat tcttaatcgc catctccagc ag                                32

SEQ ID NO: 14             moltype = DNA  length = 21
FEATURE                   Location/Qualifiers
misc_feature              1..21
                          note = Synthetic oligonucleotide
source                    1..21
                          mol_type = other DNA
                          organism = synthetic construct
SEQUENCE: 14
atccgtcttc tccccattcc g                                            21

SEQ ID NO: 15             moltype = DNA  length = 21
FEATURE                   Location/Qualifiers
misc_feature              1..21
                          note = Synthetic oligonucleotide
source                    1..21
                          mol_type = other DNA
                          organism = synthetic construct
SEQUENCE: 15
```

```
SEQ ID NO: 16           moltype = DNA   length = 1053
FEATURE                 Location/Qualifiers
misc_feature            1..1053
                        note = Synthetic oligonucleotide
source                  1..1053
                        mol_type = other DNA
                        organism = synthetic construct
SEQUENCE: 16
atgcccaaga agaagaggaa ggtggccaat ttactgaccg tacaccaaaa tttgcctgca   60
ttaccggtcg atgcaacgag tgatgaggtt cgcaagaacc tgatggacat gttcagggat  120
cgccaggcgt tttctgagca tacctggaaa atgcttctgt ccgtttgccg gtcgtgggcg  180
gcatggtgca agttgaataa ccggaaatgg tttcccgcag aacctgaaga tgttcgcgat  240
tatcttctat atcttcaggc gcgcggtctg gcagtaaaaa ctatccagca acatttgggc  300
cagctaaaca tgcttcatcg tcggtccggg ctgccacgac caagtgacag caatgctgtt  360
tcactggtta tgcggcgtat ccgaaaagaa aacgttgatg ccggtgaacg tgcaaaacag  420
gctctagcgt tcgaacgcac tgatttcgac caggttcgtt cactcatgga aaatagcgat  480
cgctgccagg atatacgtaa tctggcattt ctggggattg cttataacac cctgttacgt  540
atagccgaaa ttgccaggat cagggttaaa gatatctcac gtactgacgg tgggagaatg  600
ttaatccata ttggcagaac gaaaacgctg ttagcaccg caggtgtaga aaggcacttt   660
agcctggggg taactaaact ggtcgagcga tggatttcg tctctggtgt agctgatgat   720
ccgaataact acctgttttg ccgggtcaga aaaaatggtg ttgccgcgcc atctgccacc  780
agccagctat caactcgcgc cctggaaggg attttttgaag caactcatcg attgatttac  840
ggcgctaagg atgactctgg tcagagatac ctggcctggt ctggacacag tgcccgtgtc  900
ggagccgcgc gagatatggc ccgcgctgga gtttcaatac cggagatcat gcaagctggt  960
ggctgaccca atgtaaatat tgtcatgaac tatatccgta acctggatag tgaaacaggg 1020
gcaatggtgc gcctgctgga agatggcgat taa                              1053

SEQ ID NO: 17           moltype = DNA   length = 4203
FEATURE                 Location/Qualifiers
misc_feature            1..4203
                        note = Synthetic oligonucleotide
source                  1..4203
                        mol_type = other DNA
                        organism = synthetic construct
SEQUENCE: 17
atggccccaa agaagaagcg gaaggtcggt atccacggag tcccagcagc cgacaagaag   60
tacagcatcg gcctggacat cggcaccaac tctgtgggct gggccgtgat caccgacgag  120
tacaaggtgc ccagcaagaa attcaaggtg ctgggcaaca ccgaccggca cagcatcaag  180
aagaacctga tcggagccct gctgttcgac agcggcgaaa cagccgaggc caccccggct  240
aagagaaccg ccagaagaag ataccacaga cggaagaacc ggatctgcta tctgcaagag  300
atcttcagca acgagatggc caagtggcac gacagcttcc tgacagacag ggaagagtcc  360
ttcctggtgg aagaggataa gaagcacgag cggcacccca tcttcggcaa catcgtggac  420
gaggtggcct accacgagaa gtaccccacc atctaccacc tgagaaagaa actggtggac  480
agcaccgaca aggccgacct gcggctgatc tatctggccc tggcccacat gatcaagttc  540
cggggccact tcctgatcga gggcgaccta aaccccgaca acagcgacgt ggacaagctg  600
ttcatccagc tggtgcagac ctacaaccag ctgttcgagg aaaaccccat caacgccagc  660
ggcgtggacg ccaaggccat cctgtctgcc agactgagca gagcagacg gctgaaaat   720
ctgatcgccc agctgcccgg cgagaagaag aatggcctgt tcggaaacct gattgccctg  780
agcctgggcc tgacccccaa cttcaagagc aacttcgacc tggccgagga tgccaaactg  840
cagctgagca aggacaccta cgacgacgac ctggacaacc tgctggccca gatcggcgac  900
cagtacgccg acctgtttct ggccgccaag aacctgtccg acgccatcct gctgagcgac  960
atcctgagag tgaacaccga gatcaccaag gccccctga cgcctctat gatcaagaga 1020
tacgacgagc accaccagga cctgaccctg ctgaaagctc tcgtgcggca gcagctgcct 1080
gagaagtaca aagagatttt cttcgaccag agcaagaacg gctacgccgg ctacattgac 1140
ggcggagcca gccaggaaga gttctacaag ttcatcaagc ccatcctgga aaagatggac 1200
ggcaccgagg aactgctcgt gaagctgaac agagaggacc tgctgcgcaa gcagcggacc 1260
ttcgacaacg gcagcatccc ccaccagatc cacctgggag agctgcacgc cattctgcgg 1320
cggcaggaag atttttaccc attcctgaag gacaaccggg aaaagatcga gaagatcctg 1380
accttccgca tcccctacta cgtgggccct ctggccaggg aaacagcag attcgcctgg 1440
atgaccagaa agagcgagga aaccatcacc cctggaact cgaggaagt ggtggacaag 1500
ggcgcttccg cccagagctt catcgagcgg atgaccaact cgataagaa cctgcccaac 1560
gagaaggtgc tgcccaagca cagcctgctg tacgagtact tcaccgtgta taacgagctg 1620
accaaagtga aatacgtgac cgagggaatg agaaagcccg ccttcctgag cggcgagcag 1680
aaaaaggcca tcgtggacct gctgttcaag accaaccgga agtgaccgt gaagcagctg 1740
aaagaggact acttcaagaa aatcgagtgc ttcgactccg tggaaatctc cggcgtggaa 1800
gatcggttca acgcctccct gggcacatac cacgatctgc tgaaaattat caaggacaag 1860
gacttcctgg acaatgagga aaacgaggac atctgaagct gacccctgaca 1920
ctgtttgagg acagagagat gatcgaggaa cggctgaaaa cctatgccca cctgttcgac 1980
gacaaagtga tgaagcagct gaagcggcgg agatacaccg gctggggcag gctgagccgg 2040
aagctgatca acggcatccg ggacaagcag tccggcaaga caatcctgga tttcctgaag 2100
tccgacggct tcgccaacag aaacttcatg cagctgatcc acgacgacag cctgaccttt 2160
aaagaggaca tccagaaagc ccaggtgtcc ggccagggcg atagcctgca cgagcacatt 2220
gccaatctgg ccggcagccc cgccattaag aagggcatcc tgcagacagt gaaggtggtg 2280
gacgagctct gaaagtgat gggcggcac aagcccgaga acatcgtgat cgaaatggcc 2340
agagagaacc agaccacccc aaggggacag aagaacagcc gcgagagaat gaagcggatc 2400
gaagagggca tcaaagagct gggcagccag atcctgaaag aacaccccgt ggaaaacacc 2460
cagctgcaga acgagaagct gtacctgtac tacctgcaga atgggcggga tatgtacgtg 2520
```

-continued

```
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata agctgatcgc cagaaagaag   3420
gactgggacc ctaagaagta cggcggcttc gacagcccca ccgtggccta ttctgtgctg   3480
gtggtggcca agtggaaaaa gggcaagtcc aagaaactga agagtgtgaa agagctgctg   3540
gggatcacca tcatggaaag aagcagcttc gagaagaatc ccatcgactt tctggaagcc   3600
aagggctaca agaagtgaa aaaggacctg atcatcaagc tgcctaagta ctccctgttc   3660
gagctggaaa acgccggaa gagaatgctg gcctctgccg gcgaactgca gaagggaaac   3720
gaactggccc tgccctccaa atatgtgaac ttcctgtacc tggccagcca ctatgagaag   3780
ctgaagggct cccccgagga taatgagcag aaacagctgt ttgtggaaca gcacaagcac   3840
tacctggacg agatcatcga gcagatcagc gagttctcca agagagtgat cctggccgac   3900
gctaatctgg acaaagtgct gtccgcctac aacaagcacc gggataagcc catcagagag   3960
caggccgaga atatcatcca cctgtttacc ctgaccaatc tgggagcccc tgccgccttc   4020
aagtactttg acaccaccat cgaccggaag aggtacacca ccaccaaaga ggtgctggac   4080
gccaccctga tccaccagag catcaccggc ctgtacgaga cacgatcga cctgtctcag   4140
ctgggaggcg acaaaggcc ggcggccacg aaaaaggccg ccaggcaaa aagaaaaag   4200
taa                                                                  4203

SEQ ID NO: 18          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 18
cttcgaaatg tccgttcggt                                                  20

SEQ ID NO: 19          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 19
gaagttcgag ggcgacaccc                                                  20

SEQ ID NO: 20          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 20
aagtaaaacc tctacaaatg                                                  20

SEQ ID NO: 21          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 21
agatcgttag cagaaacaaa                                                  20

SEQ ID NO: 22          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 22
gtgtaatagc tcctgcatgg                                                  20
```

```
SEQ ID NO: 23           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 23
tcttaccagg attccatcca                                                       20

SEQ ID NO: 24           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 24
cctgccctga gtaagcgaca                                                       20

SEQ ID NO: 25           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 25
tcctggcatg tctatctgta                                                       20

SEQ ID NO: 26           moltype = DNA   length = 42
FEATURE                 Location/Qualifiers
misc_feature            1..42
                        note = Synthetic oligonucleotide
source                  1..42
                        mol_type = other DNA
                        organism = synthetic construct
SEQUENCE: 26
atggaagacg ccaaaaacat aaagaaaggc ccggcgccat tc                              42

SEQ ID NO: 27           moltype = DNA   length = 28
FEATURE                 Location/Qualifiers
misc_feature            1..28
                        note = Synthetic oligonucleotide
source                  1..28
                        mol_type = other DNA
                        organism = synthetic construct
SEQUENCE: 27
aacacttaaa atcgcagtat ccggaatg                                              28

SEQ ID NO: 28           moltype = DNA   length = 21
FEATURE                 Location/Qualifiers
misc_feature            1..21
                        note = Synthetic oligonucleotide
source                  1..21
                        mol_type = other DNA
                        organism = synthetic construct
SEQUENCE: 28
gtggtgccca tcctggtcga g                                                     21

SEQ ID NO: 29           moltype = DNA   length = 22
FEATURE                 Location/Qualifiers
misc_feature            1..22
                        note = Synthetic oligonucleotide
source                  1..22
                        mol_type = other DNA
                        organism = synthetic construct
SEQUENCE: 29
cgcttctcgt tggggtctttt gc                                                   22

SEQ ID NO: 30           moltype = DNA   length = 21
FEATURE                 Location/Qualifiers
misc_feature            1..21
                        note = Synthetic oligonucleotide
source                  1..21
                        mol_type = other DNA
                        organism = synthetic construct
SEQUENCE: 30
```

```
atccgtcttc tccccattcc g                                              21

SEQ ID NO: 31          moltype = DNA   length = 21
FEATURE                Location/Qualifiers
misc_feature           1..21
                       note = Synthetic oligonucleotide
source                 1..21
                       mol_type = other DNA
                       organism = synthetic construct
SEQUENCE: 31
gacgagctcg ctaatccagt g                                              21

SEQ ID NO: 32          moltype = DNA   length = 22
FEATURE                Location/Qualifiers
misc_feature           1..22
                       note = Synthetic oligonucleotide
source                 1..22
                       mol_type = other DNA
                       organism = synthetic construct
SEQUENCE: 32
atagagacgc tgagtccggt tc                                             22

SEQ ID NO: 33          moltype = DNA   length = 22
FEATURE                Location/Qualifiers
misc_feature           1..22
                       note = Synthetic oligonucleotide
source                 1..22
                       mol_type = other DNA
                       organism = synthetic construct
SEQUENCE: 33
cctaagccca agaggaaaca ga                                             22

SEQ ID NO: 34          moltype = DNA   length = 24
FEATURE                Location/Qualifiers
misc_feature           1..24
                       note = Synthetic oligonucleotide
source                 1..24
                       mol_type = other DNA
                       organism = synthetic construct
SEQUENCE: 34
ctgtgctggt gtgtgcaaac tata                                           24

SEQ ID NO: 35          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 35
ctgtcacagt gaaactcgtt actttgtata tc                                  32

SEQ ID NO: 36          moltype = DNA   length = 21
FEATURE                Location/Qualifiers
misc_feature           1..21
                       note = Synthetic oligonucleotide
source                 1..21
                       mol_type = other DNA
                       organism = synthetic construct
SEQUENCE: 36
acaaggctct ggcttccatt g                                              21

SEQ ID NO: 37          moltype = DNA   length = 23
FEATURE                Location/Qualifiers
misc_feature           1..23
                       note = Synthetic oligonucleotide
source                 1..23
                       mol_type = other DNA
                       organism = synthetic construct
SEQUENCE: 37
gatcaaagca aggccttgtg cat                                            23

SEQ ID NO: 38          moltype = DNA   length = 22
FEATURE                Location/Qualifiers
misc_feature           1..22
                       note = Synthetic oligonucleotide
source                 1..22
                       mol_type = other DNA
                       organism = synthetic construct
```

```
SEQUENCE: 38
tctgagcccc ttccatctga cc                                            22

SEQ ID NO: 39           moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 39
agctcagcag aagctcagca g                                             21

SEQ ID NO: 40           moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 40
cccagtcatc agttgctatg caatt                                         25

SEQ ID NO: 41           moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 41
gggtttcctt tggttcacag atcca                                         25

SEQ ID NO: 42           moltype = DNA  length = 24
FEATURE                 Location/Qualifiers
misc_feature            1..24
                        note = Synthetic oligonucleotide
source                  1..24
                        mol_type = other DNA
                        organism = synthetic construct
SEQUENCE: 42
cgttttccca caagagctaa ggct                                          24

SEQ ID NO: 43           moltype = DNA  length = 23
FEATURE                 Location/Qualifiers
misc_feature            1..23
                        note = Synthetic oligonucleotide
source                  1..23
                        mol_type = other DNA
                        organism = synthetic construct
SEQUENCE: 43
gtggtttggt cacatctcag gtg                                           23

SEQ ID NO: 44           moltype = DNA  length = 59
FEATURE                 Location/Qualifiers
misc_feature            1..59
                        note = Synthetic oligonucleotide
source                  1..59
                        mol_type = other DNA
                        organism = synthetic construct
SEQUENCE: 44
taatacgact cactataggg aagtaaaact ctacaaatgg ttttagagct agaaatagc    59

SEQ ID NO: 45           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 45
aaaagcaccg actcggtgcc                                               20

SEQ ID NO: 46           moltype = DNA  length = 59
FEATURE                 Location/Qualifiers
misc_feature            1..59
                        note = Synthetic oligonucleotide
source                  1..59
                        mol_type = other DNA
```

```
                        organism = synthetic construct
SEQUENCE: 46
taatacgact cactataggg aaacctctac aaatgtggta gtttagagct agaaatagc       59

SEQ ID NO: 47           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 47
aaaagcaccg actcggtgcc                                                  20

SEQ ID NO: 48           moltype = DNA   length = 60
FEATURE                 Location/Qualifiers
misc_feature            1..60
                        note = Synthetic oligonucleotide
source                  1..60
                        mol_type = other DNA
                        organism = synthetic construct
SEQUENCE: 48
taatacgact cactataggg cgtatagcat acattatacg gttttagagc tagaaatagc      60

SEQ ID NO: 49           moltype = DNA   length = 20
FEATURE                 Location/Qualifiers
misc_feature            1..20
                        note = Synthetic oligonucleotide
source                  1..20
                        mol_type = other DNA
                        organism = synthetic construct
SEQUENCE: 49
aaaagcaccg actcggtgcc                                                  20

SEQ ID NO: 50           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 50
cctgccctga gtaagcggta aggctagttt ta                                    32

SEQ ID NO: 51           moltype = DNA   length = 33
FEATURE                 Location/Qualifiers
misc_feature            1..33
                        note = Synthetic oligonucleotide
source                  1..33
                        mol_type = other DNA
                        organism = synthetic construct
SEQUENCE: 51
cctgccctga gtaagcgtgt aaggctagtt tta                                   33

SEQ ID NO: 52           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 52
cctgccctga gtaagcggta aggctagttt ta                                    32

SEQ ID NO: 53           moltype = DNA   length = 27
FEATURE                 Location/Qualifiers
misc_feature            1..27
                        note = Synthetic oligonucleotide
source                  1..27
                        mol_type = other DNA
                        organism = synthetic construct
SEQUENCE: 53
cctgccctgt atgtaaggct agtttta                                          27

SEQ ID NO: 54           moltype = DNA   length = 24
FEATURE                 Location/Qualifiers
misc_feature            1..24
                        note = Synthetic oligonucleotide
source                  1..24
```

```
                        mol_type = other DNA
                        organism = synthetic construct
SEQUENCE: 54
cctgccctga gtaagcctag ttta                                              24

SEQ ID NO: 55           moltype =    length =
SEQUENCE: 55
000

SEQ ID NO: 56           moltype = DNA   length = 28
FEATURE                 Location/Qualifiers
misc_feature            1..28
                        note = Synthetic oligonucleotide
source                  1..28
                        mol_type = other DNA
                        organism = synthetic construct
SEQUENCE: 56
cctgcctgag taagcgaggc tagtttta                                          28

SEQ ID NO: 57           moltype = DNA   length = 30
FEATURE                 Location/Qualifiers
misc_feature            1..30
                        note = Synthetic oligonucleotide
source                  1..30
                        mol_type = other DNA
                        organism = synthetic construct
SEQUENCE: 57
cctgccctga gtaagcgaag gctagtttta                                        30

SEQ ID NO: 58           moltype = DNA   length = 27
FEATURE                 Location/Qualifiers
misc_feature            1..27
                        note = Synthetic oligonucleotide
source                  1..27
                        mol_type = other DNA
                        organism = synthetic construct
SEQUENCE: 58
cctgccctga gtgtaaggct agtttta                                           27

SEQ ID NO: 59           moltype = DNA   length = 40
FEATURE                 Location/Qualifiers
misc_feature            1..40
                        note = Synthetic oligonucleotide
source                  1..40
                        mol_type = other DNA
                        organism = synthetic construct
SEQUENCE: 59
gcccgccctg agtaagcggt aaggctagtt ttaatttcga                             40

SEQ ID NO: 60           moltype = DNA   length = 34
FEATURE                 Location/Qualifiers
misc_feature            1..34
                        note = Synthetic oligonucleotide
source                  1..34
                        mol_type = other DNA
                        organism = synthetic construct
SEQUENCE: 60
gccctgccct gagtaagcta gttttaattt cga                                    34

SEQ ID NO: 61           moltype = DNA   length = 37
FEATURE                 Location/Qualifiers
misc_feature            1..37
                        note = Synthetic oligonucleotide
source                  1..37
                        mol_type = other DNA
                        organism = synthetic construct
SEQUENCE: 61
gccctgccct gtatgtaagg ctagttttaa ttttcga                                37

SEQ ID NO: 62           moltype = DNA   length = 43
FEATURE                 Location/Qualifiers
misc_feature            1..43
                        note = Synthetic oligonucleotide
source                  1..43
                        mol_type = other DNA
                        organism = synthetic construct
SEQUENCE: 62
gccctgccct gagtaagcgt gtaaggctag ttttaattt cga                          43
```

COMPOSITIONS AND METHODS FOR ORGAN SPECIFIC DELIVERY OF NUCLEIC ACIDS This application is a continuation of U.S. application Ser. No. 17/711,911, filed Apr. 1, 2022, which is a continuation of U.S. application Ser. No. 17/572,615, filed Jan. 10, 2022, which is a continuation of U.S. application Ser. No. 17/473,863, filed Sep. 13, 2021, now U.S. Pat. No. 11,304,911, which is a continuation of U.S. application Ser. No. 17/191,895, filed Mar. 4, 2021, now U.S. Pat. No. 11,229,609, which is a continuation of International Application No. PCT/US2019/049565, filed Sep. 4, 2019, which claims the benefit of priority to U.S. Provisional Application Ser. No. 62/726,741, filed on Sep. 4, 2018, the entire contents of each of which are hereby incorporated by reference.

This invention was made with government support under grant number CA150245 and CA190525 awarded by The National Institutes of Health. The government has certain rights in the invention.

This application contains a Sequence Listing XML, which has been submitted electronically and is hereby incorporated by reference in its entirety. Said XML Sequence Listing, created on Sep. 2, 2022, is named UTSDP3406USC4.xml and is 84,457 bytes in size.

BACKGROUND

1. Field

The present disclosure relates generally to the field of molecular biology. More particularly, it concerns tissue specific delivery of a therapeutic agent such as a nucleic acid, a protein, or a small molecule therapeutic agent in lipid nanoparticles.

2. Description of Related Art

The CRISPR/Cas (clustered regularly interspaced short palindromic repeat/CRISPR-associated protein (Cas)) technology can edit the genome in a precise, sequence dependent manner, resulting in a permanent change. Because of the ability to target disease causing mutations, it holds incredible promise for one-time cures of genetic diseases. To date, successful editing has been mediated mainly by viral vectors, which require laborious customization for every target and present challenges for clinical translation due to immunogenicity, generation of antibodies that prevent repeat administration, and concerns about rare but dangerous integration events. There remains a clear need to accomplish CRISPR/Cas editing via synthetic nanoparticles (NPs) to expand the safe and effective applications of gene editing.

CRISPR/Cas enables sequence-specific DNA editing by the RNA-guided CRISPR-associated protein 9 (Cas9) nuclease, or its homologs, that forms double-strand breaks (DSBs) in genomic DNA. Cas9 is guided by programmable RNA called single guide RNA (sgRNA). The Cas9/sgRNA complex recognizes the complementary genomic sequence with a 3' protospacer adjacent motif (PAM) sequence. Following DNA cleavage, DSB repair pathways enable directed mutagenesis, or insertions/deletions (indels) that delete the targeted gene. For therapeutic utility, transient Cas9 expression is preferred to limit off-target genomic alteration. Because both Cas9 protein and sgRNAs must be present in the same cells, co-delivery of Cas9 mRNA and sequence targeted sgRNA in one NP is an attractive method, particularly for in vivo use where tissue penetration and cellular uptake is more challenging. CRISPR/Cas editing using viruses, membrane deformation, ribonucleoprotein complex delivery, and hydrodynamic injection are functional, but have limitations that could hinder in vivo therapeutic use in the clinic, including persistent expression of Cas9 and off target editing. Furthermore, these delivery system generally are not selective for the specific organs in which editing is needed. For example, most lipid nanoparticles accumulate through the biological processes in the liver thus reducing the efficacy of the composition on delivery into the target organ.

Similarly, other therapeutic agents such as proteins and small molecule therapeutic agents could benefit from organ specific delivery. Many different types of compounds such as chemotherapeutic agents exhibit significant cytotoxicity. If these compounds could be better directed towards delivery to the desired organs, then less off target effects will be seen.

Therefore, there remains a need to develop new lipid nanoparticles which show preferential delivery to specific organs.

SUMMARY

In some aspects, the present disclosure provides lipid compositions which show organ specific delivery of the lipid composition. These compositions may be used to deliver a nucleic acid component to a specific organ.

In some aspects, the present disclosure provides compositions comprising:
(A) a therapeutic agent; and
(B) a lipid nanoparticle composition comprising:
  (1) a selective organ targeting compound;
  (2) an ionizable cationic lipid; and
  (3) a phospholipid;
wherein the composition preferentially delivers the nucleic acid to a target organ selected from the lungs, the heart, the brain, the spleen, the lymph nodes, the bones, the bone marrow, the skeletal muscles, the stomach, the small intestine, the large intestine, the kidneys, the bladder, the breast, the liver, the testes, the ovaries, the uterus, the spleen, the thymus, the brainstem, the cerebellum, the spinal cord, the eye, the ear, the tongue, or the skin. In some embodiments, the target organ is selected from the lungs, the heart, the brain, the spleen, the lymph nodes, the bones, the bone marrow, the skeletal muscles, the stomach, the small intestine, the large intestine, the kidneys, the bladder, the breast, the testes, the ovaries, the uterus, the spleen, the thymus, the brainstem, the cerebellum, the spinal cord, the eye, the ear, the tongue, or the skin.

In some embodiments, the target organ is the lungs, the lymph nodes, or the spleen. In some embodiments, the target organ is the lungs. In other embodiments, the target organ is the spleen. In other embodiments, the target organ is the liver. In other embodiments, the target organ is the lymph nodes.

In some embodiments, the selective organ targeting compound is a permanently cationic lipid. In some embodiments, the permanently cationic lipid is present in a molar percentage of the lipid nanoparticle composition from about 5% to about 20%. In some embodiments, the molar percentage of the permanently cationic lipid is present from about 12% to about 18%. In some embodiments, the molar percentage of the permanently cationic lipid is about 15%. In some embodiments, the permanently cationic lipid is present in a molar percentage of the lipid nanoparticle composition from about 20% to about 65%. In some embodiments, the molar percentage of the permanently cationic lipid is present from about 40% to about 61%. In some embodiments, the molar percentage of the permanently cationic lipid is about 50%.

In some embodiments, the permanently cationic lipid comprises a quaternary ammonium ion. In some embodiments, the permanently cationic lipid is further defined as:

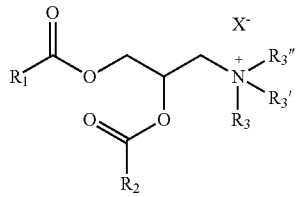

(I)

wherein:
$R_1$ and $R_2$ are each independently alkyl$_{(C8-C24)}$, alkenyl$_{(C8-C24)}$, or a substituted version of either group;
$R_3$, $R_3'$, and $R_3''$ are each independently alkyl$_{(C\leq6)}$ or substituted alkyl$_{(C\leq6)}$;
$X^-$ is a monovalent anion.

In some embodiments, $R_1$ is an alkenyl$_{(C8-C24)}$ or substituted alkenyl$_{(C8-C24)}$. In some embodiments, $R_2$ is an alkenyl$_{(C8-C24)}$ or substituted alkenyl$_{(C8-C24)}$. In other embodiments, $R_1$ is an alkyl$_{(C8-C24)}$ or substituted alkyl$_{(C8-C24)}$. In other embodiments, $R_2$ is an alkyl$_{(C8-C24)}$ or substituted alkyl$_{(C8-C24)}$. In some embodiments, $R_1$ and $R_2$ are both the same. In some embodiments, $R_3$, $R_3'$, and $R_3''$ are each identical. In some embodiments, $R_3$, $R_3'$, and $R_3''$ are each methyl. In some embodiments, $X^-$ is halide anion such as bromide or chloride. In some embodiments, the permanently cationic lipid is further defined as:

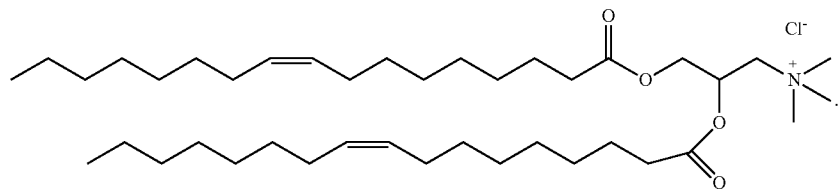

In other embodiments, the permanently cationic lipid is further defined as:

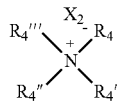

I wherein:
$R_4$ and $R_4'$ are each independently alkyl$_{(C6-C24)}$, alkenyl$_{(C6-C24)}$, or a substituted version of either group;
$R_4''$ is alkyl$_{(C\leq24)}$, alkenyl$_{(C\leq24)}$, or a substituted version of either group;
$R_4'''$ is alkyl$_{(C1-C8)}$, alkenyl$_{(C2-C8)}$, or a substituted version of either group; and
$X_2$ is a monovalent anion.

In some embodiments, $R_4$ is alkyl$_{(C6-C24)}$ or substituted alkyl$_{(C6-C24)}$ such as octadecyl. In some embodiments, $R_4'$ is alkyl$_{(C6-C24)}$ or substituted alkyl$_{(C6-C24)}$ such as octadecyl. In some embodiments, $R_4''$ is alkyl$_{(C\leq24)}$ or substituted alkyl$_{(C\leq24)}$. In some embodiments, $R_4''$ is alkyl$_{(C\leq8)}$ or substituted alkyl$_{(C\leq8)}$ such as methyl. In some embodiments, $R_4'''$ is alkyl$_{(C1-C8)}$ or substituted alkyl$_{(C1-C8)}$ such as methyl. In some embodiments, $X_2$ is a halide such as chloride or bromide. In some embodiments, the permanently cationic lipid is further defined as:

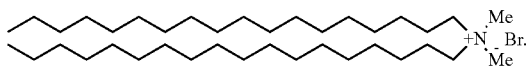 [SMILES: CCCCCCCCCCCCCCCCCC[N+](C)(C)CCCCCCCCCCCCCCCCCC]

In some embodiments, the permanently cationic lipid is further defined as:

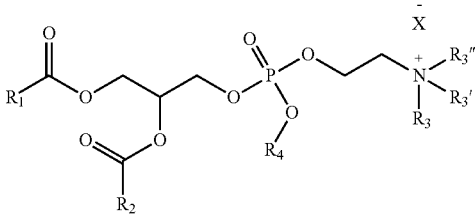

(IA)

wherein:
$R_1$ and $R_2$ are each independently alkyl$_{(C8-C24)}$, alkenyl$_{(C8-C24)}$, or a substituted version of either group;
$R_3$, $R_3'$, and $R_3''$ are each independently alkyl$_{(C\leq6)}$ or substituted alkyl$_{(C\leq6)}$;
$R_4$ is alkyl$_{(C\leq6)}$ or substituted alkyl$_{(C\leq6)}$; and
$X^-$ is a monovalent anion.

In some embodiments, $R_1$ is an alkenyl$_{(C8-C24)}$ or substituted alkenyl$_{(C8-C24)}$. In some embodiments, $R_2$ is an alkenyl$_{(C8-C24)}$ or substituted alkenyl$_{(C8-C24)}$. In other embodiments, $R_1$ is an alkyl$_{(C8-C24)}$ or substituted alkyl$_{(C8-C24)}$. In other embodiments, $R_2$ is an alkyl$_{(C8-C24)}$ or substituted alkyl$_{(C8-C24)}$. In some embodiments, $R_1$ and $R_2$ are both the same.

In some embodiments, $R_3$, $R_3'$, and $R_3''$ are each identical such as $R_3$, $R_3'$, and $R_3''$ are each methyl. In some embodiments, $R_4$ is alkyl$_{(C\leq6)}$ such as ethyl. In some embodiments, $X^-$ is halide anion such as bromide or chloride.

In some embodiments, the permanently cationic lipid is further defined as:

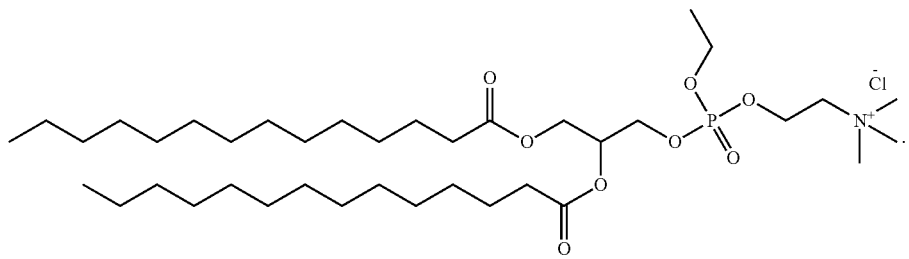 [SMILES: CCCCCCCCCCCCCC(=O)OCC(COP(=O)(OCC)OCC[N+](C)(C)C)OC(=O)CCCCCCCCCCCCC ; Cl]

In other embodiments, the selective organ targeting compound is a permanently anionic lipid. In some embodiments, the permanently anionic lipid is present in a molar percentage of the lipid nanoparticle composition from about 5% to about 50%. In some embodiments, the molar percentage of the permanently anionic lipid is present from about 10% to about 45%. In some embodiments, the molar percentage of the permanently anionic lipid is about 30%. In some embodiments, the permanently anionic lipid comprises a phosphate group.

In some embodiments, the permanently anionic lipid is further defined as:

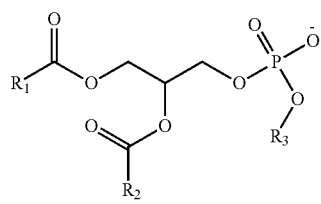

(IB)

wherein:

$R_1$ and $R_2$ are each independently alkyl$_{(C8-C24)}$, alkenyl$_{(C8-C24)}$, or a substituted version of either group;

$R_3$ is hydrogen, alkyl$_{(C\leq6)}$, or substituted alkyl$_{(C\leq6)}$, or —$Y_1$—$R_4$, wherein:

$Y_1$ is alkanediyl$_{(C\leq6)}$ or substituted alkanediyl$_{(C\leq6)}$; and $R_4$ is acyloxy$_{(C\leq8-24)}$ or substituted acyloxy$_{(C\leq8-24)}$.

In some embodiments, $R_1$ is an alkenyl$_{(C8-C24)}$ or substituted alkenyl$_{(C8-C24)}$. In other embodiments, $R_2$ is an alkenyl$_{(C8-C24)}$ or substituted alkenyl$_{(C8-C24)}$. In other embodiments, $R_1$ is an alkyl$_{(C8-C24)}$ or substituted alkyl$_{(C8-C24)}$. In other embodiments, $R_2$ is an alkyl$_{(C8-C24)}$ or substituted alkyl$_{(C8-C24)}$. In some embodiments, $R_1$ and $R_2$ are both the same.

In some embodiments, $R_3$ is hydrogen. In other embodiments, $R_3$ is —$Y_1$—$R_4$, wherein:

$Y_1$ is alkanediyl$_{(C\leq6)}$ or substituted alkanediyl$_{(C\leq6)}$; and $R_4$ is acyloxy$_{(C\leq8-24)}$ or substituted acyloxy$_{(C\leq8-24)}$.

In some embodiments, $Y_1$ is substituted alkanediyl$_{(C\leq6)}$ such as 2-hydroxypropanediyl. In some embodiments, $R_4$ is acyloxy$_{(C\leq8-24)}$ such as octadecenoate. In some embodiments, the permanently anionic lipid is further defined as:

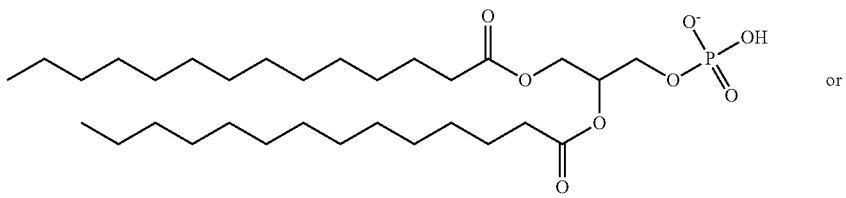

or

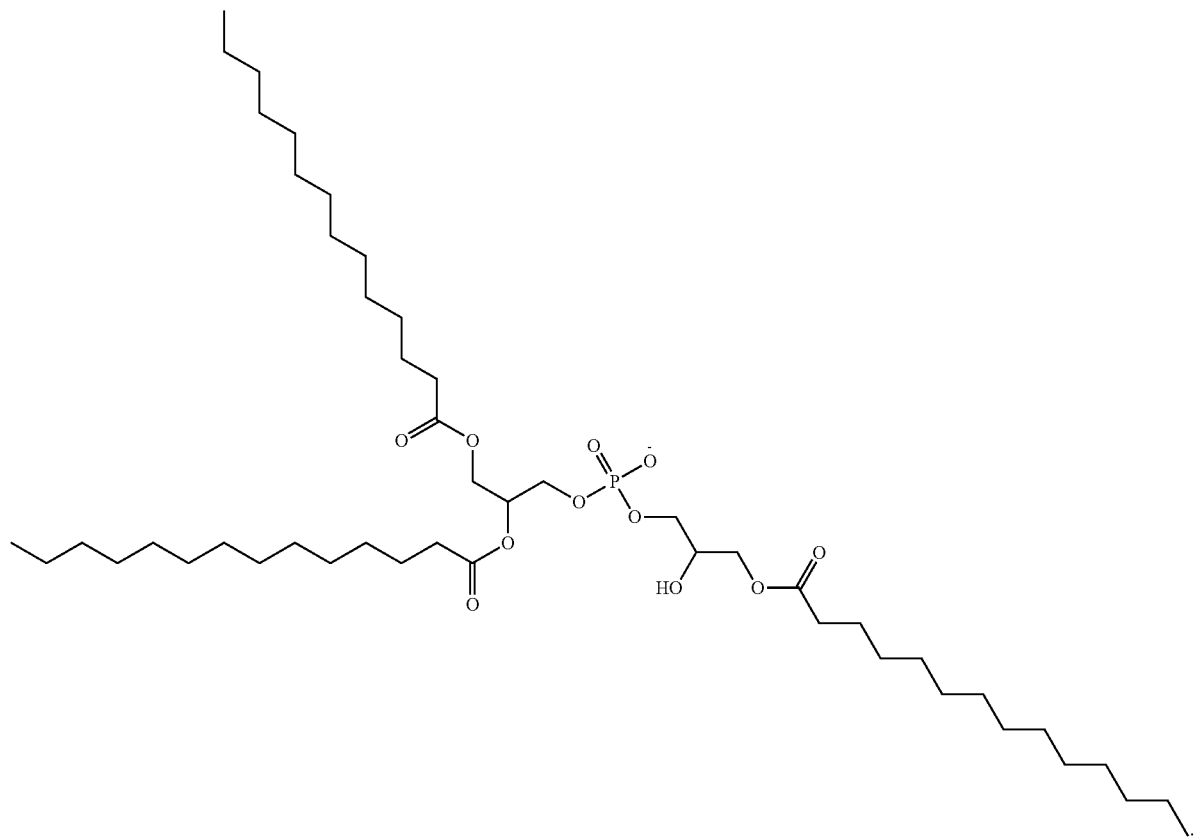

In other embodiments, the selective organ targeting compound is a $C_6$-$C_{24}$ diacyl phosphotidylcholine. In some embodiments, the diacyl phosphotidylcholine is present in a molar percentage of the lipid nanoparticle composition from about 5% to about 50%. In some embodiments, the molar percentage of the diacyl phosphotidylcholine is present from about 10% to about 45% such as about 30%.

In some embodiments, the selective organ targeting compound comprises at least two fatty acid chains, a quaternary amine, and an anionic phosphate group. In some embodiments, the diacyl phosphotidylcholine is further defined as:

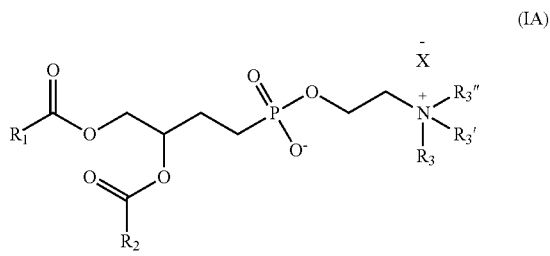

(IA)

wherein:
R$_1$ and R$_2$ are each independently alkyl$_{(C8-C24)}$, alkenyl$_{(C8-C24)}$, or a substituted version of either group;
R$_3$, R$_3$', and R$_3$" are each independently alkyl$_{(C\leq 6)}$ or substituted alkyl$_{(C\leq 6)}$; and
X$^-$ is a monovalent anion.

In some embodiments, R$_1$ is an alkenyl$_{(C8-C24)}$ or substituted alkenyl$_{(C8-C24)}$. In some embodiments, R$_2$ is an alkenyl$_{(C8-C24)}$ or substituted alkenyl$_{(C8-C24)}$. In other embodiments, R$_1$ is an alkyl$_{(C8-C24)}$ or substituted alkyl$_{(C8-C24)}$. In other embodiments, R$_2$ is an alkyl$_{(C8-C24)}$ or substituted alkyl$_{(C8-C24)}$. In some embodiments, R$_1$ and R$_2$ are both the same.

In some embodiments, R$_3$, R$_3$', and R$_3$" are each identical. In some embodiments, R$_3$, R$_3$', and R$_3$" are each methyl. In some embodiments, X$^-$ is halide anion such as bromide or chloride. In some embodiments, the diacyl phosphotidylcholine is further defined as:

further defined as 1,2-dioleoyl-sn-glycero-3-phosphoethanolamine or 1,2-distearoyl-sn-glycero-3-phosphocholine. In some embodiments, the phospholipid is 1,2-dioleoyl-sn-glycero-3-phosphoethanolamine.

In some embodiments, the compositions further comprise a steroid. In some embodiments, the steroid is present in a molar percentage of the lipid nanoparticle composition from about 39% to about 46%. In some embodiments, the molar percentage of the steroid is present from about 40% to about 43%. In some embodiments, the molar percentage of the steroid is about 40.5%. In other embodiments, the steroid is present in a molar percentage of the lipid nanoparticle composition from about 15% to about 39%. In some embodiments, the molar percentage of the steroid is present from about 20% to about 27.5%. In some embodiments, the molar percentage of the steroid is about 23.8%. In some embodiments, the steroid is cholesterol.

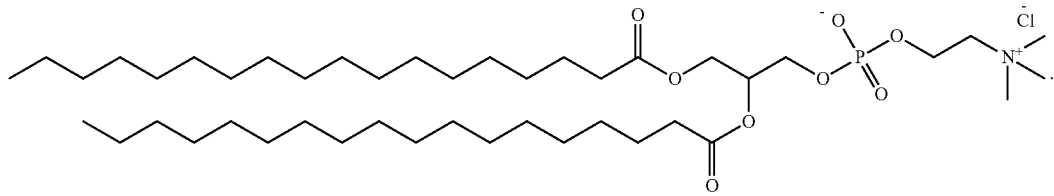 [SMILES: CCCCCCCCCCCCCCCCCC(=O)OCC(COP(=O)(O)OCC[N+](C)(C)C)OC(=O)CCCCCCCCCCCCCCCCC ; Cl]

In some embodiments, the ionizable cationic lipid is present in a molar percentage of the lipid nanoparticle composition from about 5% to about 30%. In some embodiments, the molar percentage of the ionizable cationic lipid is present from about 7.5% to about 20%. In some embodiments, the molar percentage of the ionizable cationic lipid is about 11.9%. In some embodiments, the ionizable cationic lipid is present in a molar percentage of the lipid nanoparticle composition from about 15% to about 30%. In some embodiments, the molar percentage of the ionizable cationic lipid is present from about 15% to about 25%. In some embodiments, the molar percentage of the ionizable cationic lipid is about 20.3%.

In some embodiments, the ionizable cationic lipid comprises an ammonium group which is positively charged at physiological pH and contains at least two hydrophobic groups. In some embodiments, the ammonium group is positively charged at a pH from about 6 to about 8. In some embodiments, the ionizable cationic lipid is a dendrimer or dendron. In some embodiments, the ionizable cationic lipid comprises at least two C6-C24 alkyl or alkenyl groups. In some embodiments, the ionizable cationic lipid comprises at least two C8-C24 alkyl groups.

In some embodiments, the phospholipid is present in a molar percentage of the lipid nanoparticle composition from about 8% to about 20%. In some embodiments, the molar percentage of the phospholipid is present from about 10% to about 14%. In some embodiments, the molar percentage of the phospholipid is about 11.9%. In other embodiments, the phospholipid is present in a molar percentage of the lipid nanoparticle composition from about 20% to about 23%. In some embodiments, the molar percentage of the phospholipid is present from about 20% to about 21%. In some embodiments, the molar percentage of the phospholipid is about 20.3%. In some embodiments, the phospholipid is In some embodiments, the compositions further comprise a PEGylated lipid. In some embodiments, the PEGylated lipid is present in a molar percentage of the lipid nanoparticle composition from about 0.5% to about 10.0%. In some embodiments, the molar percentage of the PEGylated lipid is present from about 0.5% to about 5.0%. In other embodiments, the molar percentage of the PEGylated lipid is present from about 2.0% to about 2.8%. In some embodiments, the molar percentage of the PEGylated lipid is about 2.4%. In other embodiments, the PEGylated lipid is present in a molar percentage of the lipid nanoparticle composition from about 3.9% to about 4.6%. In some embodiments, the molar percentage of the PEGylated lipid is present from about 4.0% to about 4.3%. In some embodiments, the molar percentage of the PEGylated lipid is about 4.1%. In some embodiments, the PEGylated lipid comprises a PEG component from about 1000 to about 10,000 Daltons. In some embodiments, the PEG lipid is a PEGylated diacylglycerol. In some embodiments, the PEG lipid is further defined by the formula:

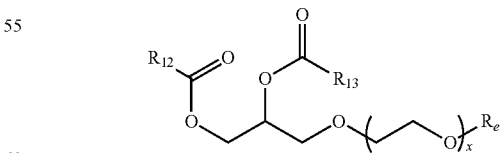

wherein:
R$_{12}$ and R$_{13}$ are each independently alkyl$_{(C\leq 24)}$, alkenyl$_{(C\leq 24)}$, or a substituted version of either of these groups;
R$_e$ is hydrogen, alkyl$_{(C\leq 8)}$, or substituted alkyl$_{(C\leq 8)}$; and
x is 1-250.

In some embodiments, the PEG lipid is dimyristoyl-sn-glycerol or a compound of the formula:

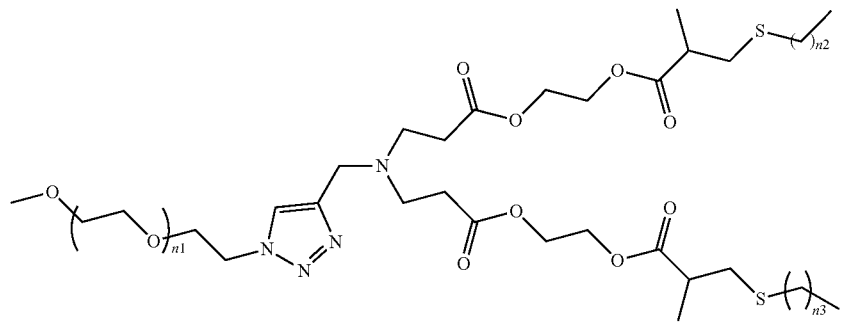

wherein:
$n_1$ is 5-250; and
$n_2$ and $n_3$ are each independently 2-25.

In some embodiments, the compositions comprise cholesterol and DMG-PEG. In some embodiments, the compositions comprise DOPE. In other embodiments, the compositions comprise DSPC. In some embodiments, the compositions further comprise DLin-MC3-DMA. In other embodiments, the compositions further comprise C12-200. In some embodiments, the compositions further comprise 3A5-SC8, 3A3-SC8, 4A1-SC8, 4A3-SC8, 5A2-SC8 with five tails, or 5A2-SC8 with six tails. In some embodiments, the compositions further comprise 5A2-SC8. In some embodiments, the compositions further comprise DOTAP. In some embodiments, the compositions comprise cholesterol, DMG-PEG, DSPC, DLin-MC3-DMA, and DOTAP.

In some embodiments, the therapeutic agent is a small molecule such as a small molecule selected from an anticancer agents, antifungal agents, psychiatric agents such as analgesics, consciousness level-altering agents such as anesthetic agents or hypnotics, nonsteroidal anti-inflammatory drugs (NSAIDS), anthelminthics, antiacne agents, antianginal agents, antiarrhythmic agents, anti-asthma agents, antibacterial agents, anti-benign prostate hypertrophy agents, anticoagulants, antidepressants, antidiabetics, antiemetics, antiepileptics, antigout agents, antihypertensive agents, anti-inflammatory agents, antimalarials, antimigraine agents, antimuscarinic agents, antineoplastic agents, antiobesity agents, antiosteoporosis agents, antiparkinsonian agents, antiproliferative agents, antiprotozoal agents, antithyroid agents, antitussive agent, anti-urinary incontinence agents, antiviral agents, anxiolytic agents, appetite suppressants, beta-blockers, cardiac inotropic agents, chemotherapeutic drugs, cognition enhancers, contraceptives, corticosteroids, Cox-2 inhibitors, diuretics, erectile dysfunction improvement agents, expectorants, gastrointestinal agents, histamine receptor antagonists, immunosuppressants, keratolytics, lipid regulating agents, leukotriene inhibitors, macrolides, muscle relaxants, neuroleptics, nutritional agents, opioid analgesics, protease inhibitors, or sedatives. In other embodiments, the therapeutic agent is a protein. In other embodiments, the therapeutic agent is a nucleic acid such as a therapeutic nucleic acid. In some embodiments, the nucleic acid is an siRNA, a miRNA, a pri-miRNA, a messenger RNA (mRNA), a clustered regularly interspaced short palindromic repeats (CRISPR) related nucleic acid, a single guide RNA (sgRNA), a CRISPR-RNA (crRNA), a trans-activating crRNA (tracrRNA), a plasmid DNA (pDNA), a transfer RNA (tRNA), an antisense oligonucleotide (ASO), a guide RNA, a double stranded DNA (dsDNA), a single stranded DNA (ssDNA), a single stranded RNA (ssRNA), and a double stranded RNA (dsRNA). In some embodiments, the compositions comprise a first nucleic acid and a second nucleic acid. In some embodiments, the first nucleic acid is a messenger RNA. In some embodiments, the second nucleic acid is a single guide RNA. In some embodiments, the first nucleic acid is a messenger RNA (mRNA) and a single guide RNA (sgRNA). In some embodiments, the nucleic acid is present in a ratio of the lipid nanoparticle composition to the nucleic acid is from about 1:1 to about 1:100. In some embodiments, the ratio is from about 1:10 to about 1:60. In some embodiments, the ratio is about 1:40.

In some embodiments, the compositions further comprise a protein. In some embodiments, the protein is a protein associated with translation or transcription. In some embodiments, the protein is associated with a CRISPR process. In some embodiments, the protein is a CRISPR associated protein. In some embodiments, the protein is Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the protein is Cas9. In some embodiments, the protein and the nucleic acid are present in a molar ratio from about 1:1 to about 1:20. In some embodiments, the molar ratio is from about 1:1 to about 1:10. In some embodiments, the molar ratio is from about 1:3 to about 1:8.

In some embodiments, the compositions have a negative zeta potential. In some embodiments, the zeta potential is from −0.25 mV to about −10 mV. In some embodiments, the zeta potential is from about −0.5 mV to about −2 mV. In some embodiments, the compositions comprise both a protein and a nucleic acid. In some embodiments, the compositions comprise Cas9 protein and a single guide nucleic acid. In some embodiments, the composition comprises Cas9 protein, a single guide nucleic acid, and a donor DNA.

In another aspect, the present disclosure provides pharmaceutical compositions comprising:
(A) a composition described herein; and
(B) an excipient.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical compositions are formulated for intravenous or intraarterial injection. In some embodiments, the excipient is a pharmaceutically acceptable carrier. In some embodiments, the pharmaceutically acceptable carrier is a solvent or solution. In some embodiments, the pharmaceutical compositions are formulated as a unit dose.

In still another aspect, the present disclosure provides methods of modulating the expression of a gene comprising delivering a nucleic acid to a cell, the method comprising contacting the cell with a composition or a pharmaceutical composition described herein under conditions sufficient to cause uptake of the nucleic acid into the cell.

In some embodiments, the cell is contacted in vitro or ex vivo. In some embodiments, the cell is contacted in vivo. In some embodiments, the modulation of the gene expression is sufficient to treat a disease or disorder such as cancer.

In still yet another aspect, the present disclosure provides methods of treating a disease or disorder in a patient comprising administering to the patient in need thereof a pharmaceutically effective amount of a composition or a pharmaceutical composition described herein, wherein the composition or pharmaceutical composition comprises a therapeutic nucleic acid or protein for the disease or disorder.

In some embodiments, the disease or disorder is cancer. In some embodiments, the methods further comprise administering one or more additional cancer therapies to the patient. In some embodiments, the cancer therapy is a chemotherapeutic compound, surgery, radiation therapy, or immunotherapy. In some embodiments, the composition or pharmaceutical composition is administered to the patient once. In other embodiments, the composition or pharmaceutical composition is administered to the patient two or more times. In some embodiments, the patient is a mammal such as a human.

In still other aspects, the present disclosure provides methods of preparing a lipid nanoparticle comprising:
(A) dissolving a permanently cationic lipid, an ionizable cationic lipid, and a phospholipid in a first solution to form a lipid solution wherein the lipid solution is formed in an organic solvent;
(B) dissolving a therapeutic agent in a buffer, wherein the buffer is a buffer with a pH from about 6.8 to about 7.6 to form a buffered therapeutic agent solution; and
(C) admixing the lipid solution to the buffered therapeutic agent solution to form a lipid nanoparticle.

In some embodiments, the organic solvent is a C1-C4 alcoholic solvent such as ethanol. In some embodiments, the buffer is an aqueous PBS buffer. In some embodiments, the methods have an encapsulating efficiency of greater than 80%.

In yet another aspect, the present disclosure provides compositions comprising:
(A) a therapeutic agent;
(B) a lipid nanoparticle composition comprising:
  (1) an ionizable cationic lipid;
  (2) a phospholipid; and
  (3) a selective organ targeting compound;
wherein the organ targeting ligand causes the preferential delivery of the composition to an organ other than the liver.

In still yet another aspect, the present disclosure provides compositions comprising:
(A) a therapeutic agent;
(B) a lipid nanoparticle composition comprising:
  (1) an ionizable cationic lipid;
  (2) a phospholipid;
  (3) a selective organ targeting compound;
  (4) a steroid; and
  (5) a PEG lipid;
wherein the organ targeting ligand causes the preferential delivery of the composition to an organ other than the liver.

In still another aspect, the present disclosure provides compositions comprising a therapeutic agent and a lipid nanoparticle composition comprising:
(A) an ionizable cationic lipid;
(B) a phospholipid; and
(C) a selective organ targeting compound;
wherein the composition has an apparent $pK_a$ from about 8 to about 13 and the composition primarily delivers the nucleic acid to the lungs.

In another aspect, the present disclosure provides compositions comprising a therapeutic agent and a lipid nanoparticle composition comprising:
(A) an ionizable cationic lipid;
(B) a phospholipid;
(C) a selective organ targeting compound;
(D) a steroid; and
(E) a PEG lipid;
wherein the composition has an apparent $pK_a$ from about 8 to about 13 and the composition primarily delivers the nucleic acid to the lungs.

In still another aspect, the present disclosure provides compositions comprising a therapeutic agent and a lipid nanoparticle composition comprising:
(A) an ionizable cationic lipid;
(B) a phospholipid; and
(C) a selective organ targeting compound;
wherein the composition has an apparent $pK_a$ from about 3 to about 6 and the composition primarily delivers the nucleic acid to the spleen.

In still yet another aspect, the present disclosure provides compositions comprising a therapeutic agent and a lipid nanoparticle composition comprising:
(A) a steroid;
(B) an ionizable cationic lipid;
(C) a phospholipid;
(D) a PEG lipid; and
(E) a selective organ targeting compound;
wherein the composition has an apparent $pK_a$ from about 3 to about 6 and the composition primarily delivers the nucleic acid to the spleen.

In another aspect, the present disclosure provides compositions comprising a therapeutic agent and a lipid nanoparticle composition comprising:
(A) an ionizable cationic lipid;
(B) a phospholipid; and
(C) a $C_6$-$C_{24}$ diacyl phosphotidylcholine;
wherein the composition primarily delivers the nucleic acid to the lymph nodes.

In still another aspect, the present disclosure provides compositions comprising a therapeutic agent and a lipid nanoparticle composition comprising:
(A) a steroid;
(B) an ionizable cationic lipid;
(C) a phospholipid;
(D) a PEG lipid; and
(E) a $C_6$-$C_{24}$ diacyl phosphotidylcholine;

wherein the composition primarily delivers the nucleic acid to the lymph nodes.

In still yet another aspect, the present disclosure provides compositions comprising a therapeutic agent and a lipid nanoparticle composition comprising:
(A) an ionizable cationic lipid;
(B) a phospholipid; and
(C) a selective organ targeting compound;
wherein the surface of the composition interacts with vitronectin and the composition primarily delivers the nucleic acid to the lungs.

In yet another aspect, the present disclosure provides compositions comprising a therapeutic agent and a lipid nanoparticle composition comprising:
(A) an ionizable cationic lipid;
(B) a phospholipid;
(C) a selective organ targeting compound;
(D) a steroid; and
(E) a PEG lipid;
wherein the surface of the composition interacts with vitronectin and the composition primarily delivers the nucleic acid to the lungs.

In still yet another aspect, the present disclosure provides compositions composition comprising a therapeutic agent and a lipid nanoparticle composition comprising:
(A) an ionizable cationic lipid;
(B) a phospholipid; and
(C) a selective organ targeting compound;
wherein the surface of the composition interacts with Apo H and the composition primarily delivers the nucleic acid to the spleen.

In another aspect, the present disclosure provides compositions composition comprising a therapeutic agent and a lipid nanoparticle composition comprising:
(A) a steroid;
(B) an ionizable cationic lipid;
(C) a phospholipid;
(D) a PEG lipid; and
(E) a selective organ targeting compound;
wherein the surface of the composition interacts with Apo H and the composition primarily delivers the nucleic acid to the spleen.

In still yet another aspect, the present disclosure provides compositions comprising a therapeutic agent and a lipid nanoparticle composition wherein a targeting protein present in a protein corona at the surface of the composition binds to a target protein substantially present in the target organ, wherein the target organ is not the liver.

In some embodiments, the targeting protein is selected from vitronectin or 132-glycoprotein I (Apo H). In some embodiments, the targeting protein is vitronectin and the target organ is the lungs. In other embodiments, the targeting protein is Apo H and the target organ is the spleen.

In some embodiments, the lipid nanoparticle composition further comprises a selective organ targeting compound which modifies the binding of the proteins on the protein corona. In some embodiments, the selective organ targeting compound is further selected from a sugar, a lipid, a small molecule therapeutic agent, a vitamin, or a protein. In some embodiments, the selective organ targeting compound is a lipid such as a permanently cationic lipid, a permanently anionic lipid, or a phosphotidylcholine. In some embodiments, the lipid nanoparticle composition further comprises an ionizable cationic lipid. In some embodiments, the lipid nanoparticle composition further comprises a phospholipid. In some embodiments, the lipid nanoparticle composition further comprises a steroid. In some embodiments, the lipid nanoparticle composition further comprises a PEG lipid.

In another aspect, the present disclosure provides compositions comprising a therapeutic agent and a lipid nanoparticle composition, wherein the lipid nanoparticle composition comprises a selective organ targeting compound and the selective organ targeting compound results in a lipid nanoparticle composition with an apparent $pK_a$ from about 3 to about 6.

In still another aspect, the present disclosure provides compositions comprising a therapeutic agent and a lipid nanoparticle composition, wherein the lipid nanoparticle composition comprises a selective organ targeting compound and the selective organ targeting compound results in a lipid nanoparticle composition with an apparent $pK_a$ from about 8 to about 13.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating certain embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Schematic illustration of DOTAP mDLNP formation and the structure of DOTAP. The molar ratio of 5A2-SC8/DOPE/Chol/DMG-PEG were fixed as 15/15/30/3 (named mDLNP). The DOTAP ratios only were then adjusted from 0 to 1200 to produce a series of DOTAP mDLNP formulations and named DOTAPY, where Y represented the percentage of DOTAP in total lipids. (FIG. 1B) Ex vivo images of luciferase in major organs at 6 h post IV injection with the dose of 0.1 mg/kg Luc mRNA (n=2). With increasing molar percentage of DOTAP, luciferase protein expression moved from liver to spleen, then to lung. (FIG. 1C) Quantification data demonstrated that DOTAP percentage is a factor for tissue specific delivery, mDLNP (0%) was the best for liver, DOTAP10-15 (similar between them) were the best for spleen, and DOTAP50 was the best for lung. Because luciferase expression was detected only in liver, spleen and lung after IV injection, the relative expression in each organ was calculated. Clearly, the more DOTAP (permanently cationic lipid) percentage in formulation, the less luminescence in liver and close to 0 when >70%. However, the more DOTAP percentage, the more luminescence in lung and close to 100% when >70%. The DOTAP5-20 showed higher percentages in spleen and DOTAP10 looked the highest.

FIGS. 2A1-2F2: The structures of lipids decide mRNA expression profile after IV injection. Generally, quaternary lipids changed mRNA delivery from liver to spleen, then to lung with increasing percentages, and zwitterionic lipids helped to deliver mRNA into spleen at higher percentages. But tertiary amine lipids could not change mRNA expression organ, instead improved delivery efficacy in liver. To further confirm the delivery trend of quaternary lipids mDLNPs, two more quaternary lipids, DDAB and EPC, were selected to perform mRNA delivery in vivo, with the same modified strategy as was done with DOTAP. (FIG. 2A1, FIG. 2B1) DDAB and EPC exhibit large structural differences between them and with DOTAP, including on three levels of comparison: the length of hydrophobic tail, saturated and unsaturated bond, and chemical structure of head group. Formulations with 5%, 15%, 40% and 50% of quaternary lipid were formed to detect size distribution and in vivo evaluation (0.1 mg/kg, 6 h, n=2). (FIG. 2A2, FIG. 2B2) Like DOTAP mDLNPs, DDAB and EPC also presented similar mRNA delivery profile. Lower cationic percent (5%) delivered mRNA into liver and spleen, then to spleen more when increased to 15%. Once increased to 40%, little mRNA expression was observed in liver and spleen, but lung exhibited high luciferase signal and then decreased at 50%. These results are very similar with DOTAP mDLNP, which suggested that functionalized mDLNP by quaternary lipids are universal and generalizable strategy for tissue targeting mRNA delivery. Then representative zwitterionic lipids, DSPC and DOCPe, were used to evaluate the mRNA delivery in vivo just like DOTAP strategy (FIG. 2C1, FIG. 2D1). The structures of DSPC and DOCPe lipids are in the general class of zwitterionic lipids. Size distributions of DSPC and DOCPe mDLNP formulations were tested by DLS before IV injection. Herein, DSPC and DOCPe showed two levels comparison in structures: saturated versus unsaturated hydrophobic tails, and charge position versus in head groups. (FIG. 2C2, FIG. 2D2) Interestingly, a similar mRNA expression profile like quaternary lipid formulations was not observed. Instead, both DSPC and DOCPe improved mRNA delivery into spleen within given range (less than 80% in DSPC and less than 50% in DOCPe), never saw any signals in lung whatever percentages (0.1 mg/kg, 6 h, n=2). Inspired by these results, ionizable tertiary amine lipids, DODAP and C12-200, were further tested with the same strategy. DODAP has the same structure with DOTAP except for the head groups (quaternary versus tertiary amine), C12-200 is an effective lipidoid used for siRNA or mRNA delivery, which has a completely different structure with DODAP. (FIG. 2E1, FIG. 2F1) Similarly, the size distributions of both modified mDLNPs were still good at certain percentages (less than 80%). (FIG. 2E2, FIG. 2F2) Surprisingly, DODAP and C12-200 could not change mRNA expression profile (different effect compared to quaternary or zwitterionic lipids). Instead, DODAP and C12-200 increased delivery of mRNA to the liver. Supporting that, DODAP20 and C12-200 showed much better delivery efficacy than original mDLNP formulation (0.1 mg/kg, 6 h, n=2). With increasing percentages of DODAP or C12-200 (50% or 80%), luciferase signal decreased a lot, but liver still was the main organ rather than spleen or lung.

(FIG. 3A) Organs distribution of Cy5.5-Luc mRNA formulations delivered by three kinds of modified mDLNP, DOTAP (quaternary lipid), DSPC (zwitterionic lipid) and DODAP (tertiary amine lipid). C57BL/6 mice were IV injected at the doses of 0.5 mg/kg and imaged at 6 h post injection (n=2). DOTAP changed the organ distribution of mRNA, compared with the original mDLNP formulation (no DOTAP), both DOTAP10 and DOTAP50 could deliver mRNA into lung, and DOTAP50 increased more, which may partly explain why DOTAP formulation mediated mRNA expression in lung at higher percentages. However, both DSPC and DODAP could not change mRNA distribution much even at 80% (DSPC) or 50% (DODAP) percentages. It was also noticed that mRNA was retained in liver for DOTAP50 and DSPC80, as showed in FIGS. 1 and 2, the former one was lung targeting NP and latter one was spleen targeting NP. Therefore, distribution was not the only factor to explain the mechanism. (FIG. 3B) The pKa of all tested and efficacious formulations were then measured, including original mDLNP, DOTAP, DDAB, EPC, DSCP, DOCPe, DODAP and C12-200 modified formulations. (FIG. 3C) Finally relationship between pKa and tissue specific mRNA delivery was plotted based on the defined rules. Here, 8 rules to score were designed as showed in the table. Obviously, all liver targeted formulations had a narrow pKa (~6-7), no significant range for spleen targeted formulation, but lung targeted delivery required high pKa (>9.25).

(FIG. 4A) Schematic illustration shows that co-delivery of Cas9 mRNA and sgTom1 activates td-tomato expression in Td-Tomato mouse. (FIG. 4B) Td-tomato expressions were induced in liver and lung when treated by mDLNP and DOTAP50 formulations, respectively. The mice were IV injected by mDLNP and DOTAP50 formulations for co-delivery of IVT Cas9 mRNA and modified sgTom1 (4/1, wt/wt) at the total doses of 2.5 mg/kg (50 µg each), then fluorescence of main organs was detected at day 10 after treatment. (FIG. 4C) T7E1 assay showed that tissue specific feature was further confirmed with in vivo PTEN editing. C57 BL6 mice were IV injected with mDLNP, DODAP20 or DOTAP50 to reach tissue specific gene editing, total dose was 2.5 mg/kg (50 µg each), weight ratio of IVT Cas9 mRNA to modified sgPTEN was 4/1, and detection time was day 10 after treatment.

(FIG. 5C) Encapsulation efficiency (EE %) was tested by Ribogreen RNA assay.

(FIG. 6A) DOTAP mDLNP mediated high Luc mRNA expression in Huh-7 cells and A549 cells and revealed that DOTAP percentages of 5%-50% were better for mRNA delivery and 10% was the best. Luc mRNA expression and cell viability were tested at 24 h post transfection with the dose of 50 ng/well mRNA (n=4). Here, DOTAP mDLNPs were formed in PBS rather than citric buffer (10 mM, pH 4.0). (FIGS. 6B & 6C) Decreased volume percentage of ethanol did not affect the characterization and mRNA delivery potency. To test the influence of ethanol for mRNA delivery, DOTAP25 was selected as a model and formed four formulations with various volume ratios of ethanol to PBS (1:3, 1:5, 1:7.5 and 1:10). All four formulations showed similar EE, size and PDI (FIG. 6B), and exhibited equality mRNA delivery potency (FIG. 6C) in FaDu cells (50 ng/well mRNA, 24 h, n=4). Therefore, this formulation was optimized using 1×PBS (pH 7.4) to instead of acidic buffer (10 mM pH 4.0) and dramatically decreased ethanol percentage, which provide a possibility that DOTAP formulations deliver those cargos that are not well-tolerated in high ethanol concentrations or acidic buffer, e.g. proteins.

(FIG. 8A) Both size and delivery efficacy were not changed too much between PBS formed and citric buffer (10 mM, pH 4.0) formed DOTAP10. (FIGS. 8B & 8C) But citric buffer formed DSPC50 and DODAP50 dramatically improved mRNA delivery effects, although no big difference on size distributions. DOTAP (or another permanently cationic lipid) may be added for LNP formation at neutral pH (e.g. 7.4 PBS buffer).

(FIG. 10A) Size distributions of Cas9/sgTom1, Cas9/sgTom2 and Cas9/sgLoxP mDLNP formulations, and td-tomato expression in liver. Mice were IV injected by three mDLNP at the total dose (Cas9/sgRNA, 4/1, wt/wt) of 3 mg/kg, organ were imaged at day 7. It looked that sgTom1 is the lead among three candidates. (FIG. 10B) SgTom1 was selected and further tested by different weight ratios (Cas9/sgRNA) of 2/1, 4/1 and 6/1 for liver gene editing. mDLNP was used for IV injection with the dose of 3 mg/kg, and td-tomato expression was detected in day 7. In this example, 4/1 worked better than 2/1 and 6/1.

(FIG. 11G) TEM images of DOTNP10-L (1/3, mol/mol). DOTAP lipid nanoparticle consists of five components, including 5A2-SC8, Cholesterol, DOPE, DMG-PEG and DOTAP. The mole ratio of 5A2-SC8, Cholesterol, DOPE, and DMG-PEG is fixed (15:15:30:5, mol/mol) and DOTNPX means DOTNP with different mole percentage of DOTAP. Here, different sgRNA including sgLUC, sgGFP, sgTOM, sgPTEN etc. were used. To distinguish them, the first letter of each gene was added at the end of DOTNP. For example, DOTNP10-L means DOTNP10 lipid nanoparticles encapsulating Cas9/sgLUC complex; DOTNP10-G means DOTNP10 lipid nanoparticles encapsulating Cas9/sgGFP complex.

(FIG. 12A) Confocal images of Hela-Luc cells after incubated with DOTNP10 encapsulating Cas9-EGFP/sgLUC complexes (1/3, mol/mol) for 1 h, 3 h, 6 h, and 24 h (9 nM of sgRNA was used). Green: EGFP fused Cas9 protein; Blue: nuclei stained with Hoechst 33342. Red arrows indicated the process of DOTNP10 entering into nucleus. (FIG. 12B) Indels percentages at LUC locus after incubated with DOTNP10-L of different mole ratios for 3 days analyzed by TIDE Sequencing (24 nM of sgRNA was used). DOTNP10 lipid nanoparticles encapsulating Cas9/sgGFP (DOTNP10-G) was used as negative control. Here, two commercial Cas9 proteins (GeneArt Cas9 and Truecut Cas9) were used. (FIG. 12C) T7EI cleavage assay of Hela-Luc cells incubated with different formulations (24 nM of sgRNA was used). 1. 100 bp DNA ladder; 2. PBS; 3. DOTNP10-G (1/3); 4. DOTNP10-L (1/1); 5. DOTNP10-L (1/3); 6. DOTNP10-L (1/5); 7. DOTNP10-L (1/3) prepared in Citrate buffer. Two commercial Cas9 proteins (GeneArt Cas9 and Truecut Cas9) were used. Among them, mole ratio at 1/3 showed the best gene editing when using Truecut Cas9 protein. (FIG. 12D) Fluorescence microscopy images of SKOV3-GFP cells incubated with DOTNP10-L and DOTNP10-G (24 nM of sgRNA was used). Here, DOTNP10-L was used as negative control. (FIG. 12E) Flow cytometry analysis of SKOV3-GFP cells incubated with DOTNP10-L and DOTNP10-G. (FIG. 12F) Mean fluorescence intensity of SKOV3-GFP cells incubated with DOTNP10-L and DOTNP10-G by flow cytometry.

(FIG. 13A) Ex vivo images of tdTomato fluorescence in major organs at 7 days post IV injection of different formulations (1.5 mg/kg of sgRNA per mouse). DOTNP5-T means DOTNP5 lipid nanoparticles encapsulating Cas9/sgTom complex; DOTNP10-T means DOTNP10 lipid nanoparticles encapsulating Cas9/sgTom complex; DOTNP50-T means DOTNP50 lipid nanoparticles encapsulating Cas9/sgTom complex. tdTomato fluorescence was only observed in liver in DOTNP5-T treated group; In DOTNP10-T group, slight fluorescence was seen in lung and if further increasing dose of DOTAP to 50% (DOTNP50-T), most of tdTomato fluorescence was observed in lung. (FIG. 13B) T7EI cleavage assay of liver and lung organs after incubating with DOTNP5-P (DOTNP5 lipid nanoparticles encapsulating Cas9/sgPTEN complex), DOTNP10-P (DOTNP10 lipid nanoparticles encapsulating Cas9/sgPTEN complex) and DOTNP50-P (DOTNP50 lipid nanoparticles encapsulating Cas9/sgPTEN complex) (2 mg/kg of sgRNA per mouse). The results are consistent with that obtained by ex vivo imaging Gene editing was only detected in liver after treated with DOTNP5-P; gene editing was obtained both in liver and in lung when incubated with DOTNP10-P; while in DOTNP50-P treatment group, most of gene editing was observed in lung.

(FIG. 17B) Ex vivo luciferase images and quantified data showed that mRNA delivery potency was dramatically improved with extra 15% to 25% of 5A2-SC8, and 20% had the highest signal (0.05 mg/kg, 6 h, n=2).

FIGS. 20A-20C show (20A) Details of DOTAP and 18PA SORT LNPs, including molar ratios, molar percentages, weight ratios of total lipid to mRNA, sizes, PDI and zeta potentials. (20B) LNPs were formulated using a modified ethanol dilution method. SORT lipids are included in the ethanol phase and sgRNA/mRNA are encapsulated during LNP formation. (20C) The chemical structures of lipids used in standard mDLNP and DOTAP/18PA SORT formulations are shown. For the development of SORT, a degradable dendrimer-based ionizable cationic lipid named 5A2-SC8 was the focused of the LNPs that can deliver siRNAs/miRNAs to extend survival in a genetically engineered mouse model of MYC-driven liver cancer (Zhou et al., 2016; Zhang et al., 2018a; Zhang et al., 2018b) and toggle polyploidy in the liver. An LNP molar composition that was optimized for mRNA delivery was focused to the liver named mDLNPs (Cheng et al., 2018). This liver-targeted base mRNA formulation of 5A2-SC8/DOPE/Cholesterol/DMG-PEG2000=15/15/30/3 (mol) were prepared and supplemented with SORT lipids to prepare SORT LNPs (details in 20A). For the sake of further clarity, the traditional 4-component LNPs are composed of ionizable cationic lipids (herein defined as containing an amino group with $pK_a<8$), zwitterionic phospholipids (defined as a lipid bearing equal number of positive and negative charges), cholesterol, and poly(ethylene glycol) (PEG) lipids (most commonly, PEG2000-DMG). SORT LNPs include a $5^{th}$ lipid, such as a permanently cationic lipid (defined as positively charged without $pK_a$ or $pK_a>8$) or a permanently anionic lipid (defined as negatively charged).

FIGS. 33A-33C show CRISPR/Cas gene editing in the spleen was achieved in both Td-Tom transgenic mice and wild type C57/BL6 mice by co-delivering Cas9 mRNA and sgRNA. (33A) Schematic illustration shows that co-delivery of Cas9 mRNA and sgTom1 activates Td-Tom expression in Td-Tom mice. (33B) Td-Tom expression was induced in the spleen and liver by the spleen-targeted formulation 30% 18PA SORT LNP. Quantification data showed that editing in the spleen was higher than in the liver. Td-Tom fluorescence of main organs was detected at day 2 after IV treatment with co-delivery of Cas9 mRNA and modified sgTom1 (2/1, wt/wt) at the total doses of 4 mg/kg. (33C) T7E1 assay indicated that specific PTEN editing of spleen was obtained by co-delivery of Cas9 mRNA (IVT) and sgPTEN. C57/BL6 mice were IV injected with 30% 18PA SORT LNPs at total dose of 4 mg/kg (Cas9 mRNA/sgPTEN, 2/1, wt/wt), and PTEN editing was detected at day 2. In this case, no liver editing was observed, suggesting that spleen-specific editing can be achieved.

FIG. 34 shows DODAP-20 SORT LNPs achieved nearly 100% TdTom editing in hepatocytes administration of a single 0.3 mg/kg Cre mRNA dose. As shown in the flow cytometry histogram, there is full separation between TdTom− control mice and TdTom+ 20% DODAP treated mice. After liver perfusion, the resected livers of mice treated with 20% DODAP SORT LNPs were surprisingly bright red compared to control livers. Even without fluorescence excitation, the livers glowed red due to complete activation of TdTom expression. TdTom mice were injected with 0.3 mg/kg Cre mRNA, then sacrificed after two days (n=3). Hepatocytes were isolated by two-step collagenase perfusion and TdTom fluorescence was analyzed by flow cytometry.

FIGS. 41A-C show (41A) table of 5A2-DOT-X LNPs showing the molar ratios and percentages used to formulate 5A2-DOT-5 (5 mole % DOTAP), 5A2-DOT-10, 5A2-DOT-20, 5A2-DOT-30, 5A2-DOT-40, 5A2-DOT-50, and 5A2-DOT-60 (60 mole % DOTAP) LNPs. A total lipids/sgRNA ratio of 40:1 (wt.) was used for all LNPs. (41B) Gene editing in HeLa-Luc cells following treatment with different 5A2-DOT-X Cas9/sgLuc RNP formulations was detected using the T7EI assay. (41C) Gene editing was analyzed using Sanger sequencing and ICE analysis.

FIG. 42 show representative TEM images of 5A2-DOT-10 encapsulating Cas9/sgLuc RNP complexes with molar ratio of 1/3. 5A2-DOT-10 Cas9/sgLuc was prepared at total lipid concentration of 2 mg/mL in PBS buffer. 3 μL of the nanoparticle solutions was dropped onto carbon TEM grids and allowed to deposit for 1 min before blotting with filter paper. Then the TEM grids were imaged using Transmission Electron Microscopy (FEI Tecnai G2 Spirit Biotwin).

Figures 1A, 1B, 1C:
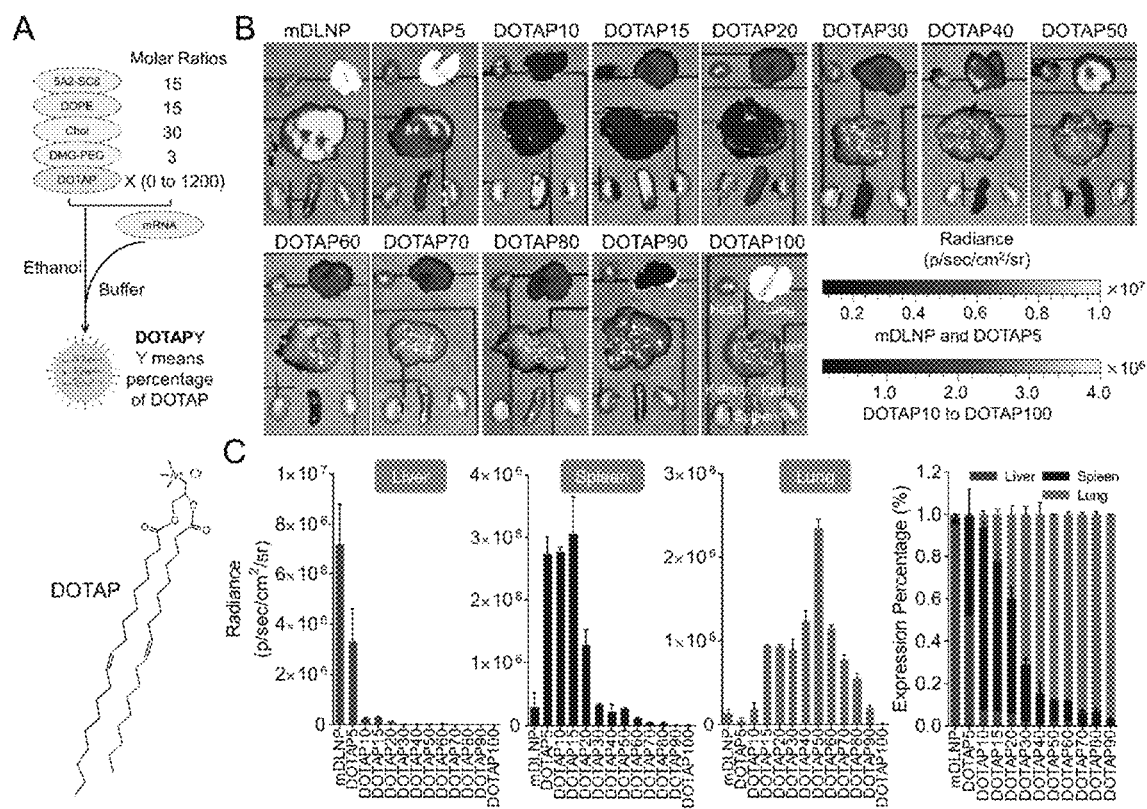
FIGS. 1A-C: DOTAP mDLNP formulations mediated excellent mRNA delivery efficacy at low doses after IV injection and demonstrated tissue specific delivery features with given percentage of DOTAP.

Neutral buffer was required for RNP encapsulation and delivery. (46K) Indels (%) at GFP loci in genomic DNA isolated from HeLa-GFP cells after treatment with 5A2-DOT-10 Cas9/sgGFP LNPs prepared using different buffers were measured using ICE analysis. All neutral buffers showed high gene editing in cells, demonstrating the importance of neutral buffers in nanoparticle preparation. Please note that FIGS. 44E and 44F have been reproduced above in FIG. 45 to assemble relevant data together for enhanced clarity.

FIGS. 47A-47J show highly efficient multiplexed genome editing was achieved in vivo. (47A) Schematic illustration shows how delivery of Cas9/sgTOM RNPs activates Td-Tom expression in Td-Tomato transgenic mice. 5A2-DOT-X LNPs were injected into Td-Tom mice locally (via intra-muscle or intra-brain injections) and systemically (via i.v. injection through tail vein). In vivo imaging of Td-Tom mice after intra-muscle (1 mg/kg sgTom) (47B) or intra-brain (0.15 mg/kg sgTOM) (47D) injection of 5A2-DOT-10 Cas9/sgTOM showed bright red fluorescence in the leg muscle or brain tissue (respectively). Successful CRISPR/Cas gene editing was further confirmed by confocal imaging of (47C) muscle and (47E) brain tissue sections. 5A2-DOT-10 enabled higher gene editing efficiency than positive control RNAiMAX, which has previously been used for local RNP injections. (47F) In vivo imaging of Td-Tom mice after intravenous (IV) injection of 5A2-DOT-X Cas9/sgTOM LNPs with different molar percentages of DOTAP. Td-Tom fluorescence, as a downstream readout of DNA editing, showed that low DOTAP percentages facilitated liver editing while high DOTAP percentages facilitated lung editing (1.5 mg/kg sgTOM, IV). (47G) Successful CRISPR/Cas gene editing was further confirmed by confocal imaging. (47H) The T7EI cleavage assay was performed on DNA isolated from liver and lung tissues after systemic IV treatment with 5A2-DOT-5, 5A2-DOT-10, 5A2-DOT-50, and 5A2-DOT-60 encapsulating Cas9/sgPTEN. Indels (%) was calculated and reported. (47I) 5A2-DOT-50 LNPs containing pooled sgRNAs for 6 targets (sgTOM, sgP53, sgPTEN, sgEm14, sgALK, and sgRB1) (5A2-DOT-50-Pool) were administered to td-Tom mice IV at total RNA dose of 2 mg/kg (0.33 mg/kg each sgRNA). Gene editing at the TOM loci was confirmed by in vivo imaging and (47J) editing of the other 5 loci was confirmed using the T7EI cleavage assay on lung tissues.

FIGS. 48A-48H show 5A2-DOT-X LNPs simplify generation of complex mouse models. (48A) To create an in situ liver-specific cancer model, 5A2-DOT-5 LNPs encapsulating Cas9/sgP53/sgPTEN/sgRB1 RNPs were injected into adult C57BL/6 mice weekly (3 injections, 2.5 mg/kg total sgRNA, IV, n=4). After 12, 15, and 20 weeks, mice were sacrificed and livers were collected to analyze tumor generation. (48B) T7EI cleavage results from genomic DNA extracted from livers confirmed gene editing occurred at all three loci. (48C) Representative photograph of a mouse liver containing tumors excised 20 weeks after injection. (48D) H&E and Ki67 staining further confirmed progressive tumor formation. Higher tumor proliferation biomarker Ki67 expression was detected in tumor lesions. Scale bar=100 µm. (48E) To create an in situ lung-specific cancer model, 5A2-DOT-50 LNPs encapsulating Cas9/sgEm14/sgAlk RNPs were injected into adult C57BL/6 mice once (2 mg/kg) or twice (1.5 mg/kg weekly for 2 weeks) (IV, n=5). After 10, 16, and 24 weeks, mice were sacrificed and lungs were collected to analyze tumor generation. (48F) T7EI cleavage results from genomic DNA extracted from lungs confirmed gene editing occurred at loci of Em14 and Alk. PCR amplicons of Em14-Alk rearrangements were also detected in all lungs treated with 5A2-DOT-50 LNPs. (48G) Em14-Alk rearrangements were further confirmed by sub-cloning and DNA sequencing (Predicted=SEQ ID NO: 50; Clone1=SEQ ID NO: 51; Clone2=SEQ ID NO: 52; Clone3=SEQ ID NO: 53; Clone4=SEQ ID NO: 54; Clone5=SEQ ID NO: 55; Clone6=SEQ ID NO: 56; Clone7=SEQ ID NO: 57; Clone8=SEQ ID NO: 58). (48H) H&E and Ki67 staining further confirmed progressive tumor formation. Higher tumor proliferation biomarker Ki67 expression was detected in lung tumor lesions. Scale bar=100 µm.

Figures 49A, 49B:
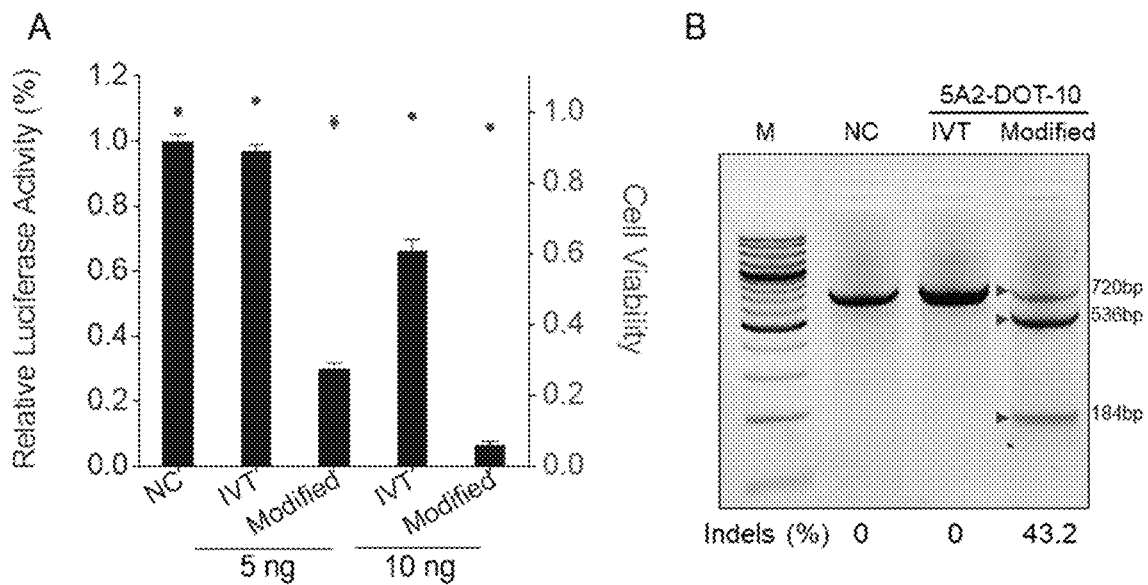

FIGS. 49A & 49B show gene editing efficiency of unmodified sgRNA synthesized by in vitro transcription (IVT) comparing to chemically modified and synthesized sgRNA (2'-methyl 3'-phosphorothioate modifications in the first and last 3 nucleotides). (49A) Relative luciferase activity in Hela-Luc-Cas9 cells after treatment with IVT sgRNA and chemically modified sgRNA encapsulated inside nanoparticles. (49B) T7EI assay detecting gene editing efficiency of Cas9/IVT sgRNA and Cas9/chemically modified sgRNA encapsulated nanoparticles. Cleavage bands at 536 bp and 184 bp were observed clearly with modified sgRNA treatment group.

Figure 50:
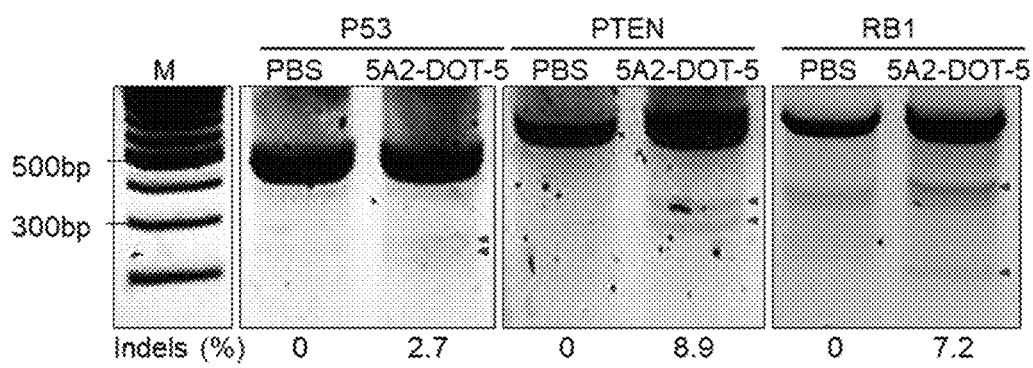

FIG. 50 shows gene editing of P53, PTEN and RB1 genes in mouse liver after treatment with 5A2-DOT-5 LNPs encapsulating Cas9/sgP53/sgPTEN/sgRB1 RNPs. T7EI assay detecting the gene editing of liver genomic DNA at PTEN, P53 and RB1 genome loci, after treatment weekly for two weeks. PBS treatment group was used as control. Cleavage bands were detected at 261 bp and 215 bp of PCR amplicons targeting P53; cleavage bands were detected at 345 bp and 293 bp of PCR amplicons targeting PTEN; cleavage bands were detected at 395 bp and 207 bp of PCR amplicons targeting RB1.

Figure 51:
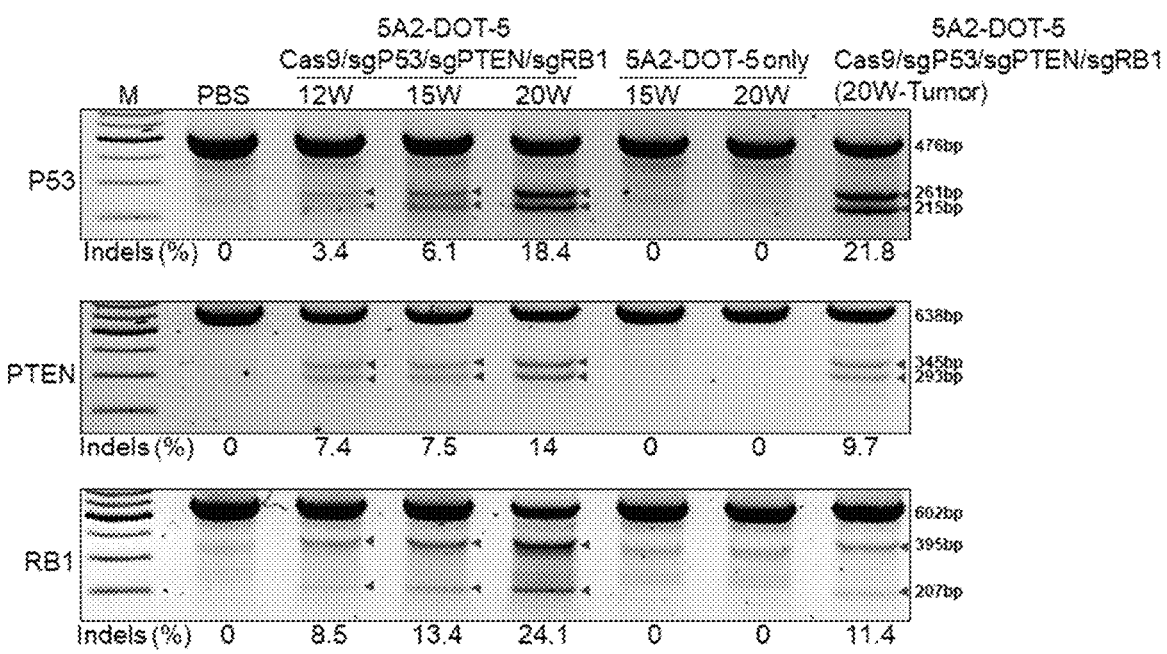

FIG. 51 shows T7EI assay detecting the gene editing of P53, PTEN and RB1 genes in mouse liver after treatment with 5A2-DOT-5 LNPs encapsulating Cas9/sgP53/sgPTEN/sgRB1 RNPs. PBS treatment and 5A2-DOT-5 only (no Cas9/sgRNA) treatment groups were used as control. The T7EI result of genome DNA extracted from tumor of mice after treated with 5A2-DOT-5 LNPs encapsulating Cas9/sgP53/sgPTEN/sgRB1 RNPs for 20 weeks demonstrated the tumor generation was induced by knockout of these three genes, as cleavage bands were detected at all three genome loci.

Figure 52:

FIG. 52 shows representative photograph of a mouse liver and excised tumors excised from a mouse in the group treated with 5A2-DOT-5 LNPs encapsulating Cas9/sgP53/sgPTEN/sgRB1 RNPs for 15 weeks.

Figures 53A, 53B, 53C:
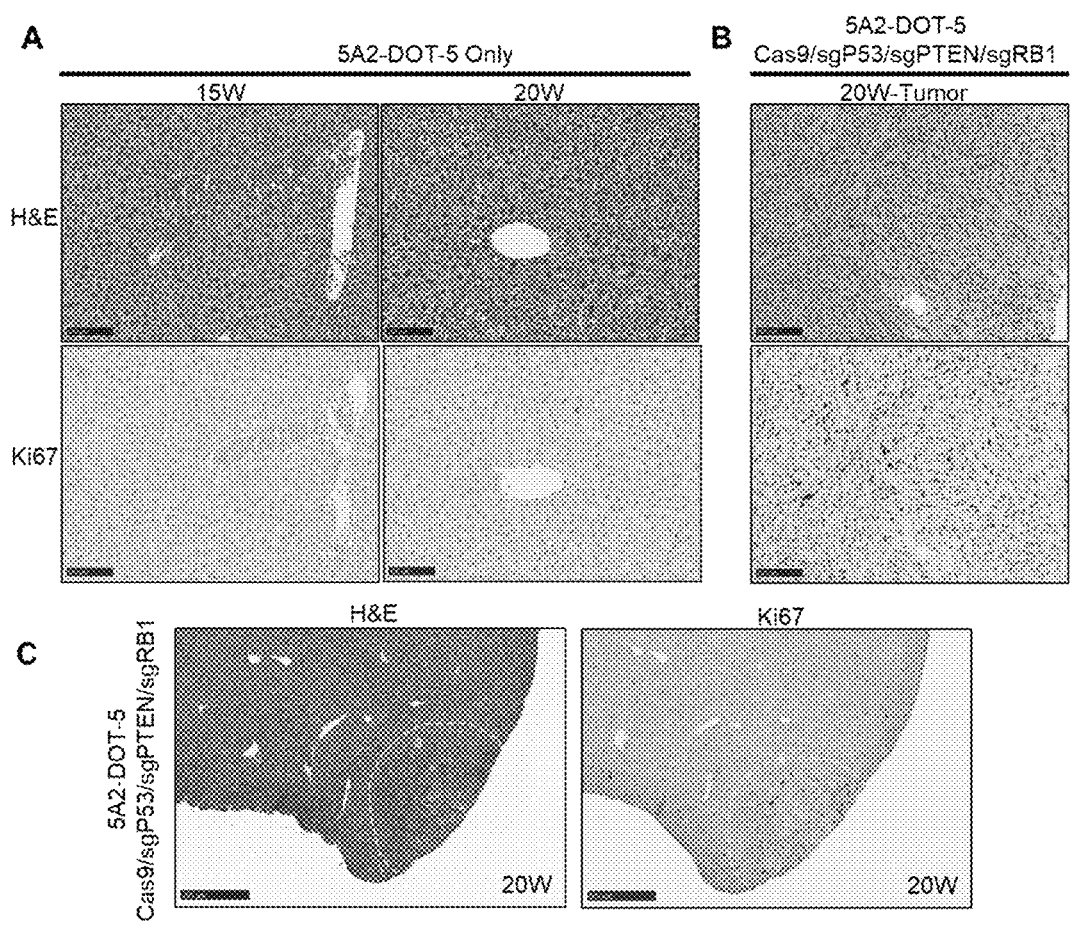
Figures 54A, 54B, 54C, 54D:
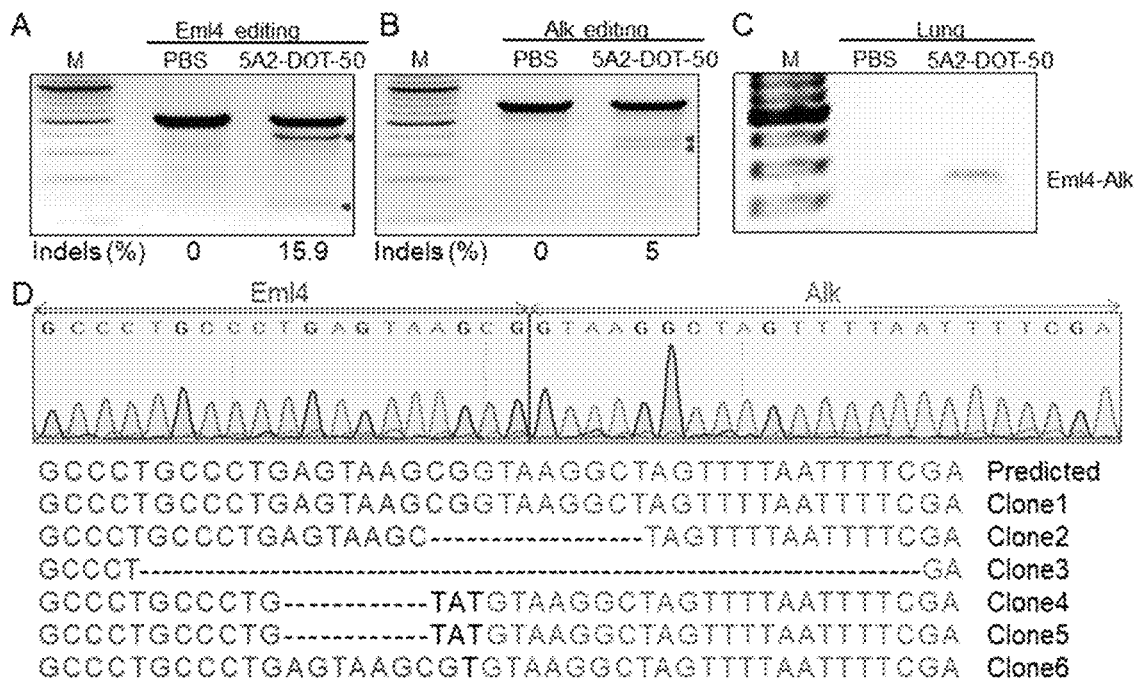

FIGS. 53A-53C show H&E and Ki67 staining images of mouse livers following treatment with 5A2-DOT-5 LNPs only (no Cas9/sgRNA) (control) for 15 weeks and 20 weeks (53A), tumors excised from a mouse in the group treated with 5A2-DOT-5 LNPs encapsulating Cas9/sgP53/sgPTEN/sgRB1 RNPs for 20 weeks (53B). No morphological changes were detected with 5A2-DOT-5 LNPs only treatments, suggesting nanovectors alone could not lead to tumors. Scale bar: 100 µm. (53C) Large view images of mouse liver tumor generation after treated with 5A2-DOT-5 LNPs encapsulating Cas9/sgP53/sgPTEN/sgRB1 RNPs for 20 weeks. Scale bar: 500 µm.

FIGS. 54A-54D show generation of Em14-Alk rearrangements in mouse lungs after treatment with 5A2-DOT-50 LNPs encapsulating Cas9/sgEm14/sgAlk RNPs for 7 days (2 mg/kg of total sgRNA). Em14 editing (54A) and Alk editing (54B) were detected in genomic DNA extracted from mouse lungs by T7EI assay. (54C) PCR analysis was performed on genomic DNA extracted from mouse lungs to determine Em14-Alk inversion. (54D) The PCR amplicons were sub-cloned and the sequences of 6 independent clones were listed, together with a representative chromatogram presented on the upper panel. The chromatogram was exactly the same as predicted for Em14-Alk rearrangement. (Predicted=SEQ ID NO: 59; Clone1=SEQ ID NO: 59; Clone2=SEQ ID NO: 60; Clone4=SEQ ID NO: 61; Clone5=SEQ ID NO: 61; Clone6=SEQ ID NO: 62)

Figure 55:
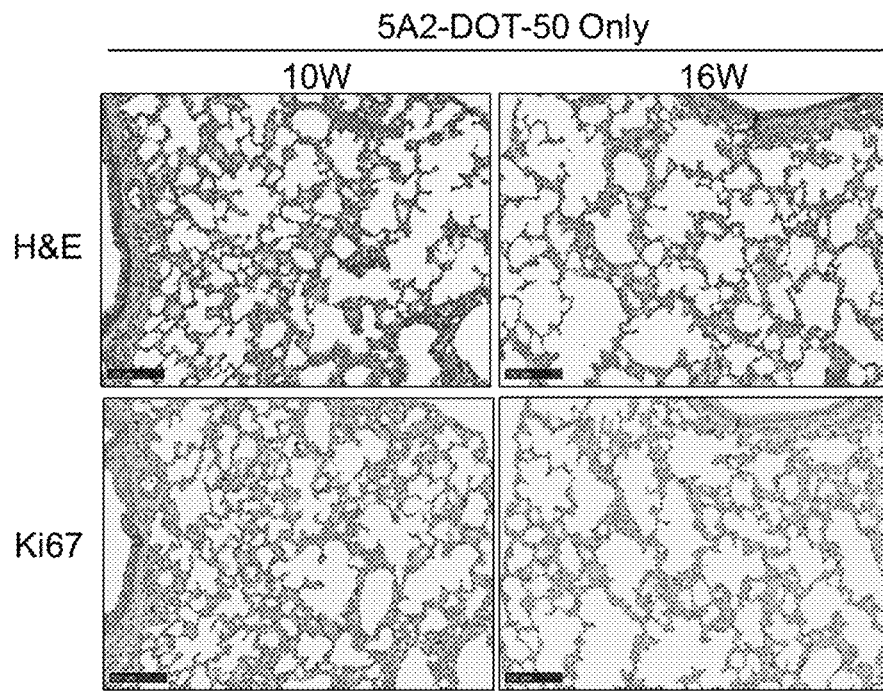

FIG. 55 shows H&E and Ki67 staining images of mouse livers treated with 5A2-DOT-50 LNPs Only (no Cas9/sgRNA) for 10 weeks and 16 weeks (LNP dose equal to 1 mg/kg of total sgRNA). No morphological changes were detected in 5A2-DOT-50 LNPs Only injected animals Scale bar: 100 µm.

Figure 56:
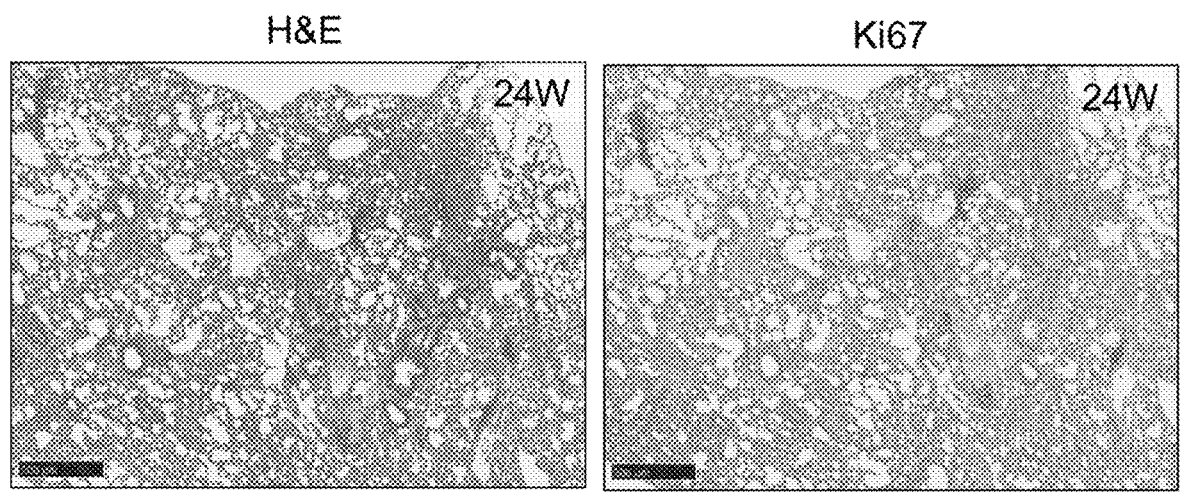

FIG. 56 shows large view images of mouse lung tumor generation after treated with 5A2-DOT-50 LNPs encapsulating Cas9/sgEm14/sgAlk RNPs for 24 weeks. Scale bar: 500 µm. Several tumor lesions (highlighted) were observed from both H&E and Ki67 staining images.

Figure 57:
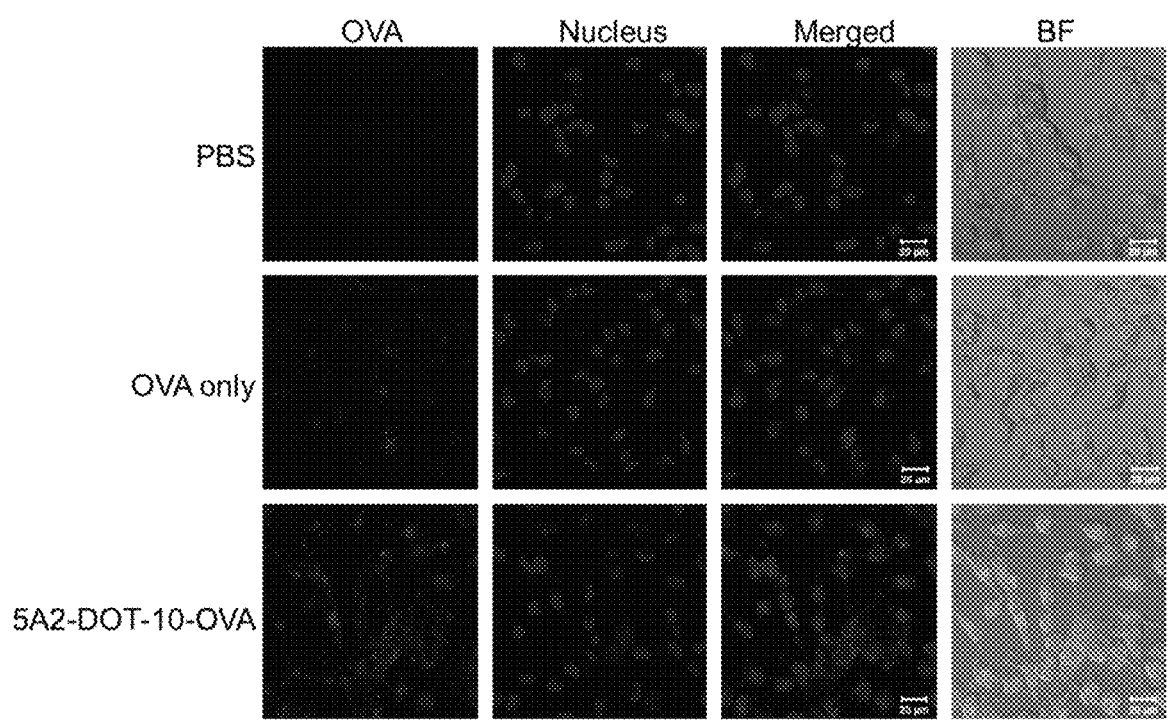

FIG. 57 shows 5A2-DOT-10 LNPs could deliver ovalbumin (OVA) protein efficiently into the cytoplasm of HeLa-Luc cells. Cells were treated with free rhodamine-labeled OVA protein and 5A2-DOT-10 LNPs encapsulating rhodamine-labeled OVA for 22 h before imaging by confocal microscopy.

DESCRIPTION OF ILLUSTRATIVE EMBODIMENTS

Described herein is a lipid nanoparticle (LNP), composed of 1) a permanently cationic lipid, 2) an ionizable cationic lipid, and 3) a phospholipid and may optionally contain either cholesterol and lipid PEG or both. Inclusion of the permanently cationic lipid serves to direct the LNP to a specific organ such as the lungs, the lymph nodes, or the spleen. The data presented herein indicate that this effect is general, and the components are modular with each category indicating that 5A2-SC8 can be replaced by any ionizable cationic lipid, DOTAP can be replaced by any cationic lipid, and DOPE can be replaced by any phospholipid. In some embodiments, cholesterol and lipid PEG are also included, but formulations without cholesterol or lipid PEG are feasible. These carriers can deliver mRNA, sgRNA, and proteins to specific organs in vivo, thus solving a major challenge.

A. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, for example, the formula

includes

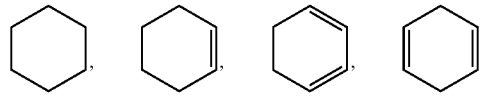

and

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ⁓ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀" means a single bond where the group attached to the thick end of the wedge is "into the page". The symbol " ⁓ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

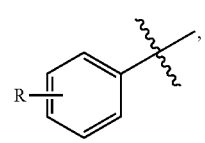

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

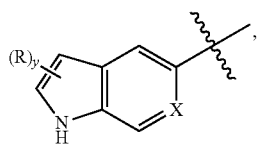

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen.

The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —CCH, —CCCH$_3$, and —CH$_2$CCCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

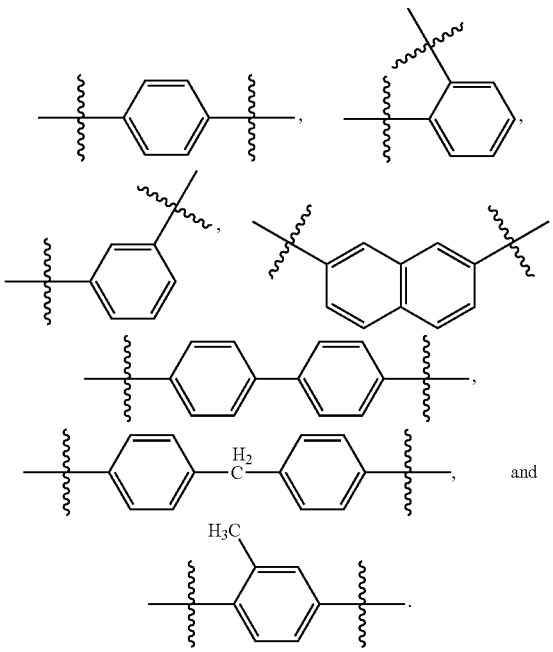

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O) CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from are nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

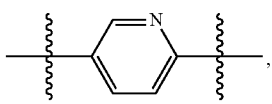

-continued

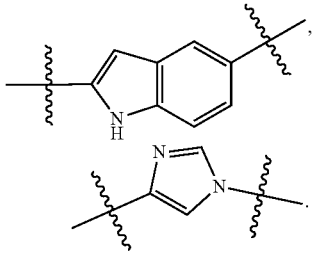

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —C(O)NHCH₃, —C(O)N(CH₃)₂, —OC(O)CH₃, —NHC (O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

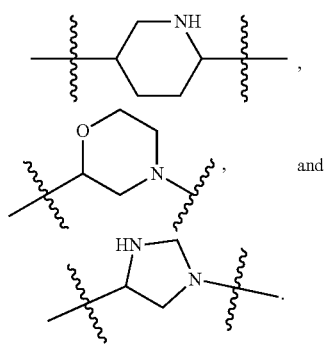

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "alkylaminodiyl" refers to the divalent group —NH-alkanediyl-, —NH-alkanediyl-NH—, or -alkanediyl-NH-alkanediyl-. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc. Within the context of the dendrimer, the repeating unit may also be described as the branching unit, interior layers, or generations. Similarly, the terminating group may also be described as the surface group.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. Cationic Ionizable Lipids

In some aspects of the present disclosure, composition containing compounds containing lipophilic and cationic components, wherein the cationic component is ionizable, are provided. In some embodiments, the cationic ionizable lipids contain one or more groups which is protonated at physiological pH but may deprotonated at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some embodiments, these cationic ionizable lipids are dendrimers, which are a polymer exhibiting regular dendritic branching, formed by the sequential or generational addition of branched layers to or from a core and are characterized by a core, at least one interior branched layer, and a surface branched layer. (See Petar R. Dvornic and Donald A. Tomalia in Chem. in Britain, 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to described compounds described herein which have a dendron like appearance (e.g. molecules which radiate from a single focal point).

While dendrimers are polymers, dendrimers may be preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bio-attachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol.

Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some aspects, the dendrimers that may be used in the present compositions are assembled using the differential reactivity of the acrylate and methacrylate groups with amines and thiols. The dendrimers may include secondary or tertiary amines and thioethers formed by the reaction of an acrylate group with a primary or secondary amine and a methacrylate with a mercapto group. Additionally, the repeating units of the dendrimers may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine ($-NH_2$) or a carboxylic acid ($-CO_2H$). In still other embodiments, the terminating group is an aliphatic or aromatic group containing one or more hydrogen bond donors such as a hydroxide group, an amide group, or an ester.

The cationic ionizable lipids of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Cationic ionizable lipids may occur as racemates and racemic mixtures, single enantiomers, diastereomeric mixtures and individual diastereomers. In some embodiments, a single diastereomer is obtained. The chiral centers of the cationic ionizable lipids of the present disclosure can have the S or the R configuration. Furthermore, it is contemplated that one or more of the cationic ionizable lipids may be present as constitutional isomers. In some embodiments, the compounds have the same formula but different connectivity to the nitrogen atoms of the core. Without wishing to be bound by any theory, it is believed that such cationic ionizable lipids exist because the starting monomers react first with the primary amines and then statistically with any secondary amines present. Thus, the constitutional isomers may present the fully reacted primary amines and then a mixture of reacted secondary amines.

Chemical formulas used to represent cationic ionizable lipids of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The cationic ionizable lipids of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the cationic ionizable lipids of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a cationic ionizable lipids provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments, the ionizable cationic lipid is present in an amount from about from about 20 to about 23. In some embodiments, the molar percentage is from about 20, 20.5, 21, 21.5, 22, 22.5, to about 23 or any range derivable therein. In other embodiments, the molar percentage is from about 7.5 to about 20. In some embodiments, the molar percentage is from about 7.5, 8, 9, 10, 11, 12, 13, 14, 15, 16, 17, 18, 19, to about 20 or any range derivable therein.

C. Selective Organ Targeting (Sort) Compound

In some aspects, the present disclosure comprise one or more selective organ targeting (SORT) compound which leads to the selective delivery of the composition to a particular organ. This compound may be a lipid, a small molecule therapeutic agent, a sugar, a vitamin, or a protein.

In some embodiments, the selective organ targeting (SORT) compound is present in the composition in a molar ratio from about 2%, 4%, 5%, 10%, 15%, 20%, 22%, 24%, 26%, 28%, 30%, 32%, 34%, 36%, 38%, 40%, 45%, 50%, 55%, 60%, 65%, to about 70%, or any range derivable therein. In some embodiments, the SORT compound may be present in an amount from about 5% to about 40%, from about 10% to about 40%, from about 20% to about 35%, from about 25% to about 35%, or from about 28% to about 34%.

In some embodiments, the SORT compound may be a lipid. A lipid is a small molecule with two or more alkyl or alkenyl chains of $C_6$-$C_{24}$. A small molecule therapeutic agent is a compound containing less than 100 non-hydrogen atoms and a weight of less than 2,000 Daltons. A sugar is a molecule comprising a molecular formula $C_nH_{2n}O_n$, wherein n is from 3 to 7 or a combination of multiple molecules of that formula. A protein is a sequence of amino acids comprising at least 3 amino acid residues. Proteins without a formal tertiary structure may also be referred to as a peptide. The protein may also comprise an intact protein with a tertiary structure. A vitamin is a macronutrient and consists of one or more compounds selected from Vitamin A, Vitamin $B_1$, Vitamin $B_2$, Vitamin $B_3$, Vitamin $B_5$, Vitamin $B_6$, Vitamin $B_7$, Vitamin $B_9$, Vitamin $B_{12}$, Vitamin C, Vitamin D, Vitamin E, and Vitamin K 1. Permanently Cationic Lipid In some aspects, the present disclosure provides one or more lipids with one or more hydrophobic components and a permanently cationic group. The permanently cationic lipid may contain an group which has a positive charge regardless of the pH. One permanently cationic group that may be used in the permanently cationic lipid is a quaternary ammonium group. These permanently cationic lipids include such structures as those described in the formula below:

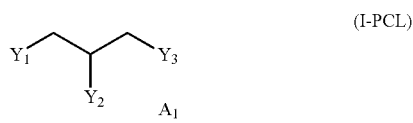
(I-PCL)

wherein:
- $Y_1$, $Y_2$, or $Y_3$ are each independently $X_1C(O)R_1$ or $X_2N^+R_3R_4R_5$; provided at least one of $Y_1$, $Y_2$, and $Y_3$ is $X_2N^+R_3R_4R_5$;
- $R_1$ is $C_1$-$C_{24}$ alkyl, $C_1$-$C_{24}$ substituted alkyl, $C_1$-$C_{24}$ alkenyl, $C_1$-$C_{24}$ substituted alkenyl;
- $X_1$ is O or $NR_a$, wherein $R_a$ is hydrogen, $C_1$-$C_4$ alkyl, or $C_1$-$C_4$ substituted alkyl;
- $X_2$ is $C_1$-$C_6$ alkanediyl or $C_1$-$C_6$ substituted alkanediyl;
- $R_3$, $R_4$, and $R_5$ are each independently $C_1$-$C_{24}$ alkyl, $C_1$-$C_{24}$ substituted alkyl, $C_1$-$C_{24}$ alkenyl, $C_1$-$C_{24}$ substituted alkenyl;
- $A_1$ is an anion with a charge equal to the number of $X_2N^+R_3R_4R_5$ groups in the compound.

In another embodiment, the permanently cationic lipid is further defined by the formula:

(II-PCL)

wherein:
- $R_6$-$R_9$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; provided at least one of $R_6$-$R_9$ is a group of $C_5$-$C_{24}$; and
- $A_2$ is a monovalent anion.

In another embodiments, the permanently cationic lipid is further defined by the formula:

(III-PCL)

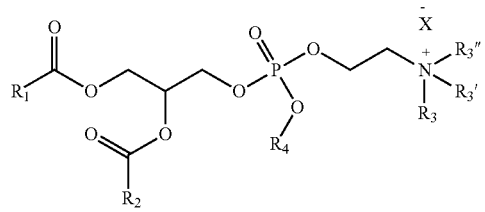

wherein:
- $R_1$ and $R_2$ are each independently alkyl$_{(C8-C24)}$, alkenyl$_{(C8-C24)}$, or a substituted version of either group;
- $R_3$, $R_3'$, and $R_3''$ are each independently alkyl$_{(C\leq 6)}$ or substituted alkyl$_{(C\leq 6)}$;
- $R_4$ is alkyl$_{(C\leq 6)}$ or substituted alkyl$_{(C\leq 6)}$; and
- $X^-$ is a monovalent anion.

In some embodiments, the permanently cationic lipid is present in an amount from about 4 to about 16 molar percentage of the total lipid composition. The composition may contain from about 5, 6, 7, 8, 9, 10, 11, 12, 13, 14, or 15 molar percentage, or any range derivable therein. In other embodiments, the composition may comprise from about 18 to about 66 molar percentage of the total lipid composition. In some embodiments, the compositions may contain from about 18, 20, 22, 24, 26, 28, 30, 32, 34, 36, 38, 40, 42, 44, 46, 48, 50, 52, 54, 56, 58, 60, 62, 64, or 66 molar percentage, or any range derivable therein.

2. Permanently Anionic Lipid

In some aspects, the present disclosure provides one or more lipids with one or more hydrophobic components and a permanently anionic group. One anionic group that may be used in the permanently anionic lipid is a phosphate group. The phosphate group may be a compound which is deprotonated and possesses a negative charge at a pH below 8, 9, 10, 11, 12, 13 or 14. The hydrophobic components may be one or more $C_6$-$C_{24}$ alkyl or alkenyl groups. The compound may have one hydrophobic group, two hydrophobic groups, or three hydrophobic groups.

In some embodiments, the permanently anionic lipid has a structure of the formula:

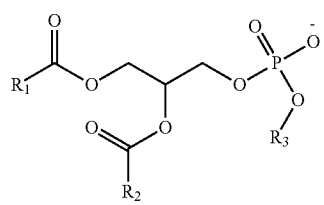
(IB)

wherein:
- $R_1$ and $R_2$ are each independently alkyl$_{(C8-C24)}$, alkenyl$_{(C8-C24)}$, or a substituted version of either group;
- $R_3$ is hydrogen, alkyl$_{(C\leq 6)}$, or substituted alkyl$_{(C\leq 6)}$, or —$Y_1$—$R_4$, wherein:
  - $Y_1$ is alkanediyl$_{(C\leq 6)}$ or substituted alkanediyl$_{(C\leq 6)}$; and
  - $R_4$ is acyloxy$_{(C\leq 8-24)}$ or substituted acyloxy$_{(C\leq 8-24)}$.

3. Phosphotidylcholine

In some aspects, the present disclosure provides one or more lipids with one or more hydrophobic components, a cationic amine group, and a negatively charged phosphate group. The cationic amine group may be a quaternary amine with three methyl groups attached to the nitrogen atom. The hydrophobic components may be one or more $C_6$-$C_{24}$ alkyl or alkenyl groups. The compound may have one hydrophobic group, two hydrophobic groups, or three hydrophobic groups. In some embodiments, the phosphotidylcholine compound is further defined as:

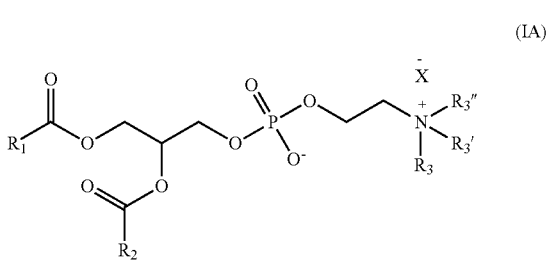

(IA)

wherein:
R$_1$ and R$_2$ are each independently alkyl$_{(C8-C24)}$, alkenyl$_{(C8-C24)}$, or a substituted version of either group;
R$_3$, R$_3'$, and R$_3''$ are each independently alkyl$_{(C\leq6)}$ or substituted alkyl$_{(C\leq6)}$; and
X$^-$ is a monovalent anion.

D. Additional Lipids in the Lipid Nanoparticles

In some aspects of the present disclosure, compositions containing one or more lipids are mixed with the cationic ionizable lipids to create a composition. In some embodiments, the cationic ionizable lipids are mixed with 1, 2, 3, 4, or 5 different types of lipids. It is contemplated that the cationic ionizable lipids can be mixed with multiple different lipids of a single type. In some embodiments, the cationic ionizable lipids compositions comprise at least a steroid or a steroid derivative, a PEG lipid, and a phospholipid.

In some embodiments, the lipid nanoparticles are preferentially delivered to a target organ. In some embodiments, the target organ is selected from the lungs, the heart, the brain, the spleen, the bone marrow, the bones, the skeletal muscles, the stomach, the small intestine, the large intestine, the kidneys, the bladder, the breast, the liver, the testes, the ovaries, the uterus, the spleen, the thymus, the brainstem, the cerebellum, the spinal cord, the eye, the ear, the tongue, or the skin. Alternatively, the composition may be preferentially delivered to a target organ system such as the nervous system, the cardiovascular system, or the respiratory system or a part of one of these organ system. As used herein, the term "preferentially delivered" is used to refer to a composition which is delivered to the target organ or organ system in at least 25% of the amount administered. This term is used to refer to a composition in which at least 25%, 50%, or at least 75% of the amount administered.

1. Steroids and Steroid Derivatives

In some aspects of the present disclosure, the cationic ionizable lipids are mixed with one or more steroid or a steroid derivative to create a composition. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula below:

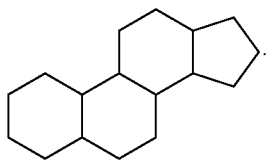 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

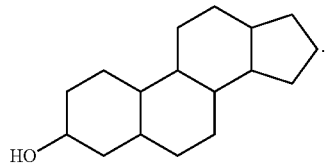 [SMILES: OC1CCC2C(CCC3C4CCCC4CCC23)C1]

In some embodiments of the present disclosure, the steroid or steroid derivative is a cholestane or cholestane derivative. In a cholestane, the ring structure is further defined by the formula:

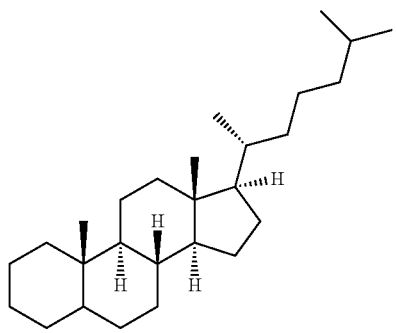

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestene and a sterol or a derivative thereof.

In some embodiments, the compositions may further comprise a molar percentage of the steroid to the total lipid composition from about 40 to about 46. In some embodiments, the molar percentage is from about 40, 41, 42, 43, 44, 45, to about 46 or any range derivable therein. In other embodiments, the molar percentage of the steroid relative to the total lipid composition is from about 15 to about 40. In some embodiments, the molar percentage is 15, 16, 18, 20, 22, 24, 26, 28, 30, 32, 34, 36, 38, or 40, or any range derivable therein.

2. PEG or PEGylated Lipid

In some aspects of the present disclosure, the polymers are mixed with one or more PEGylated lipids (or PEG lipid) to create a lipid composition. In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present disclosure are taught by U.S. Pat. No. 5,820,873, WO 2010/141069, or U.S. Pat. No. 8,450,298, which is incorporated herein by reference.

In another aspect, the PEG lipid has the formula:

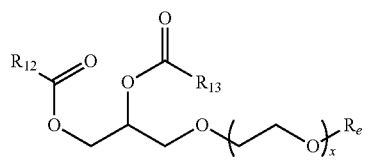

wherein: $R_{12}$ and $R_{13}$ are each independently alkyl$_{(C \leq 24)}$, alkenyl$_{(C \leq 24)}$, or a substituted version of either of these groups; $R_e$ is hydrogen, alkyl$_{(C \leq 8)}$, or substituted alkyl$_{(C \leq 8)}$; and x is 1-250. In some embodiments, $R_e$ is alkyl$_{(C \leq 8)}$ such as methyl. $R_{12}$ and $R_{13}$ are each independently alkyl$_{(C \leq 4-20)}$. In some embodiments, x is 5-250. In one embodiment, x is 5-125 or x is 100-250. In some embodiments, the PEG lipid is 1,2-dimyristoyl-sn-glycerol, methoxypolyethylene glycol.

In another aspect, the PEG lipid has the formula:

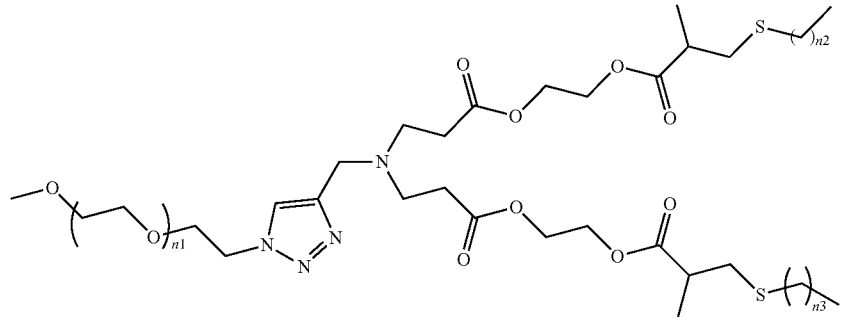

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments, the compositions may further comprise a molar percentage of the PEG lipid to the total lipid composition from about 4.0 to about 4.6. In some embodiments, the molar percentage is from about 4.0, 4.1, 4.2, 4.3, 4.4, 4.5, to about 4.6 or any range derivable therein.

In other embodiments, the molar percentage is from about 1.5 to about 4.0. In some embodiments, the molar percentage is from about 1.5, 1.75, 2, 2.25, 2.5, 2.75, 3, 3.25, 3.5, 3.75, to about 4.0 or any range derivable therein.

3. Phospholipid

In some aspects of the present disclosure, the polymers are mixed with one or more phospholipids to create a composition. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine.

In some embodiments, the compositions may further comprise a molar percentage of the phospholipid to the total lipid composition from about 20 to about 23. In some embodiments, the molar percentage is from about 20, 20.5, 21, 21.5, 22, 22.5, to about 23 or any range derivable therein. In other embodiments, the molar percentage is from about 7.5 to about 20. In some embodiments, the molar percentage is from about 7.5, 8, 9, 10, 11, 12, 13, 14, 15, 16, 17, 18, 19, to about 20 or any range derivable therein.

E. Therapeutic Agents

1. Nucleic Acids

In some aspects of the present disclosure, the lipid compositions comprise one or more nucleic acids. In some embodiments, the lipid composition comprises one or more nucleic acids present in a weight ratio to the lipid composition from about 5:1 to about 1:100. In some embodiments, the weight ratio of nucleic acid to lipid composition is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any range derivable therein. In some embodiments, the weight ratio is about 1:40. In addition, it should be clear that the present disclosure is not limited to the specific nucleic acids disclosed herein. The present disclosure is not limited in scope to any particular source, sequence, or type of nucleic acid, however, as one of ordinary skill in the art could readily identify related homologs in various other sources of the nucleic acid including nucleic acids from non-human species (e.g., mouse, rat, rabbit, dog, monkey, gibbon, chimp, ape, baboon, cow, pig, horse, sheep, cat and other species). It is contemplated that the nucleic acid used in the present disclosure can comprises a sequence based upon a naturally-occurring sequence. Allowing for the degeneracy of the genetic code, sequences that have at least about 50%, usually at least about 60%, more usually about 70%, usually about 80%, preferably at least about 90% and most preferably about 95% of nucleotides that are identical to the nucleotide sequence of the naturally-occurring sequence. In another embodiment, the nucleic acid is a complementary sequence to a naturally occurring sequence, or complementary to 75%, 80%, 85%, 90%, 95% and 100%. Longer polynucleotides encoding 250, 500, 1000, 1212, 1500, 2000, 2500, 3000 or longer are contemplated herein.

The nucleic acid used herein may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present disclosure may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the nucleic acid comprises one or more antisense segments which inhibits expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

2. Modified Nucleobases

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In some embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, $O(CH_2)_2O(CH_2)_2N(CH_3)_2$, and N-substituted acetamide (O—$CH_2$—C(=O)—$N(R_m)$$(R_n)$ where each $R_m$ and $R_n$ is, independently, H, an amino protecting group or substituted or unsubstituted $C_1$-$C_{10}$ alkyl.

In some embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, $O(CH_2)_2$—O—$N(CH_3)_2$, —$O(CH_2)_2O$$(CH_2)_2N(CH_3)_2$, and O—$CH_2$—C(=O)—N(H)$CH_3$.

In some embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —$C(R_aR_b)$—N(R)—O— or, —$C(R_aR_b)$—O—N(R)—; 4'-$CH_2$-2', 4'-$(CH_2)_2$-2', 4'-$(CH_2)$—O-2' (LNA); 4'-$(CH_2)$—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845); 4'-C($CH_3$)($CH_3$)—O-2' and analogs thereof, (see, e.g., WO 2009/006478); 4'-$CH_2$—N($OCH_3$)-2' and analogs thereof (see, e.g., WO2008/150729); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672); 4'-$CH_2$—C(H)($CH_3$)-2' (see, e.g., Chattopadhyaya et al., J. Org. Chem., 2009, 74, 118-134); and 4'-$CH_2$—C(=$CH_2$)-2' and analogs thereof (see, PCT International Application WO 2008/154401).

In some embodiments, such 4' to 2' bridges independently comprise from 1 to 4 linked groups independently selected from —$[C(R_a)(R_b)]_n$—, —$C(R_a)$=$C(R_b)$—, —$C(R_a)$=N—, —C(=$NR_a$)—, —C(=O)—, —C(=S)—, —Si$(R_a)_2$—, —S(=O)$_x$—, and —N($R_a$)—; wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$, alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-$(CH_2)_3$-2') BNA, and (K) Methoxy(ethyleneoxy) (4'-CH ($CH_2OMe$)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794, 499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-$CH_2$—O-2') bicyclic nucleosides have been incorporated into antisense oligonucleotides that showed antisense activity (Frieden et al., Nucleic Acids Research, 2003, 21, 6365-6372).

In some embodiments, substituted sugar moieties comprise one or more non-bridging sugar substituent and one or more bridging sugar substituent (e.g., 5'-substituted and 4'-2' bridged sugars; PCT International Application WO 2007/134181, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfur, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US 2005/0130923) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In some embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In some embodiments, at least one of $q_1$, $q_2$, $q_3$, $q_4$, $q_5$, $q_6$ and $q_7$ is methyl. In some embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO 2008/101157 for other disclosed 5',2'-bis substituted nucleosides) and replacement of the ribosyl ring oxygen atom with S and further substitution at the 2'-position (see U.S. Patent Publication US 2005/0130923) or alternatively 5'-substitution of a bicyclic nucleic acid (see PCT International Application WO 2007/134181 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., 2007).

In some embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In some embodiments, oligonucleotides comprise one or more RNA-like nucleosides. In some embodiments, oligonucleotides comprise one or more DNA-like nucleotides.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., 1991; and those disclosed by Sanghvi, Y. S., 1993.

Representative United States Patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

In some embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), a or (3 such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(═O)—N(H)-5'), amide-4 (3'-CH$_2$—N(H)—C(═O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., 1989), cholic acid (Manoharan et al., 1994), a thioether, e.g., hexyl-5-tritylthiol (Manoharan et al., 1992; Manoharan et al., 1993), a thiocholesterol (Oberhauser et al., 1992), an aliphatic chain, e.g., dodecandiol or undecyl residues (Saison-Behmoaras et al., 1991; Kabanov et al., 1990; Svinarchuk et al., 1993), a phospholipid, e.g., di-hexadecyl-rac-glycerol or triethylammonium 1,2-di-O-hexadecyl-rac-glycero-3-H-phosphonate (Manoharan et al., 1995; Shea et al., 1990), a polyamine or a polyethylene glycol chain (Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

3. Proteins

In some embodiments, the compositions may further comprise one or more proteins. Some proteins may include enzymes such as nuclease enzymes. The compositions described herein may comprise one or more CRISPR associated proteins (e.g. CRISPR enzyme) including a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2.

The protein in the compositions described herein may be Cas9 (e.g., from S. pyogenes or S. pneumonia). The CRISPR enzyme can direct cleavage of one or both strands at the location of a target sequence, such as within the target sequence and/or within the complement of the target sequence. The CRISPR enzyme may be mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, the present disclosure provides compounds containing one or more therapeutic proteins. The therapeutic proteins that may be included in the composition include a wide range of molecules such as cytokines, chemokines, interleukins, interferons, growth factors, coagulation factors, anti-coagulants, blood factors, bone morphogenic proteins, immunoglobulins, and enzymes. Some non-limiting examples of particular therapeutic proteins include Erythropoietin (EPO), Granulocyte colony-stimulating factor (G-CSF), Alpha-galactosidase A, Alpha-L-iduronidase, Thyrotropin α, N-acetylgalactosamine-4-sulfatase (rhASB), Dornase alfa, Tissue plasminogen activator (TPA) Activase, Glucocerebrosidase, Interferon (IF) β-1a, Interferon β-1b, Interferon γ, Interferon α, TNF-α, IL-1 through IL-36, Human growth hormone (rHGH), Human insulin (BHI), Human chorionic gonadotropin a, Darbepoetin a, Follicle-stimulating hormone (FSH), and Factor VIII.

4. Small Molecule Therapeutic Agents

In some aspects, the present disclosure provides compositions comprising a therapeutic agent. The therapeutic agent may be a small molecule such as a 7-Methoxypteridine, 7-Methylpteridine, abacavir, abafungin, abarelix, acebutolol, acenaphthene, acetaminophen, acetanilide, acetazolamide, acetohexamide, acetretin, acrivastine, adenine, adenosine, alatrofloxacin, albendazole, albuterol, alclofenac, aldesleukin, alemtuzumab, alfuzosin, alitretinoin, allobarbital, allopurinol, all-transretinoic acid (ATRA), aloxiprin, alprazolam, alprenolol, altretamine, amifostine, amiloride, aminoglutethimide, aminopyrine, amiodarone HCl, amitriptyline, amlodipine, amobarbital, amodiaquine, amoxapine, amphetamine, amphotericin, amphotericin B, ampicillin, amprenavir, amsacrine, amylnitrate, amylobarbitone, anastrozole, anrinone, anthracene, anthracyclines, aprobarbital, arsenic trioxide, asparaginase, aspirin, astemizole, atenolol, atorvastatin, atovaquone, atrazine, atropine, atropine azathioprine, auranofin, azacitidine, azapropazone, azathioprine, azintamide, azithromycin, aztreonum, baclofen, barbitone, BCG live, beclamide, beclomethasone, bendroflumethiazide, benezepril, benidipine, benorylate, benperidol, bentazepam, benzamide, benzanthracene, benzathine penicillin, benzhexol HCl, benznidazole, benzodiazepines, benzoic acid, bephenium hydroxynaphthoate, betamethasone, bevacizumab (avastin), bexarotene, bezafibrate, bicalutamide, bifonazole, biperiden, bisacodyl, bisantrene, bleomycin, bleomycin, bortezomib, brinzolamide, bromazepam, bromocriptine mesylate, bromperidol, brotizolam, budesonide, bumetanide, bupropion, busulfan, butalbital, butamben, butenafine HCl, butobarbitone, butobarbitone (butethal), butoconazole, butoconazole nitrate, butylparaben, caffeine, calcifediol, calciprotriene, calcitriol, calusterone, cambendazole, camphor, camptothecin, camptothecin analogs, candesartan, capecitabine, capsaicin, captopril, carbamazepine, carbimazole, carbofuran, carboplatin, carbromal, carimazole, carmustine, cefamandole, cefazolin, cefixime, ceftazidime, cefuroxime axetil, celecoxib, cephradine, cerivastatin, cetrizine, cetuximab, chlorambucil, chloramphenicol, chlordiazepoxide, chlormethiazole, chloroquine, chlorothiazide, chlorpheniramine, chlorproguanil HCl, chlorpromazine, chlorpropamide, chlorprothixene, chlorpyrifos, chlortetracycline, chlorthalidone, chlorzoxazone, cholecalciferol, chrysene, cilostazol, cimetidine, cinnarizine, cinoxacin, ciprofibrate, ciprofloxacin HCl, cisapride, cisplatin, citalopram, cladribine, clarithromycin, clemastine fumarate, clioquinol, clobazam, clofarabine, clofazimine, clofibrate, clomiphene citrate, clomipramine, clonazepam, clopidogrel, clotiazepam, clotrimazole, clotrimazole, cloxacillin, clozapine, cocaine, codeine, colchicine, colistin, conjugated estrogens, corticosterone, cortisone, cortisone acetate, cyclizine, cyclobarbital, cyclobenzaprine, cyclobutane-spirobarbiturate, cycloethane-spirobarbiturate, cycloheptane-spirobarbiturate, cyclohexane-spirobarbiturate, cyclopentane-spirobarbiturate, cyclophosphamide, cyclopropane-spirobarbiturate, cycloserine, cyclosporin, cyproheptadine, cyproheptadine HCl, cytarabine, cytosine, dacarbazine, dactinomycin, danazol, danthron, dantrolene sodium, dapsone, darbepoetin alfa, darodipine, daunorubicin, decoquinate, dehydroepiandrosterone, delavirdine, demeclocycline, denileukin, deoxycorticosterone, desoxymethasone, dexamethasone, dexamphetamine, dexchlorpheniramine, dexfenfluramine, dexrazoxane, dextropropoxyphene, diamorphine, diatrizoicacid, diazepam, diazoxide, dichlorophen, dichlorprop, diclofenac, dicumarol, didanosine, diflunisal, digitoxin, digoxin, dihydrocodeine, dihydroequilin, dihydroergotamine mesylate, diiodohydroxyquinoline, diltiazem HCl, diloxamide furoate, dimenhydrinate, dimorpholamine, dinitolmide, diosgenin, diphenoxylate HCl, diphenyl, dipyridamole, dirithromycin, disopyramide, disulfiram, diuron, docetaxel, domperidone, donepezil, doxazosin, doxazosin HCl, doxorubicin (neutral), doxorubicin HCl, doxycycline, dromostanolone propionate, droperidol, dyphylline, echinocandins, econazole, econazole nitrate, efavirenz, ellipticine, enalapril, enlimomab, enoximone, epinephrine, epipodophyllotoxin derivatives, epirubicin, epoetinalfa, eposartan, equilenin, equilin, ergocalciferol, ergotamine tartrate, erlotinib, erythromycin, estradiol, estramustine, estriol, estrone, ethacrynic acid, ethambutol, ethinamate, ethionamide, ethopropazine HCl, ethyl-4-aminobenzoate (benzocaine), ethylparaben, ethinylestradiol, etodolac, etomidate, etoposide, etretinate, exemestane, felbamate, felodipine, fenbendazole, fenbuconazole, fenbufen, fenchlorphos, fenclofenac, fenfluramine, fenofibrate, fenoldepam, fenoprofen calcium, fenoxycarb, fenpiclonil, fentanyl, fenticonazole, fexofenadine, filgrastim, finasteride, flecamide acetate, floxuridine, fludarabine, fluconazole, fluconazole, flucytosine, fludioxonil, fludrocortisone, fludrocortisone acetate, flufenamic acid, flunanisone, flunarizine HCl, flunisolide, flunitrazepam, fluocortolone, fluometuron, fluorene, fluorouracil, fluoxetine HCl, fluoxymesterone, flupenthixol decanoate, fluphenthixol decanoate, flurazepam, flurbiprofen, fluticasone propionate, fluvastatin, folic acid, fosenopril, fosphenytoin sodium, frovatriptan, furosemide, fulvestrant, furazolidone, gabapentin, G-BHC (Lindane), gefitinib, gemcitabine, gemfibrozil, gemtuzumab, glafenine, glibenclamide, gliclazide, glimepiride, glipizide, glutethimide, glyburide, Glyceryltrinitrate (nitroglycerin), goserelin acetate, grepafloxacin, griseofulvin, guaifenesin, guanabenz acetate, guanine, halofantrine HCl, haloperidol, hydrochlorothiazide, heptabarbital, heroin, hesperetin, hexachlorobenzene, hexethal, histrelin acetate, hydrocortisone, hydroflumethiazide, hydroxyurea, hyoscyamine, hypoxanthine, ibritumomab, ibuprofen, idarubicin, idobutal, ifosfamide, ihydroequilenin, imatinib mesylate, imipenem, indapamide, indinavir, indomethacin, indoprofen, interferon alfa-2a, interferon alfa-2b, iodamide, iopanoic acid, iprodione, irbesartan, irinotecan, isavuconazole, isocarboxazid, isoconazole, isoguanine, isoniazid, isopropylbarbiturate, isoproturon, isosorbide dinitrate, isosorbide mononitrate, isradipine, itraconazole, itraconazole, itraconazole (Itra), ivermectin, ketoconazole, ketoprofen, ketorolac, khellin, labetalol, lamivudine, lamotrigine, lanatoside C, lansoprazole, L-DOPA, leflunomide, lenalidomide, letrozole, leucovorin, leuprolide acetate, levamisole, levofloxacin, lidocaine, linuron, lisinopril, lomefloxacin, lomustine, loperamide, loratadine, lorazepam, lorefloxacin, lormetazepam, losartan mesylate, lovastatin, lysuride maleate, Maprotiline HCl, mazindol, mebendazole, Meclizine HCl, meclofenamic acid, medazepam, medigoxin, medroxyprogesterone acetate, mefenamic acid, Mefloquine HCl, megestrol acetate, melphalan, mepenzolate bromide, meprobamate, meptazinol, mercaptopurine, mesalazine, mesna, mesoridazine, mestranol, methadone, methaqualone, methocarbamol, methoin, methotrexate, methoxsalen, methsuximide, methyclothiazide, methylphenidate, methylphenobarbitone, methyl-p-hydroxybenzoate, methylprednisolone, methyltestosterone, methyprylon, methysergide maleate, metoclopramide, metolazone, metoprolol, metronidazole, Mianserin HCl, miconazole, midazolam, mifepristone, miglitol, minocycline, minoxidil, mitomycin C, mitotane, mitoxantrone, mofetilmycophenolate, molindone, montelukast, morphine, Moxifloxacin HCl, nabumetone, nadolol, nalbuphine, nalidixic acid, nandrolone, naphthacene, naphthalene, naproxen, naratriptan HCl, natamycin, nelarabine, nelfinavir, nevirapine, nicardipine HCl, nicotin amide, nicotinic acid, nicoumalone, nifedipine, nilutamide, nimodipine, nimorazole, nisoldipine, nitrazepam, nitrofurantoin, nitrofurazone, nizatidine, nofetumomab, norethisterone, norfloxacin, norgestrel, nortriptyline HCl, nystatin, oestradiol, ofloxacin, olanzapine, omeprazole, omoconazole, ondansetron HCl, oprelvekin, ornidazole, oxaliplatin, oxamniquine, oxantelembonate, oxaprozin, oxatomide, oxazepam, oxcarbazepine, oxfendazole, oxiconazole, oxprenolol, oxyphenbutazone, oxyphencyclimine HCl, paclitaxel, palifermin, pamidronate, p-aminosalicylic acid, pantoprazole, paramethadione, paroxetine HCl, pegademase, pegaspargase, pegfilgrastim, pemetrexeddisodium, penicillamine, pentaerythritol tetranitrate, pentazocin, pentazocine, pentobarbital, pentobarbitone, pentostatin, pentoxifylline, perphenazine, perphenazine pimozide, perylene, phenacemide, phenacetin, phenanthrene, phenindione, phenobarbital, phenolbarbitone, phenolphthalein, phenoxybenzamine, phenoxybenzamine HCl, phenoxymethyl penicillin, phensuximide, phenylbutazone, phenytoin, pindolol, pioglitazone, pipobroman, piroxicam, pizotifen maleate, platinum compounds, plicamycin, polyenes, polymyxin B, porfimersodium, posaconazole (Posa), pramipexole, prasterone, pravastatin, praziquantel, prazosin, prazosin HCl, prednisolone, prednisone, primidone, probarbital, probenecid, probucol, procarbazine, prochlorperazine, progesterone, proguanil HCl, promethazine, propofol, propoxur, propranolol, propylparaben, propylthiouracil, prostaglandin, pseudoephedrine, pteridine-2-methyl-thiol, pteridine-2-thiol, pteridine-4-methyl-thiol, pteridine-4-thiol, pteridine-7-methyl-thiol, pteridine-7-thiol, pyrantelembonate, pyrazinamide, pyrene, pyridostigmine, pyrimethamine, quetiapine, quinacrine, quinapril, quinidine, quinidine sulfate, quinine, quininesulfate, rabeprazole sodium, ranitidine HCl, rasburicase, ravuconazole, repaglinide, reposal, reserpine, retinoids, rifabutine, rifampicin, rifapentine, rimexolone, risperidone, ritonavir, rituximab, rizatriptan benzoate, rofecoxib, ropinirole HCl, rosiglitazone, saccharin, salbutamol, salicylamide, salicylic acid, saquinavir, sargramostim, secbutabarbital, secobarbital, sertaconazole, sertindole, sertraline HCl, simvastatin, sirolimus, sorafenib, sparfloxacin, spiramycin, spironolactone, stanolone, stanozolol, stavudine, stilbestrol, streptozocin, strychnine, sulconazole, sulconazole nitrate, sulfacetamide, sulfadiazine, sulfamerazine, sulfamethazine, sulfamethoxazole, sulfanilamide, sulfathiazole, sulindac, sulphabenzamide, sulphacetamide, sulphadiazine, sulphadoxine, sulphafurazole, sulphamerazine, sulpha-methoxazole, sulphapyridine, sulphasalazine, sulphinpyrazone, sulpiride, sulthiame, sumatriptan succinate, sunitinib maleate, tacrine, tacrolimus, talbutal, tamoxifen citrate, tamulosin, targretin, taxanes, tazarotene, telmisartan, temazepam, temozolomide, teniposide, tenoxicam, terazosin, terazosin HCl, terbinafine HCl, terbutaline sulfate, terconazole, terfenadine, testolactone, testosterone, tetracycline, tetrahydrocannabinol, tetroxoprim, thalidomide, thebaine, theobromine, theophylline, thiabendazole, thiamphenicol, thioguanine, thioridazine, thiotepa, thotoin, thymine, tiagabine HCl, tibolone, ticlopidine, tinidazole, tioconazole, tirofiban, tizanidine HCl, tolazamide, tolbutamide, tolcapone, topiramate, topotecan, toremifene, tositumomab, tramadol, trastuzumab, trazodone HCl, tretinoin, triamcinolone, triamterene, triazolam, triazoles, trifluromazine, trimethoprim, trimipramine maleate, triphenylene, troglitazone, tromethamine, tropicamide, trovafloxacin, tybamate, ubidecarenone (coenzyme Q10), undecenoic acid, uracil, uracil mustard, uric acid, valproic acid, valrubicin, valsartan, vancomycin, venlafaxine HCl, vigabatrin, vinbarbital, vinblastine, vincristine, vinorelbine, voriconazole, xanthine, zafirlukast, zidovudine, zileuton, zoledronate, zoledronic acid, zolmitriptan, zolpidem, and zopiclone.

F. Kits

The present disclosure also provides kits. Any of the components disclosed herein may be combined in the form of a kit. In some embodiments, the kits comprise a composition as described above or in the claims.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the lipid nanoparticle components are combined in a single container. In other embodiments, some or all of the lipid nanoparticle components are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Preparation of DOTAP Modified Lipid Nanoparticles

Lipid nanoparticles (LNPs) are the most efficacious carrier class for in vivo nucleic acid delivery. Historically, effective LNPs are composed of 4 components: an ionizable cationic lipid, zwitterionic phospholipid, cholesterol, and lipid poly(ethylene glycol) (PEG). However, these LNPs result in only general delivery of nucleic acids, rather than organ or tissue targeted delivery. LNPs typically delivery RNAs only to the liver. Therefore, new formulations of LNPs were sought in an effort to provide targeted nucleic acid delivery.

The four canonical types of lipids were mixed in a 15:15:30:3 molar ratio, with or without the addition of a permanently cationic lipid. Briefly, LNPs were prepared by mixing 5A2-SC8 (ionizable cationic), DOPE (zwitterionic), cholesterol, DMG-PEG, and DOTAP (permanently cationic) in the ratios shown in Table 0.1.

TABLE 0.1

Molar Ratios and Percentages of Lipids in modified LNPS.

| Name | Molar Ratios | | | | | Molar Percentage (%) | | | | | Lipids/mRNA |
|---|---|---|---|---|---|---|---|---|---|---|---|
| | 5A2-SC8 | DOPE | Chol | DMG-PEG | DOTAP | 5A2-SC8 | DOPE | Chol | DMG-PEG | DOTAP | (wt/wt) |
| mDLNP | 15 | 15 | 30 | 3 | 0 | 23.8 | 23.8 | 47.6 | 4.8 | 0.0 | 40 |
| DOTAP5 | 15 | 15 | 30 | 3 | 3.3 | 22.6 | 22.6 | 45.2 | 4.5 | 5.0 | 40 |
| DOTAP10 | 15 | 15 | 30 | 3 | 7 | 21.4 | 21.4 | 42.9 | 4.3 | 10.0 | 40 |
| DOTAP15 | 15 | 15 | 30 | 3 | 11 | 20.3 | 20.3 | 40.5 | 4.1 | 14.9 | 40 |
| DOTAP20 | 15 | 15 | 30 | 3 | 16 | 19.0 | 19.0 | 38.0 | 3.8 | 20.3 | 40 |
| DOTAP25 | 15 | 15 | 30 | 3 | 21 | 17.9 | 17.9 | 35.7 | 3.6 | 25.0 | 40 |
| DOTAP30 | 15 | 15 | 30 | 3 | 27 | 16.7 | 16.7 | 33.3 | 3.3 | 30.0 | 40 |
| DOTAP35 | 15 | 15 | 30 | 3 | 34 | 15.5 | 15.5 | 30.9 | 3.1 | 35.1 | 40 |
| DOTAP40 | 15 | 15 | 30 | 3 | 42 | 14.3 | 14.3 | 28.6 | 2.9 | 40.0 | 40 |
| DOTAP45 | 15 | 15 | 30 | 3 | 52 | 13.0 | 13.0 | 26.1 | 2.6 | 45.2 | 40 |
| DOTAP50 | 15 | 15 | 30 | 3 | 63 | 11.9 | 11.9 | 23.8 | 2.4 | 50.0 | 40 |
| DOTAP55 | 15 | 15 | 30 | 3 | 77 | 10.7 | 10.7 | 21.4 | 2.1 | 55.0 | 40 |
| DOTAP60 | 15 | 15 | 30 | 3 | 95 | 9.5 | 9.5 | 19.0 | 1.9 | 60.1 | 40 |

TABLE 0.1-continued

Molar Ratios and Percentages of Lipids in modified LNPS.

| Name | Molar Ratios | | | | | Molar Percentage (%) | | | | | Lipids/mRNA (wt/wt) |
|---|---|---|---|---|---|---|---|---|---|---|---|
| | 5A2-SC8 | DOPE | Chol | DMG-PEG | DOTAP | 5A2-SC8 | DOPE | Chol | DMG-PEG | DOTAP | |
| DOTAP65 | 15 | 15 | 30 | 3 | 117 | 8.3 | 8.3 | 16.7 | 1.7 | 65.0 | 40 |
| DOTAP70 | 15 | 15 | 30 | 3 | 150 | 7.0 | 7.0 | 14.1 | 1.4 | 70.4 | 40 |
| DOTAP75 | 15 | 15 | 30 | 3 | 190 | 5.9 | 5.9 | 11.9 | 1.2 | 75.1 | 40 |
| DOTAP80 | 15 | 15 | 30 | 3 | 260 | 4.6 | 4.6 | 9.3 | 0.9 | 80.5 | 40 |
| DOTAP85 | 15 | 15 | 30 | 3 | 357 | 3.6 | 3.6 | 7.1 | 0.7 | 85.0 | 40 |
| DOTAP90 | 15 | 15 | 30 | 3 | 570 | 2.4 | 2.4 | 4.7 | 0.5 | 90.0 | 40 |
| DOTAP95 | 15 | 15 | 30 | 3 | 1200 | 1.2 | 1.2 | 2.4 | 0.2 | 95.0 | 40 |
| DOTAP100 | 0 | 0 | 0 | 0 | 100 | 0.0 | 0.0 | 0.0 | 0.0 | 100.0 | 40 |

For preparation of the mDLNP formulation, 5A2-SC8, DOPE, Cholesterol and DMG-PEG were dissolved in ethanol at the given molar ratios (15:15:30:3). The mRNA was dissolved in citrate buffer (10 mM, pH 4.0). The mRNA was then diluted into the lipids solution to achieve a weight ratio of 40:1 (total lipids:mRNA) by rapidly mixing the mRNA into the lipids solution at a volume ratio of 3:1 (mRNA: lipids, v/v). This solution was then incubated for 10 min at room temperature. For formation of DOTAP modified mDLNP formulations, mRNA was dissolved in 1×PBS or citrate buffer (10 mM, pH 4.0), and mixed rapidly into ethanol containing 5A2-SC8, DOPE, Cholesterol, DMG-PEG and DOTAP, fixing the weight ratio of 40:1 (total lipids:mRNA) and volume ratio of 3:1 (mRNA:lipids). As shown in Table 1, each formulation is named DOTAPX where X represents the DOTAP molar percentage in total lipids.

Example 2—Characterization of DOTAP Modified mDLNP Formulations

Figures 5A, 5B, 5C:
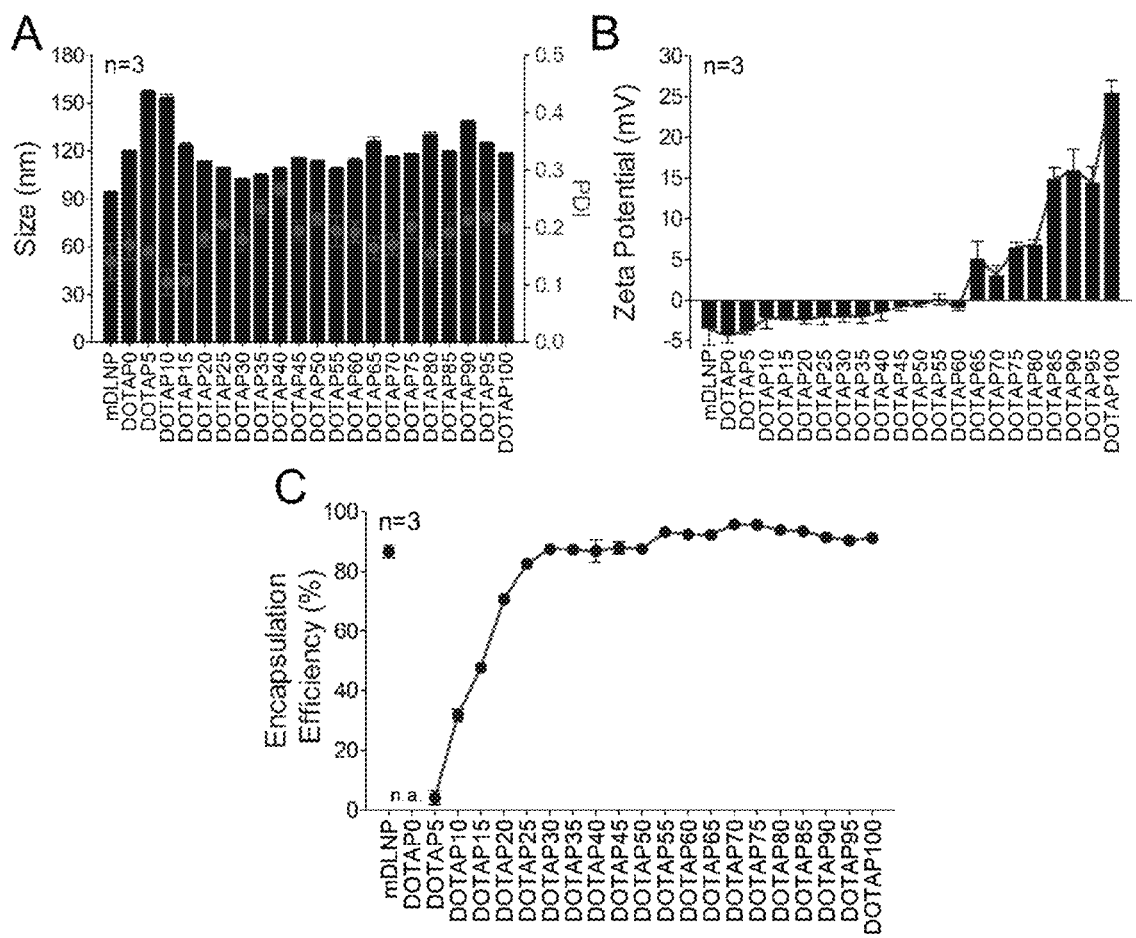
FIGS. 5A-C: Characterization of DOTAP mDLNP formulations (n=3). Size, PDI (FIG. 5A) and zeta-potential (FIG. 5B) were detected by Dynamic Light Scattering (DLS).

To characterize the different mDLNP formulations, size, polydispersity index and zeta-potential were examined by dynamic light scattering, 3 separate times for each formulation. Size and polydispersity index are shown in FIG. 5A, indicating regardless of DOTAP concentration, the formulations all fell within a size range of about 90 nm to about 160 nm, while the polydispersity indices varied from about 0.1 to about 0.3, indicating relative homogeneity of size. Zeta potential is shown for each formulation in FIG. 5B and shows that the zeta potential generally increases with the concentration of DOTAP.

Next, encapsulation efficiency was tested using a Ribogreen RNA assay (Zhao et al., 2016). Briefly, mRNA was encapsulated with about 85% efficiency in mDLNPs without DOTAP (FIG. 5C) when the mRNA was dissolved in acidic buffer (10 mM citrate, pH 4). Low pH is required to protonate the ionizable amine in the ionizable cationic lipid (e.g. 5A2-SC8, C12-200, DLin-MC3-DMA) to allow electrostatic complexation with negatively charged mRNA. For all other formulations on this plot, mixing was performed at pH 7.4 using mRNA dissolved in PBS. Clearly, with low concentrations of DOTAP, encapsulation efficiency was low, but increased to >80% with a molar percentage of DOTAP above 25% (FIG. 5C). The encapsulation efficiency was between about 80% and about 95% for all formulations with a molar percentage of greater than 25% DOTAP. Therefore, the potential to use neutral pH PBS mixing is a feature of the permanently cationic lipid strategy. This strategy allows for tissue specific delivery and for high Cas9 protein encapsulation. The addition of a permanently cationic lipid allows formation of LNPs at neutral pH. These encapsulation results are when PBS was used as a buffer. When acidic buffers are used (e.g. citrate buffer (10 mM, pH 4.0)), then the encapsulation efficiency is high (>90%) for all formulations from 0 to 100% DOTAP.

Finally, pKa was determined using 2-(p-toluidino)-6-naphthalenesulfonic acid (TNS) assay (FIG. 3B) (Zhao et al., 2016). The relationship between pKa and tissue specific mRNA delivery was plotted based on the defined rules. Here 8 rules were designed to score as showed in the table. Obviously, liver targeted formulations had a narrow pKa (~6-7), no significant range for spleen targeted formulation, but lung targeted delivery required high pKa (>9.25). Together distribution and pKa detection into consideration, it was concluded that internal charges of NPs is one factor that affects mRNA distributions, and that global/apparent LNP pKa is another factor determines the mRNA-mediated protein expression profiles in organs.

Figures 6A, 6B, 6C:
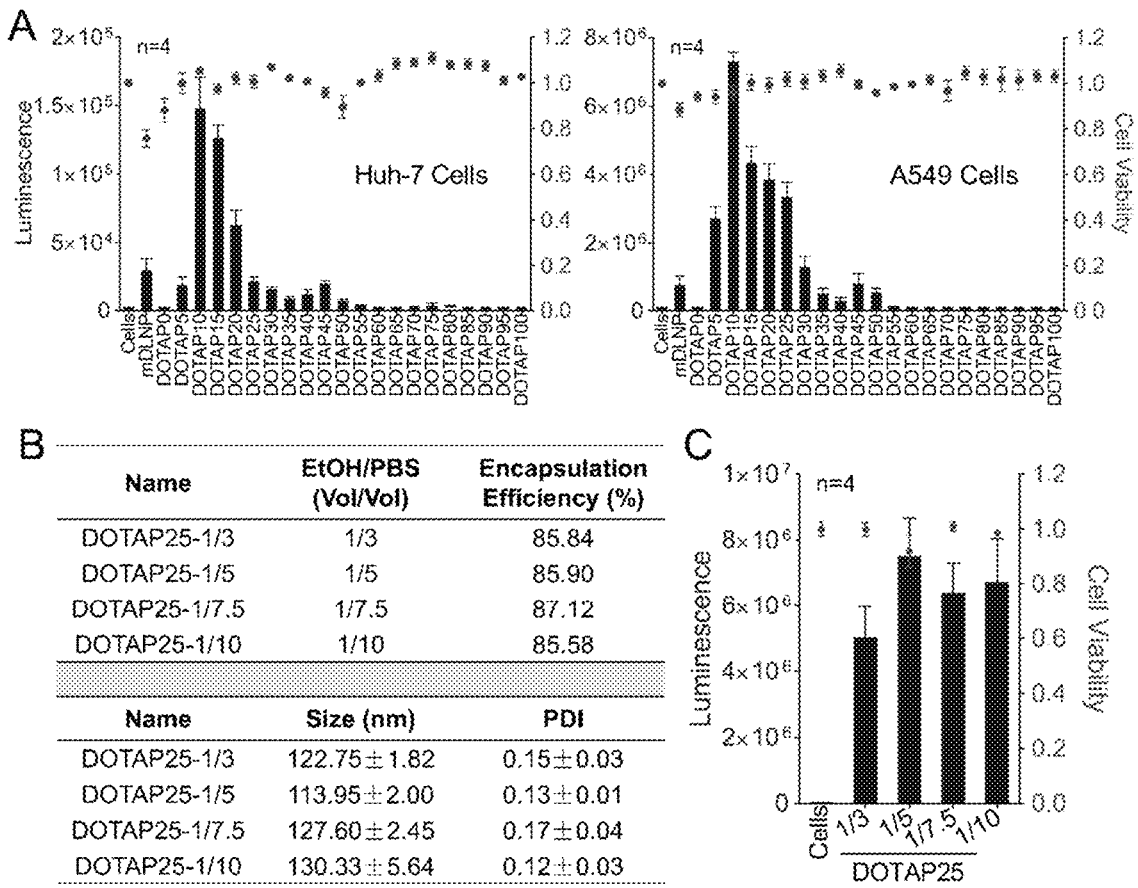
FIGS. 6A-C: DOTAP formulations showed excellent mRNA delivery efficiency and exhibited a delivery potential for these cargos that were not well-tolerated with ethanol or acidic buffer, e.g. proteins.

Example 3—Efficacy of Permanently Cationic Lipid Modified mDLNPs for mRNA Delivery To examine the delivery efficacy by which LNPs including a permanently cationic lipid are able to deliver active cargo in vitro, the DOTAP modified mDLNPs were loaded with mRNA encoding luciferase, and Huh-7 liver cells and A549 adenocarcinomic human alveolar basal epithelial cells were transfected with the 50 ng/well of mRNA. These cells were cultured for 24 hours before luciferase expression and cell viability were examined. As shown in FIG. 6A, DOTAP percentages of 5%-50% were better for mRNA delivery and expression in the Huh-7 liver cells in vitro, and 10% DOTAP appeared to have the greatest delivery and expression of luciferase (FIG. 6A). It is noted that delivery characteristics in vivo may be different. Generally, these studies may not be useful to predict in vivo activity, nor tissue tropism due to the additional in vivo barriers, organ distribution, and cellular specify of the SORT LNPs. Additionally, cell viability was examined and it was found that 10% DOTAP yielded high viability within the mDLNPs which exhibited robust luciferase expression (FIG. 6A). Examination of the same transfection with the A549 lung cancer cell line showed similar results, with cells transfected with the DOTAP10 formulation exhibiting nearly double the fluorescence of any of the other formulations and maintaining a high cell viability (FIG. 6A). DOTAP SORT LNPs were formed in PBS (pH 7.4) rather than citric buffer (10 mM, pH 4.0), but may formed in either buffer system. This is an attribute because it allows encapsulation and delivery of cargos that are not stable in ethanol or acidic buffer, e.g. proteins.

To determine the effect of ethanol concentration within the formulation, DOTAP25 was selected and prepared with various ethanol to PBS ratios (1:3, 1:5, 1:7.5 ad 1:10) (FIG. 6B). All four formulations showed similar encapsulation efficiency, size, and PDI (FIG. 2B). mRNA delivery efficiency was also measured by transfecting FaDu hypopharynx carcinoma cells with 50 ng/well of mRNA in each formulation. The delivery efficiency of each formulation was similar, with very little effect on cell viability as well (FIG. 6C). Therefore, these formulations appear applicable to a number of cell types, including liver, lung, and throat. Further, this formulation has also been successfully modified to use 1×PBS (pH 7.4) instead of acidic buffer (pH 4.0), and these data show that the ethanol percentage can be dramatically decreased, which provide for the possibility that DOTAP formulations may deliver cargo that are much more sensitive to high ethanol concentrations and acidic buffers, e.g. proteins.

Next, to test the ability of these mDLNPs to deliver mRNA in vivo, mice were injected with a dose of 0.1 mg/kg of Luc mRNA in each of the formulations. FIG. 1B shows ex vivo images of luciferase in major organs at 6 h post IV injection of each formulation. Interestingly, with increasing molar percentage of DOTAP, luciferase expression moved from liver to spleen, then to lung, demonstrating organ specific delivery. These data were quantitated, revealing that DOTAP percentage is a factor for tissue targeting delivery, and that mDLNP (0% DOTAP) is the best for liver delivery, while 5-15% DOTAP are the best for spleen and DOTAP50 (50%) is the best for lung delivery (FIG. 1B). Assuming that luciferase expression was detected only in liver, spleen and lung after IV injection, the percentage of luciferase expressed in each organ can be calculated (FIG. 1C). These data clearly indicate that with increasing molar DOTAP percentage in the formulation, there is decreasing delivery to and expression in the liver, with close to zero expression seen in the liver when DOTAP percentage is greater than 70% (FIG. 1B, 1C). However, the greater the DOTAP percentage, the more luminescence is seen in lung tissues, with close to 100% of luminescence seen in the lung when DOTAP percentage is greater than 80% (FIG. 1C). Concentrations of DOTAP 5 and 30 molar percentage showed higher percentages of luminescence in spleen tissues, while DOTAP10 showed the highest relative luminescence in the spleen compared to other tissues (FIG. 1C). These results indicate that lipid concentrations can be tailored for specific tissue delivery, following injection.

Figures 3A, 3B, 3C:
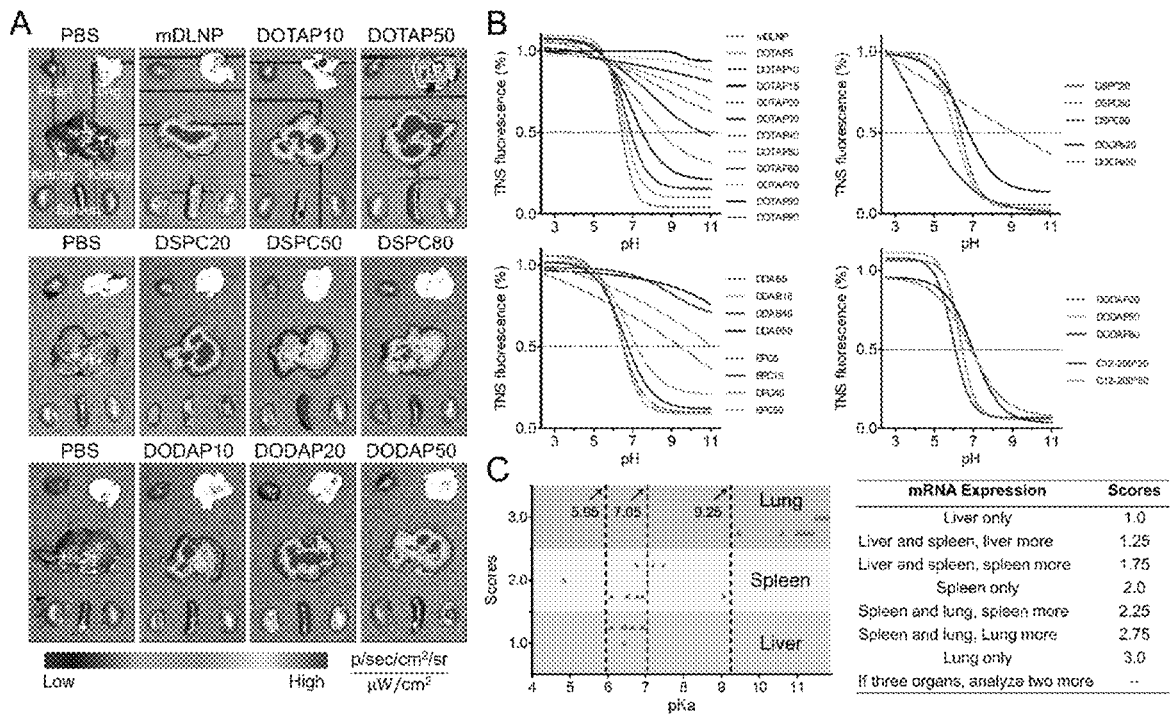
FIGS. 3A-C: To determine why various lipids may induce huge differences for mRNA expression in organs, distribution assay and pKa detection was then performed. Both biodistribution and pKa played roles for mRNA expression profiles in organs.
Figure 7:
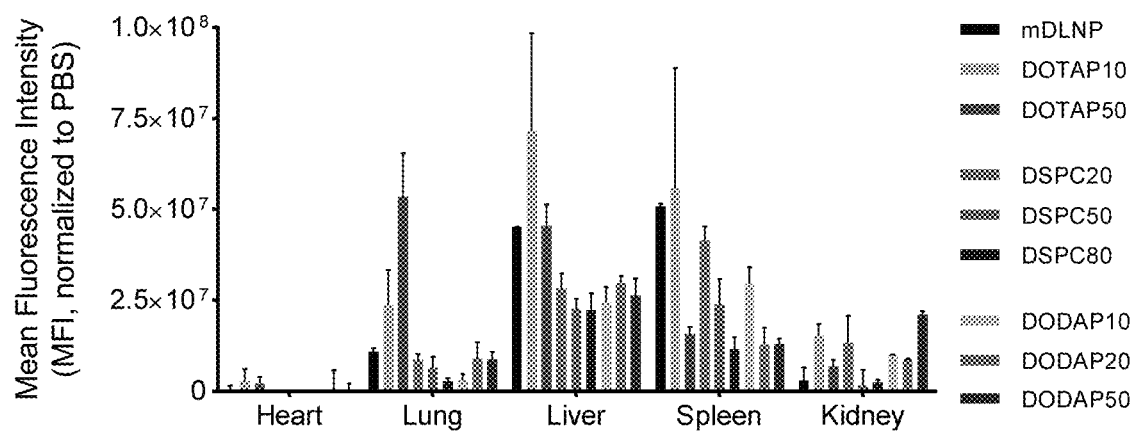
FIG. 7: The quantification data of biodistribution in main organs. C57 BL6 mice were IV injected by various Cy5.5-Luc mRNA formulations at the doses of 0.5 mg/kg (n=2). Heart, lung, liver, spleen and kidney were isolated, imaged and quantified after 6 h.
Figures 8A, 8B, 8C:
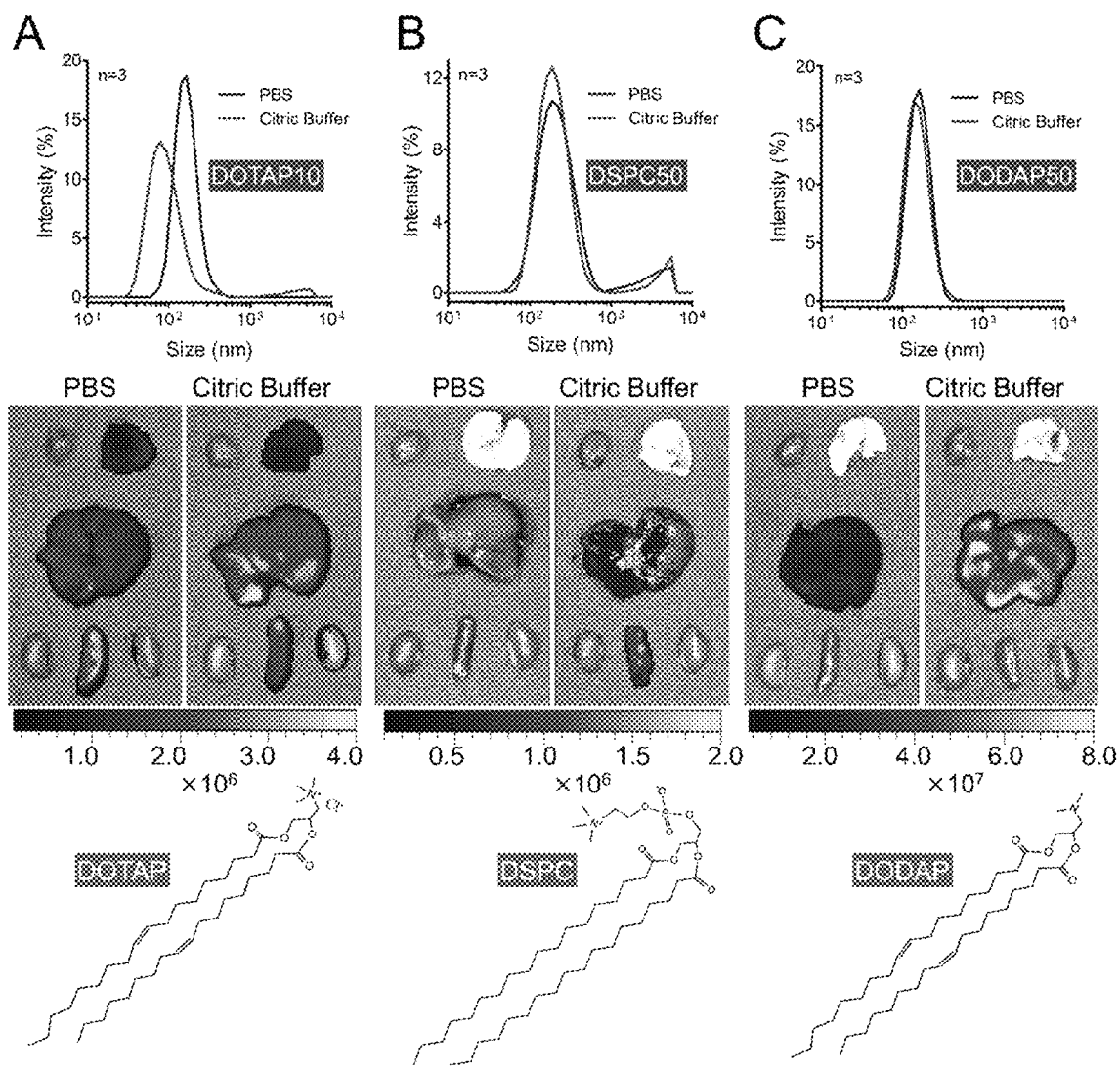
FIGS. 8A-8C: There were no big differences for size distribution and Luc mRNA delivery efficacy for DOTAP10 formulation formed by PBS or citric buffer, but not applied in DSPC50 and DODAP50. To test the buffer effects on mRNA delivery efficacy in vivo, DOTAP10 (quaternary lipid), DSPC50 (zwitterionic lipid) and DODAP50 (tertiary amine lipid) were chosen. C57 BL6 mice were IV injected by each Luc mRNA formulation at the dose of 0.1 mg/kg, after 6 h, main organs were isolated and imaged (n=2).
Figure 9:
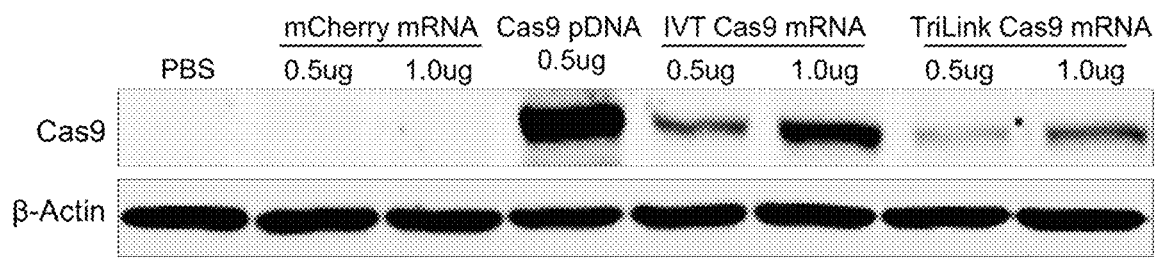
FIG. 9: Western blot result of IVT Cas9 mRNA quality test delivered by mDLNP. To achieve tissue specific gene editing, Cas9 mRNA and sgRNA were designed to be co-delivered. Firstly, Cas9 mRNA was made by IVT and analyzed by western blot for quality test. In this assay, both Cas9 pDNA delivered by Lipofectamine 2000 and commercial Cas9 mRNA (TriLink). mDLNP were positive controls, and mCherry mDLNP was negative control. 293T cells were seeded in 12-well plate the day before transfection, and cells were treated for 24 h by each condition before performing western blot. IVT Cas9 mRNA worked much better than commercial mRNA, therefore, IVT Cas9 mRNA was used to perform gene editing in vivo.

To test the organ biodistributions of specific DOTAP formulations in greater depth, PBS or liver targeting NPs (mDLNP), spleen targeting NPs (DOTAP10) and lung targeting NPs (DOTAP50) were injected into C57BL/6 mice (n=2) at a dose of 0.5 mg/kg Cy5-Luc mRNA (dye labeled mRNA to track RNA LNPs). 6 h post injection, major organs were collected and imaged (FIG. 3A). The organ distribution of formulations was changed by the amount of DOTAP, and accumulation in liver gradually moved to lung with increasing DOTAP percentages, but regardless of DOTAP percentage, there are still NPs present in the liver (FIG. 7, FIG. 8). Taking this data into account with that of FIG. 1, it is clear that organ distribution is not enough to analyze tissue targeted delivery efficacy (mRNA translation to protein). Further, considering the similar size distribution and EE between these formulations, zeta-potential and pKa may play roles in tissue targeting mRNA expression.

In an effort to understand whether the effects of the addition of DOTAP to mDLNPS were limited, or whether the distributions shown above are universal to permanent cationic lipid formulated mDLNPs, mDLNPs were generated with inclusion of another popular cationic lipid, Didodecyldimethylammonium Bromide (DDAB) (FIG. 2A1). DDAB has two hydrophobic tails with 18 carbons and no unsaturated bonds, and has a completely different head group than DOTAP (FIG. 1C). DDAB5, DDAB15, DDAB40 and DDAB50 formulations were selected for in vivo delivery (0.1 mg/kg, 6 h, n=2). Similar to the DOTAP formulations above, there was very little difference in size distribution (FIG. 2A1), even though DDAB percentage in the NPs varied by 10 fold (5% to 50%). Similar to DOTAP NPs, in vivo luciferase expression showed a trend that luminescence moved from the liver to spleen, then to lung with increasing DDAB percentages (FIG. 2A2).

mDLNPs were formed with a third permanent cationic lipid with the headgroup 1,2-dimyristoyl-sn-glycero-3-ethylphosphocholine chloride which has similar structure with DOTAP, but with shorter, 14 carbon, hydrophobic tails ((14:0) EPC) (FIG. 2B1). Similar to the DDAB strategy, (14:0) EPC5, (14:0) EPC15, (14:0) EPC40 and (14:0) EPC50 formulations were prepared and the size distribution (FIG. 2B1) and in vivo Luc mRNA delivery (0.1 mg/kg, 6 h, n=2) were examined (FIG. 2B2). Similar to the mDLNPs analyzed above, the particle size was generally uniform (FIG. 2B1), and as expected, luminescence moved from liver to spleen, then to lung with increasing (14:0) EPC molar percentages (FIG. 2B2). Taking all of these data together, which include different hydrophobic tails, saturated and unsaturated bonds, and different head groups, it appears that cationic lipid formulated mDLNP for tissue targeting mRNA delivery is universal.

In an effort to understand whether the effects of the addition of DOTAP to LNPs were specific to permanently cationic lipids, the effects of adding zwitterionic lipids instead of permanently cationic lipids in mDLNP formulations was examined Two representative zwitterionic lipids, phospholipids with different chemical structures: DSPC and DOCPe were tested. Additionally, it was also tested to determine if the addition of zwitterionic lipids (instead of permanently cationic lipids) would affect tissue specific delivery efficacy. FIGS. 2C1 and 2D1 show the chemical structures of DSPC and DOCPe lipids (zwitterionic lipids). There are differences in both the positions of the positive and negative charged functional headgroups and in the hydrophobic domains (saturated versus unsaturated), suggesting that any observed effect would be general/universal for zwitterionic lipids. mDLNPs formulated with either DSPC or DOCPe were similar (FIGS. 2C1, 2D1). Interestingly, the inclusion of zwitterionic lipids into 5-component modified DLNPs did not change the protein expression profile from liver to lungs as was the case for DOTAP and other permanently cationic lipids. Instead, both DSPC and DOCPe improved mRNA delivery into spleen within given range (less than 80% in DSPC and less than 50% in DOCPe). There was no protein expression in lungs for any percentages (0.1 mg/kg, 6 h, n=2) (FIGS. 2C2, 2D2). Therefore, inclusion of additional zwitterionic lipid can aid spleen delivery, but cannot tune delivery efficacy from liver to spleen to lungs like the inclusion of permanently cationic lipids.

In an effort to understand whether the effects of the addition of DOTAP to LNPs were specific to permanently cationic lipids, the effects of adding ionizable cationic lipids instead of permanently cationic lipids in mDLNP formulations were examined. Two representative ionizable cationic lipids with different chemical structures: C12-200 and DODAP, were tested. DODAP has a same structure with DOTAP except for the head groups (quaternary versus tertiary amine) C12-200 is an effective lipidoid used for siRNA and mRNA delivery containing ionizable tertiary amines (also no quaternary amines), which has a completely different structure with DODAP. (FIGS. 2E1, 2F1) Similarly, the size distributions of both modified mDLNPs were still uniform at certain percentages (less than 80%). (FIGS. 2E1, 2F1) Surprisingly, the inclusion of ionizable cationic lipids into 5-component modified DLNPs did not change the protein expression profile from liver to spleen to lungs as was the case for DOTAP and other permanently cationic lipids. Instead, the inclusion of ionizable cationic lipids into DLNPs increased mRNA delivery efficacy of mRNA to the liver. These showed much better delivery efficacy than original mDLNP (0.1 mg/kg, 6 h, n=2) without additional ionizable cationic lipid (only 5A2-SC8). With increasing percentages of DODAP or C12-200 (50% or 80%), luciferase signal decreased a lot, but liver still was the main organ rather than spleen or lung. Therefore, it was concluded that organ specific effects can be attributed to inclusion specific ratios of permanently cationic lipids. Moreover, this data shows that permanently cationic lipids produce different effects than ionizable cationic lipids. These data further show that these trends are universal with respect to classes of lipids.

Figures 10A, 10B:
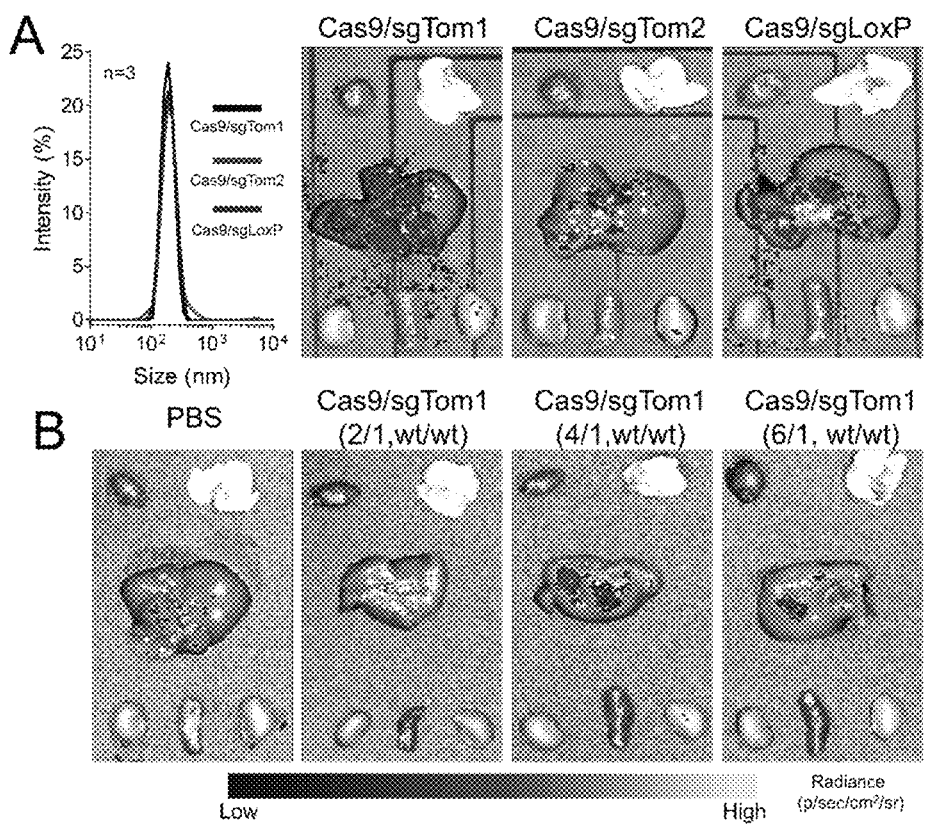
FIGS. 10A & 10B: sgRNAs screening and weight ratio (Cas9 mRNA/sgRNA) optimization in Td-Tomato mice. To reach maximum gene editing in Td-Tomato mice, sgRNA sequences were screened and optimized weight ratio of Cas9 mRNA to sgRNA.

Example 4—CRISPR/Cas9 Gene Editing Using Modified mDLNPs that Co-Deliver Cas9 mRNA and sgRNA First, three sgRNAs targeting Td-Tomato mice were compared to determine which sgRNA would be most effective in subsequent experiments. These sgRNAs are sgTom1, sgTom2 and sgLoxP. As is shown in FIG. 10A, sgTom1 and sgLoxP were delivered and expressed with similar results, and were more successful at inducing TdTomato than sgTom2 (FIG. 10A). Considering the weak PAM of sgLoxP (NAG), sgTom1 was finally chosen for further experiments.

Figures 4A, 4B, 4C:
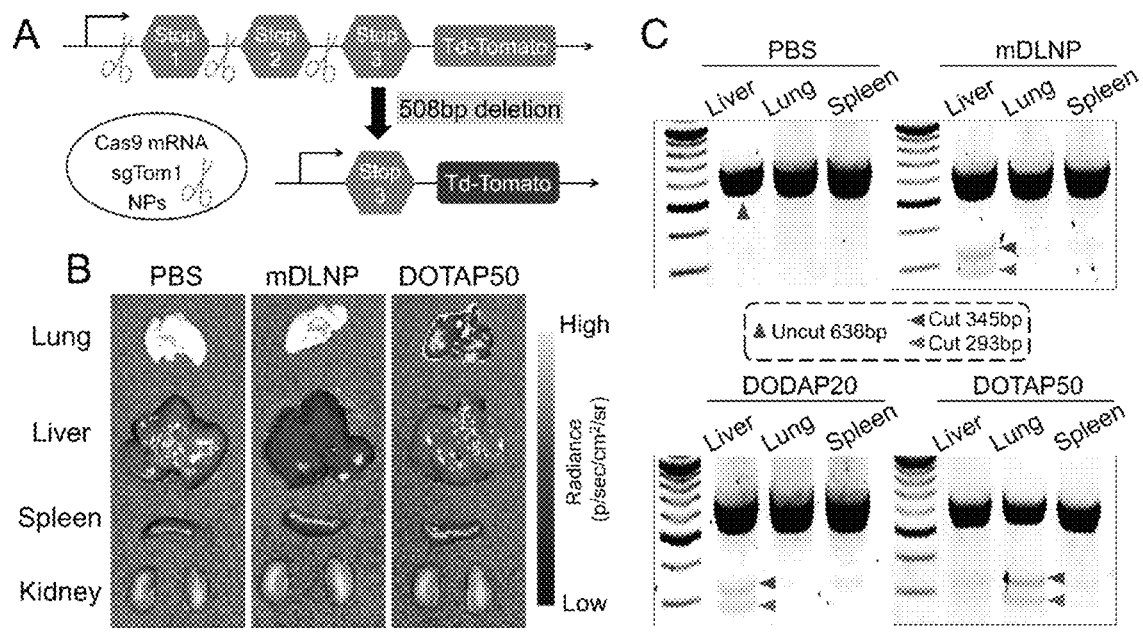
FIGS. 4A-4C: Liver and lung gene editing were achieved both in Td-Tomato and C57BL/6 mice.

Given the tissue specific mRNA (luc mRNA) delivery shown with DOTAP NPs, and that both DDAB and EPC modified NPs showed similar delivery trends, DOTAP modified mDLNPs were then used for Cas9 mRNA/sgRNA co-delivery aimed at achieving tissue specific gene editing. To examine co-delivery in vivo, genetically engineered mice containing a homozygous Rosa26 promoter Lox-Stop-Lox tdTomato (tdTO) cassette present in all cells were used (FIG. 4A). Co-delivery of DOTAP modified mDLNPs housing Cas9-mRNA and sgRNA against LoxP or against Tom enabled deletion of the Stop cassette and induction of tdTO expression (FIG. 4B). The mice were IV injected by mDLNP and DOTAP50 formulations for co-delivery of IVT Cas9 mRNA and modified sgTom1 (4/1, wt/wt) at the total doses of 2.5 mg/kg (50 ug each), then fluorescence of main organs was detected at day 10 after treatment. (FIG. 4B). Liver and lung specific CRISPR/Cas gene editing was achieved. Spleen specific editing was also achieved. However, due to very high background red autofluorescence, spleen editing was not quantifiable using this TdTomato reporter mouse.

To further examine tissue specific editing, PTEN was selected as an endogenous target. C57BL/6 mice were IV injected with mDLNP, DODAP20 or DOTAP50 to reach tissue specific gene editing. The total dose was 2.5 mg/kg (50 ug each), weight ratio of IVT Cas9 mRNA to modified sgPTEN was 4/1, and detection time was day 10 after treatment. sgRNA targeting PTEN was used. A T7E1 assay showed that tissue specific feature was further confirmed with in vivo PTEN editing. (FIG. 4C).

Example 5—CRISPR/Cas9 Gene Editing Using Modified mDLNPs that Deliver Cas9 Protein/sgRNA Ribonucleoproteins (RNPs Building on the discovery that inclusion of a permanently cationic lipid (e.g. DOTAP) into traditional LNP formulations containing an ionizable cationic lipid, a zwitterionic lipid, cholesterol, and a PEGylated lipid, it was investigated whether this formulation methodology could also deliver other cargoes that are sensitive to ethanol and/or low pH acidic aqueous buffers. The key element of the DOTAP strategy is that formulations can be prepared using PBS at neutral pH. It was therefore examined if this methodology could also encapsulate and deliver large proteins, such as Cas9, for gene editing applications. DOTNP lipid nanoparticles therefore consist of five components: an ionizable cationic lipids (e.g. 5A2-SC8), a zwitterionic lipid (e.g. DOPE), Cholesterol, DMG-PEG, and modular inclusion of a permanently cationic lipid (e.g. DOTAP). The mole ratio of 5A2-SC8, Cholesterol, DOPE, and DMG-PEG was fixed (15:15:30:5, mol/mol) and DOTNPX means DOTNP with different mole percentage of DOTAP.

Figures 11A, 11B, 11C, 11D, 11E, 11F, 11G:
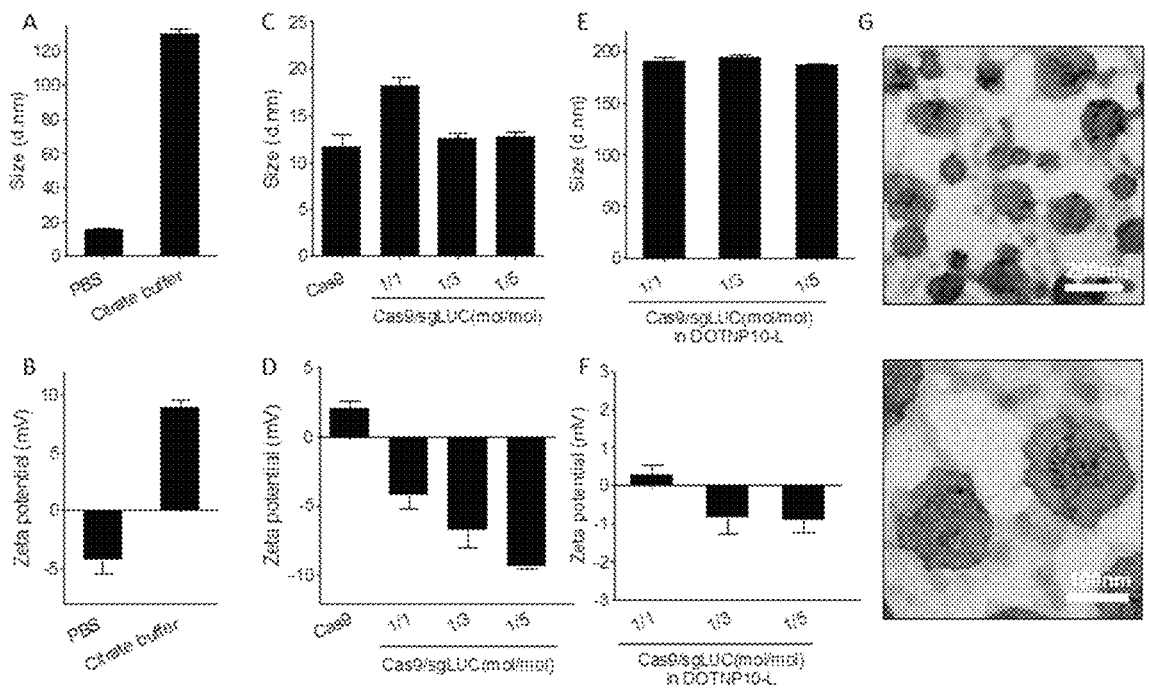
FIGS. 11A-11G: Characterization of Cas9/sgRNA complex and DOTNP lipid nanoparticles after encapsulating Cas9/sgRNA complex. Size (FIG. 11A) and Zeta potential (FIG. 11B) of Cas9/sgLUC complex (mol/mol=1/1) in PBS (pH7.4) and in Citrate Buffer (pH4.2). Size of Cas9/sgLUC complex prepared in citrate buffer is very big (larger than 100 nm) and the zeta potential is positively charged, so it is impossible to be encapsulated by lipid nanoparticles. However, the size of Cas9/sgLUC complex prepared in PBS is compact (less than 20 nm) and has negative charges, so it is able to be encapsulated by lipid nanoparticles. Size (FIG. 11C) and Zeta potential (FIG. 11D) of Cas9/sgLUC complex prepared with different Cas9/sgRNA mole ratios (1/1, 1/3, and 1/5). Compared with Cas9/sgLUC complex (1/1, mol/mol), higher mole ratios (1/3 and 1/5, mol/mol) showed smaller size and more negative charges, which are beneficial for lipid nanoparticle encapsulation. Size (FIG. 11E) and Zeta potential (FIG. 11F) of DOTNP10 lipid nanoparticles encapsulating Cas9/sgLUC complex (named DOTNP10-L) when preparing with different mole ratios (1/1, /3, 1/5).

The first characterized Cas9/sgRNA complexes were examined if they are sensitive to acidic pH. The size (diameter) (FIG. 11A) and Zeta potential (FIG. 11B) of Cas9/sgLUC complex (mol/mol=1/1) was measured in PBS (pH 7.4) and in citrate Buffer (pH 4.2). The size of Cas9/sgLUC complexes prepared in citrate buffer is large (greater than 100 nm) and the zeta potential is positively charged. These two attributes (size larger than a typical efficacious LNP) and positive charge (charge incompatible to complex with positively charged lipids), render it impossible to be effectively encapsulated by lipid nanoparticles. However, the size of Cas9/sgLUC complexes prepared in PBS is compact (less than 20 nm) and has negative charges. Therefore, it can be encapsulated by lipid nanoparticles when formulated at neutral pH. Next, Cas9/sgRNA complexes with different Cas9 protein to sgRNA molar ratios were prepared and characterized. Size (FIG. 11C) and Zeta potential (FIG. 11D) of Cas9/sgLUC complexes prepared with different Cas9/sgRNA mole ratios (1/1, 1/3, and 1/5). Compared with Cas9/sgLUC complex (1/1, mol/mol), higher mole ratios (1/3 and 1/5, mol/mol) showed smaller size and more negative charges, which may be beneficial for lipid nanoparticle encapsulation. The compositions were prepared and characterized DOTNP lipid nanoparticles after encapsulating Cas9/sgRNA complexes. Size (FIG. 11E) and Zeta potential (FIG. 11F) of DOTNP10 lipid nanoparticles encapsulating Cas9/sgLUC complex (named DOTNP10-L) when preparing with different mole ratios (1/1, /3, 1/5). This data indicates encapsulation of Cas9/sgRNA RNPs into monodisperse LNPs. FIG. 11G shows TEM images of DOTNP10-L (1/3, mol/mol) LNPs with encapsulated RNPs. Following this initial study, different sgRNA were used including sgLUC, sgGFP, sgTOM, and sgPTEN. To distinguish them, the first letter of each gene was added at the end of DOTNP. For example, DOTNP10-L means DOTNP10 lipid nanoparticles encapsulating Cas9/sgLUC complex; DOTNP10-G means DOTNP10 lipid nanoparticles encapsulating Cas9/sgGFP complex.

TABLE 7

Characterizations of DOTAP10, DSPC50 and DODAP50 formulations formed by PBS and citric buffer, including size, PDI and encapsulation efficacy.

|  | DOTAP10 | | DSPC50 | | DODAP50 | |
| --- | --- | --- | --- | --- | --- | --- |
|  | PBS | Citric Buffer | PBS | Citric Buffer | PBS | Citric Buffer |
| Size (nm) | 155.4 | 85.1 | 208.9 | 202.0 | 153.5 | 148.0 |
| PDI | 0.09 | 0.21 | 0.30 | 0.29 | 0.08 | 0.15 |
| EE (%) | 34.9 | 54.9 | 0 | 43.7 | 14.4 | 36.2 |

TABLE 8

Listed all primers used in this research work, including the length of PCR product and their purposes.

| Name | Forward Primers (5' to 3') | Reverse Primers (5' to 3') | Length | Notes |
| --- | --- | --- | --- | --- |
| Cas9 | ATATATGGATCCGCCACCATGGCCCCAAAGAAGAAGCGGAAGGTC | ATATATGAATTCTTACTTTTTCTTTTTTGCCTGGCCGGCCTTTTTCGTGGCCGCCGGCCTTTTGTCGCCTCCCAG | 4233 bp | For IVT clone |
| Ca9 Seq-1 | CTGAGCGACATCCTGAGAGTGAAC | | | For sequencing to confirm the whole Cas9 sequences |
| Ca9 Seq-2 | | AGCAGGTCCTCTCTGTTCAG | | |
| Ca9 Seq-3 | GACGGCTTCGCCAACAGAAACTTC | | | |
| Ca9 Seq-4 | | TTTGATGCCCTCTTCGATCCG | | |
| Ca9 Seq-5 | GGGAGATCGTGTGGGATAAG | | | |
| Ca9 Seq-6 | | ACTTCTTAGGGTCCCAGTCC | | |
| Ca9 Seq-7 | AAGAGAGTGATCCTGGCCGAC | | | |
| PTEN | ATCCGTCTTCTCCCCATTCCG | GACGAGCTCGCTAATCCAGTG | 638 bp | For T7E1 assay |
| IVT sgTom1 | TAATACGACTCACTATAGGGAAGTAAAACCTCTACAAATGGTTTTAGAGCTAGAAATAGC | AAAAGCACCGACTCGGTGCC | 120 bp | For IVT template preparation. Red indicated sgRNA sequences |
| IVT sgTom2 | TAATACGACTCACTATAGGGAAACCTCTATAAATGTGGTAGTTTTAGAGCTAGAAATAGC | AAAAGCACCGACTCGGTGCC | 120 bp | |
| IVT sgLoxP | TAATACGACTCACTATAGGGGGTATAGCATACATTATACGGTTTTAGAGCTAGAAATAGC | AAAAGCACCGACTCGGTGCC | 120 bp | |

(Cas9 = SEQ ID NOS: 3-4; Ca9 Seq-1 = SEQ ID NO: 5; Ca9 Seq-2 = SEQ ID NO: 6; Ca9 Seq-3 = SEQ ID NO: 7; Ca9 Seq-4 = SEQ ID NO: 8; Ca9 Seq-5 = SEQ ID NO: 9; Ca9 Seq-6 = SEQ ID NO: 10; Ca9 Seq-7 = SEQ ID NO: 11; PTEN = SEQ ID NOS: 14-15; IVT sgTom1 = SEQ ID NOS: 44-45; IVT sgTom2 = SEQ ID NOS: 46-47; IVT sgLoxP = SEQ ID NOS: 48-49)

Figures 12A, 12B, 12C, 12D, 12E, 12F:
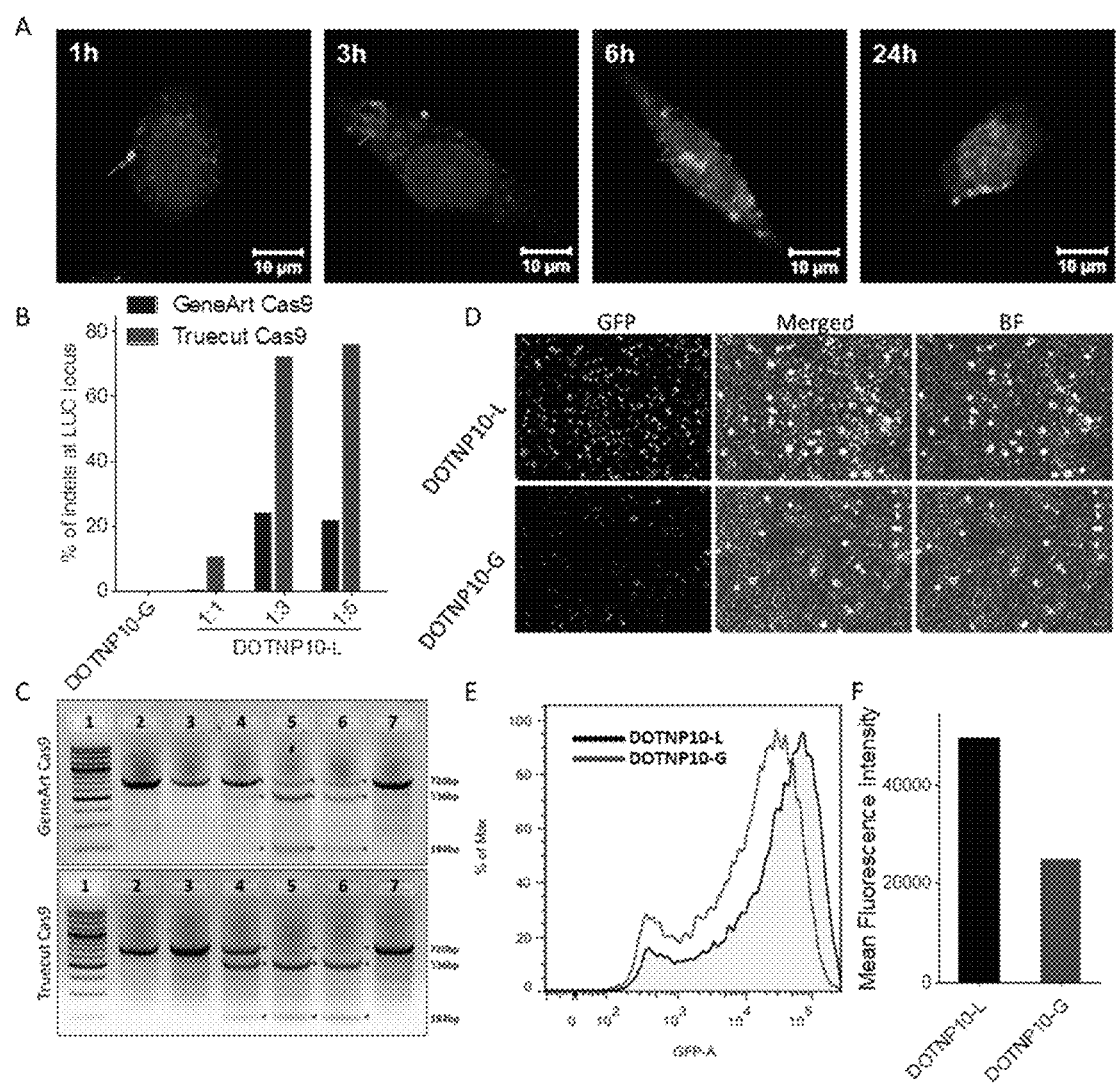
FIGS. 12A-12F: DOTNP lipid nanoparticles were able to deliver Cas9/sgRNA complex into nucleus and exhibited efficient gene editing in vitro.

To examine if DOTNP lipid nanoparticles could deliver Cas9/sgRNA RNP complexes into the nucleus and mediate efficient gene editing in vitro, a series of experiments were performed. First, DOTNPs containing Cas9/sgRNA RNPs that were tagged by a green fluorescent EGFP were tracked by confocal microscopy (FIG. 12A). Images of Hela-Luc cells after incubation with DOTNP10 encapsulating Cas9-EGFP/sgLUC complexes (1/3, mol/mol) for 1 h, 3 h, 6 h, and 24 h (9 nM of sgRNA was used) showed that the DOTNPs were internalized into cells and that the Cas9 RNP trafficked to the nucleus. Green: EGFP fused Cas9 protein; Blue: nuclei stained with Hoechst 33342. Red arrows indicated the process of DOTNP10 entering into nucleus. (FIG. 12B)

Next, it was examined if DOTNP lipid nanoparticles could deliver Cas9/sgRNA RNP complexes could cut targeted Luciferase DNA. The percentages of DNA indels (insertions and deletions) was quantified using the TIDE assay ay the LUC locus following incubation with DOTNP10-L of different mole ratios for 3 days (24 nM of sgRNA was used). DOTNP10 lipid nanoparticles encapsulating Cas9/sgGFP (DOTNP10-G) was used as negative control. Here, two commercial Cas9 proteins (GeneArt Cas9 and Truecut Cas9) were used. (FIG. 12B). Next, a T7EI cleavage assay of Hela-Luc cells incubated with different formulations (24 nM of sgRNA) was performed to demonstrate DNA editing (FIG. 12C). Among the conditions tested, mole ratio at 1/3 showed the best gene editing when using Truecut Cas9 protein. Next, fluorescence microscopy was used to test editing of GFP (FIG. 12D). Images of SKOV3-GFP cells incubated with DOTNP10-L (control, does not target GFP) and DOTNP10-G (does target GFP) (24 nM of sgRNA) which showed on target editing demonstrated by disappearance of GFP protein expression. Finally, flow cytometry was used to analyze SKOV3-GFP cells incubated with DOTNP10-L and DOTNP10-G (FIG. 12E). (FIG. 12F) Mean fluorescence intensity of SKOV3-GFP cells incubated with DOTNP10-L and DOTNP10-G by flow cytometry showed editing of GFP by CRSPR/Cas.

Figures 13A, 13B:
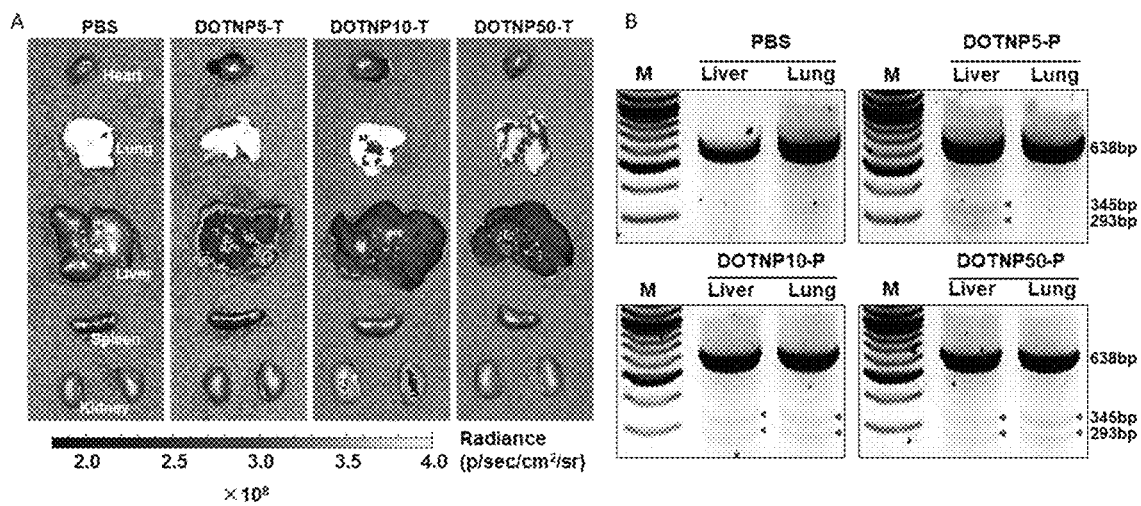
FIGS. 13A & 13B: DOTNPs showed tissue-specific gene editing in vivo.

Next, it was examined if DOTNP lipid nanoparticles could deliver Cas9/sgRNA RNP complexes in vivo to achieve CRISPR/Cas-mediated gene editing. As before, the genetically engineered TdTomato mouse model was employed. 1.5 mg/kg of sgRNA were delivered per mouse with the following formulations: DOTNP5-T means DOTNP5 LNPs encapsulating Cas9/sgTom complex; DOTNP10-T means DOTNP10 LNPs encapsulating Cas9/sgTom complex; DOTNP50-T means DOTNP50 LNPs encapsulating Cas9/sgTom complex. Following IV injection of these formulations, tdTomato fluorescence was quantified ex vivo in major organs 7 days post injection (FIG. 13A). tdTomato fluorescence was only observed in the liver for the DOTNP5-T treated group; In DOTNP10-T group, slight fluorescence was seen in lung and if further increasing dose of DOTAP to 50% (DOTNP50-T), most of tdTomato fluorescence was observed in lung. Therefore, similar to the mRNA delivery experiments summarized above, the DOTAP methodology also allows tissue specific gene editing of Cas9/sgRNA ribonucleoprotein (RNP) complexes. To further examine delivery, LNPs containing sgRNA against PTEN were delivered. Using the T7EI cleavage assay of liver and lung organs, it was determined that IV injection of DOTNP5-P (DOTNP5 LNPs encapsulating Cas9/sgPTEN complex), DOTNP10-P (DOTNP10 LNPs encapsulating Cas9/sgPTEN complex) and DOTNP50-P (DOTNP50 LNPs encapsulating Cas9/sgPTEN complex) (2 mg/kg of sgRNA per mouse) mediate gene editing (FIG. 13B). The results are consistent with that obtained by ex vivo imaging. Gene editing was only detected in liver after treated with DOTNP5-P; gene editing was obtained both in liver and in lung when incubated with DOTNP10-P; while in DOTNP50-P treatment group, most of gene editing was observed in lung.

The data provided herein show that lipid nanoparticles may be prepared with varying compositions in order to specifically target the payload to specific tissues. Particularly, lipid nanoparticles with low concentrations of permanently cationic lipids (≤10%) are effective for delivering nucleic acids to the liver, and LNPs with less than 30% permanently cationic lipid are effective for delivering nucleic acids to the spleen, LNPs with greater than 30% permanently cationic lipid effectively deliver nucleic acids to the lungs. These findings appear to be universal, with head groups, saturation, and tail length having little effect.

Example 6—Additional of Another Lipid into Known Four Lipid Compositions Result in the Change of Delivery Target The generalizability of the approach (methodology) to include a "fifth" lipid into established 4-component LNPs was then explored.

Figures 14A, 14B:
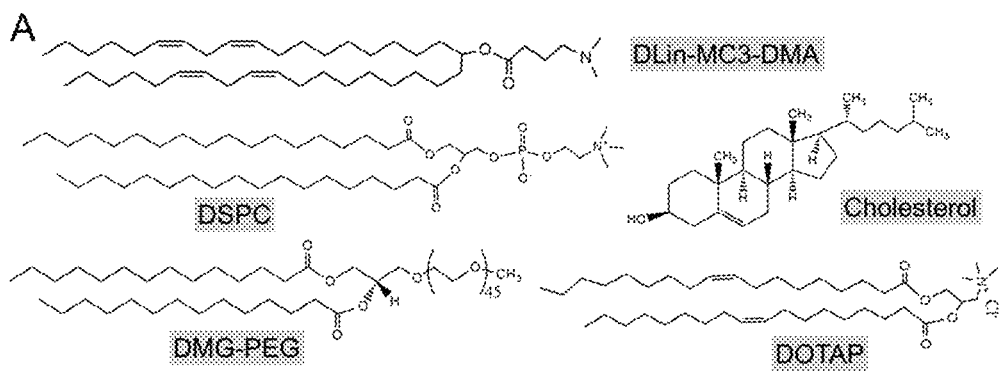
FIGS. 14A & 14B show the details of MC3 LNPs and DOTAP modified MC3 formulations, including (FIG. 14A) structures of each component, (FIG. 14B) molar ratios, weight ratios of total lipid to mRNA, sizes and PDI.
Figures 15A, 15B:
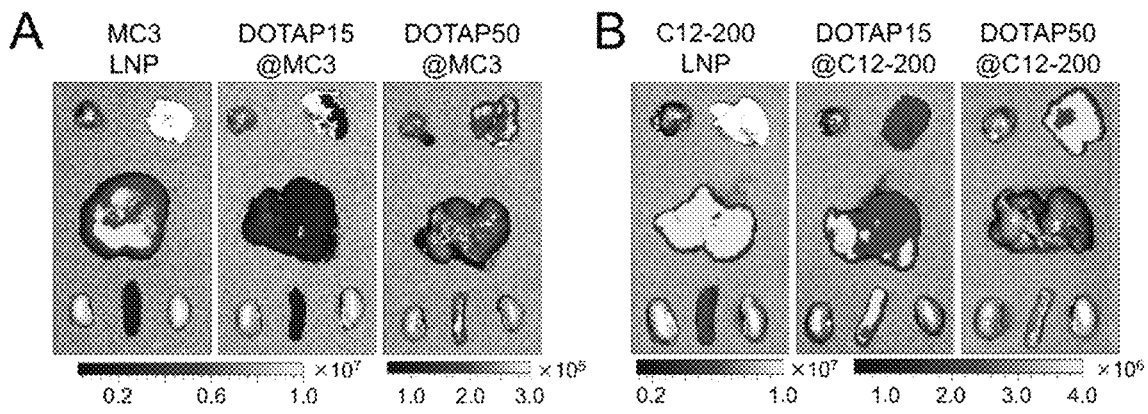
FIGS. 15A & 15B show DLin-MC3-DMA (FIG. 15A) and C12-200 (FIG. 15B) were selected and evaluated with the DOTAP strategy at the doses of 0.1 mg/kg (6 h, n=2). With increasing DOTAP percentages from 0 to 50%, both MC3 and C12-200 based LNPs showed identical mRNA expression profiles like mDLNP where luciferase signal moved from liver to spleen and finally to lung.
Figures 16A, 16B:
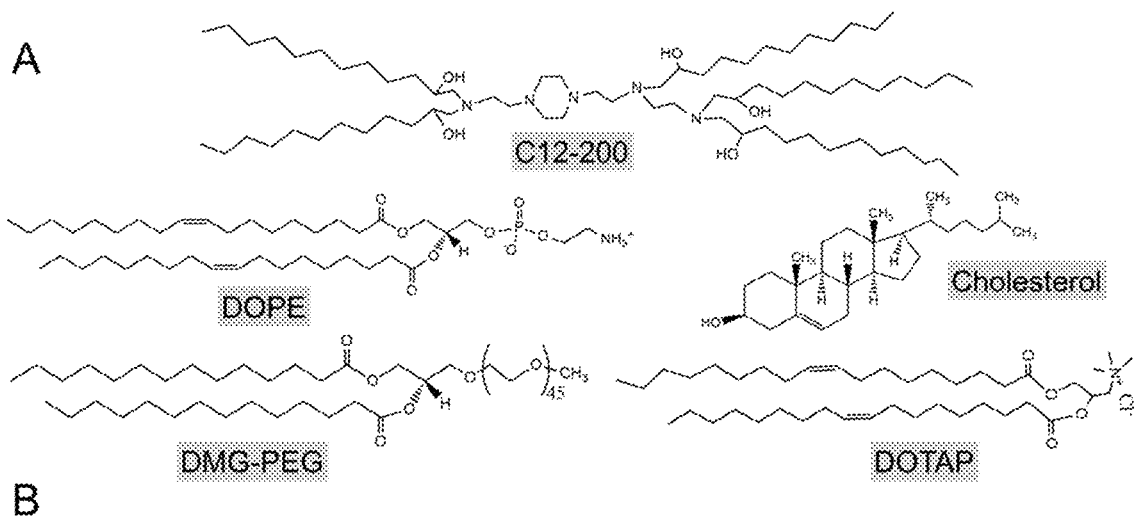
FIGS. 16A & 16B show the details of C12-200 LNPs and DOTAP modified C12-200 formulations, including (FIG. 16A) structures of each component, (FIG. 16B) molar ratios, weight ratios of total lipid to mRNA, sizes and PDI.

To examine if the inclusion of a permanently cationic lipid (e.g. DOTAP) could alter the tissue specificity of other ionizable cationic lipids, two well known and well established ionizable cationic lipid LNP systems were selected. DLin-MC3-DMA was selected and it was formulated with DSPC, Cholesterol, and PEG-DMG. The same molar composition as Patisiran/Onpattro (Alnylam Pharmaceuticals) was produced and supplemented with 15% or 50% of DOTAP (extra 5th lipid into Onpattro 4 lipid formulation) (FIG. 14). DLin-MC3-DMA LNPs are considered the "gold standard" for both siRNA and mRNA delivery. To date, they have only been shown to deliver to the liver following IV administration. As shown in FIG. 15A, DOTAP altered mRNA expression profiles in organs for DLin-MC3-DMA based LNPs (0.1 mg/kg Luciferase mRNA, 6 h). With increasing percentage of DOTAP, luciferase signal moved from liver to spleen and finally to lung, which was exactly the same with the phenomenon for 5A2-SC8 mDLNPs. To further study the universality of this approach, we included DOTAP into C12-200 LNPs (FIG. 16). While DLin-MC3-DMA is a two-tailed lipid with a single dimethylamine headgroup that is considered a stable nucleic acid lipid nanoparticle (SNALP), C12-200 is a representative "lipidoid" that can be formulated into lipid-like LNPs. All three are ionizable cationic lipids. Identical to the results with 5A2-SC8 and DLin-MC3-DMA, inclusion of 15 or 50% DOTAP into C12-200 LNPs changed luciferase protein expression following mRNA delivery from the liver to spleen to lungs (FIG. 15B). Thus, the $5^{th}$ lipid methodology (such as adding a permanently cationic lipid) is generalizable to other ionizable cationic lipid LNPs.

Example 7—Additional of Another Lipid into Known Four Lipid Compositions Result in Improved Delivery Furthermore, the generalizability of the approach (methodology) by asking if additional ionizable cationic lipid would improve liver delivery was explored.

Figures 17A, 17B:
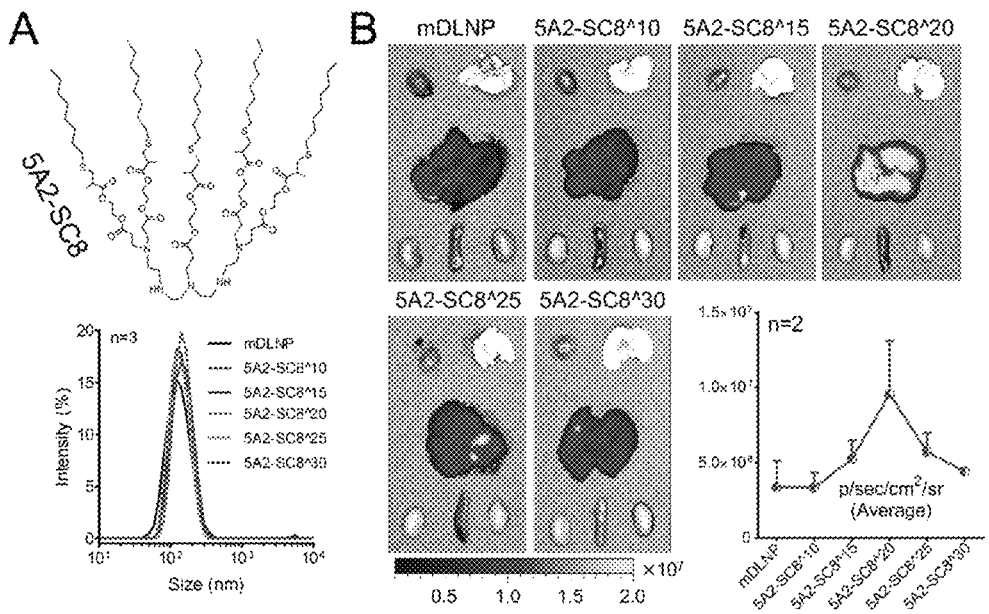
FIGS. 17A & 17B show (FIG. 17A) Further optimization of mDLNP. As the key lipid in mDLNP, 5A2-SC8 was used as the "fifth" lipid to modify mDLNP to form four formulations with extra percentage of 10% to 30%.
Figure 18:
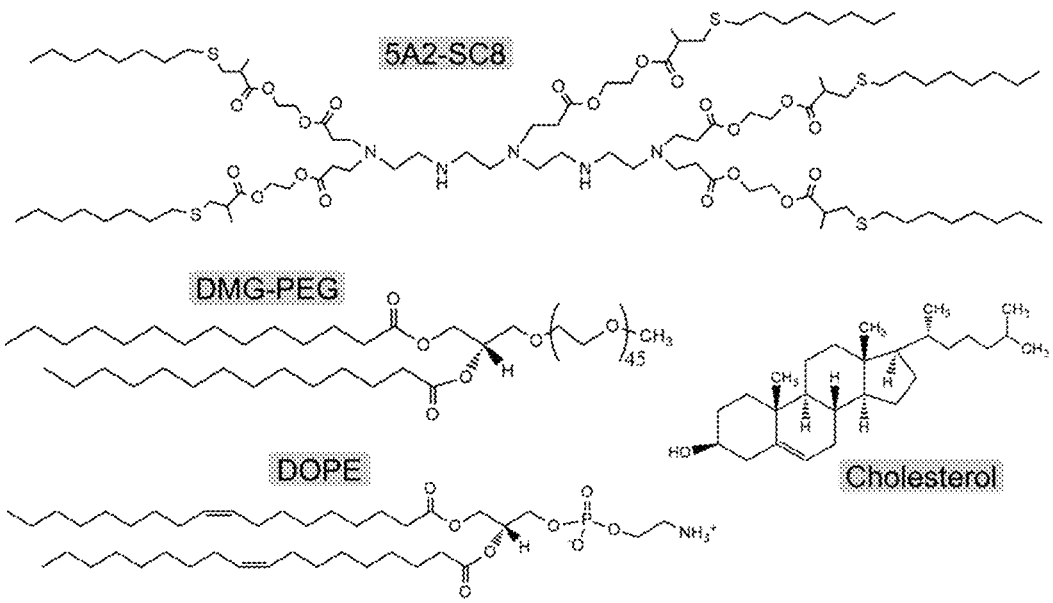
FIG. 18 shows the structures of 5A2-SC8, DOPE, Cholesterol and DMG-PEG. mDLNP is an effective and safe mRNA delivery carrier for liver targeting therapeutics developed by previous work, which is consisted with 5A2-SC8, DOPE, Cholesterol and DME-PEG at the molar ratio of 15/15/30/3.

To examine if the ionizable cationic lipid generally promotes liver delivery, additional 5A2-SC8 ionizable cationic lipids was included as the "fifth" lipid into LNPs containing appropriate ratios of 5A2-SC8, DOPE, Cholesterol, and PEG DMG. Extra 5A2-SC8 was included at percentages of 10 to 30 (FIG. 17A and FIG. 18). To avoid saturated luminescence, a low 0.05 mg/kg dose of mRNA dose was tested (IV, 6 h). As shown in FIG. 17B, both ex vivo images and quantified data demonstrated that increased extra 15% to 25% of 5A2-SC8 did help improve mRNA delivery potency in the liver. 5A2-SC8A20 (5A2-SC8 LNPs plus 20% extra 5A2-SC8) increased Luciferase 2-3 times higher than the original mDLNP formulation.

Example 8—Studies Relating to Selective Organ Targeting Compositions

Figures 19A, 19B, 19C, 19D, 19E, 19F, 19G:
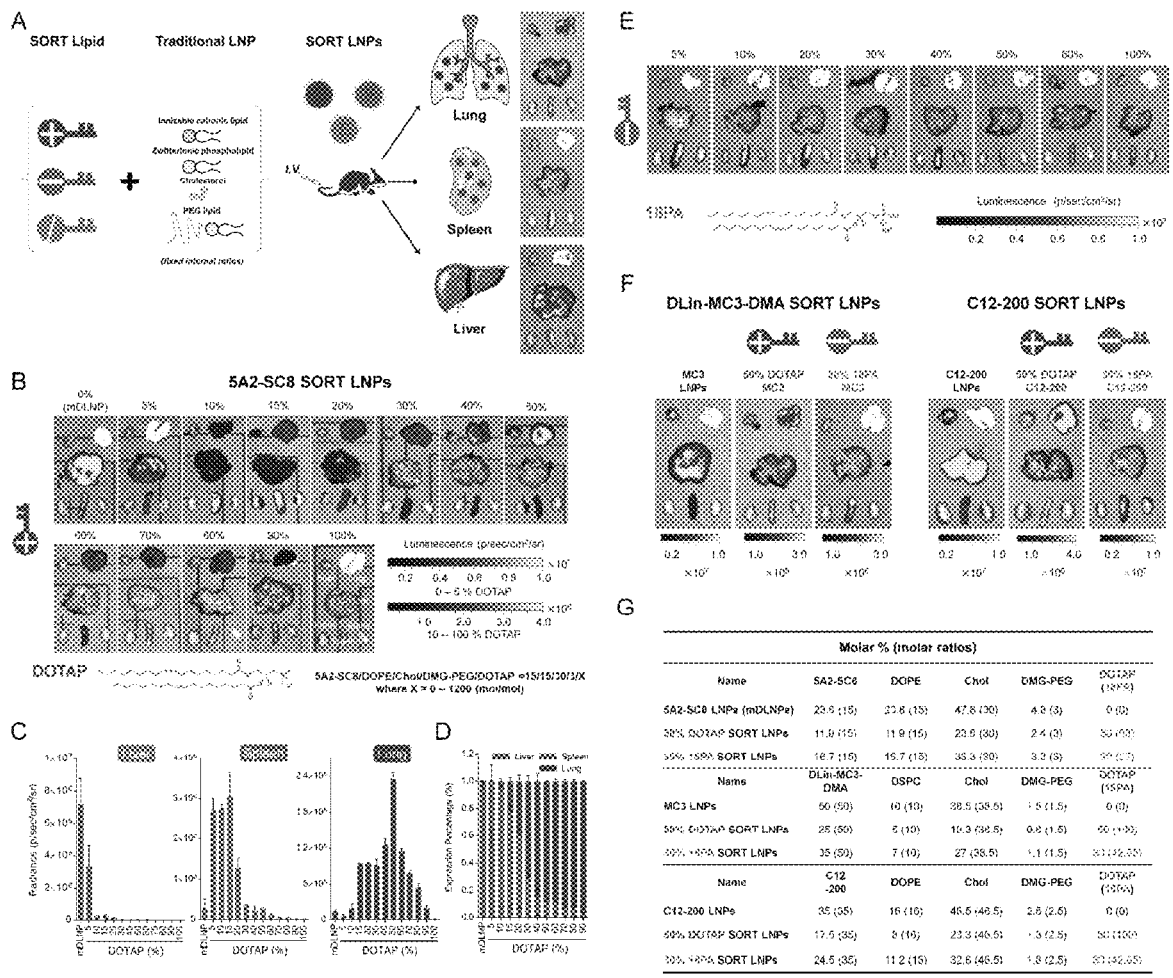
FIGS. 19A-19G show selective ORgan Targeting (SORT) allows lipid nanoparticles (LNPs) to be systematically and predictably engineered to accurately edit cells in specific organs. (19A) Addition of a supplemental component (termed a SORT lipid) to traditional LNPs systematically alters the in vivo delivery profile and mediates tissue specific delivery as a function of the percentage and biophysical property of the SORT lipid. This universal methodology successfully redirected multiple classes of nanoparticles. Shown here are bioluminescence images of mice injected intravenously with 0.1 mg/kg Luciferase mRNA inside of lung- and spleen-specific DLin-MC3-DMA LNPs (Onpattro SNALPs) and liver enhanced 5A2-SC8 degradable dendrimer-based LNPs (DLNPs). Inclusion of SORT lipids into 4-component 5A2-SC8, DLin-MC3-DMA, and C12-200 LNPs created 5-component SORT LNPs. (19B) 5A2-SC8 SORT LNPs were formulated with a molar ratio of 5A2-SC8/DOPE/Chol/DMG-PEG/SORT Lipid=15/15/30/3/X (mol/mol), where X was adjusted from 0 to 1200 to make series of LNPs with 0% to 100% SORT lipid (fraction of total lipids). Here, inclusion of a permanently cationic lipid (DOTAP) systematically shifted luciferase protein expression from the liver to spleen to lung as a function of DOTAP percentage (0.1 mg/kg Luc mRNA, 6 h). (19C) Quantification data demonstrated that SORT lipid percentage is a factor for tissue specific delivery; 0% (mDLNPs) was optimal for liver; 5-15% was optimal for spleen; and 50% was optimal for lungs. (19D) Relative luciferase expression in each organ demonstrated that fractional expression could be predictable tuned. (19E) Inclusion of an anionic SORT lipid enabled selective mRNA delivery to the spleen. Luciferase expression was observed only in spleen when introducing 18PA lipid into mDLNPs up to 40% (0.1 mg/kg Luc mRNA, 6 h). (19F) Ex vivo images of luminescence in major organs at 6 h post IV injection of DLin-MC3-DMA SORT LNPs with the dose of 0.1 mg/kg Luc mRNA. With increasing molar percentage of DOTAP, luciferase expression moved from liver to lung. 18PA mediated exclusive delivery of Luc mRNA to the spleen. The same trend was observed for modified C12-200 LNPs (0.1 mg/kg, 6 h). (19G) Details of selected SORT lipid formulations.

This disclosure describes a strategy termed Selective ORgan Targeting (SORT) that allows nanoparticles to be systematically engineered for accurate delivery of diverse cargoes including mRNA, Cas9 mRNA/sgRNA, and Cas9 ribonucleoprotein (RNP) complexes to the lungs, spleens, and livers of mice following intravenous (IV) administration (FIG. 19A). Traditional LNPs are composed of ionizable cationic lipids, zwitterionic phospholipids, cholesterol, and poly(ethylene glycol) (PEG) lipids. This disclosure shows that addition of a supplemental component (termed a SORT compound or a selective organ targeting compound) precisely alters the in vivo RNA delivery profile and mediates tissue specific gene delivery and editing as a function of the percentage and biophysical property of the added SORT lipid. This disclosure shows evidence of a theory for tissue specific delivery, establish that this methodology is useful for various nanoparticle systems, and provide a method for LNP design to edit therapeutically relevant cells.

Effective intracellular delivery materials have conventionally relied on an optimal balance of ionizable amines to bind and release RNAs (pKa between 6.0-6.5) and nanoparticle stabilizing hydrophobicity (Kanasty et al., 2013; Jayaraman et al., 2012; Nelson et al., 2013; Hao et al., 2015). Without wishing to be bound by any theory, it is believed that internal and/or external charge may be a factor for tuning tissue tropism. Intravenous administration of the developed SORT LNPs enabled high levels of tissue specific gene editing. SORT is compatible with various methods of deploying gene editing machinery, including mRNA, Cas9 mRNA/sgRNA, and Cas9 RNPs (the systemic RNP delivery). Lung-targeted SORT LNPs edited 40% of epithelial cells and 65% of endothelial cells; spleen-targeted SORT LNPs edited 13% of B cells and 10% of T cells; and enhanced liver-targeted SORT LNPs edited 93% of hepatocytes following a single, low dose injection.

A. Discovery and Development of SORT

To examine the hypothesis that internal charge adjustment could mediate tissue specific delivery, a strategy was conceived to add a $5^{th}$ lipid to already established LNP compositions with validated efficacy in liver hepatocytes. The rationale was to tune efficacious LNP formulations without destroying the core 4-component ratios that are normally used for mediating RNA encapsulation and endosomal escape (Wittrup et al., 2015; Cheng et al., 2018).

The effect of adding a permanently cationic lipid (defined as positively charged without pKa or pKa >8) to a degradable dendrimer ionizable (pKa <8) cationic lipid named 5A2-SC8 used in mDLNPs (Zhou et al., 2016; Zhang et al., 2018a; Zhang et al., 2018b) was examined, which effectively delivered fumarylacetoacetate hydrolase (FAH) mRNA to liver hepatocytes and extended survival in FAH knockout mice (Cheng et al., 2018). This initial base mDLNP formulation consisted of 5A2-SC8, 1,2-dioleoyl-sn-glycero-3-phosphoethanolamine (DOPE), cholesterol, DMG-PEG (15/15/30/3, mol/mol), and mRNA (5A2-SC8/mRNA, 20/1, wt/wt) (FIG. 20). A series of LNPs were then formed by systematically increasing the percentage of additional permanently cationic lipid from 5 to 100% of total lipids (FIGS. 19B & 20). 1,2-dioleoyl-3-trimethylammonium-propane (DOTAP), a well-known quaternary amino lipid, was initially selected as the SORT lipid to add into LNP formulations. DOTAP-modified SORT formulations thus included five lipid components, where 5A2-SC8/DOPE/Chol/DMG-PEG was fixed at 15/15/30/3 (mol/mol), and DOTAP was added at molar ratios from 0 to 1200 to make a titrated series of formulations (FIG. 20).

Figures 21A, 21B:
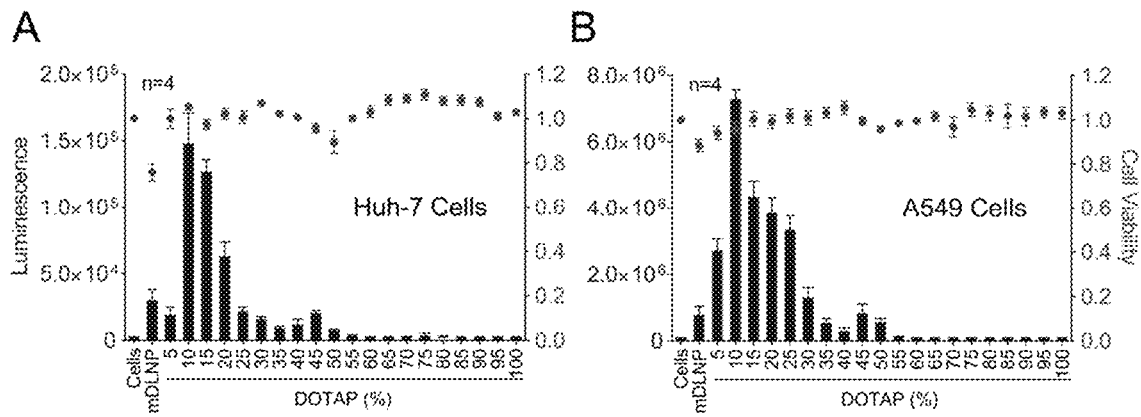
FIGS. 21A & 21B show In vitro Luciferase (Luc) mRNA delivery results for DOTAP-modified SORT mDLNPs in (FIG. 21A) Huh-7 liver cells and (FIG. 21B) A549 lung cells as a function of the incorporated DOTAP percentage. Luc mRNA delivery results showed that LNPs with DOTAP percentages of 5%-50% delivered the most mRNA in both Huh-7 liver cells and A549 lung cells. SORT LNPs with 10% DOTAP were much more efficacious in vitro than the previously reported base mDLNP. No appreciable cytotoxicity was observed for any formulation and all were uniform (low PDI) with diameters ranging from 90 nm to 150 nm (FIG. 20). Measurements of surface charge revealed that DOTAP was encapsulated inside together with mRNA and not on the LNP surface as the zeta potentials were close to 0 when DOTAP was less than 60%. The surface charge became positive only at percentages above 65% (FIG. 20), revealing that PEG lipid-coated SORT LNPs with selective tissue tropism could be discovered that possess a near neutral surface charge, which is an attribute for clinical translation. Cells were seeded into 96-well plates at a density of $1 \times 10^4$ cells per well the day before transfection. Luc mRNA expression and cell viability were measured at 24 h post treatment with the dose of 50 ng/well Luc mRNA (n=4).

The effects of SORT modification was then evaluated by delivering Luciferase (Luc) mRNA intravenously (IV) at dose of 0.1 mg/kg. With increasing molar percentage of DOTAP, resulting luciferase protein expression moved progressively from liver to spleen, and then to lung, demonstrating a clear and precise organ specific delivery trend with a threshold that allowed exclusive lung delivery (FIG. 19B). DOTAP percentage was the key factor that tuned tissue specificity. Base LNPs (0% DOTAP) were optimal for liver delivery, which was anticipated since they had been previously optimized for hepatocyte delivery (Cheng et al., 2018). With addition of 10-15% DOTAP, the resulting SORT LNPs could now deliver mRNA to cells in the spleen. Increasing the permanently cationic SORT lipid further, it was found that 50% DOTAP was optimal for lung delivery (FIG. 19C). It is worth noting that although 50% DOTAP SORT LNPs are efficacious for mRNA delivery to the lungs in vivo, they were not as efficacious for in vitro delivery (FIG. 21). Moreover, 50% DOTAP SORT LNPs possess a neutral zeta potential surface charge (−0.52 mV) (FIG. 20), indicating that tissue tropism is not due to positive charge related MPS uptake. Calculating the relative expression in each organ, the use of DOTAP as a SORT lipid completely altered delivery from liver to lungs (FIG. 19D). Given that it has been estimated that >99% of current IV nanomedicines are sequestered by the MPS (Wilhelm et al., 2016; Gustafson et al., 2015), these new SORT nanoparticles therefore overcome one longstanding challenges in nanomedicine.

With the functional role of the permanently cationic SORT lipid elucidated, without wishing to be bound by any theory, it is believed that inclusion of other lipids may also alter tissue tropism. To explore this potential, negatively charged 1,2-dioleoyl-sn-glycero-3-phosphate (18PA) was incorporated as a SORT lipid in a similar manner as DOTAP (FIG. 20). At 10-40% 18PA incorporation, SORT LNPs now mediated completely selective delivery to the spleen with no luciferase expression in any other organ (FIG. 19E). Thus, negatively charged SORT lipids allow for explicit delivery to the spleen. These results indicated that SORT lipid percentage can be tailored for specific tissue mRNA delivery via IV injection.

B. SORT is Generalizable to Other LNP Types and Lipid Classes

Figures 22A, 22B, 22C:
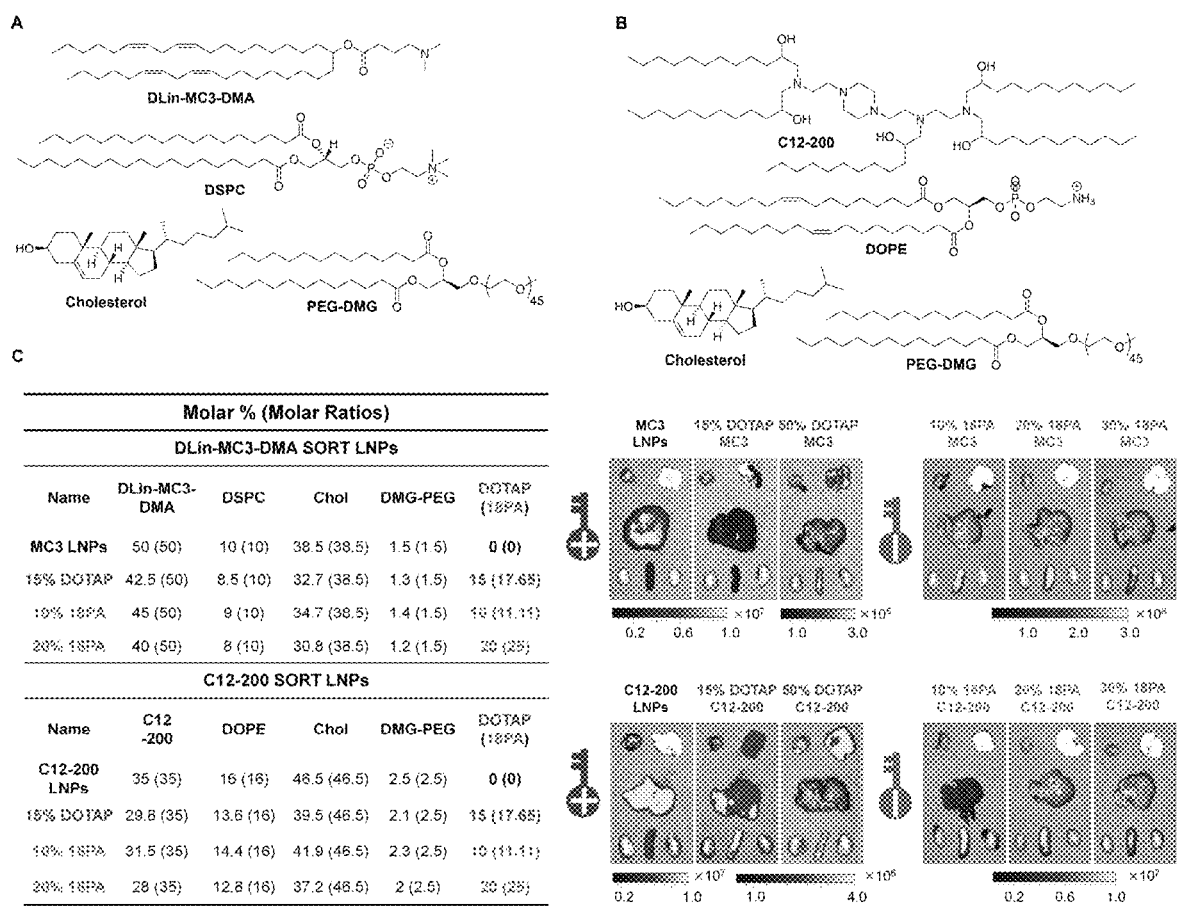
FIGS. 22A-22C show chemical structures of lipids used in (22A) DLin-MC3-DMA SNALPS (Jayaraman et al., 2012) and (22B) C12-200 LLNPs (Love et al., 2010) are shown. Liver-targeted base mRNA formulations of DLin-MC3-DMA/DSPC/Cholesterol/DMG-PEG2000=50/10/38.5/1.5 (mol) and C12-200/DOPE/Cholesterol/DMG-PEG2000=35/16/46.5/2.5 (mol) were prepared and later supplemented with SORT lipids to prepare SORT LNPs. (22C) Table and results of additional SORT formulations using DLin-MC3-DMA and C12-200. The weight ratio of total lipids/mRNA was 20/1 (wt/wt) for all DLin-MC3-DMA and C12-200 LNPs.

It was then explored if the SORT methodology could be applied to other classes of established 4-component LNPs to test whether SORT is universal. First, DLin-MC3-DMA was formulated with DSPC, cholesterol, and PEG-DMG with the same molar composition as FDA-approved Onpattro (Patisiran) (30) (FIG. 22), considered the "gold standard" for both siRNA and mRNA delivery. To date, they have only been shown to deliver to the liver following IV administration, which was confirmed here as well (FIG. 19F). As expected, supplementing DLin-MC3-DMA LNPs with DOTAP altered the protein expression profile of the Onpattro formulation. With increasing SORT lipid percentage, the luciferase signal moved from the liver to spleen to lung, which was exactly the same phenomenon for the initially tested 5A2-SC8 DLNPs. To further study the universality of the approach, DOTAP was included into C12-200 LNPs (FIGS. 19G & 22), which are also well validated for RNA delivery to the liver (Kove et al., 2010; Kauffman et al., 2015). Identical to the results with 5A2-SC8 and DLin-MC3-DMA LNPs, inclusion of 15 or 50% DOTAP into C12-200 LNPs changed luciferase protein expression following mRNA delivery from the liver to spleen to lungs (FIGS. 19G & 22). Additionally, inclusion of 18PA as a SORT lipid mirrored the results with 5A2-SC8 and mediated exclusive delivery of Luc mRNA to the spleen for both DLin-MC3-DMA SNALPs and C12-200 LLNPs (FIGS. 19F-G). While DLin-MC3-DMA is a two-tailed lipid with a single dimethylamine headgroup that forms stable nucleic acid lipid nanoparticles (SNALPs), C12-200 is a representative lipidoid that forms lipid-like LNPs (LLNPs). Thus, the SORT methodology was shown to be generalizable to other classes of ionizable cationic lipid LNPs, which will allow existing liver-targeting LNPs to be easily altered to deliver mRNA to the spleen or lungs. Specifically, the SORT technology may allow FDA-approved Onpattro to be quickly redeveloped for treatment of diseases in the lung and spleen.

Figures 23A, 23B, 23C:
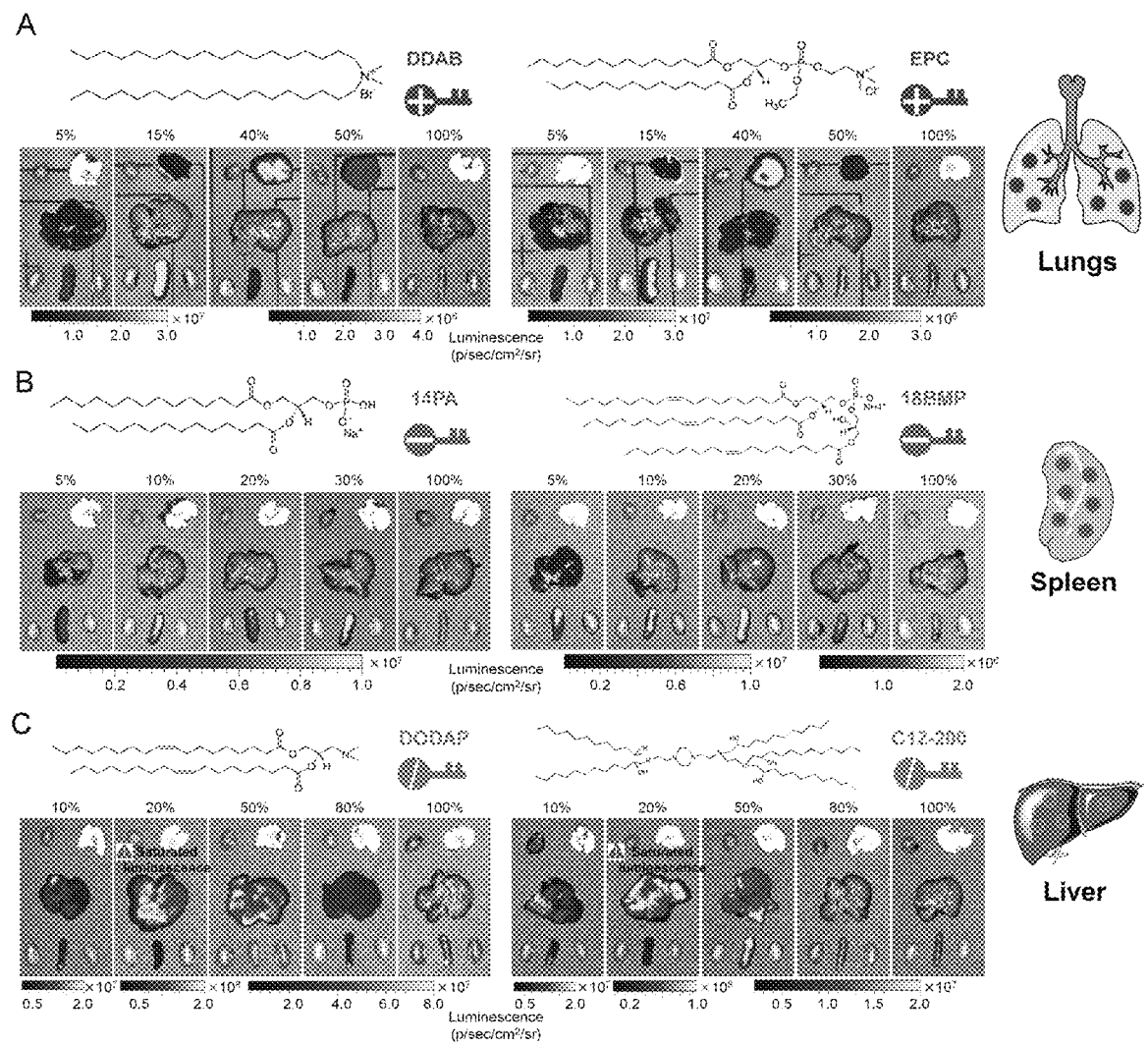
FIGS. 23A-23C show SORT relies on general biophysical properties and not exact chemical structures. (23A) SORT lipids could be divided into specific groups with defined biophysical properties. Permanently cationic SORT lipids (DDAB, EPC, and DOTAP) all resulted in the same mRNA delivery profile (liver to spleen to lung based on SORT lipid percentage) (0.1 mg/kg Luc mRNA, 6 h). (23B) Anionic SORT lipids (14PA, 18BMP, 18PA) all resulted in the same mRNA delivery profile (exclusively spleen based on SORT lipid percentage). (23C) Ionizable cationic SORT lipids with tertiary amino groups (DODAP, C12-200) enhanced liver delivery without any luciferase expression in the lungs (0.1 mg/kg Luc mRNA, 6 h).

To understand whether the tissue tropism profiles observed were specific to exact chemical structures or generalizable to defined chemical classes, multiple permanently cationic, anionic, zwitterionic, and ionizable cationic SORT lipids were evaluated (FIG. 23). First, 5A2-SC8 LNPs was generated with two additional permanently cationic lipids: didodecyldimethylammonium bromide (DDAB) and 1,2-dimyristoyl-sn-glycero-3-ethylphosphocholine chloride (EPC). These lipids all contain quaternary amino groups, but there are major chemical differences in the polar head group, linker region, and hydrophobic domain (e.g. degree of saturation). LNPs containing 5, 15, 40, 50, and 100% DDAB or EPC were formulated and characterized. The in vivo luciferase expression profile matched that of the DOTAP LNPs, where the luminescence activity systematically shifted from the liver to spleen, then to lung with increasing DDAB or EPC percentages (0.1 mg/kg, 6 h). Once the percentage was increased to 40%, high luciferase signal was observed exclusively in the lungs (FIG. 23A). 1,2-dimyristoyl-sn-glycero-3-phosphate (14PA) and sn-(3-oleoyl-2-hydroxy)-glycerol-1-phospho-sn-3'-(1',2'-dioleoyl)-glycerol (18BMP) was generated as representative anionic lipids with very different structures compared to 18PA. All anionic SORT lipids promoted exclusive delivery to the spleen (FIG. 23B). This flexibility provides ways to balance multiple factors including potency, selectivity, and tolerability by optimizing the SORT compound.

Figures 24A, 24B:
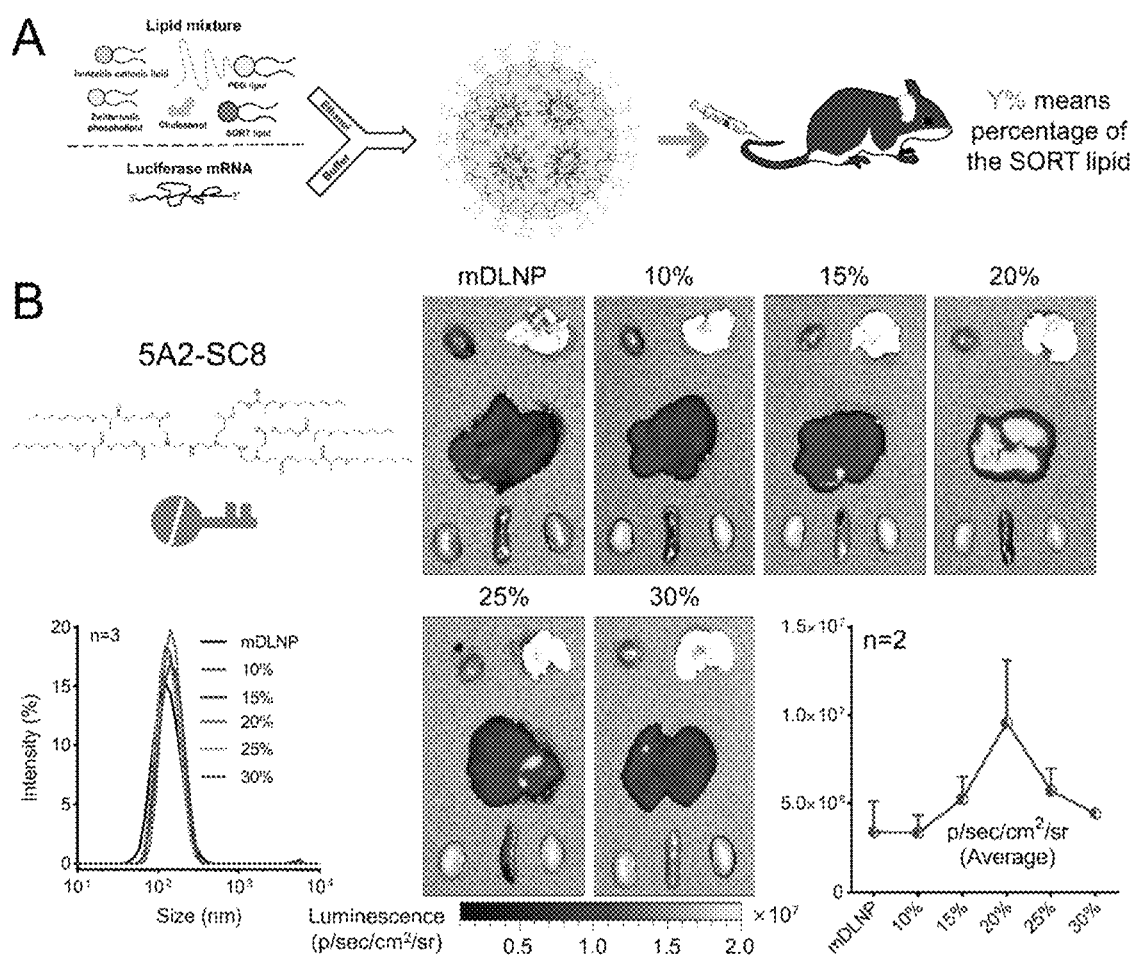
FIGS. 24A & 24B show SORT was further applied to utilize ionizable cationic lipids as SORT lipids to further enhance mDLNP liver delivery. (24A) Schematic illustration of SORT. (24B) 5A2-SC8 was used as a SORT lipid, supplementing base the mRNA mDLNP formulation (5A2-SC8/DOPE/Cholesterol/DMG-PEG2000=15/15/30/3 (mol)) with additional 5A2-SC8 using the SORT method. Ex vivo luciferase images and quantified data showed that mRNA delivery potency was dramatically improved when an extra 15%-25% SORT lipid was added. Maximal expression was produced with 20% incorporation (0.05 mg/kg, 6 h, n=2). SORT thus allowed development of a $2^{nd}$ generation mDLNP with increased efficacy.
Figures 25A, 25B:
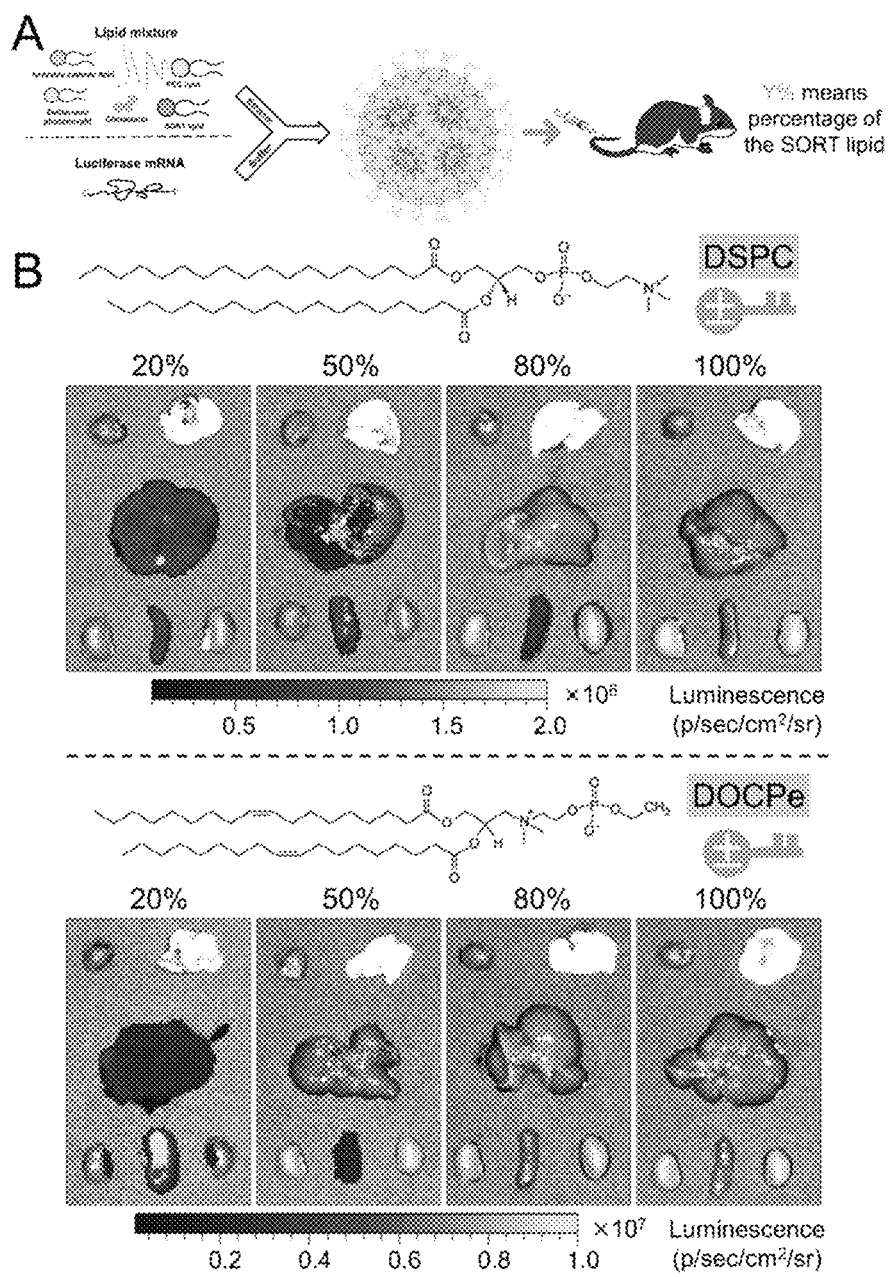
FIGS. 25A & 25B show the effects of zwitterionic SORT lipids were evaluated. Inclusion of zwitterionic SORT lipids into liver-targeted mDLNPs altered expression from the liver to the spleen with increasing incorporation of the SORT lipid. 80% DSPC and 50% DOCPe SORT LNPs delivered mRNA exclusively to the spleen after IV injection. (25A) Schematic illustration of SORT method. (25B) Ex vivo images of luminescence in major organs at 6 h post IV injection. DSPC and DOCPe, zwitterionic lipids with different structures, improved Luc mRNA delivery into spleen with increased percentages (0.1 mg/kg, 6 h, n=2).

Inspired by these findings, other ionizable cationic lipids were added to established formulations. As expected, addition of DODAP or C12-200 to 5A2-SC8 LNPs did not significantly alter tissue tropism, but surprisingly did enhance liver delivery >10-fold at 20% incorporation (FIG. 23C). Supplementing already established 5A2-SC8 LNPs with additional 5A2-SC8 as a SORT lipid dramatically improved liver mRNA delivery, producing $10^7$ photons/sec/$cm^2$ at the extremely low dose of 0.05 mg/kg. SORT thus offers a new strategy to further improve liver targeting LNP systems (FIG. 24). The effect of using zwitterionic lipids (DOCPe and DSPC) were also evaluated as SORT lipids. While the tissue tropism was found to move from liver to spleen, it was not as selective compared to use of cationic or anionic SORT lipids (FIG. 25).

Figure 26A:
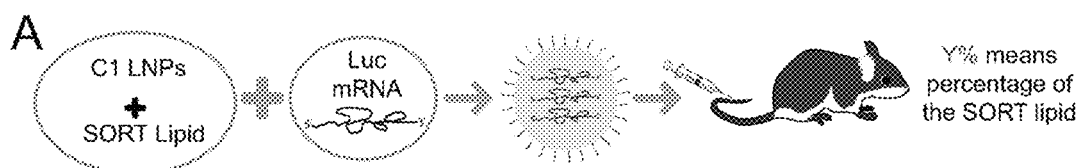
FIGS. 26A & 26B SORT was evaluated as a potential strategy to "activate" inactive LNP formulations. (26A) Schematic illustration of supplementing an inactive Cl formulation with a SORT lipid to test if SORT can endow activity. (26B) The detailed information of Cl LNPs (inactive LNPs) and DOTAP (or DODAP) Cl SORT LNPs, including lipid molar ratios, molar percentages, weight ratios of total lipids to mRNA, sizes, and PDI. Cl LNPs were prepared in a way that allowed for mRNA encapsulation and favorable biophysical properties (uniform <200 nm size). However, no protein expression at all resulted following IV injection of Cl LNPs. Thus, it was asked if SORT could "activate" dead LNPs. DODAP and DOTAP SORT lipids were evaluated. DODAP@Cl LNPs delivered mRNA into spleen and liver, and DOTAP@Cl LNPs delivered mRNA into lung and spleen (0.1 mg/kg, 6 h, n=2). Therefore, SORT can activate dead LNPs and provide tissue selectivity.
Figure 26B:
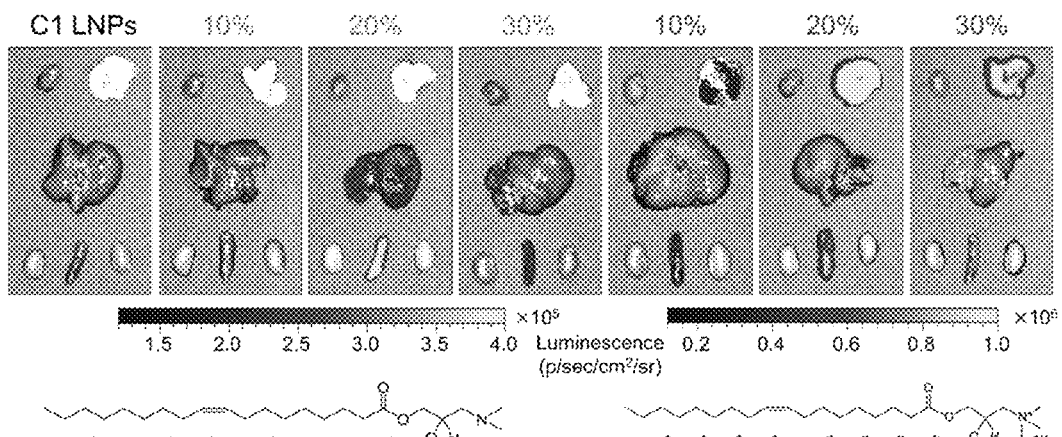

To test the limits of the SORT methodology, it was examined if SORT could "activate" otherwise inactive formulations. Indeed, supplementing a completely inactive formulation with DODAP or DOTAP resulted in tissue specific delivery to the spleen and lung (FIG. 26). Taking these results together, the SORT is a modular and universal strategy to achieve tissue targeted delivery.

Figure 27A:
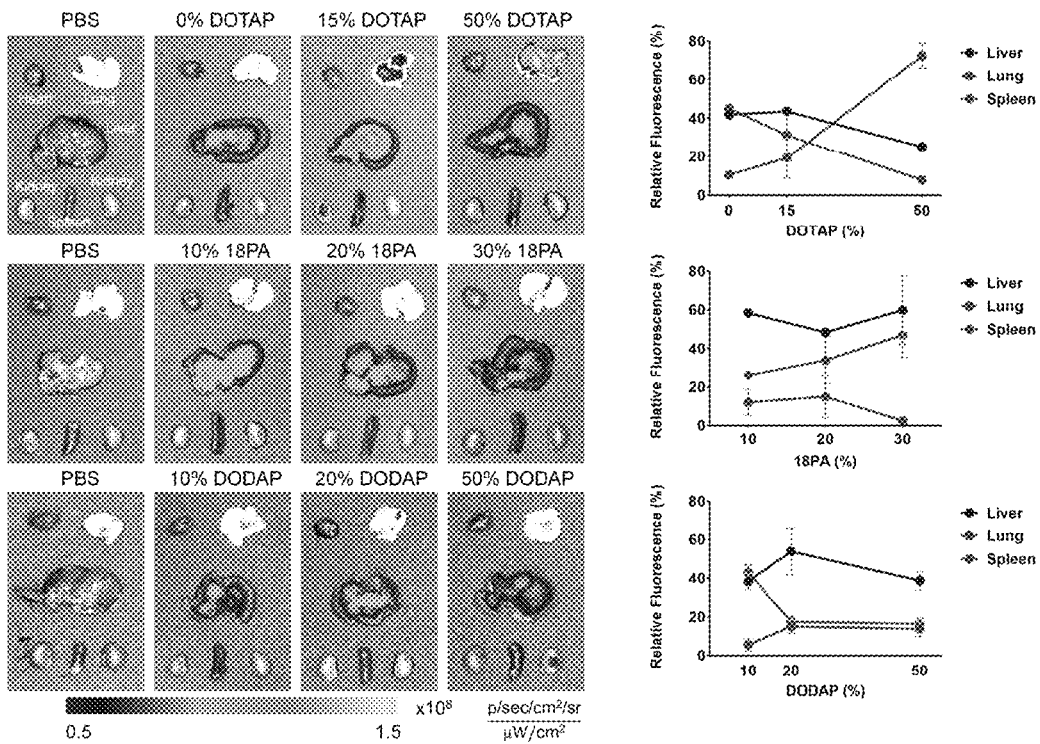
FIGS. 27A & 27B show SORT altered LNP biodistribution and revealed a correlation between relative apparent pKa and organ specificity. (27A) Fluorescent Cy5-labeled mRNA was employed to track biodistribution of SORT LNPs. Inclusion of DOTAP as a SORT lipid increased mRNA accumulation in the lungs, partially explaining the ability to deliver RNA to mouse lungs. 18PA increased uptake into the spleen. DODAP slightly increased liver and decreased spleen accumulation (0.5 mg/kg, 6 h). Note that this data describes SORT LNP location, not the ability to productively delivery mRNA intracellularly. (27B) The relative apparent pKas of all 67 effective mRNA formulations were measured by the TNS assay and plotted versus in vivo delivery efficacy in different organs (functional delivery by mRNA translated to protein). All liver targeted formulations had a narrow pKa (6-7), as expected. Surprisingly, high pKa (>9) was required for lung-targeted delivery and lower pKa (<6) aided spleen delivery. Note that all SORT LNPs contain ionizable cationic lipids (for endosomal escape) along with a mixture of other charged and uncharged lipids (that collectively mediate tissue tropism).
Figures 28A, 28B:
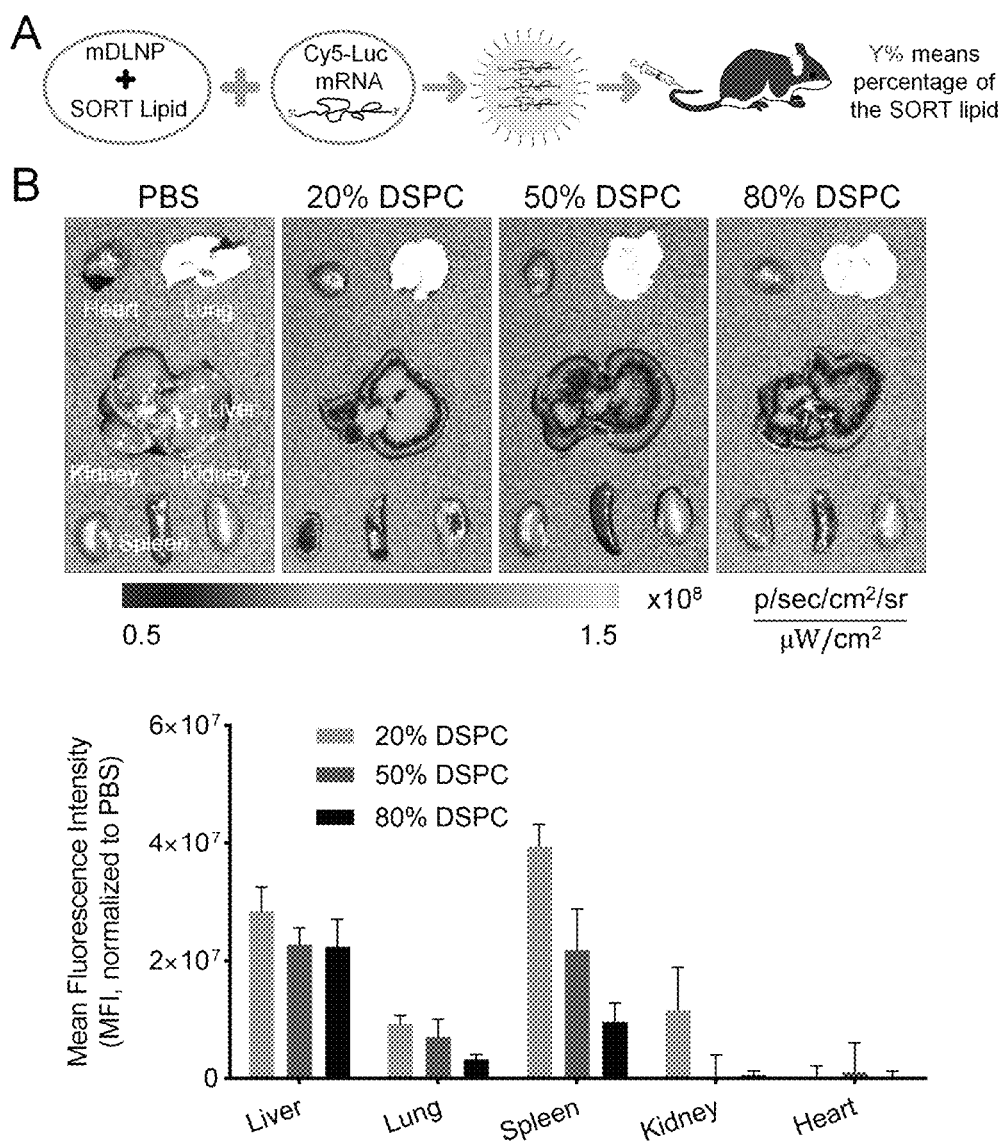
FIGS. 28A & 28B show Cy5-labeled mRNA was employed to track biodistribution of SORT LNPs. Organ distributions of DSPC mDLNPs after IV injection. (28A) Schematic illustration of SORT. (28B) Cy5 fluorescence and quantified data of major organs treated by DSPC mDLNPs (0.5 mg/kg, 6 h, n=2).

C. SORT Alters Protein Corona, LNP Biodistribution, and Apparent pKa to Mediate Organ Specific Delivery Mechanistic experiments were conducted to explore how and why inclusion of extra lipids in defined categories controls mRNA delivery to different organs. It is logical that LNPs that deliver to cells within the lungs should biodistribute (accumulate) in the lungs. Cy5-labeled mRNA was delivered to track the in vivo distribution of 5A2-SC8 LNPs containing SORT lipids with lung (DOTAP quaternary amino lipid), spleen (18PA anionic lipid and DSPC zwitterionic lipid) and liver (DODAP ionizable tertiary amino lipid) tropism (FIGS. 27A & 28). All LNPs were injected IV at a dose of 0.5 mg/kg Cy5-labeled mRNA and imaging was performed after 6 hours. As shown in FIG. 27A, DOTAP altered biodistribution with a progressive increase in lung accumulation as a function of DOTAP percentage. Incorporation of 18PA increased uptake into the spleen. DODAP slightly increased liver and decreased spleen accumulation. Interestingly, there was no protein expression at all in the liver for lung- and spleen-specific SORT LNPs, even though these LNPs still accumulated in the liver. This suggests that organ biodistribution is required for organ specific efficacy but is not the only factor to explain the mechanism of tissue targeted delivery.

Without wishing to be bound by any theory, it is believed that the changes in biodistribution and activity in defined cell populations could be due to alteration of the protein corona, where the binding of specific protein(s) creates a functionally active biological identity. Using quantitative mass spectroscopy analysis, it was found that the addition of SORT molecules dramatically changes both the specific proteins that most tightly bind and the overall protein corona composition. Without wishing to be bound by any theory it is believed that lung-specific SORT LNPs selectively and most abundantly bound vitronectin, which can interact with positively-charged lipids and binds αvβ3 integrins that are highly expressed on both endothelial and epithelial cells of the lungs. This mechanism of endogenous targeting draws a direct comparison to adenoviruses that exploit the αvβ5 integrin to target the bronchial epithelium. Spleen-specific SORT LNPs most tightly bound β2-glycoprotein I, which has been shown to interact with negatively-charged lipids and potentially plays a role in spleen localization with immune cell populations in the spleen. It is worth noting that the complex mixture of bound proteins may also play a role. This ensemble effect was also viewed as a potential mechanism for targeting of multiple cell types and as a way to further enrich specificity to specific cell types within one organ using alternative SORT molecules. It has previously been shown that Apolipoprotein E binds to DLin-MC3-DMA Onpattro LNPs and that efficacy is lost in Apo E knockout animals. Thus, there is strong evidence that Apo E is required for receptor-mediated targeting and uptake in hepatocytes, presumably by LDL receptor, and that the described protein corona mechanism can control cellular specificity and efficacy. To see that mDLNPs also strongly associate with Apo E was therefore encouraging, providing further evidence of their hepatocyte efficacy and strengthening the validity of the protein corona assays. Liver-enhanced SORT LNPs retain Apo E binding but also are enriched in albumin, suggesting a possible expansion of cell types within the liver. These data cumulatively show that the chemical structure of the SORT molecule can direct a specific protein corona that alters organ tropism and cellular specificity. Without wishing to be bound by any theory, it is believed that the identity of the SORT molecule can control the protein corona identity suggesting that SORT molecules could include a sugar, a lipid, a small molecule therapeutic agent, a vitamin, small molecules, hydrophilic molecules, hydrophobic molecules, amphipathic molecules, peptides, protein, and the like.

Figure 27B:
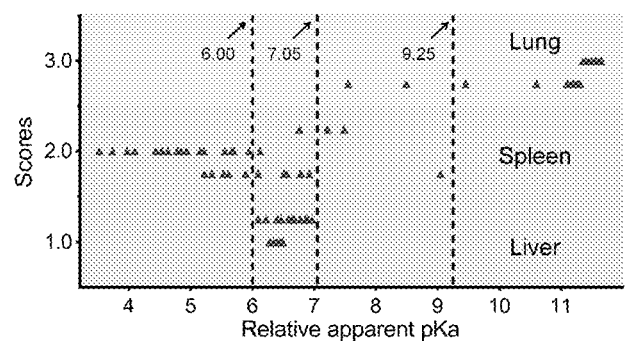
Figure 29:
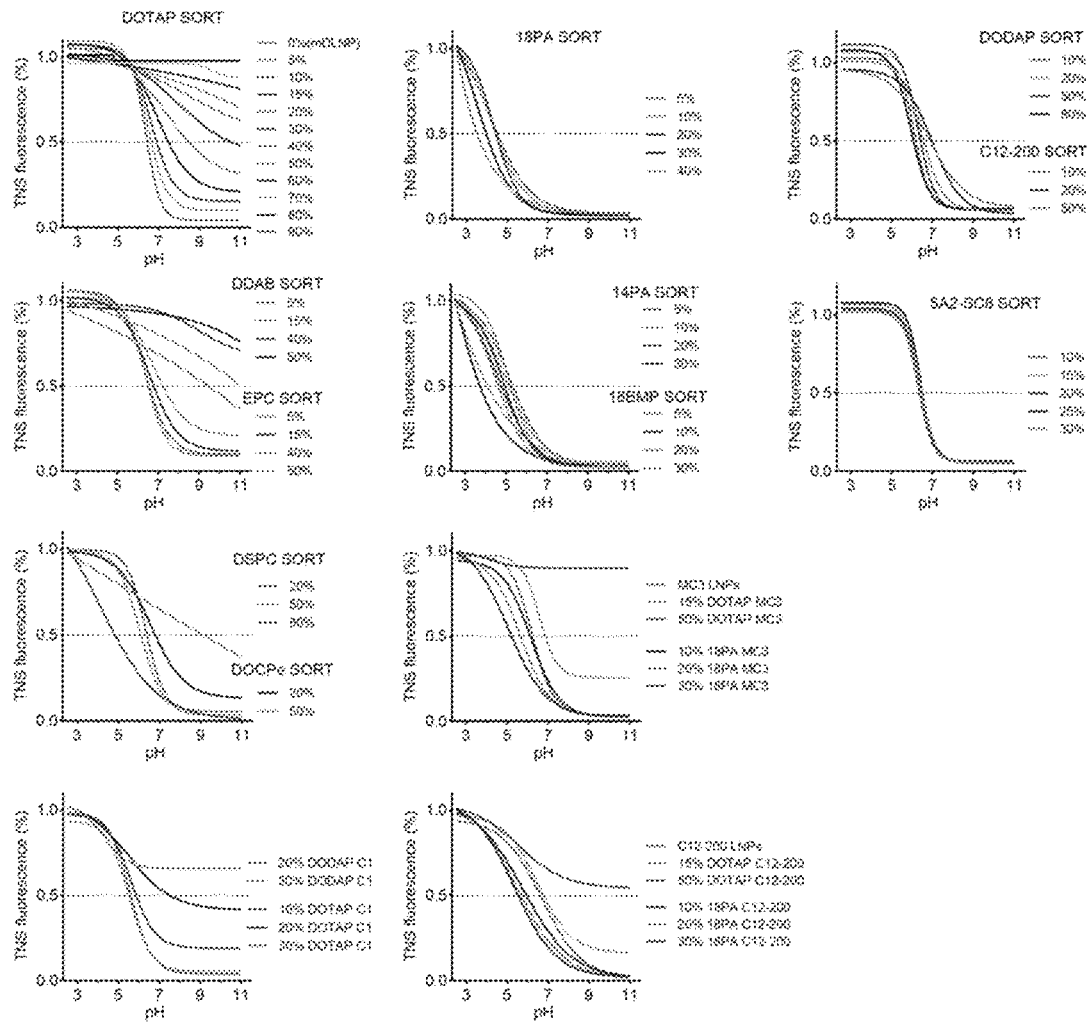
FIG. 29 shows a modified TNS assay was used to measure global/apparent pKa of mRNA formulations. 67 NPs successful formulations (high in vivo efficacy) were evaluated in total. The relative pKa were estimated compared to base LNP formulation (no added SORT lipid) when 50% of normalized signal was produced. The TNS assay has been historically used to measure LNPs with a single ionizable cationic lipid and neutral (non-ionizable) helper lipids, producing a value that captures the ionization behavior of a cationic lipid within a self-assembled LNP. A modified method was used here because SORT LNPs with high percentages (>40%) of the permanently cationic lipid (e.g. DOTAP) do not buffer charge well even though they contain ionizable cationic lipid. Due to the complexity of SORT LNPs that contain a variety of charged lipids (not a single ionizable cationic lipid as in traditional LNPs), the focus was on the relative signal at 50%, which correlated with in vivo tissue specific activity.
Figures 30A, 30B:
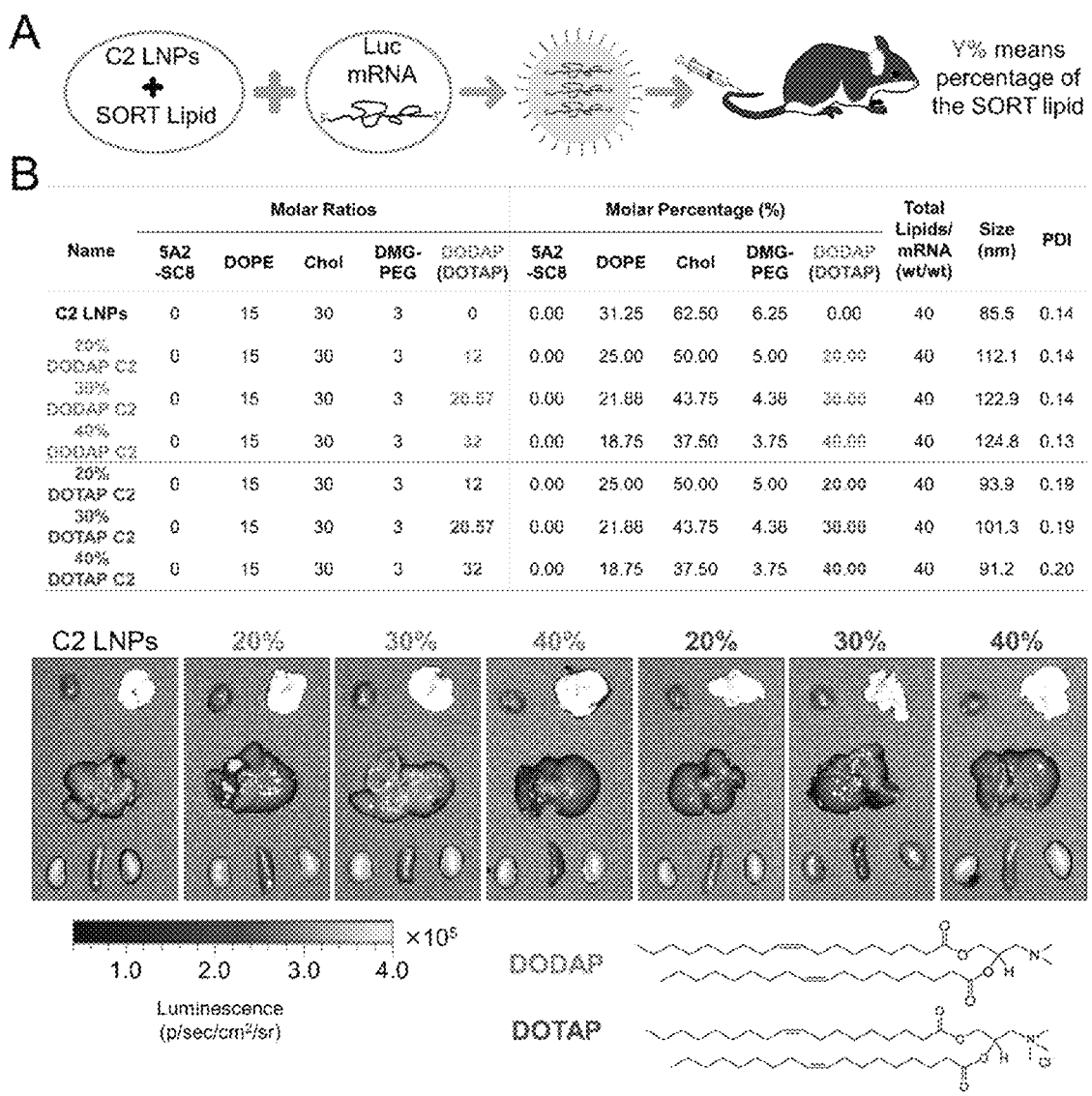
FIGS. 30A & 30B show inclusion of an ionizable lipid (e.g. 5A2-SC8) was required for efficacy. LNPs that contained SORT lipids, but no ionizable cationic lipid were inactive. (30A) Schematic illustration of SORT C2 LNPs. (30B) Details of C2 and SORT lipids C2 LNPs. Ex vivo luciferase images showed that both DODAP and DOTAP failed to enable significant mRNA delivery of C2 LNPs. These results indicate that the ionizable amino lipid is required for successful mRNA delivery (0.1 mg/kg, 6 h, n=2).

The apparent/global $pK_a$ was examined because it has been established as a parameter that correlates LNPs with functional activity. For example, it has been shown that $pK_a$ around 6.4 is optimal for delivery to hepatocytes (Jayaraman et al., 2012). The apparent $pK_a$ was analyzed using the TNS assay for all efficacious in vivo formulations (67 LNPs) (FIGS. 27B & 29, Table 1). Because SORT involves inclusion of additional charged lipids, the resulting TNS titration curves capture the ionization behavior of more complex mixed species LNPs. As such, the relative $pK_a$ was instead estimated when 50% of normalized signal was produced. When plotting relative $pK_a$ with respect to tissue tropism, SORT LNPs grouped into defined apparent $pK_a$ ranges (FIG. 27B). As expected, all efficacious liver targeted formulations had a very narrow $pK_a$ within the well-established 6-7 range (Jayaraman et al., 2012). All lung targeted formulations were located in the high $pK_a$ range (>9). Conversely, spleen tropic SORT LNPs grouped to the low $pK_a$ range (2-6). These results confirm that 6-7 is optimal for delivery to the liver but reveal the finding that high $pK_a$ mediates lung delivery and low $pK_a$ mediates spleen delivery. It should be note that all SORT LNPs still contain ionizable cationic lipids, which are considered useful for endosomal escape (Wittrup et al., 2015) due to their ability to acquire charge. Control experiments were performed and confirmed that inclusion of an ionizable cationic lipid was required for efficacy (FIG. 30). Thus, SORT allows retention of the molecules with specific microspecies $pK_a$ that are required for efficacy in desired molar proportions, while inclusion of SORT lipids modifies the apparent pKa. Without wishing to be bound by any theory, it is believed a two-part mechanism may play a role. SORT LNPs selectively bind specific proteins in the serum that enable receptor-mediated efficacy in cells in the lungs or spleen, very similar to how lipoprotein particles (e.g. LDL) natively transport cholesterol. This controlled and predictable endogenous targeting mechanism enables SORT LNPs to reach non-liver targets. The second part involves how the SORT molecules alter the properties of the non-hepatic targeting SORT LNPs such that they no longer possess the physiochemical properties for liver efficacy (e.g. global/apparent $pK_a$ 6.4), which provides the precision. It is also noted that other and more complicated factors, such as cell-specific endocytic trafficking differences, may also play a role. Taking results into consideration, it is suggested that the internal charges of LNP nanostructures mediate biodistribution and that the apparent $pK_a$ correlates with protein expression profiles in specific organs. This particular value may be used to continue to develop other organ-specific nanoparticles.

TABLE 1

Details of DDAB, EPC, 14PA, 18BMP, DODAP, C12-200,5A2-SC8, DSPC, and DOCPe modified mDLNP formulations (SORT LNPs), including molar ratio and percentage of each component, weight ratios of total lipids to mRNA, size, and PDI.

| Name | Molar Ratios | | | | | Molar Percentage (%) | | | | | Lipids/mRNA (wt/wt) | Size (nm) | PDI |
|---|---|---|---|---|---|---|---|---|---|---|---|---|---|
| | 5A2-SC8 | DOPE | Chol | DMG-PEG | $X^a$ | 5A2-SC8 | DOPE | Chol | DMG-PEG | $X^a$ | | | |
| 5% DDAB | 15 | 15 | 30 | 3 | 3.315 | 22.62 | 22.62 | 45.24 | 4.52 | 5.00 | 40 | 193.5 | 0.14 |
| 15% DDAB | 15 | 15 | 30 | 3 | 11.12 | 20.24 | 20.24 | 40.47 | 4.05 | 15.00 | 40 | 167.7 | 0.13 |
| 40% DDAB | 15 | 15 | 30 | 3 | 42 | 14.29 | 14.29 | 28.57 | 2.86 | 40.00 | 40 | 143.8 | 0.13 |
| 50% DDAB | 15 | 15 | 30 | 3 | 63 | 11.90 | 11.90 | 23.81 | 2.38 | 50.00 | 40 | 174.7 | 0.21 |
| 100% DDAB | 0 | 0 | 0 | 0 | 100 | 0.00 | 0.00 | 0.00 | 0.00 | 100.00 | 40 | 3174.3 | 0.23 |
| 5% EPC | 15 | 15 | 30 | 3 | 3.315 | 22.62 | 22.62 | 45.24 | 4.52 | 5.00 | 40 | 195.3 | 0.14 |
| 15% EPC | 15 | 15 | 30 | 3 | 11.12 | 20.24 | 20.24 | 40.47 | 4.05 | 15.00 | 40 | 166.3 | 0.14 |
| 40% EPC | 15 | 15 | 30 | 3 | 42 | 14.29 | 14.29 | 28.57 | 2.86 | 40.00 | 40 | 116.7 | 0.15 |
| 50% EPC | 15 | 15 | 30 | 3 | 63 | 11.90 | 11.90 | 23.81 | 2.38 | 50.00 | 40 | 105.7 | 0.17 |
| 100% EPC | 0 | 0 | 0 | 0 | 100 | 0.00 | 0.00 | 0.00 | 0.00 | 100.00 | 40 | 455.9 | 0.32 |
| 5% 14PA | 15 | 15 | 30 | 3 | 3.315 | 22.62 | 22.62 | 45.24 | 4.52 | 5.00 | 40 | 92.8 | 0.18 |
| 10% 14PA | 15 | 15 | 30 | 3 | 7 | 21.43 | 21.43 | 42.86 | 4.29 | 10.00 | 40 | 98.6 | 0.18 |
| 20%14PA | 15 | 15 | 30 | 3 | 16.75 | 19.05 | 19.05 | 38.10 | 3.81 | 20.00 | 40 | 105.7 | 0.17 |
| 30% 14PA | 15 | 15 | 30 | 3 | 27 | 16.67 | 16.67 | 33.33 | 3.33 | 30.00 | 40 | 107.3 | 0.19 |
| 100% MPA | 0 | 0 | 0 | 0 | 100 | 0.00 | 0.00 | 0.00 | 0.00 | 100.00 | 40 | 2607.3 | 0.28 |
| 5% 18BMP | 15 | 15 | 30 | 3 | 3.315 | 22.62 | 22.62 | 45.24 | 4.52 | 5.00 | 40 | 112.0 | 0.13 |
| 10% 18BMP | 15 | 15 | 30 | 3 | 7 | 21.43 | 21.43 | 42.86 | 4.29 | 10.00 | 40 | 131.4 | 0.10 |
| 20% 18BMP | 15 | 15 | 30 | 3 | 15.75 | 19.05 | 19.05 | 38.10 | 3.81 | 20.00 | 40 | 172.9 | 0.12 |
| 30% 18BMP | 15 | 15 | 30 | 3 | 27 | 16.67 | 16.67 | 33.33 | 3.33 | 30.00 | 40 | 195.9 | 0.13 |
| 100% 18BMP | 0 | 0 | 0 | 0 | 100 | 0.00 | 0.00 | 0.00 | 0.00 | 100.00 | 40 | 87.4 | 0.21 |
| 10% DODAP | 15 | 15 | 30 | 3 | 7 | 21.43 | 21.43 | 42.86 | 4.29 | 10.00 | 40 | 138.5 | 0.11 |
| 20% DODAP | 15 | 15 | 30 | 3 | 15.75 | 19.05 | 19.05 | 38.10 | 3.81 | 20.60 | 40 | 122.4 | 0.18 |
| 50% DODAP | 15 | 15 | 30 | 3 | 63 | 11.90 | 11.90 | 23.81 | 2.38 | 50.00 | 40 | 148.0 | 0.15 |
| 80% DODAP | 15 | 15 | 30 | 3 | 252 | 4.76 | 4.76 | 9.52 | 0.95 | 80.00 | 40 | 180.4 | 0.13 |
| 100% DODAP | 0 | 0 | 0 | 0 | 100 | 0.00 | 0.00 | 0.00 | 0.00 | 100.00 | 40 | 932.8 | 0.74 |
| 10% C12-200 | 15 | 15 | 30 | 3 | 7 | 21.43 | 21.43 | 42.86 | 4.29 | 10.00 | 40 | 179.7 | 0.11 |
| 20% C12-200 | 15 | 15 | 30 | 3 | 15.75 | 19.05 | 19.05 | 38.10 | 3.81 | 20.00 | 40 | 141.3 | 0.19 |
| 50% C12-200 | 15 | 15 | 30 | 3 | 63 | 11.90 | 11.90 | 23.81 | 2.38 | 50.00 | 40 | 156.1 | 0.16 |
| 80% C12-200 | 15 | 15 | 30 | 3 | 252 | 4.76 | 4.76 | 9.52 | 0.95 | 80.00 | 40 | 273.2 | 0.21 |
| 100% C12-200 | 0 | 0 | 0 | 0 | 100 | 0.00 | 0.00 | 0.00 | 0.00 | 100.00 | 40 | 2505.3 | 1.00 |
| 10% 5A2-SC8 | 15 | 15 | 30 | 3 | 7 | 21.43 | 21.43 | 42.86 | 4.29 | 10.00 | 40 | 127.1 | 0.14 |
| 15% 5A2-SC8 | 15 | 15 | 30 | 3 | 11.12 | 20.24 | 20.24 | 40.47 | 4.05 | 15.00 | 40 | 130.9 | 0.13 |
| 20% 5A2-SC8 | 15 | 15 | 30 | 3 | 15.75 | 19.05 | 19.05 | 38.10 | 3.81 | 20.00 | 40 | 137.6 | 0.10 |
| 25% 5A2-SC8 | 15 | 15 | 30 | 3 | 21 | 17.86 | 17.86 | 35.71 | 3.57 | 25.00 | 40 | 126.0 | 0.12 |
| 30% 5A2-SC8 | 15 | 15 | 30 | 3 | 27 | 16.67 | 16.67 | 33.33 | 333 | 30.00 | 40 | 134.7 | 0.10 |
| 20% DSPC | 15 | 15 | 30 | 3 | 15.75 | 19.05 | 19.05 | 38.10 | 3.81 | 20.00 | 40 | 115.7 | 0.19 |
| 50% DSPC | 15 | 15 | 30 | 3 | 63 | 11.90 | 11.90 | 23.81 | 2.38 | 50.00 | 40 | 202.0 | 0.29 |
| 80% DSPC | 15 | 15 | 30 | 3 | 252 | 4.76 | 4.76 | 9.52 | 0.95 | 80.00 | 40 | 1024.7 | 0.67 |
| 100% DSPC | 0 | 0 | 0 | 0 | 100 | 0.00 | 0.00 | 0.00 | 0.00 | 100.00 | 40 | 2134.8 | 0.99 |
| 20% DOCPe | 15 | 15 | 30 | 3 | 15.75 | 19.05 | 19.05 | 38.10 | 3.81 | 20.00 | 40 | 147.7 | 0.15 |
| 50% DOCPe | 15 | 15 | 30 | 3 | 63 | 11.90 | 11.90 | 23.81 | 2.38 | 50.00 | 40 | 173.6 | 0.20 |
| 80% DOCPe | 15 | 15 | 30 | 3 | 252 | 4.76 | 4.76 | 9.52 | 0.95 | 80.00 | 40 | 127.7 | 0.21 |
| 100% DOCPe | 0 | 0 | 0 | 0 | 100 | 0.00 | 0.00 | 0.00 | 0.00 | 100.00 | 40 | 93.7 | 0.36 |

$^a$X represents DDAB, EPC, 14PA, 18BMP, DODAP, C12-200, 5A2-SC8, DSPC and DOCPe.

D. SORT Allows Lung, Liver, and Spleen Specific Gene Editing Following IV Administration Given the ability of SORT LNPs to target specific organs, these finding were then applied to tissue specific gene editing via IV injection. The CRISPR/Cas (clustered regularly interspaced short palindromic repeat/CRISPR-associated protein (Cas)) technology can edit the genome in a precise and sequence dependent manner and has rapidly developed for use in diverse applications, including for potential correction of disease-causing mutations (Jinek et al., 2012; Cong et al., 2013; Mali et al., 2013; Hendel et al., 2015; Yin et al., 2016; Yin et al., 2017; Wang et al., 2018; Amoasii et al., 2018). Gene editing can be achieved by local administration injections (Zuris et al., 2015; Sun et al., 2015; Chew et al., 2016; Staahl et al., 2017). However, many serious genetic disorders arise from mutations in cells deep in organs, where correction of specific cells will be required to cure disease. Such correction may be best achieved by systemic administration. It has been recently reported that IV co-delivery of Cas9 mRNA and sgRNA is a safe and effective strategy to enable gene editing (Miller et al., 2017; Yin et al., 2017; Finn et al., 2018). To date, however, there have been no reports of LNPs rationally engineered to edit cells in organs outside of the liver.

Figures 31A, 31B, 31C, 31D, 31E:
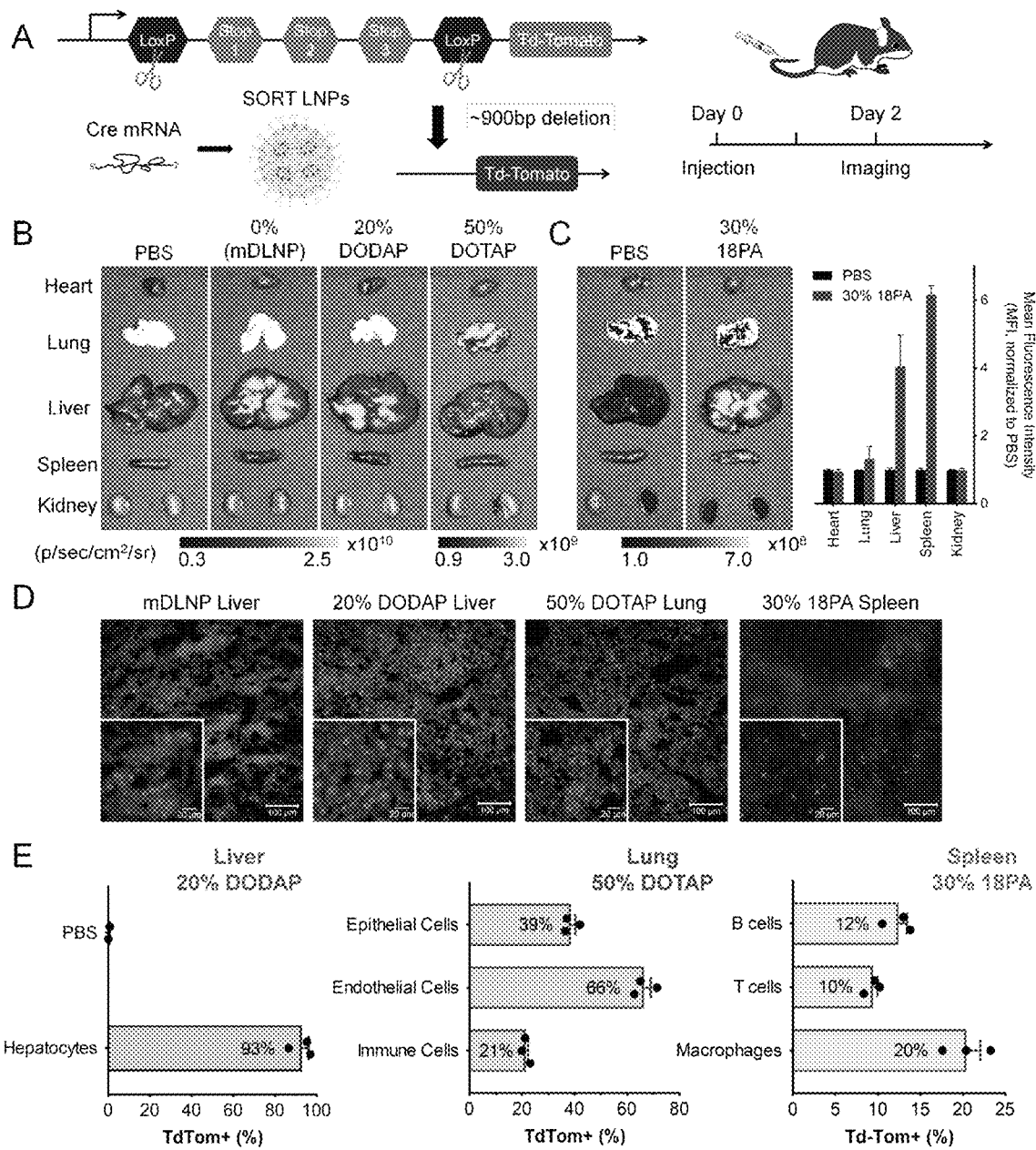
FIGS. 31A-31E show SORT LNPs enabled tissue specific gene editing in Td-Tomato mice by Cre mRNA delivery. (31A) Schematic illustration shows that delivery of Cre mRNA activates Td-Tom expression in Td-Tom transgenic mice. (31B) mDLNP and 20% DODAP LNPs induced Td-Tom fluorescence specifically in the liver and 50% DOTAP LNPs selectively edited the lung. Td-Tom fluorescence of main organs was detected 2 days following IV injection of Cre mRNA-loaded LNPs (0.3 mg/kg). (31C) 30% 18PA SORT LNPs induced gene editing in the spleen (note high liver background fluorescence in PBS injected mice). (31D) Confocal microscopy was employed to further verify effective tissue editing. Scale bars=20 μm and 100 μm. (31E) FACS was used to quantify the percentage of TdTom$^+$ cells within defined cell type populations of the liver, lung, and spleen (day 2, 0.3 mg/kg).
Figure 32:
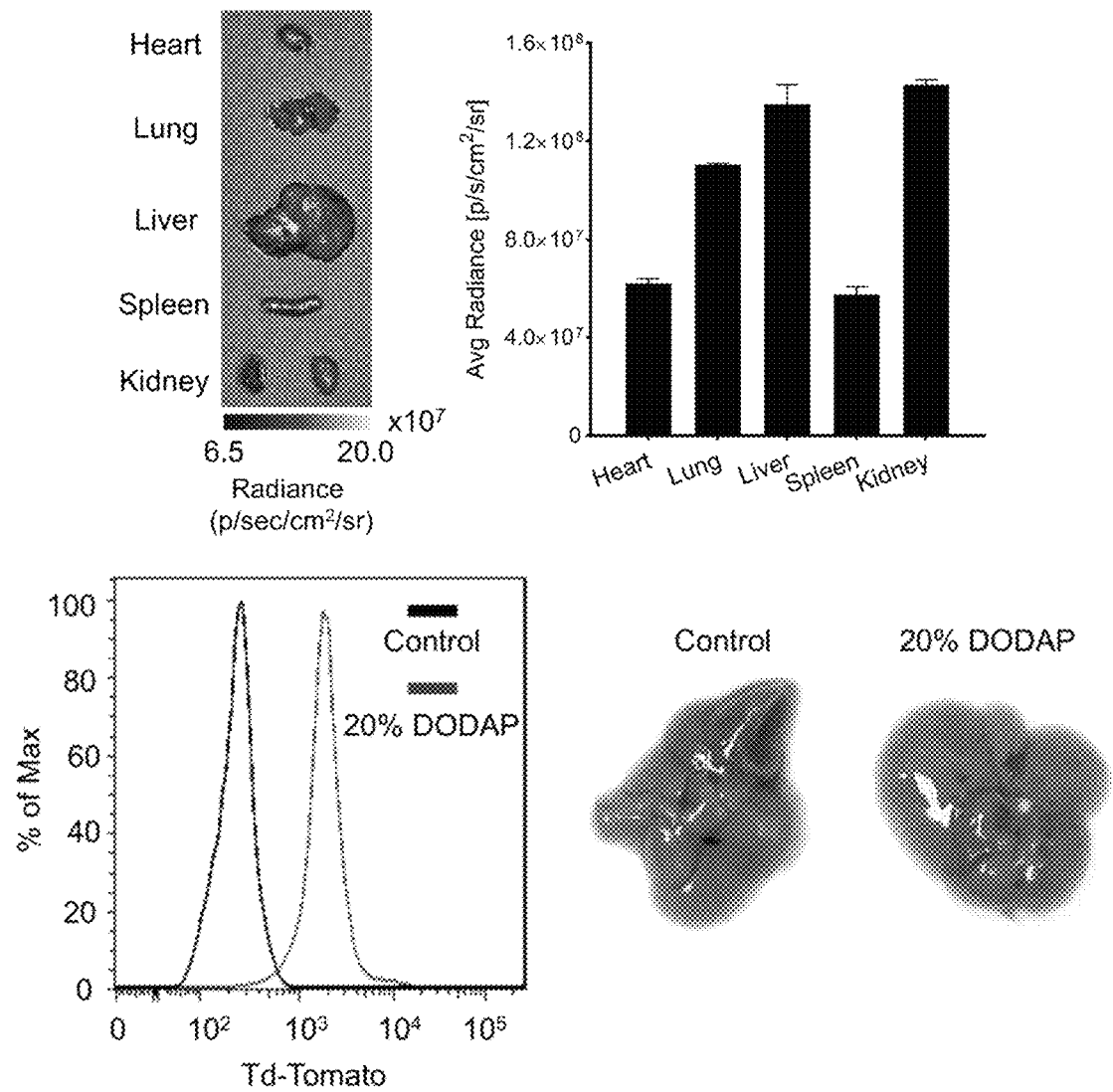
FIG. 32 shows B6.Cg-Gt(ROSA) 26Sor$^{tm9(CAG-tdTomato)Hze}$/J (Ai9) mice exhibit some autofluorescence in the absorption region for TdTom. Moreover, there is a large difference for TdTom autofluorescence between different organs (n=2). Liver and kidney show the highest signal and spleen shows the lowest. Although this does not interfere with detection of editing in most organs (when the excitation settings are properly adjusted to eliminate background), it does complicate detection of spleen TdTom expression because background spleen is so much lower than other organs.

To examine and quantify the ability of SORT LNPs to mediate organ-specific gene editing, genetically engineered tdTomato (tdTom) reporter mice containing a LoxP flanked stop cassette (Tabebordbar et al., 2016) were utilized that prevents expression of the tdTom protein (Staahl et al., 2017). Once the stop cassette is deleted, tdTom fluorescence is turned on, allowing detection of gene edited cells (FIG. 31A). Cre recombinase mRNA (Cre mRNA) were initially delivered to activate tdTom in edited cells. Fluorescent tissues were readily apparent (FIG. 31B) in selected organs treated with liver, lung, and spleen selective SORT LNPs. It should be noted that separate controls had to be used for each experiment because these mice have some background organ fluorecense, which is weakest in the spleen compared to other organs (FIGS. 31C & 32). This makes detection of spleen specificity more challenging to differentiate in the tdTom mouse model. When endogenous PTEN was subsequently edited, spleen specific SORT LNPs showed clean DNA cutting by the T7E1 assay only in the spleen (FIG. 33C) without any cutting of DNA in the liver or lungs.

Nevertheless, tdTom positive cells were easily seen by confocal imaging of tissue sections (FIG. 31D).

Figure 35:
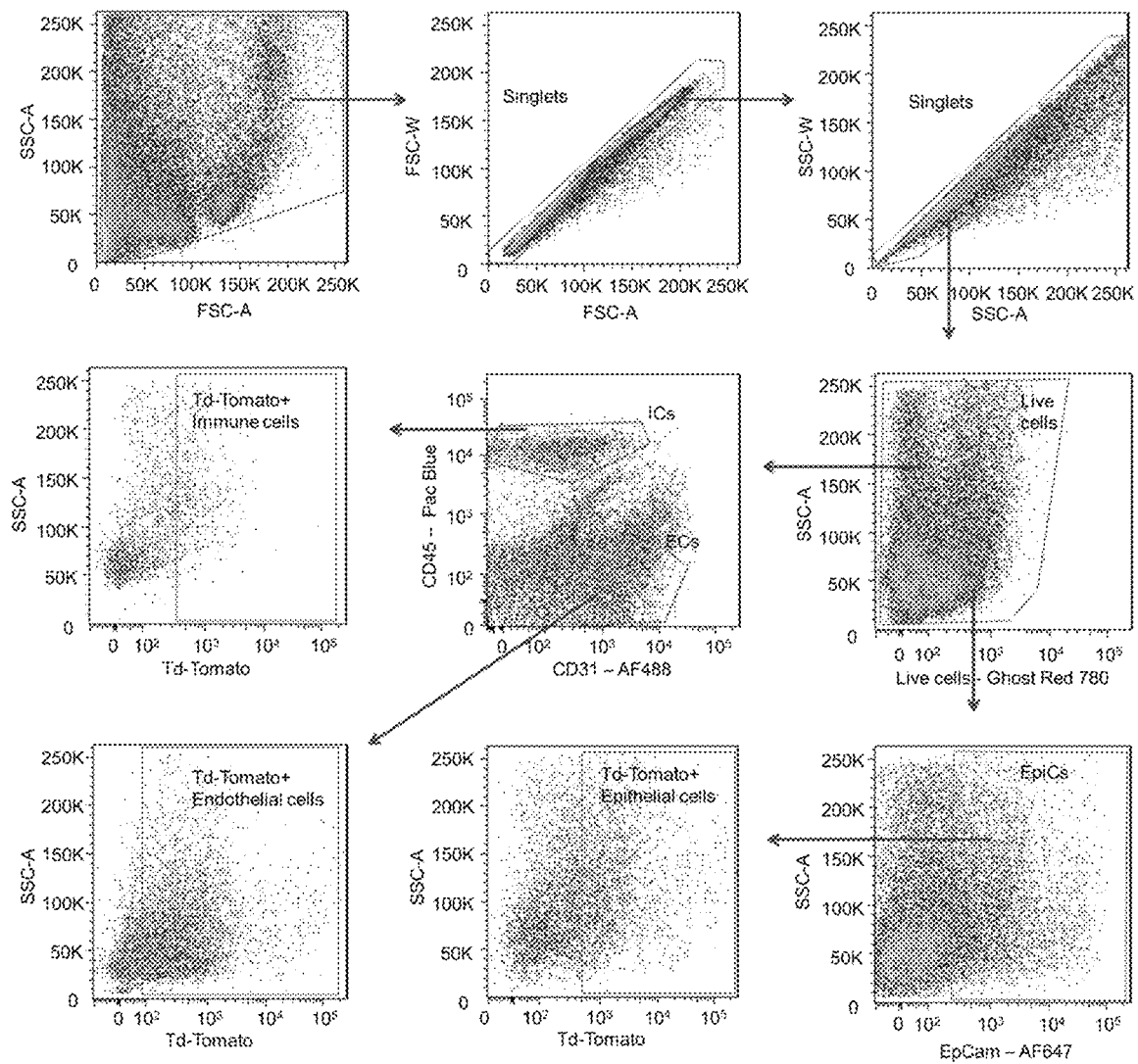
FIG. 35 shows the FACS gating strategy for analysis of TdTom+ expression in lung cells is described. Ghost Red 780 was used to distinguish live and dead cells. EpCam+ was used to define epithelial cells, CD45+ and CD31− used to define immune cells, and CD45− and CD31+ were used to define endothelial cells. Gates for Td-Tom+ in cell types were drawn based on PBS injected control mice. Td-Tom mice were injected with Cre mRNA formulations and Td-Tom+ in given cell types was detected by flow after two days (n=3).
Figure 36:
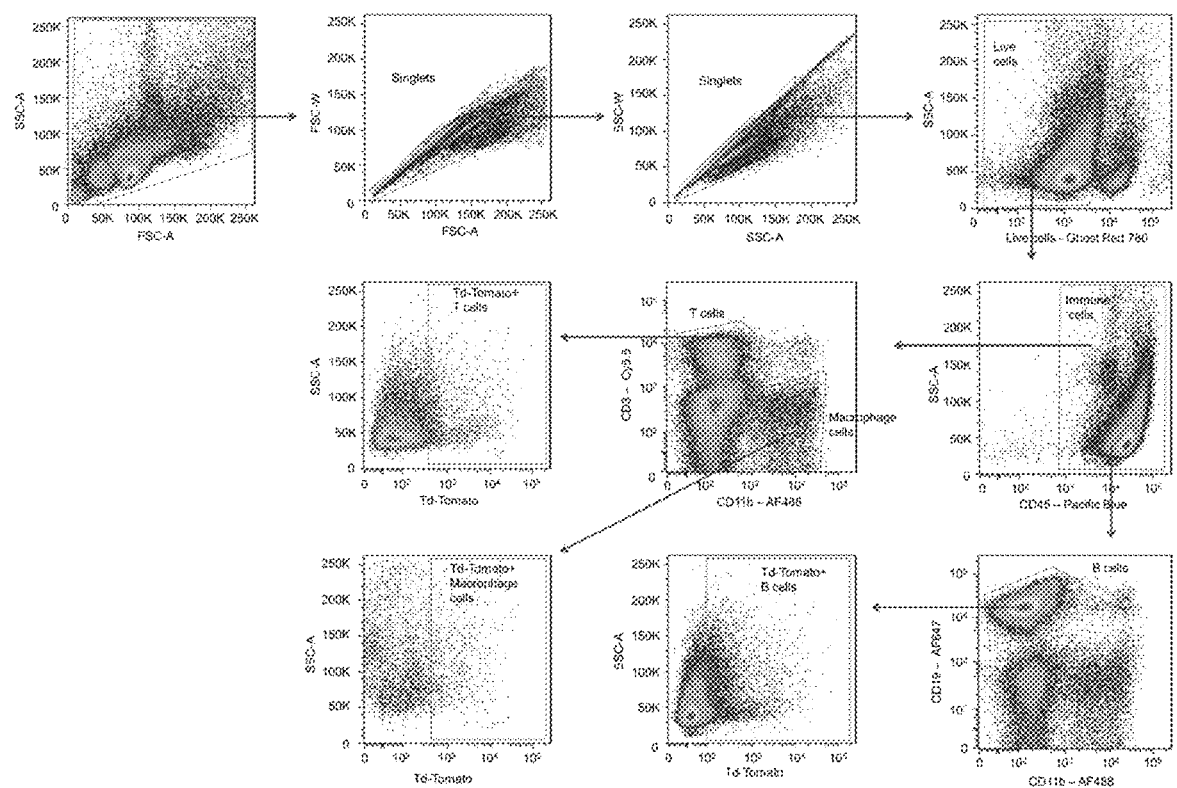
FIG. 36 shows the FACS gating strategy for analysis of TdTom+ expression in splenic cells is described. Ghost Red 780 was used to distinguish live and dead cells. CD44+ was used to distinguish immune cells, then CD3+ and CD11b− were used for T cells, CD3− and CD11b+ were used for macrophage cells, CD19+ and CD11b− were used for B cells. Gates for Td-Tom+ in cell types were drawn based on PBS injected control mice. Td-Tom mice were injected with Cre mRNA formulations and Td-Tomato+ in given cell types was detected by flow after two days (n=3).

E. SORT Enables High Levels of Editing in Specific and Therapeutically Relevant Cell Populations Gene editing of specific cell types within the liver, lung, and spleen using flow cytometry of single cells extracted from edited organs were quantified (FIG. 31E). Liver-specific SORT (20% DODAP) 5A2-SC8 LNPs edited ~93% of all hepatocytes in the liver following a single injection of 0.3 mg/kg Cre mRNA (FIGS. 31E & 34). This is the highest level of hepatocyte gene editing reported to date. Lung-specific SORT (50% DOTAP) 5A2-SC8 LNPs edited ~40% of all epithelial cells, ~65% of all endothelial cells, and ~20% of immune cells in the lungs at the same dose (FIGS. 31E & 35). Given that epithelial cells are a primary target for correction of mutations in CFTR that cause cystic fibrosis, this result establishes lung-specific SORT LNPs as a compelling delivery system with immediate application for correcting CFTR mutations. Finally, spleen-specific SORT (30% 18PA) 5A2-SC8 LNPs edited ~13% of all B cells, ~10% of all T cells, and ~20% of all macrophages (FIGS. 31E & 36). Due to the improved selectivity over prior studies, spleen-specific SORT LNPs could be applicable to treat non-Hodgkin's B cell lymphoma and other immune disorders. Although the initial focus was on single, low dose injection quantification, higher levels of editing are achievable by administering higher doses or multiple injections.

Figures 37A, 37B, 37C, 37D, 37E, 37F, 37G:
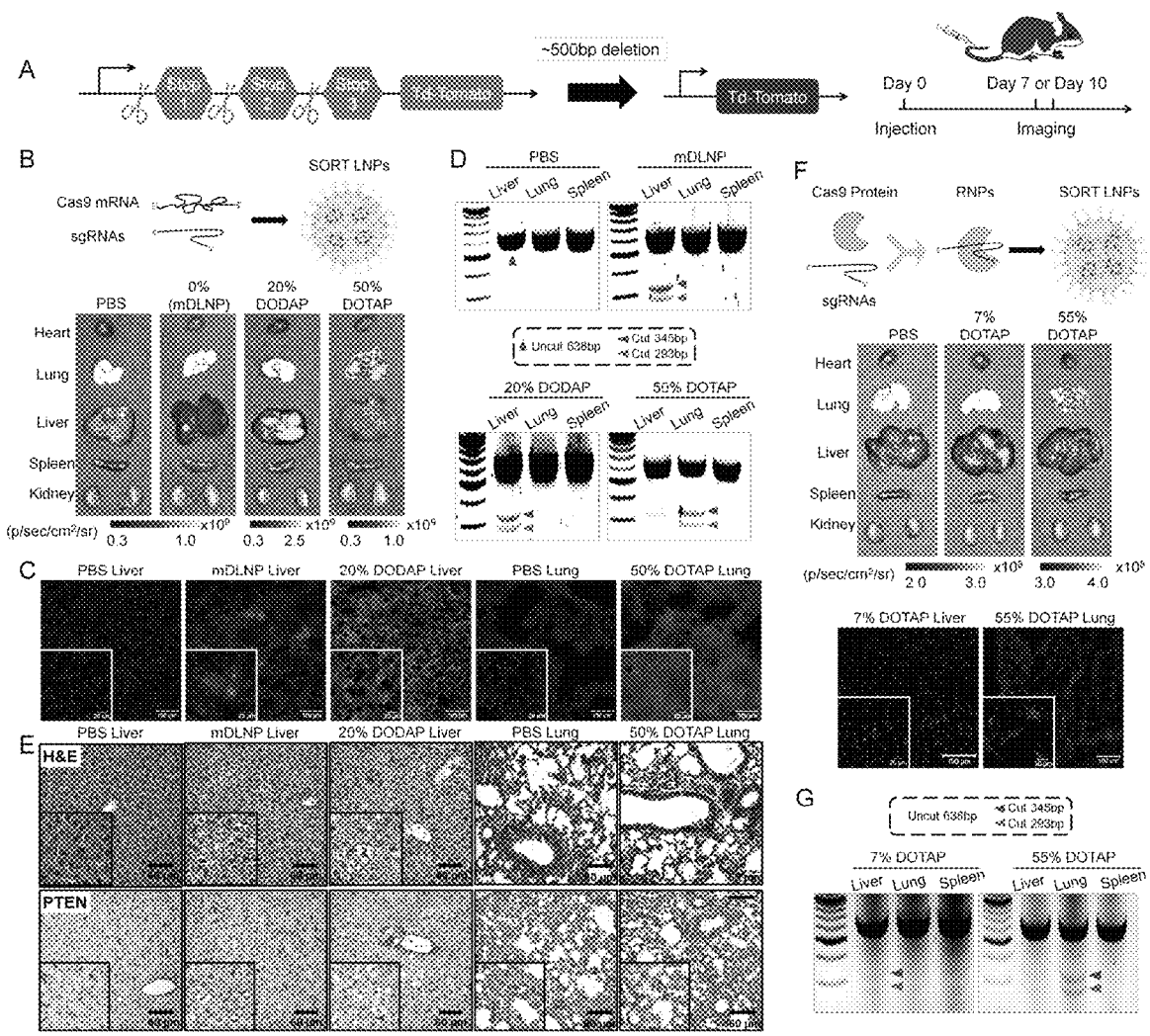
FIG. 37A-37G show SORT LNPs mediated tissue-specific CRISPR/Cas gene editing of Td-Tom transgenic mice and C57/BL6 wild type mice by co-delivering Cas9 mRNA and sgRNA and by delivering Cas9 RNPs. (37A) Schematic illustration shows that co-delivery of Cas9 mRNA (or Cas9 protein) and sgTom1 activates Td-Tom expression in Td-Tom transgenic mice. (37B) mDLNP and 20% DODAP LNPs induced Td-Tom fluorescence specifically in the liver and 50% DOTAP LNPs selectively edited the lung. Td-Tom fluorescence was detected 10 days following IV injection of Cas9 mRNA and modified sgTom1 (4/1, wt/wt) at a total dose of 2.5 mg/kg. (37C) tdTom expression was confirmed by confocal imaging of tissue sections. Scale bars=20 μm and 100 μm (37D) Cas9 mRNA and sgPTEN were co-delivered in SORT LNPs to selectively edit the liver, lung, and spleen of C57/BL6 mice (total dose of 2.5 mg/kg (Cas9 mRNA/sgPTEN, 4/1, wt/wt; measured 10 days following a single injection). The T7E1 assay indicated that tissue specific PTEN editing was achieved. (37E) H&E sections and IHC further confirmed successful PTEN editing. Clear cytoplasm indicated lipid accumulation in H&E sections and PTEN loss in IHC images. Scale bar=60 μm. (37F) Delivery of Cas9/sgTom1 ribonucleoprotein (RNP) complexes in 7% DOTAP or 55% DOTAP SORT LNPs induced Td-Tom fluorescence specifically in the liver and lungs, respectively. Td-Tom fluorescence was detected 7 days following IV injection of Cas9/sgTom1 RNPs at a dose of 1.5 mg/kg sgTom1. tdTom expression was confirmed by confocal imaging of tissue sections. Scale bars=20 μm and 100 μm (37G) Liver- and lung-tropic SORT LNPs also delivered Cas9/sgPTEN RNPs to selectively edit the liver and lungs C57/BL6 mice (1.5 mg/kg sgPTEN; measured 7 days following a single injection). The T7E1 assay indicated that tissue specific PTEN editing was achieved.
Figure 38:
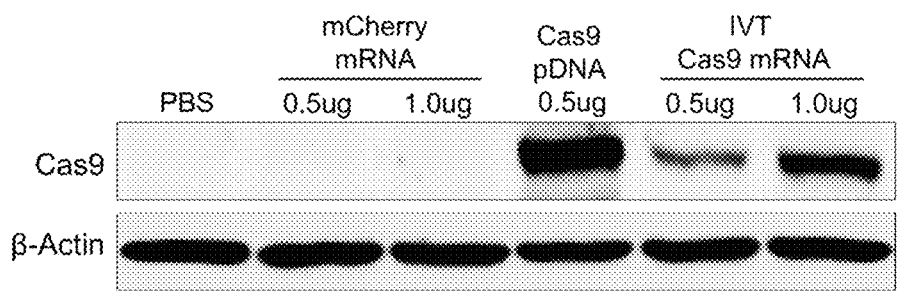
FIG. 38 shows IVT Cas9 mRNA was evaluated by western blot. 293T cells were seeded in 12-well plate the day before transfection, cells were treated for 24 h by each condition before performing western blot. Cas9 pDNA was delivered by Lipofectamine 2000 and mRNAs were delivered by mDLNPs.
Figures 39A, 39B:
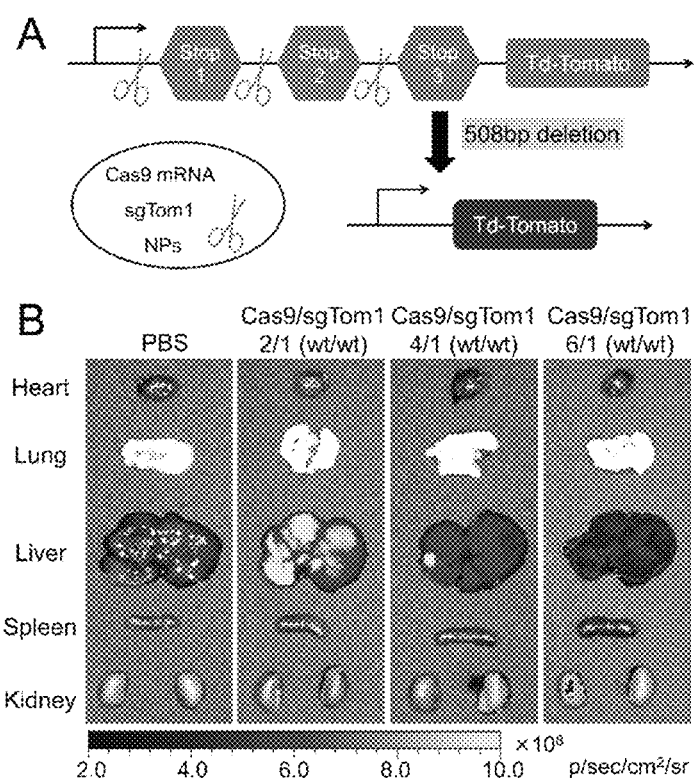
FIGS. 39A & 39B show weight ratios of IVT Cas9 mRNA to sgTom1 were optimized via Cas9 mRNA and sgRNA co-delivery strategy. (39A) Schematic illustration shows that co-delivery of Cas9 mRNA and sgTom1 activates Td-Tom expression in transgenic mouse. (39B) Td-Tom fluorescence of major organs was imaged at day 7 after IV injection, indicating that 2/1 of Cas9/sgTom1 (wt/wt) was optimal. The total RNA dose was 1 mg/kg, IVT Cas9 mRNA and modified sgTom1 were co-encapsulated by mDLNPs.

F. SORT Allows Tissue Specific Gene Editing Via IV Co-Delivery of Cas9 mRNA/sgRNA and by Delivery of Cas9 RNPs The ability of SORT LNPs to achieve tissue specific CRISPR/Cas gene editing via IV co-delivery of Cas9 mRNA and sgRNA in a single nanoparticle (FIGS. 37A, 38, & 39, Table 2) were next examined. The liver and lung targeting SORT LNPs were injected at a dose of 2.5 mg/kg total RNA (4:1 mRNA:sgRNA, wt:wt) and quantified gene editing 10 days following a single IV injection. As shown in FIG. 37B, strong tdTom fluorescence in the liver was observed for both the base LNP and 20% DODAP SORT LNP treated mice, and strong fluorescence in the lung of 50% DOTAP SORT LNP treated mice. All results were consistent with the Luc mRNA delivery results. Due to fast turnover of splenic immune cells in mice (Kamath et al., 2000), the weight ratio of Cas9/sgRNA was optimized to be 2/1 (FIG. 39) and tested the spleen editing two days after injection. Accounting for background autofluorescence, bright tdTom fluorescence was observed in the spleen of 30% 18PA-treated mice, and clear T7E1 cleavage bands were detected exclusively in DNA isolated from the spleen (no editing of liver or lungs) (FIG. 33). The fluorescence was then confirmed by imaging tissue sections with confocal microscopy (FIG. 37C).

Next, the direct delivery of Cas9 RNPs was explored, which is the most challenging strategy for synthetic carriers. The use of permanently cationic SORT lipids enabled Cas9 protein/sgtdTom complexes to be encapsulated with control over tissue tropism. IV injection of 7% DOTAP SORT LNPs enabled liver editing, while 55% DOTAP SORT LNPs enabled exclusive lung editing (FIG. 37F). These data indicate that the described methodology enables liver, lung, and spleen specific CRISPR/Cas gene editing.

To go beyond reporter mice, the ability of tissue specific LNPs to edit an endogenous target was tested. PTEN was selected because it is a well-established tumor suppressor expressed in most cells. Wild type C57BL/6 mice were injected with SORT LNPs co-loaded with Cas9 mRNA and sgPTEN (2.5 mg/kg total RNA). Generation of insertions and deletions (indels) was quantified 10 days following a single IV injection. As shown in FIG. 37D, clear DNA cleavage bands were observed in specific tissues by T7E1 assay which demonstrated that both base LNPs and 20% DODAP SORT LNPs mediated effective PTEN editing in liver, but not at all in lung or spleen. Remarkably, 50% DOTAP SORT LNPs showed PTEN editing exclusively in the lungs. To further confirm PTEN editing, H&E staining and immunohistochemistry (IHC) of tissue sections was performed. As shown in FIG. 37E, cells in tissue sections obviously displayed clear cytoplasm, which is a known phenotype of PTEN loss due to lipid accumulation (Xue et al., 2014). Moreover, negative staining of PTEN was observed in IHC sections in both liver and lung tissues, providing clear evidence for PTEN editing. Although spleen specific 18PA SORT LNP editing was more challenging to distinguish in the tdTom mouse model, clear spleen PTEN editing could be observed in wild type mice with the optimized weight ratio of Cas9/sgPTEN (2/1) and detection time (2 days). No editing of DNA in the liver or lungs was observed by the T7E1 assay performed on 18PA SORT LNP injected mice (FIG. 33). Finally, SORT was applied to Cas9 RNPs and examined endogenous editing of PTEN. As before, 7% and 55% DOTAP SORT LNPs containing Cas9 protein/sgPTEN enabled liver and lung specific editing, respectively (FIG. 37G). These results, targeting an endogenous gene, demonstrate rationally guided tissue selective gene editing achieved by synthetic carriers.

G. Materials and Methods

I. Materials 5A2-SC8 (Zhou et al., 2016), DLin-MC3-DMA (Jayaraman et al., 2012), and C12-200 (Love et al., 2010) were synthesized and purified by following published protocols. 1,2-dioleoyl-3-trimethylammonium-propane (DOTAP), dimethyldioctadecylammonium (DDAB), 1,2-dimyristoyl-sn-glycero-3-ethylphosphocholine (EPC), 1,2-dioleoyl-sn-glycero-3-phosphate (sodium salt) (18PA), 1,2-dimyristoyl-sn-glycero-3-phosphate (sodium salt) (14PA), sn-(3-oleoyl-2-hydroxy)-glycerol-1-phospho-sn-3'-(1',2'-dioleoyl)-glycerol (ammonium salt) (18:1 Hemi BMP, 18BMP), 1,2-dioleoyl-3-dimethylammonium-propane (DODAP), 1,2-distearoyl-sn-glycero-3-phosphocholine (DSPC), 2-((2,3-bis(oleoyloxy)propyl)dimethylammonio) ethyl ethyl phosphate (DOCPe) and 1,2-dioleoyl-sn-glycero-3-phosphoethanolamine (DOPE) were purchased from Avanti Polar Lipids. Cholesterol was purchased from Sigma-Aldrich. 1,2-Dimyristoyl-sn-glycerol-methoxy(poly ((ethylene glycol) MW 2000) (DMG-PEG2000) was purchased from NOF America Corporation. Cas9 protein was purchased from Thermo Fisher. The ONE-Glo+Tox Luciferase Reporter assay kit was purchased from Promega Corporation. Pur-A-Lyzer Midi Dialysis Kits (WMCO, 3.5 kDa) were purchased from Sigma-Aldrich. 4',6-Diamidino phenylindole dihydrochloride (DAPI) was purchased from Thermo Fisher Scientific. Cas9 mRNA was produced by in vitro translation (IVT). Cy5-labelled firefly luciferase mRNA (Cy5-Luc mRNA), unlabeled firefly luciferase mRNA (Luc mRNA), and mCherry mRNA were purchased from TriLink BioTechnologies. D-Luciferin (Sodium Salt) was purchased from Gold Biotechnology. Modified sgTom1 and sgPTEN (Table 2) were purchased from Synthego.

TABLE 2

Relative apparent pKa values of SORT LNPs measured by the TNS assay.

| mDLNP based LNPs | | | | | | MC3 and C12-200 based LNPs | | C1 based LNPs | |
|---|---|---|---|---|---|---|---|---|---|
| Name | PKa | Name | pKa | Name | pKa | Name | pKa | Name | pKa |
| mDLNP O | 6.46 O | 15% DDAB C | 7.21 C | 10% 14PA A | 5.15 A | 50% C12-200 I | 6.89 I | MC3 LNPs O | 6.28 O |
| 5% DOTAP C | 6.67 C | 40% DDAB C | >11.0 C | 20% 14PA A | 4.78 A | 10% 5A2-SC8 I | 6.34 I | 15% DOT MC3 C | 6.86 C |
| 10% DOTAP C | 6.92 C | 50% DDAB C | >11.0 C | 30% 14PA A | 3.73 A | 15% 5A2-SC8 I | 6.40 I | 50% DOT MC3 C | >11 C |
| 15% DOTAP C | 7.48 C | 5% EPC C | 6.51 C | 15% 18BMP A | 5.22 A | 20% 5A2-SC8 I | 6.44 I | 10% 18PA MC3 A | 6.12 A |
| 20% DOTAP C | 8.49 C | 15% EPC C | 6.76 C | 10% 18BMP A | 4.93 A | 25% 5A2-SC8 I | 6.49 I | 20% 18PA MC3 A | 5.66 A |
| 30% DOTAP C | 10.6 C | 40% EPC C | 9.45 C | 20% 18BMP A | 4.63 A | 30% 5A2-SC8 I | 6.48 I | 30% 18PA MC3 A | 5.21 A |
| 40% DOTAP C | >11.0 C | 50% EPC C | >11.0 C | 30% 18BMP A | 4.09 A | 20% DSPC Z | 6.40 Z | C12-200 LNPs O | 6.64 O |
| 50% DOTAP C | >11.0 C | 5% 18PA A | 4.53 A | 10% DODAP I | 6.22 I | 50% DSPC Z | 6.09 Z | 15% DOT C12-200 C | 6.77 C |
| 60% DOTAP C | >11.0 C | 10% 18PA A | 4.44 A | 20% DODAP I | 6.46 I | 80% DSPC Z | 4.84 Z | 50% DOT C12-200 C | >11 C |
| 70% DOTAP C | >11.0 C | 20% 18PA A | 4.43 A | 50% DODAP I | 6.44 I | 20% DOCPe Z | 6.78 Z | 10% 18PA C12-200 A | 5.95 A |
| 80% DOTAP C | >11.0 C | 30% 18PA A | 3.97 A | 80% DODAP I | 6.09 I | 50% DOCPe Z | 9.05 Z | 20% 18PA C12-200 A | 5.69 A |
| 90% DOTAP C | >11.0 C | 40% 18PA A | 3.52 A | 10% C12-200 I | 6.58 I | | | 30% 18PA C12-200 A | 5.55 A |
| 5% DDAB C | 6.55 C | 5% 14PA A | 5.34 A | 20% C12-200 I | 6.96 I | | | | |

|                            | 20% DODAP C1 I | 5.61 I |
|                            | 30% DODAP C1 I | 5.53 I |
|                            | 10% DOTAP C1 C | 5.89 C |
|                            | 20% DOTAP C1 C | 7.55 C |
|                            | 30% DOTAP C1 C | >11 C |

O = Original LNPs  C = Cationic Lipids + LNPs  A = Anionic Lipids + LNPs  I = Ionizable Lipids + LNPs  Z = Zwitterionic Lipids + LNPs

II. Nanoparticle Formation

RNA-loaded LNP formulations were formed using the ethanol dilution method (Zhou et al., 2016). The liver-targeted mRNA formulation (mDLNP) was developed and reported in a previous paper (Cheng et al., 2018), and the base formulations were prepared as previously described (Jayaraman et al., 2012; Love et al., 2010). Unless otherwise stated, all lipids with specified molar ratios were dissolved in ethanol and RNA was dissolved in 10 mM citrate buffer (pH 4.0). The two solutions were rapidly mixed at an aqueous to ethanol ration of 3:1 by volume (3:1, aq.:ethanol, vol:vol) to satisfy a final weight ratio of 40:1 (total lipids: mRNA), then incubated for 10 min at room temperature. To prepare SORT LNP formulations containing anionic SORT lipids (such as 18PA, 14PA and 18BMP), the anionic lipids were dissolved in tetrahydrofuran (THF) first then mixed with other lipid components in ethanol, finally yielding formulations with mRNA buffer (10 mM, pH 3.0) as described above. All formulations were named based on the additional lipids. Taking DOTAP mDLNP as an example, the internal molar ratio of mDLNP was fixed as reported in a published paper with 5A2-SC8/DOPE/Cholesterol/DMG-PEG of 15/15/30/3 (Cheng et al., 2018). DOTAP, as the additional lipid, was dissolved into the above ethanol lipid mixture with specified amount, making the molar ratio of 5A2-SC8/DOPE/Cholesterol/DMG-PEG/DOTAP equal to 15/15/30/3/X, then rapidly mixed with aq. mRNA solutions following the above standard protocol, finally producing SORT LNPs named Y % DOTAP, where Y means the molar percent of DOTAP in total lipids. Formulations with other additional lipids were formed similarly with the above methods (FIG. 20 and Table 3). For Cas9/sgRNA ribonucleoprotein (RNP) encapsulation, 1×PBS was used for formulation and the molar ratio of Cas9 and sgRNA was fixed at 1:3. After SORT LNP formation, the fresh LNP formulations were diluted with 1×PBS to 0.5 ng/μL mRNA (with final ethanol concentration <5%) for in vitro assays and size detection. For in vivo experiments, the formulations were dialyzed (Pur-A-Lyzer Midi Dialysis Kits, WMCO 3.5 kDa, Sigma-Aldrich) against 1×PBS for 2 h and diluted with PBS to 15 μL/g for intravenous (IV) injections.

TABLE 3 sgRNA sequences

| Name | Sequences (5' to 3') | PAM (5' to 3') | Notes |
| --- | --- | --- | --- |
| sgTom1 | AAGTAAAACCTCTACAAATG (SEQ ID NO: 1) | TGG | Chemical modified sgTom1 and sgPTEN were selected |
| sgPTEN | AGATCGTTAGCAGAAACAAA (SEQ ID NO: 2) | AGG | |

III. Characterization of mRNA Formulations

Size distribution and polydispersity index (PDI) were measured using Dynamic Light Scattering (DLS, Malvern MicroV model; He—Ne laser, λ=632 nm), zeta-potential was measured after diluting with 1×PBS. To measure the apparent $pK_a$ of mRNA formulations, the 2-(p-toluidino)-6-naphthalenesulfonic acid (TNS) assay was employed (Cheng et al., 2018; McLaughlin and Harary, 1976; Bailey and Cullis, 1994; Heyes et al., 2005), with some modification. mRNA formulations (60 µM total lipids) and the TNS probe (2 µM) were incubated for 5 min with a series of buffers, containing 10 mM HEPES, 10 mM MES (4-morpholineethanesulfonic acid), 10 mM ammonium acetate and 130 mM NaCl (the pH ranged from 2.5 to 11). The mean fluorescence intensity of each well (black bottom 96-well plate) was measured by a Tecan plate reader with $\lambda_{Ex}$=321 nm and $\lambda_{Em}$=445 nm and data was normalized to the value of pH 2.5. Typically, the apparent pKa is defined by the pH at half-maximum fluorescence. Although this method was useful for estimating LNP global/apparent $pK_a$ for most all LNPs, it could not be used for SORT LNPs containing >40% permanently cationic lipid because these LNPs are always charged. Therefore, the relative pKa was instead estimated compared to base LNP formulation (no added SORT lipid) when 50% of normalized signal was produced. This alternative calculation did not change the $pK_a$ for most LNPs but did allow estimation of permanently cationic SORT LNPs that agreed with experimental results for tissue selective RNA delivery. Thus, it can be suggested that the standard TNS assay be used when LNPs contain a single ionizable cationic lipid and the alternative 50% normalized signal method be used for systems such as SORT that contain complex mixtures of multiple lipids harboring a variety of charge states.

IV. In Vitro Luciferase Expression and Cell Viability Tests

Huh-7 or A549 cells were seeded into white 96-well plates at a density of 1×10⁴ cells per well the day before transfection. The media was replaced by 150 µL fresh DMEM medium (5% FBS), then 50 µL Luc mRNA formulations were added with fixed 25 ng mRNA per well. After incubation for another 24 h, ONE-Glo+Tox kits were used to detect mRNA expression and cytotoxicity based on Promega's standard protocol.

V. Animal Experiments

All animal experiments were approved by the Institution Animal Care and Use Committees of The University of Texas Southwestern Medical Center and were consistent with local, state and federal regulations as applicable. C57BL/6 mice were obtained from the UTSW Mouse Breeding Core Facility. B6.Cg-Gt(ROSA) 26Sor$^{tm9(CAG-tdTomato)Hze}$/J mice (also known as Ai9 or Ai9 (RCL-tdT) mice) were obtained from The Jackson Laboratory (007909) and bred to maintain homozygous expression of the Cre reporter allele that has a loxP-flanked STOP cassette preventing transcription of a CAG promoter-driven red fluorescent tdTomato protein. Following Cre-mediated recombination, Ai9 mice will express tdTomato fluorescence. Ai9 mice are congenic on the C57BL/6J genetic background.

VI. In Vivo Luc mRNA Delivery and Biodistribution

C57BL/6 mice with weight of 18-20 g, were IV injected by various Luc mRNA formulations at a dose of 0.1 or 0.05 mg/kg. n=2-4 per group. After 6 h, mice were intraperitoneal (IP) injected with D-Luciferin (150 mg/kg) and imaged by an IVIS Lumina system (Perkin Elmer). For biodistribution, C57BL/6 mice were IV injected with Cy5-Luc mRNA formulations at a dose of 0.5 mg/kg. Ex vivo imaging (Cy5 channel) was performed 6 h post injection.

VII. mRNA Synthesis

Optimized Cre recombinase mRNA and Cas9 mRNA was produced by in vitro transcription (IVT). Briefly, NLS-Cre fragment and Cas9 fragment were prepared by PCR program using pCAG-CreERT2 and pSpCas9(BB)-2A-GFP (PX458) as PCR template, respectively. Then, the these fragments were cloned into pCS2+MT vector with optimized 5'(3')-untranslated regions (UTR) and poly A sequences. IVT reactions were performed following standard protocols but with N1-methylpseudouridine-5'-triphosphate replacing the typical UTP. Finally, the mRNA was capped (Cap-1) by Vaccinia Capping Enzyme and 2' methyltransferase (NEB). Table 4 shows the primers used herein.

TABLE 4

Primers including the length of PCR products and their purposes

| Name | Forward Primers (5' to 3') | Reverse Primers (5' to 3') | Length | Notes |
| --- | --- | --- | --- | --- |
| Cas9 | ATATATGGATCCGCCACCATGGC CCCAAAGAAGAAGCGGAAGGTC (SEQ ID NO: 3) | ATATATGAATTCTTACTTTTTCTTT TTTGCCTGGCCGGCCTTTTCGTGGC CGCCGGCCTTTTGTCGCCTCCCAG (SEQ ID NO: 4) | 4233 bp | For IVT clone |
| Ca9 Seq-1 | CTGAGCGACATCCTGAGAGTGAAC (SEQ ID NO: 5) | | | For sequencing to confirm |
| Ca9 Seq-2 | | AGCAGGTCCTCTCTGTTCAG (SEQ ID NO: 6) | | the whole Cas9 sequences |

TABLE 4-continued

Primers including the length of PCR products and their purposes

| Name | Forward Primers (5' to 3') | Reverse Primers (5' to 3') | Length | Notes |
|---|---|---|---|---|
| Ca9 Seq-3 | GACGGCTTCGCCAACAGAAACTTC (SEQ ID NO: 7) | | | |
| Ca9 Seq-4 | | TTTGATGCCCTCTTCGATCCG (SEQ ID NO: 8) | | |
| Ca9 Seq-5 | GGGAGATCGTGTGGGATAAG (SEQ ID NO: 9) | | | |
| Ca9 Seq-6 | | ACTTCTTAGGGTCCCAGTCC (SEQ ID NO: 10) | | |
| Ca9 Seq-7 | AAGAGAGTGATCCTGGCCGAC (SEQ ID NO: 11) | | | |
| NLS-Cre | ATATATGGATCCGCCACCATGGCCAAGAAGAAGAGGAAGGTGGCCAATTACTGACCGTACACCAAAATTTGCCTG (SEQ ID NO: 12) | ATATATGAATTCTTAATCGCCATCTCCAGCAG (SEQ ID NO: 13) | 1083 bp | For IVT clone |
| PTEN | ATCCGTCTTCTCCCCATTCCG (SEQ ID NO: 14) | GACGAGCTCGCTAATCCAGTG (SEQ ID NO: 15) | 638 bp | For T7E1 assay |

The code sequences for NLS-Cre and Cas9 as following:

(SEQ ID NO: 16)
NLS-Cre:
ATGCCCAAGAAGAAGAGGAAGGTGGCCAATTTACTGACCGTACACCAA
AATTTGCCTGCATTACCGGTCGATGCAACGAGTGATGAGGTTCGCAAG
AACCTGATGGACATGTTCAGGGATCGCCAGGCGTTTTCTGAGCATACC
TGGAAAATGCTTCTGTCCGTTTGCCGGTCGTGGGCGGCATGGTGCAAG
TTGAATAACCGGAAATGGTTTCCCGCAGAACCTGAAGATGTTCGCGAT
TATCTTCTATATCTTCAGGCGCGGTCTGGCAGTAAAAACTATCCAG
CAACATTTGGGCCAGCTAAACATGCTTCATCGTCGGTCCGGGCTGCCA
CGACCAAGTGACAGCAATGCTGTTTCACTGGTTATGCGGCGTATCCGA
AAAGAAAACGTTGATGCCGGTGAACGTGCAAAACAGGCTCTAGCGTTC
GAACGCACTGATTTCGACCAGGTTCGTTCACTCATGGAAAATAGCGAT
CGCTGCCAGGATATACGTAATCTGGCATTTCTGGGGATTGCTTATAAC
ACCCTGTTACGTATAGCCGAAATTGCCAGGATCAGGGTTAAAGATATC
TCACGTACTGACGGTGGGAGAATGTTAATCCATATTGGCAGAACGAAA
ACGCTGGTTAGCACCGCAGGTGTAGAGAAGGCACTTAGCCTGGGGGTA
ACTAAACTGGTCGAGCGATGGATTTCCGTCTCTGGTGTAGCTGATGAT
CCGAATAACTACCTGTTTTGCCGGGTCAGAAAAAATGGTGTTGCCGCG
CCATCTGCCACCAGCCAGCTATCAACTCGCGCCCTGGAAGGGATTTTT
GAAGCAACTCATCGATTGATTTACGGCGCTAAGGATGACTCTGGTCAG
AGATACCTGGCCTGGTCTGGACACAGTGCCCGTGTCGGAGCCGCGCGA
GATATGGCCCGCGCTGGAGTTTCAATACCGGAGATCATGCAAGCTGGT
GGCTGGACCAATGTAAATATTGTCATGAACTATATCCGTAACCTGGAT
AGTGAAACAGGGGCAATGGTGCGCCTGCTGGAAGATGGCGATTAA (SEQ ID NO: 17)
SV40 NLS-Cas9-Nucleoplasmin NLS:
ATGGCCCCAAAGAAGAAGCGGAAGGTCGGTATCCACGGAGTCCCAGCA
GCCGACAAGAAGTACAGCATCGGCCTGGACATCGGCACCAACTCTGTG
GGCTGGGCCGTGATCACCGACGAGTACAAGGTGCCCAGCAAGAAATTC
AAGGTGCTGGGCAACACCGACCGGCACAGCATCAAGAAGAACCTGATC
GGAGCCCTGCTGTTCGACAGCGGCGAAACAGCCGAGGCCACCCGGCTG
AAGAGAACCGCCAGAAGAAGATACACCAGACGGAAGAACCGGATCTGC
TATCTGCAAGAGATCTTCAGCAACGAGATGGCCAAGGTGGACGACAGC
TTCTTCCACAGACTGGAAGAGTCCTTCCTGGTGGAAGAGGATAAGAAG
CACGAGCGGCACCCCATCTTCGGCAACATCGTGGACGAGGTGGCCTAC
CACGAGAAGTACCCCACCATCTACCACCTGAGAAAGAAACTGGTGGAC
AGCACCGACAAGGCCGACCTGCGGCTGATCTATCTGGCCCTGGCCCAC
ATGATCAAGTTCCGGGGCCACTTCCTGATCGAGGGCGACCTGAACCCC
GACAACAGCGACGTGGACAAGCTGTTCATCCAGCTGGTGCAGACCTAC
AACCAGCTGTTCGAGGAAAACCCCATCAACGCCAGCGGCGTGGACGCC
AAGGCCATCCTGTCTGCCAGACTGAGCAAGAGCAGACGGCTGGAAAAT
CTGATCGCCCAGCTGCCCGGCGAGAAGAAGAATGGCCTGTTCGGAAAC
CTGATTGCCCTGAGCCTGGGCCTGACCCCCAACTTCAAGAGCAACTTC
GACCTGGCCGAGGATGCCAAACTGCAGCTGAGCAAGGACACCTACGAC
GACGACCTGGACAACCTGCTGGCCCAGATCGGCGACCAGTACGCCGAC
CTGTTTCTGGCCGCCAAGAACCTGTCCGACGCCATCCTGCTGAGCGAC
ATCCTGAGAGTGAACACCGAGATCACCAAGGCCCCCCTGAGCGCCTCT
ATGATCAAGAGATACGACGAGCACCACCAGGACCTGACCCTGCTGAAA
GCTCTCGTGCGGCAGCAGCTGCCTGAGAAGTACAAAGAGATTTTCTTC -continued
```
GACCAGAGCAAGAACGGCTACGCCGGCTACATTGACGGCGGAGCCAGC

CAGGAAGAGTTCTACAAGTTCATCAAGCCCATCCTGGAAAAGATGGAC

GGCACCGAGGAACTGCTCGTGAAGCTGAACAGAGAGGACCTGCTGCGG

AAGCAGCGGACCTTCGACAACGGCAGCATCCCCCACCAGATCCACCTG

GGAGAGCTGCACGCCATTCTGCGGCGGCAGGAAGATTTTTACCCATTC

CTGAAGGACAACCGGGAAAAGATCGAGAAGATCCTGACCTTCCGCATC

CCCTACTACGTGGGCCCTCTGGCCAGGGGAAACAGCAGATTCGCCTGG

ATGACCAGAAAGAGCGAGGAAACCATCACCCCCTGGAACTTCGAGGAA

GTGGTGGACAAGGGCGCTTCCGCCCAGAGCTTCATCGAGCGGATGACC

AACTTCGATAAGAACCTGCCCAACGAGAAGGTGCTGCCCAAGCACAGC

ACTGCTGTACGAGTACTTCACCGTGTATAACGAGCTGACCAAGTGAAA

TACGTGACCGAGGGAATGAGAAAGCCCGCCTTCCTGAGCGGCGAGCAG

AAAAAGGCCATCGTGGACCTGCTGTTCAAGACCAACCGGAAAGTGACC

GTGAAGCAGCTGAAAGAGGACTACTTCAAGAAAATCGAGTGCTTCGAC

TCCGTGGAAATCTCCGGCGTGGAAGATCGGTTCAACGCCTCCCTGGGC

ACATACCACGATCTGCTGAAAATTATCAAGGACAAGGACTTCCTGGAC

AATGAGGAAAACGAGGACATTCTGGAAGATATCGTGCTGACCCTGACA

CTGTTTGAGGACAGAGAGATGATCGAGGAACGGCTGAAAACCTATGCC

CACCTGTTCGACGACAAAGTGATGAAGCAGCTGAAGCGGCGGAGATAC

ACCGGCTGGGGCAGGCTGAGCCGGAAGCTGATCAACGGCATCCGGGAC

AAGCAGTCCGGCAAGACAATCCTGGATTTCCTGAAGTCCGACGGCTTC

GCCAACAGAAACTTCATGCAGCTGATCCACGACGACAGCCTGACCTTT

AAAGAGGACATCCAGAAAGCCCAGGTGTCCGGCCAGGGCGATAGCCTG

CACGAGCACATTGCCAATCTGGCCGGCAGCCCCGCCATTAAGAAGGGC

ATCCTGCAGACAGTGAAGGTGGTGGACGAGCTCGTGAAAGTGATGGGC

CGGCACAAGCCCGAGAACATCGTGATCGAAATGGCCAGAGAGAACCAG

ACCACCCAGAAGGGACAGAAGAACAGCCGCGAGAGAATGAAGCGGATC

GAAGAGGGCATCAAAGAGCTGGGCAGCCAGATCCTGAAAGAACACCCC

GTGGAAAACACCCAGCTGCAGAACGAGAAGCTGTACCTGTACTACCTG

CAGAATGGGCGGGATATGTACGTGGACCAGGAACTGGACATCAACCGG

CTGTCCGACTACGATGTGGACCATATCGTGCCTCAGAGCTTTCTGAAG

GACGACTCCATCGACAACAAGGTGCTGACCAGAAGCGACAAGAACCGG

GGCAAGAGCGACAACGTGCCCTCCGAAGAGGTCGTGAAGAAGATGAAG

AACTACTGGCGGCAGCTGCTGAACGCCAAGCTGATTACCCAGAGAAAG

TTCGACAATCTGACCAAGGCCGAGAGAGGCGGCCTGAGCGAACTGGAT

AAGGCCGGCTTCATCAAGAGACAGCTGGTGGAAACCCGGCAGATCACA

AAGCACGTGGCACAGATCCTGGACTCCCGGATGAACACTAAGTACGAC

GAGAATGACAAGCTGATCCGGGAAGTGAAAGTGATCACCCTGAAGTCC

AAGCTGGTGTCCGATTTCCGGAAGGATTTCCAGTTTTACAAAGTGCGC

GAGATCAACAACTACCACCACGCCCACGACGCCTACCTGAACGCCGTC

GTGGGAACCGCCCTGATCAAAAAGTACCCTAAGCTGGAAAGCGAGTTC
```

```
GTGTACGGCGACTACAAGGTGTACGACGTGCGGAAGATGATCGCCAAG

AGCGAGCAGGAAATCGGCAAGGCTACCGCCAAGTACTTCTTCTACAGC

AACATCATGAACTTTTTCAAGACCGAGATTACCCTGGCCAACGGCGAG

ATCCGGAAGCGGCCTCTGATCGAGACAAACGGCGAAACCGGGGAGATC

GTGTGGGATAAGGGCCGGGATTTTGCCACCGTGCGGAAAGTGCTGAGC

ATGCCCCAAGTGAATATCGTGAAAAAGACCGAGGTGCAGACAGGCGGC

TTCAGCAAAGAGTCTATCCTGCCCAAGAGGAACAGCGATAAGCTGATC

GCCAGAAAGAAGGACTGGGACCCTAAGAAGTACGGCGGCTTCGACAGC

CCCACCGTGGCCTATTCTGTGCTGGTGGTGGCCAAAGTGGAAAAGGGC

AAGTCCAAGAAACTGAAGAGTGTGAAAGAGCTGCTGGGGATCACCATC

ATGGAAAGAAGCAGCTTCGAGAAGAATCCCATCGACTTTCTGGAAGCC

AAGGGCTACAAAGAAGTGAAAAAGGACCTGATCATCAAGCTGCCTAAG

TACTCCCTGTTCGAGCTGGAAAACGGCCGGAAGAGAATGCTGGCCTCT

GCCGGCGAACTGCAGAAGGGAAACGAACTGGCCCTGCCCTCCAAATAT

GTGAACTTCCTGTACCTGGCCAGCCACTATGAGAAGCTGAAGGGCTCC

CCCGAGGATAATGAGCAGAAACAGCTGTTTGTGGAACAGCACAAGCAC

TACCTGGACGAGATCATCGAGCAGATCAGCGAGTTCTCCAAGAGAGTG

ATCCTGGCCGACGCTAATCTGGACAAAGTGCTGTCCGCCTACAACAAG

CACCGGGATAAGCCCATCAGAGAGCAGGCCGAGAATATCATCCACCTG

TTTACCCTGACCAATCTGGGAGCCCCTGCCGCCTTCAAGTACTTTGAC

ACCACCATCGACCGGAAGAGGTACACCAGCACCAAAGAGGTGCTGGAC

GCCACCCTGATCCACCAGAGCATCACCGGCCTGTACGAGACACGGATC

GACCTGTCTCAGCTGGGAGGCGACAAAAGGCCGGCGGCCACGAAAAAG

GCCGGCCAGGCAAAAAAGAAAAAGTAA
```

VIII. Western Blot

The quality of IVT Cas9 mRNA was analyzed by western blot. 293T cells were seeded into 12-well plate with the density of $1\times10^5$ cells per well the day before transfection. Cells were treated with various formulations in 600 µL total volume for another 24 h, including mCherry mDLNP (0.5 µg mRNA per well), mCherry mDLNP (1.0 µg mRNA per well), IVT Cas9 mDLNP (0.5 µg mRNA per well), IVT Cas9 mDLNP (1.0 µg mRNA per well) and Lipofectamine2000/ Cas9 pDNA (0.5 µg pDNA per well). After washing three times with 1×PBS, 100 µL lysis buffer (50 mM Tris HCl, pH 7.4, with 150 mM NaCl, 1 mM EDTA and 1% TRITON X-100) and 1 µL protein inhibitor cocktail (100×, Thermo Fisher) were added into each well and rocked for 20 min at RT. Cell lysates were collected into 1.6 mL tubes and centrifuged for 10 min (13,000 g) at 4° C. Supernatants were collected into new tubes and stored in −80° C. if not used immediately. Before executing a western blot, protein concentrations were measured using a BCA assay kit (ThermoFisher). Fifteen microgram total proteins were loaded and separated by 4-20% polyacrylamide gel (ThermoFisher). Separated proteins were then transferred into polyvinylidene membrane (BioRad) and blocked by 5% BSA (dissolved in PBST) for 1 h at RT. Primary antibodies were applied overnight at 4° C. After washing four times using PBST, the membrane was incubated by secondary antibody for 1 h at RT then imaged with ECL substrate after washing four times by PBST (ThermoFisher).

IX. Gene Editing (Cre mRNA) in Td-Tomato Mice Model

Cre mRNA formulations were prepared as described above and performed IV injections (0.3 mg/kg Cre mRNA). After two days, mice (n=4 per group) were sacrificed and major organs were imaged by IVIS Lumina system (Perkin Elmer).

X. Cell Isolation and Staining for Flow Cytometry

To test the Td-Tomato$^+$ cells in cell types of each organ, cell isolation and staining was performed after 2 days of treatment with Cre mRNA formulations (0.3 mg/kg), then analyzed by flow cytometry.

For hepatocyte isolation, two-step collagenase perfusion was executed as described before (Cheng et al., 2018). Briefly, mice were anesthetized by isofluorane and fixed. Perfusion was started with liver perfusion medium (Thermo Fisher Scientific, 17701038) for 7-10 min, then switched to liver digestion medium (Thermo Fisher Scientific, 17703034) for another 7-10 min. The liver was collected into a plate containing 10 mL of liver digestion medium and cut to release the hepatocytes. Then the released hepatocytes were collected and washed twice with hepatocyte wash medium (Thermo Fisher Scientific, 17704024) and once with 1×PBS. After further isolated by straining and low speed (50×g) centrifugation, the hepatocytes were analyzed by FACS Aria II SORP machine (BD Biosciences).

For isolation and staining of spleen cell types, the removed spleen was minced up by a sterile blade and homogenized in 250 µL of 1× digestion medium (45 units/µL Collagenase I, 25 units/µL DNAse I and 30 units/µL Hyaluronidase). The spleen solution was transferred into a 15 mL tube that contained 5-10 mL of 1× digestion medium. Next, the spleen solution was filtered using a 70 µm filter and washed once with 1×PBS. A cell pellet was obtained by centrifuging for 5 min at the speed of 300×g. The supernatant was removed and the cell pellet was resuspended in 2 mL of 1×RBC lysis buffer (BioLegend, 420301) and incubated on ice for 5 min After incubation, 4 mL of cell staining buffer (BioLegend) was added to stop RBC lysis. The solution was centrifuged again at 300×g for 5 min to obtain a cell pellet. The single cells were resuspended in cell staining buffer and added into flow tubes that contained antibodies (100 µL total volume). The cells were incubated with antibodies for 20 min in the dark at 4° C. The stained cells were washed twice with 1 mL 1×PBS, then resuspended in 500 µL 1×PBS for flow cytometry analysis. The antibodies used were Pacific Blue anti-mouse CD45 (BioLegend, 103126), Alexa Fluor 488 anti-mouse/human CD11b (BioLegend, 101217), Alexa Fluor 647 anti-mouse CD19 (BioLegend, 115522) and PerCP-Cyanine5.5 Anti-Mouse CD3e (145-2C11) (Tonbo Biosciences, 65-0031). Ghost Dye Red 780 (Tonbo Biosciences, 13-0865-T500) was used to discriminate live cells.

For isolation and staining of lung cell types, isolated lungs were minced up by a sterile blade and then transferred into 15 mL tube that contained 10 mL 2× digestion medium (90 units/µL Collagenase I, 50 units/µL DNAse I and 60 units/µL Hyaluronidase) and incubated at 37° C. for 1 h with shaking. After incubation, any remaining lung tissue was homogenized. The following steps were similar with the spleen protocol described above. The antibodies here used were Pacific Blue anti-mouse CD45 (BioLegend, 103126), Alexa Fluor 488 anti-mouse CD31 (BioLegend, 102414) and Alexa Fluor 647 anti-mouse CD326 (Ep-CAM) (BioLegend, 118212). Ghost Dye Red 780 (Tonbo Biosciences, 13-0865-T500) was used to discriminate live cells.

XI. Gene Editing (Cas9 mRNA/sgRNA and Cas9/sgRNA RNPs) in Td-Tomato Mice Model

To evaluate in vivo gene editing, Td-Tom mice were selected for comparable weight and same sex. Cas9 mRNA and sgRNA was co-delivered to tdTomato (td-Tom) mice. Cas9 mRNA/sgTom1 (4/1, wt/wt) were co-delivered by various formulations with the total RNA dose equal to 2.5 mg/kg. 10 days following IV injection, the main organs were removed and imaged on an IVIS Lumina system. For spleen-targeted formulations, the total RNA dose was 4 mg/kg and the weight ratio of Cas9 mRNA to sgTom1 was 2/1, with a detection time was 2 days. For RNP delivery, the mole ratio of Cas9 protein to sgRNA was fixed at 1:3, the injection dose was 1.5 mg/kg RNA, and the detection time was day 7 after injection (n=2-4 per group). To confirm Td-Tom expression, tissue sections were further prepared and imaged by confocal microscopy. Briefly, tissue blocks were embedded into optimal cutting temperature compound (OCT) (Sakura Finetek) and cyro-sectioned (8 µm) on a Cryostat instrument (Leica Biosystems). Mounted tissue slices were stained with 4,6-diamidino-2-phenylindole (DAPI, Vector Laboratories) before imaging by confocal microscopy on a Zeiss LSM 700.

XII. Gene Editing (Cas9 mRNA/sgPTEN and Cas9/sgRNA RNPs) in C57BL/6 Mice

To examine endogenous gene editing in vivo, PTEN was selected. Wild type C57BL/6 mice were IV injected with various carriers by co-delivery of Cas9 mRNA and modified sgPTEN at a total dose of 2.5 mg/kg (4/1, mRNA/sgRNA, wt/wt) (n=2-4 per group). After 10 days, tissues were collected, and genomic DNA was extracted using a PureLink Genomic DNA Mini Kit (ThermoFisher). For spleen-targeted formulations, the total RNA dose was 4 mg/kg, Cas9 mRNA/sgTom1 was 2/1 (wt/wt), and the detection time was 2 days after injection. For RNP delivery, the mole ratio of Cas9 protein to sgRNA was fixed at 1:3, the injection dose was 1.5 mg/kg RNA, and the detection time was day 7 after injection (n=2-4 per group). After obtaining PTEN PCR products, the T7E1 assay (NEB) was performed to confirm gene editing efficacy by the standard protocol. Furthermore, evaluation of PTEN editing was executed on tissue sections by H&E staining and immunohistochemistry (IHC). Briefly, paraformaldehyde (PFA) fixed tissues were embedded in paraffin, sectioned and H&E stained by the Molecular Pathology Core at UTSW. The 4 µm sections were performed in the standard fashion and detected with Elite ABC Kit and DAB Substrate (Vector Laboratories) for IHC.

Example 9: Formulation Using Neutral Buffer

Figures 40A, 40B, 40C, 40D, 40E, 40F, 40G, 40H, 40I:
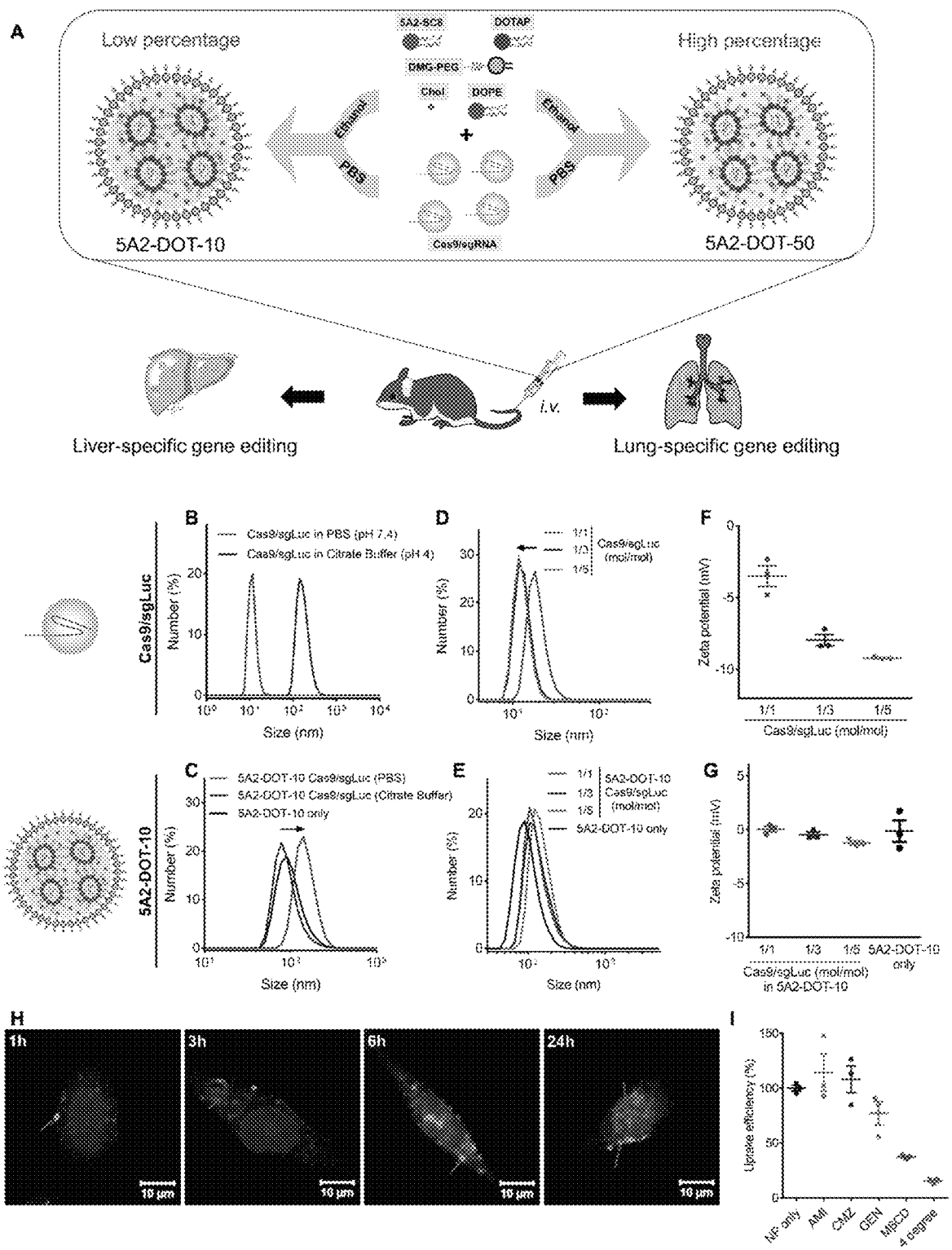
FIGS. 40A-40I show a modular approach was developed to enable systemic nanoparticle delivery of CRISPR/Cas9 ribonucleoproteins (RNPs) for tissue-specific genome editing. (40A) Addition of a permanently cationic supplemental component (e.g. DOTAP) into traditional LNP formulations enabled encapsulation and protection of Cas9/sgRNA complexes using neutral buffers during nanoparticle formation. Precise tuning of the DOTAP percentage mediated tissue-specific gene editing. (40B) Size distribution of Cas9/sgLuc RNPs prepared in PBS buffer (pH 7.4) and citrate buffer (pH 4.0). The size increase is likely due to denaturization. (40C) Size distribution of 5A2-DOT-10 encapsulating Cas9/sgLuc RNPs prepared in PBS and citrate buffer. 5A2-DOT-10 prepared without RNPs was used as control. (40D) Size distribution of Cas9/sgRNA RNPs with Cas9/sgLuc molar ratio of 1/1, 1/3 and 1/5. (40E) Size distribution of 5A2-DOT-10 encapsulating Cas9/sgLuc with molar ratio of 1/1, 1/3 and 1/5. (40F) Zeta potential of Cas9/sgRNA RNPs showing decreasing charge. (40G) No significant difference of zeta potential was observed for 5A2-DOT-10 encapsulating Cas9/sgLuc with different molar ratios. (40H) Time-dependent cellular uptake of 5A2-DOT-10 LNPs encapsulating EGFP-fused Cas9/sgRNAs showing cytoplasmic release and gradual entry into the nucleus. (40I) Inhibition of 5A2-DOT-10 LNP uptake was studied using specific endocytosis inhibitors. AMI: inhibitor of macropinocytosis; CMZ: inhibitor of clathrin-mediated endocytosis; GEN: inhibitor of caveolae-mediated endocytosis; MβCD: lipid rafts-mediated endocytosis; 4 degree: energy mediated endocytosis.

Cas9 RNPs was observed to denature in acidic buffer, resulting in an increase of hydrodynamic size from 10 nm to 150 nm (FIG. 40B). This makes RNP encapsulation into monodisperse nanoparticles difficult if not impossible. These studies focus on lipid nanoparticles (LNPs) because they are the most efficacious class of RNA delivery carriers (Wang et al., 2017; Doudna & Charpentier, 2014; Hajj & Whitehead, 2017; Sander & Joung, 2014) in preclinical models and in humans (Wood, 2018). Among the four components of LNPs [ionizable cationic lipids, zwitterionic phospholipids, cholesterol, and poly(ethylene glycol) (PEG) lipids)], ionizable cationic lipids with $pK_a$ around 6.4 are useful for activity because they bind negatively charged RNAs at the pH of mixing (e.g. pH 4 when the amines are protonated), lose charge at neutral pH before cellular uptake, and then acquire charge again as the pH in endosomes decreases to fuse with endosomal membranes and enable release of cargoes to the cytoplasm. However, this feature prevents effective encapsulation of cargoes at neutral pH because ionizable cationic lipids are uncharged at neutral pH. To overcome this challenge, the addition of a $5^{th}$ component, specifically a cationic lipid that would be positively charged at neutral pH, would allow for encapsulation of RNAs and proteins using neutral buffers (instead of acidic buffers), thus preserving the tertiary structure and stability of RNPs (FIG. 40A).

Figure 43:
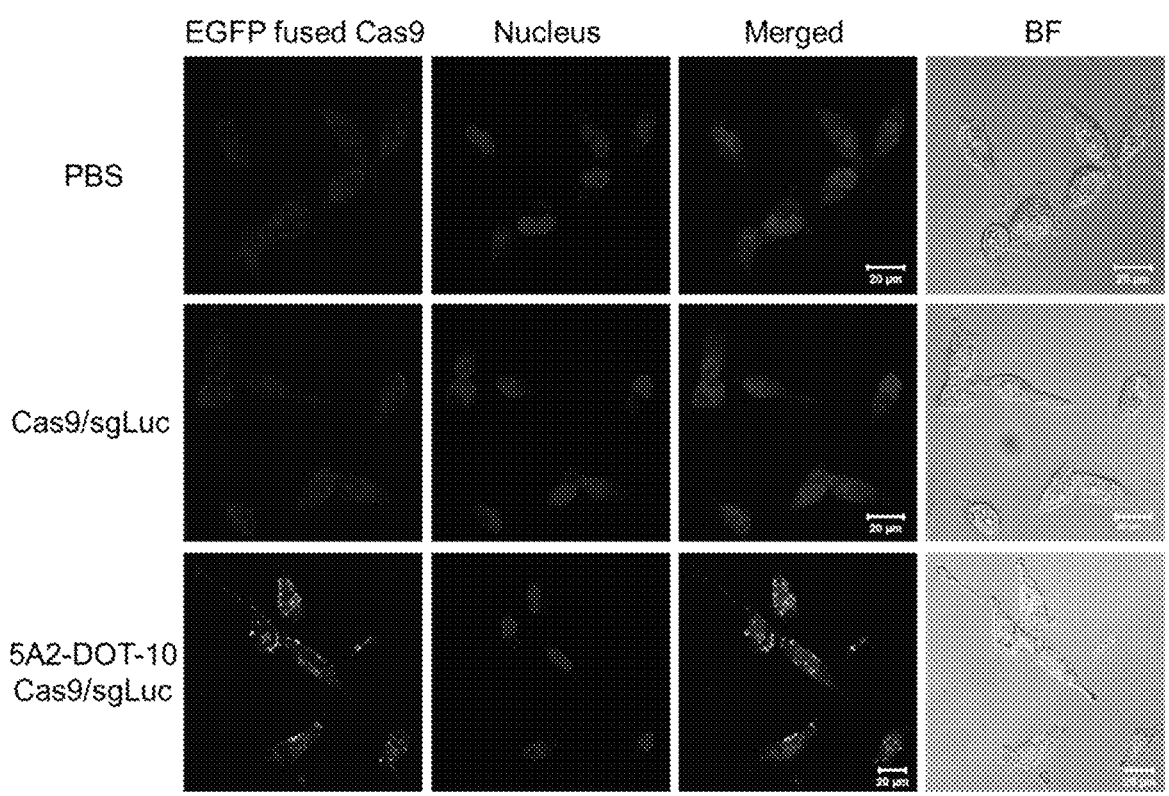
FIG. 43 shows confocal images showing cellular uptake of PBS (control), free Cas9/sgLuc complexes (control), and 5A2-DOT-10 Cas9/sgLuc in Hela-Luc cells 20 hr following treatment. Cas9-EGFP fusion protein was used to track the subcellular distribution of Cas9/sgRNA complexes. The Cas9/sgLuc complexes exhibited no detectable green fluorescence above background (PBS) inside cells, while bright green signals were detected after treated with 5A2-DOT-10.

To evaluate this strategy, 5A2-SC8 was selected as the ionizable cationic lipid because 5A2-SC8 LNPs safely deliver short siRNAs/miRNAs and long mRNAs to mice with compromised liver function, including MYC-driven liver cancer (Zhou et al., 2016; Zhang et al., 2018a; Zhang et al., 2018b) or genetic knockout of fumarylacetoacetate hydrolase (FAH) (Cheng et al., 2018). Introduction of a permanently cationic lipid (e.g. DOTAP) into traditional 4-component 5A2-SC8 LNP formulations indeed allowed controlled self-assembly to occur by mixing an ethanol solution of lipids with a PBS solution of RNPs (1/3, v/v). The incorporation of DOTAP was evaluated from 5 to 60 mole % of total lipids (FIG. 41), which revealed higher levels of gene editing at 10-20% in vitro and formation of stable RNP-loaded nanoparticles with size <200 nm (FIG. 42). Initially using sgRNA targeting reporter Luciferase (sgLuc), the size of LNPs with 10 mole % DOTAP incorporation (5A2-DOT-10: 5A2-SC8/DOPE/Chol/DMG-PEG/DOTAP=15/15/30/3/7 (mol/mol)) was observed, prepared using PBS buffer were slightly larger than nanoparticles without RNP loading. Identical LNPs prepared using low PH buffer did not change size, implying that RNPs were not encapsulated (FIG. 40C). To determine the optimal mole ratio between Cas9 protein and sgRNA, Cas9/sgRNA complexes at 1/1, 1/3 and 1/5 (mol/mol) were prepared, which decreased RNP size (FIG. 40D) and increased negative charge (FIG. 40F). The RNP ratio did not alter the size or zeta potential of the resulting LNPs after encapsulation (FIG. 1E, 1G). The surface charge of all LNPs was neutral, which not only indicates successful encapsulation, but is also useful for minimizing in vivo uptake by the immune mononuclear phagocyte system (MPS) system. To further examine whether 5A2-DOT-10 could successfully mediate delivery of RNPs into the nucleus, LNPs with encapsulated fluorescent EGFP-fused Cas9 protein were tracked. Free RNPs alone were unable to enter cells, as no green fluorescence above background was detectable (FIG. 43). Bright green fluorescence was observed in the cytoplasm of cells after 5A2-DOT-10 treatment for 3 hours. EGFP-fused Cas9 proteins were then observed to gradually enter the nucleus within 6 hours (FIG. 40H) due to the presence of nuclear localization signals on Cas9. Endocytosis was energy dependent and mainly dependent on lipid rafts, as treatment of MβCD, an inhibitor of lipid raft-based endocytosis, significantly inhibited cellular uptake of nanoparticles (FIG. 40I).

Figures 44A, 44B, 44C, 44D, 44E, 44F, 44G, 44H:
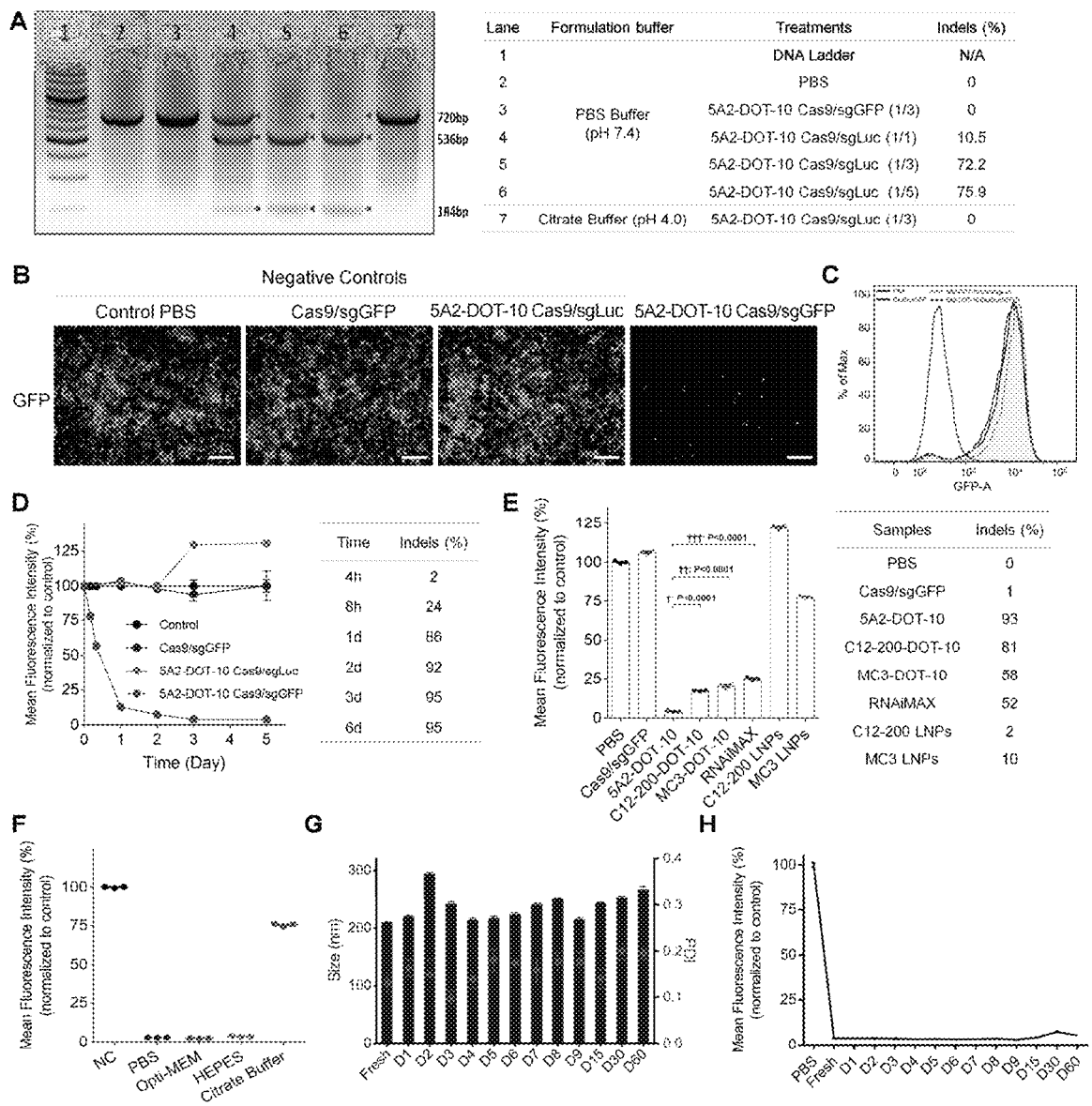
FIGS. 44A-44H show gene editing occurs quickly and effectively in vitro. (44A) T7EI cleavage assay of DNA isolated from HeLa-Luc cells treated with various nanoparticles and controls. Highly effective gene editing was mediated by 5A2-DOT-10 delivering Cas9/sgLuc RNPs (1/3 and 1/5). Indels (%) at Luc loci was quantified by ICE analysis. Note that gene editing was 0% for LNPs prepared using low pH citrate buffer (the currently used and established method). (44B) Fluorescence microscopy images of HeLa-GFP cells after treatment with various formulations. Scale bar=100 μm. 5A2-DOT-10 Cas9/sgGFP treatment significantly decreased GFP fluorescence. (44C) Flow cytometry analysis of HeLa-GFP cells after treatment with various formulations. The peak of GFP positive cells shifted completely to the left only for the 5A2-DOT-10 Cas9/sgGFP group, indicating almost all GFP positive cells went dark. (44D) Time-dependent GFP fluorescence intensity of HeLa-GFP cells after various treatments. Permanent GFP fluorescence loss after day 2 was observed with 5A2-DOT-10 Cas9/sgGFP treatment, while ICE analysis of Sanger sequencing data showed that indels was maintained at higher than 90% after day 2. (44E & 44F) Mean Fluorescence Intensity (%) of HeLa-GFP cells after treatment with Cas9/sgGFP alone, Cas9/sgGFP-loaded 5A2-SC8, C12-200, DLin-MC3-DMA LNP formulations containing 10% supplemental DOTAP, Cas9/sgGFP-loaded traditional C12-200 and DLin-MC3-DMA LNPs nanoformulations, and Cas9/sgGFP-loaded RNAiMAX. The GFP fluorescence significantly decreased after treated with all three DOTAP-modified formulations. The ICE analysis of Sanger sequencing data further confirmed the highest gene editing efficiency was with 5A2-DOT-10 LNPs. Mean±s.e.m. (n=3). Statistical significance was determined using a two-sided Student's t-test. †: t value=42.69, degrees of freedom (df)=4 ($P<0.0001$); ††: t value=16.75, degrees of freedom (df)=4 ($P<0.0001$); †††: t value=37.53, degrees of freedom (df)=4 ($P<0.0001$). P value <0.05 was considered statistically significant. (44G) 5A2-DOT-10 Cas9/sgGFP LNPs were stored at 4° C. for 2 months. The nanoparticle diameter and PDI was monitored over time. (44H) Periodic treatment of HeLa-GFP cells with stored LNPs showed that no activity was lost, indicating long-term LNP and RNP stability and potential for translation. All cells in the experiments above were treated with 24 nM sgRNA.
Figures 45A, 45B:
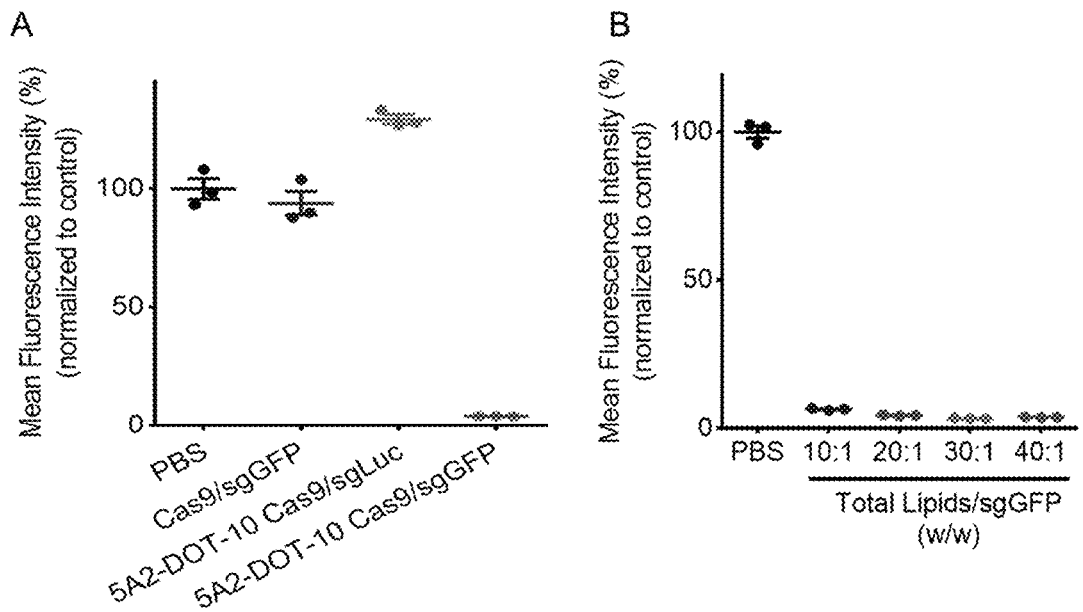
FIGS. 45A & 45B show gene editing of different nanoformulations in Hela-GFP cells. (45A) Mean fluorescence intensity (%) of Hela-GFP cells after treated with Cas9/sgGFP alone, 5A2-DOT-10 Cas9/sgLuc, and 5A2-DOT-10 Cas9/sgGFP (at total lipids/sgGFP weight ratio of 40:1). (45B) Mean fluorescence intensity (%) of Hela-GFP cells after treatment of 5A2-DOT-10 Cas9/sgGFP prepared with total lipids/sgGFP weight ratio at 10:1, 20:1, 30:1 and 40:1.

To quantify gene editing efficacy, HeLa-Luc and HeLa-GFP reporter cells were employed. Examining different Cas9/sgLuc ratios, gene editing was higher at 1/3 and 1/5 (FIG. 44A). The result of a T7 Endonuclease I (T7EI) assay demonstrated that most all target DNA bands (720 bp) were cut into two cleavage bands (536 bp and 184 bp). No cleavage bands were observed with control treatment groups. To test the hypothesis that neutral pH buffer is required to encapsulate RNPs with preservation of Cas9 function, the gene editing efficiency of 5A2-DOT-10 prepared using pH 4 citrate buffer was also evaluated. No cleavage bands were observed at all (FIG. 44A). The negative result was further confirmed by Sanger sequencing, providing additional evidence that the conventional acid-based formulation methods could not produce efficacious NPs. Switching to GFP-expressing cells, 5A2-DOT-10 encapsulating Cas9/sgGFP induced Indels into GFP DNA and knocked out nearly all GFP expression. Control groups exhibited similar fluorescence intensity with PBS-treated cells (FIG. 44B), which was confirmed by flow cytometry (FIGS. 44C & 45). Permanent gene editing was apparent by an indefinite loss of GFP in growing cells and confirmed by Sanger sequencing, where Inference of CRISPR Edits (ICE) analysis showed that indels reached 95% (FIG. 44D). With an eye towards clinical translation, RNP-loaded 5A2-DOT-10 stability was monitored at 4° C. for 2 months. LNPs did not change size and remained uniform (PDI<0.2) (FIG. 44G). Continual testing of 5A2-DOT-10 nanoparticles revealed constant gene editing activity, even after 60 days storage (FIG. 44H).

Figures 46A, 46B, 46C, 46D, 46E, 46F, 46G, 46H, 46I, 46J, 46K:
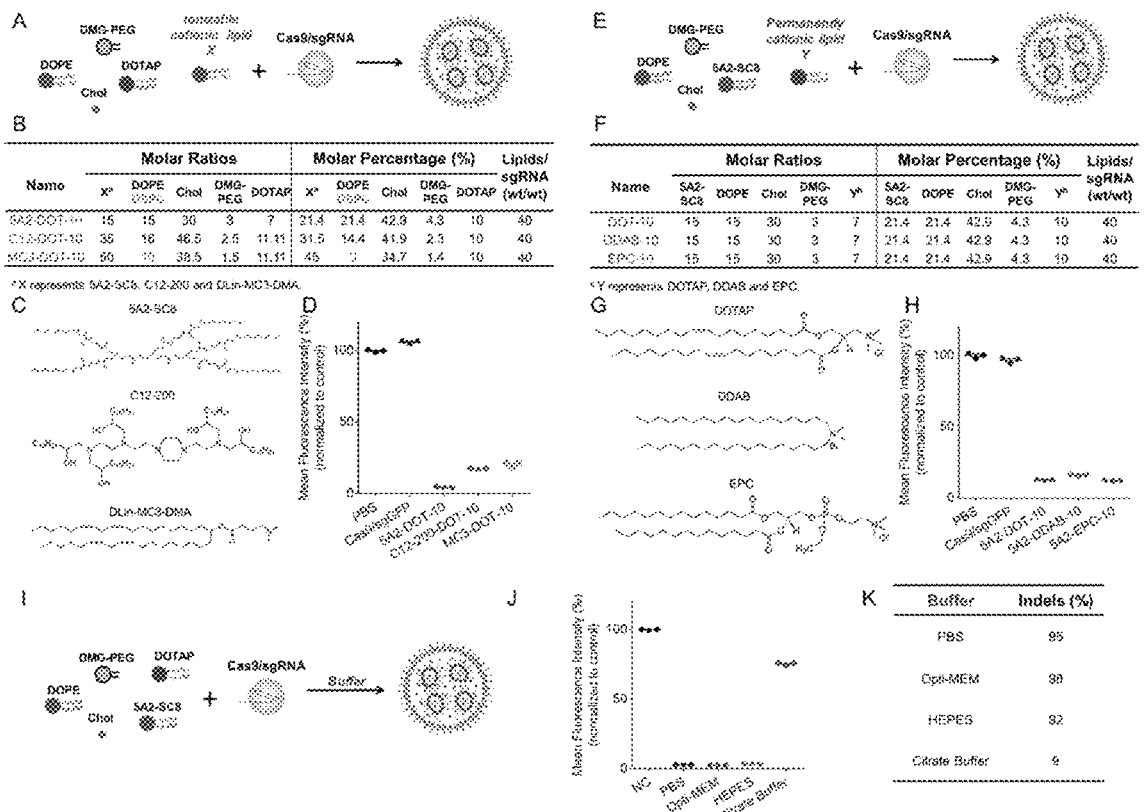
FIGS. 46A-46K show the generalizable RNP delivery strategy (FIG. 40A) is universal for ionizable cationic lipid nanoparticles (DLNPs, LLNPs, SNALPs) and for other cationic lipids that are positively charged at pH 7.4 and for other neutral buffers. (46A) Scheme of LNP formulation with different ionizable lipids. (46B) Details of LNP formulations with different ionizable lipids, including determinate molar ratio and percentage of each component, and the weight ratio of total lipids to sgRNA. (46C) Chemical structures of ionizable cationic lipids used in formulations, including 5A2-SC8, C12-200, and Dlin-MC3-DMA. (46D) Mean Fluorescence Intensity (%) of HeLa-GFP cells following treatment with Cas9/sgGFP RNPs encapsulated in 5A2-DOT-10, C12-200-DOT-10, and MC3-DOT-10. The GFP fluorescence significantly decreased after treatment with all three formulations. (46E) Scheme of LNP formulation preparation with different permanently cationic lipids. (46F) Details of LNP formulations with different permanently cationic lipids, including determinate molar ratio and percentage of each component, and the weight ratio of total lipids to sgRNA. (46G) Chemical structures of permanently cationic lipids used in formulations, including DOTAP, DDAB, and EPC. (46H) Mean Fluorescence Intensity (%) of HeLa-GFP cells after treatment with Cas9/sgGFP RNPs encapsulated in 5A2-DOT-10, 5A2-DDAB-10, and 5A2-EPC-10. Instead of DOTAP, other cationic lipids (DDAB and EPC) were also able to achieve efficient gene editing. (46I) Scheme of LNP formulation in different buffers. (46J) Mean Fluorescence Intensity (%) of HeLa-GFP cells after treatment with 5A2-DOT-10 formulated using different buffers, including PBS, Opti-MEM, HEPES, and Citrate Buffer.

The strategy of adding a permanently cationic lipid into classical 4-component LNPs to achieve efficient RNP delivery was not limited to the dendrimer-based ionizable lipid, 5A2-SC8. To prove this, supplemental DOTAP was included into nanoformulations prepared using other classes of ionizable materials: the well-known DLin-MC3-DMA lipid used in FDA-approved Onpattro (Wood, 2018) and the C12-200 lipidoid (FIGS. 46A-B). Even though they have very different chemical structures compared to 5A2-SC8 (FIG. 46C), all DOTAP-modified nanoparticles could efficiently edit cells whereas previously established C12-200 or MC3 formulations without DOTAP showed low editing efficiency (FIG. 44E). 5A2-DOT-10 also achieved higher editing efficiency than the positive control RNAiMAX. Because 5A2-DOT-10 LNPs were more efficacious than MC3-DOT-10 and C12-200-DOT-10, all subsequent experiments were performed using 5A2-SC8. In addition to DOTAP, other cationic lipids, including DDAB and EPC, were also introduced into LNP formulations (FIGS. 46E-G). The results were similar for all three cationic lipids with different chemical structures (FIG. 46H). These results indicate that this strategy is universal for ionizable cationic lipid nanoparticles (DLNPs, LLNPs, SNALPs) and for other cationic lipids that are positively charged at pH 7.4. Because this methodology allowed adjustment of the FDA-approved Onpattro formulation to enable delivery of RNPs, this approach offers different directions for clinically translatable treatment of human diseases.

A key to successful RNP delivery is replacement of the standard acidic buffer with PBS buffer to maintain protein stability. To test if this methodology is compatible with other neutral buffers, LNPs in PBS, Opti-MEM medium, and HEPES were formulated. Formulations prepared in citrate buffer (pH 4) were used as a control (FIG. 46I). Significant and equivalent gene editing (>90%) was achieved using LNPs prepared in all three neutral buffer conditions, but not in acidic buffer (FIG. 44F). ICE analysis of sequencing results was consistent with that shown by flow cytometry (FIG. 46K).

Figures 47A, 47B, 47C, 47D, 47E, 47F, 47G, 47H, 47I, 47J:
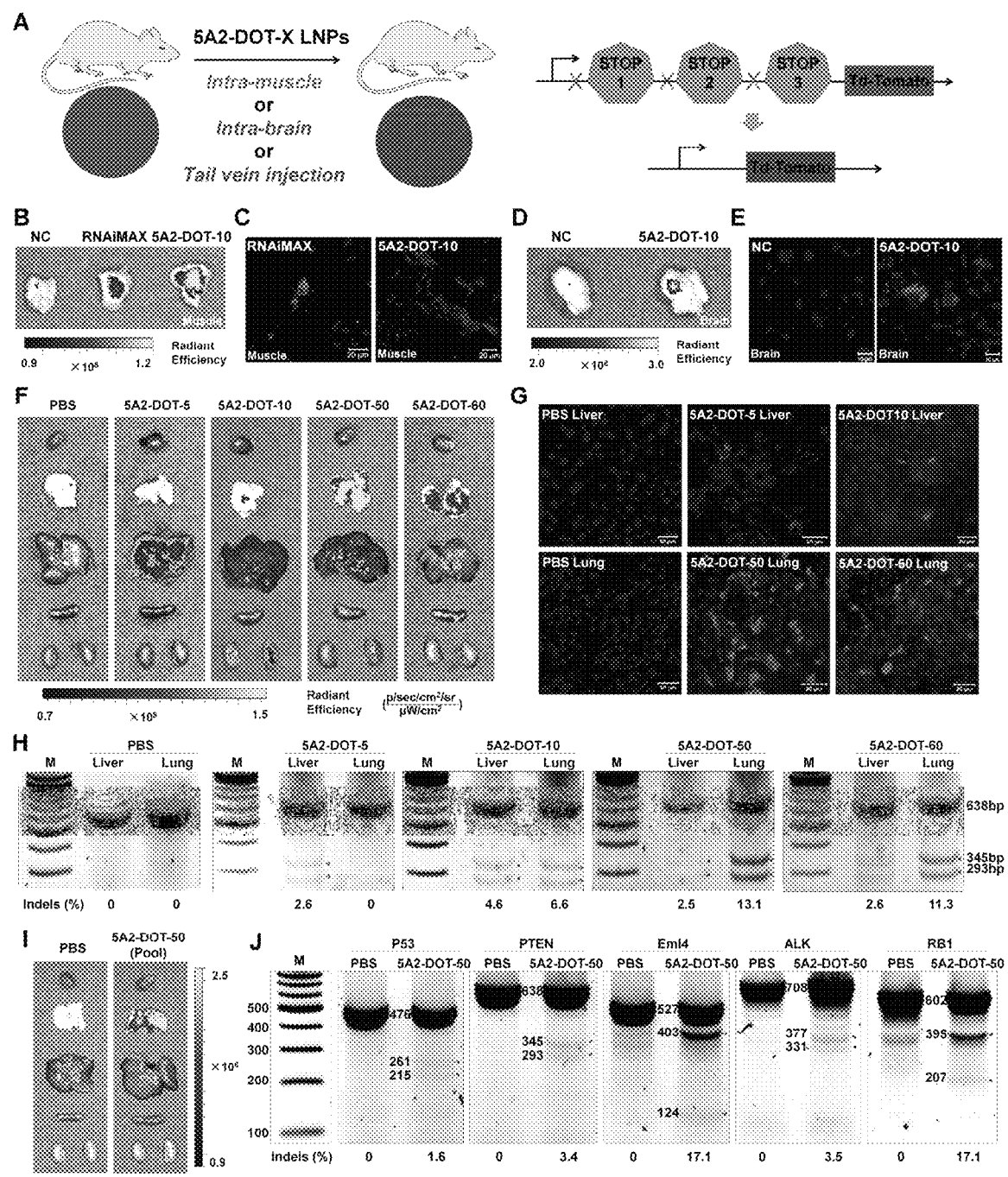

To examine in vivo gene editing, 5A2-DOT-10 encapsulating Cas9/sgTOM complexes to the Td-Tomato mouse model (FIG. 47A) were delivered. In these mice, CRISPR-mediated deletion of the Lox-Stop-Lox cassette turns on downstream tdTom expression in successfully edited cells. 5A2-DOT-10 LNPs loaded with Cas9/sgTOM RNPs were injected into the left leg of mice by intramuscular injection at dose of 1 mg/kg sgTOM. Due to previous use for direct injection gene editing, (Zuris et al., 2015) RNAiMAX complexed with Cas9/sgTOM RNPs was used for comparison. Higher Td-Tom fluorescence was observed in the muscle treated with 5A2-DOT-10 than in mice treated with RNAiMAX (FIG. 47B). Imaging of tissue sections further confirmed gene editing producing brighter red fluorescence in the 5A2-DOT-10 treatment group (FIG. 47C). 5A2-DOT-10 were injected into the brains of Td-Tom mice (0.15 mg/kg of sgTOM). Again, bright red signal was observed near the injection site, confirming editing of mouse brains (FIG. 47D-E).

The improved stability and efficacy of 5A2-DOT-10 could mediate successful systemic gene editing in tissues were evaluated. To examine this strategy for RNP delivery, LNPs were prepared with different molar percentages of DOTAP (5-60%) and delivered RNPs to Td-Tom mice IV (1.5 mg/kg of sgTOM). Td-Tom fluorescence was observed exclusively in the liver 7 days following injection of 5A2-DOT-5. Increasing the incorporated DOTAP percentage from 5 to 60% resulted in gradual fluorescence (CRISPR-guided gene editing) from liver to lung. 5A2-DOT-60 enabled mainly lung editing (FIG. 47F). These results indicate that deep tissue editing can be achieved in a tissue-specific manner by adjusting the inner lipid component chemistry and molar ratios. Tissue-specific editing was further confirmed by confocal imaging of tissue sections (FIG. 47G). The editing of an endogenous target, Pten, were then evaluated by systemically injecting LNPs encapsulating Cas9/sgPTEN RNPs into wild-type C57BL/6 mice. Clear T7EI cleavage bands were only detected in liver for 5A2-DOT-5 treated mice and in the lungs for 5A2-DOT-50 and 5A2-DOT-60 treated mice (FIG. 47H).

To evaluate whether it is possible to simultaneously edit multiple genes in vivo, Cas9 protein and six different sgRNAs into 5A2-DOT-50. sgTOM, sgP53, sgPTEN, sgEm14, sgALK and sgRB1 were loaded into Cas9 proteins were encapsulated. Td-Tom mice with 5A2-DOT-50 (Pool) by tail vein injection (0.33 mg/kg of each sgRNA) were then treated. After one week, bright Td-Tom fluorescence was detected in the lungs, indicating gene editing of TOM (FIG. 47I). Clear T7EI cleavage bands were observed at all other 5 genome loci, demonstrating 5A2-DOT-50 were able to edit multiple genes simultaneously and effectively (FIG. 47J) at low doses. Quantification analyses revealed editing efficiencies of targets up to 22% (FIGS. 47 & 48) in the lungs. The sgRNAs with end modifications of the first and last 3 nucleotides were used herein to enhance sgRNA stability and reproducibility (FIG. 49) (Finn et al., 2018; Hendel et al., 2015). Reports have shown that precise modifications to additional nucleotides can increase in vivo gene editing 2- to 4-fold compared to end-modified sgRNAs, (Finn et al., 2018; Yin et al., 2017) suggesting that the editing efficiencies reported herein could be higher with further sgRNA optimization. Nevertheless, the high potency and tissue specificity of 5A2-DOT-50 allowed for simultaneous editing of 6 targets in the lungs with one injection.

Animal models are traditionally generated by transgenesis or gene engineering in embryonic stem cells, which is time consuming and costly. Direct mutation of tumor- and other disease-related genes in adult mice using CRISPR/Cas provides a feasible approach for rapid generation of models. This has only been accomplished using costly lentiviruses that must be engineered for each target and by hydrodynamic injection into the liver (Xue et al., 2014; Maddalo et al., 2014). Since mutation of multiple genes is typically required to generate functional cancer models, the development of an inexpensive and effective non-viral nanoparticle-based approach for multiplexing is highly desirable. Since 5A2-DOT-X LNPs are potent, can simultaneously edit multiple targets, can be administered repeatedly, and provide tissue specificity, they provide a path to generate a wide variety of animal models.

Figures 48A, 48B, 48C, 48D, 48E, 48F, 48G, 48H:
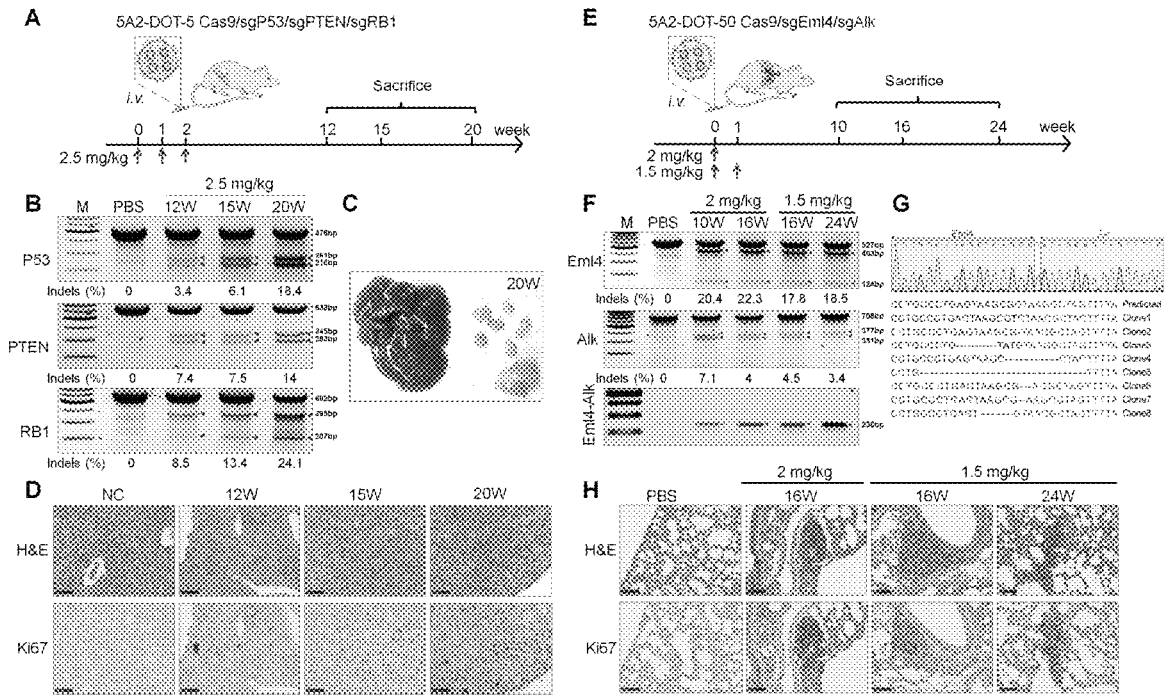

5A2-DOT-5 were employed to simultaneously knockout three tumor suppressor genes (P53, PTEN, and RB1) selectively in the liver. These genes have been identified in many human cancers, including liver. C57BL/6 mice were treated with weekly IV injections of 2.5 mg/kg total sgRNA for 3 weeks and detected the gene editing efficiency in mice livers (FIG. 48A). The clear cleavage bands at all three gene loci were observed after treatments of 2, 12, 15, and 20 weeks by T7EI assay (FIGS. 48B, 50, & 51). The cleavage bands were much brighter as time progressed, indicating tumor growth. When the mice were sacrificed at 15 weeks and 20 weeks, visible tumors were found on the liver, together with several metastatic tumors in the abdominal cavities (FIGS. 48C & 52). The tumor generation by H&E staining and IHC staining targeting tumor proliferation biomarker Ki67 (FIGS. 48D & 53) were also detected at various time points.

To generate a challenging lung cancer mouse model, the Em14-Alk chromosomal rearrangement was focused on, which is a complex mutation found in many solid human tumors, especially non-small cell lung cancers (Maddalo et al., 2014; Blasco et al., 2014). The Em14-Alk fusion protein generated after rearrangement between Em14 and Alk promotes cancer development. Exploiting the high potency and lung-targeting specificity of 5A2-DOT-50, once (at dose of 2 mg/kg of total sgRNA) or twice (at dose of 1.5 mg/kg of total sgRNA, weekly) IV doses were injected and evaluated the tumor generation process (FIG. 48E). Indel generation was detectable at all examined time points from extracted lung DNA from mice in both groups (FIGS. 48F & 54). Clear gene rearrangement bands were detected in the lungs of 5A2-DOT-50-treated mice, confirming successfully generated chromosomal rearrangements (FIGS. 48F & 54). The Em14-Alk rearrangement bands were much brighter as time progressed, suggesting proliferation of edited cells. The sequencing results after sub-cloning of these PCR amplicons further confirmed the Em14-Alk rearrangements (FIGS. 48G & 54). Several tumor lesions were observed in the lungs after 16 weeks and 24 weeks from H&E staining and Ki67 staining (FIGS. 48H, 55, & 56). These results show that a single injection of 5A2-DOT-50 LNPs could successfully generate chromosomal rearrangements and lead to lung tumor generation in adult mice. These LNPs are therefore positioned to accelerate in situ creation of a variety of disease models.

B. Materials and Methods

I. Materials.

5A2-SC8 (Zhou et al., 2016), DLin-MC3-DMA (Jayaraman et al., 2012), and C12-200 (Love et al., 2010) were synthesized and purified by following published protocols. 1,2-dioleoyl-sn-glycero-3-phosphoethanolamine (DOPE), 1,2-dioleoyl-3-trimethylammonium-propane (DOTAP), dimethyldioctadecylammonium (DDAB), 1,2-dimyristoyl-sn-glycero-3-ethylphosphocholine (EPC), and 1,2-distearoyl-sn-glycero-3-phosphocholine (DSPC) were purchased from Avanti Polar Lipids. Cholesterol was purchased from Sigma-Aldrich. 1,2-Dimyristoyl-sn-glycerol-methoxy (poly((ethylene glycol) MW 2000) (DMG-PEG2000) was purchased from NOF America Corporation. The ONE-Glo+ Tox Luciferase Reporter assay kit was purchased from Promega Corporation. Pur-A-Lyzer Midi Dialysis Kits (WMCO, 3.5 kDa) were purchased from Sigma-Aldrich. 4',6-Diamidino-2-phenylindole dihydrochloride (DAPI), Hoechst 33342, DLS Ultramicro cuvettes, Lipofectamine RNAiMAX Transfection Reagent, and Lab-Tek chambered cover glass units were purchased from Thermo Fisher Scientific. Cas9 protein and Ki-67 monoclonal antibody was purchased from Thermofisher. GenCrispr NLS Cas9-EGFP Nuclease was purchased from GenScript. Modified sgRNAs were purchased from Synthego.

II. Cas9/sgRNA Complex Preparation.

Separate solutions of Cas9 proteins and sgRNAs in the notated buffers were mixed together at equal volumes. After mixing, the RNPs were allowed to form over 5 minutes of incubation at room temperature for full Cas9/sgRNA complex self-assembly. The mole ratios of Cas9 protein to sgRNA used were 1/1, 1/3 and 1/5.

III. Optimized Nanoparticle Formulations and Characterization.

Ionizable cationic lipids (5A2-SC8, C12-200, or DLin-MC3-DMA) (Zhou et al., 2016; Jayaraman et al., 2012; Love et al., 2010), zwitterionic lipids (DOPE or DSPC), cholesterol, DMG-PEG, and permanently cationic lipids (DOTAP, DDAB, or EPC) were dissolved in ethanol at given molar ratios. Cas9/sgRNA complexes were dissolved in 1×PBS buffer. The Cas9/sgRNA RNP complexes solution in PBS buffer was pipette mixed rapidly into the lipids solution in ethanol at a volume ratio of 3:1 (Cas9/sgRNA RNPs: lipids, v/v), such that the weight ratio of total lipids to sgRNA was 40:1 (wt), then incubated for 15 min at room temperature. Afterwards, the fresh formulations were directly characterized and used for in vitro assays. For animal experiments, the formulations were dialyzed (Pur-A-Lyzer Midi Dialysis Kits, WMCO 3.5 kDa) against 1×PBS for 1 h to remove ethanol before topical injections (intra-muscle or intra-brain injection) or systemic injection (intravenous injection). The size distribution and zeta potential of nanoformulations were measured using Dynamic Light Scattering (DLS, Malvern; He—Ne Laser, 2=632 nm; detection angle=173°).

IV. RNAiMAX Formulations.

For preparation of RNAiMAX complexing RNPs, the Cas9/sgRNA complex was prepared in Opti-MEM and mixed gently with Lipofectamine RNAiMAX Transfection Reagent diluted in Opti-MEM (at dose of 1 μL RNAiMAX/ μg sgRNA). The mixture solution was incubated at room temperature for 30 minutes to complete the complexation.

V. Standard LNP Formulations.

For preparation of C12-200 and MC3 LNPs encapsulating RNPs, Cas9/sgRNA RNP complexes solution in citrate buffer (pH 4.0) was pipette mixed rapidly into the lipids solution in ethanol at a volume ratio of 3:1 (Cas9/sgRNA RNPs:total lipids, v/v), such that the weight ratio of total lipids to sgRNA was 40:1 (wt/wt), then incubated for 15 mM at room temperature. The molar ratio of C12-200/DOPE/Chol/DMG-PEG was 35/16/46.5/2.5 for C12-200 LNPs; the molar ratio of DLin-MC3-DMA/DSPC/Chol/DMG-PEG was 50/10/38.5/1.5 for MC3 LNPs.

VI. Cellular Uptake and Uptake Mechanism of 5A2-DOT-10 Cas9/sgLuc Treatment.

To examine cellular uptake, HeLa-Luc cells were seeded into Lab-Tek Chambered Coverglass (8 wells) at a density of $2\times10^4$ cells per well and incubated at 37° C. overnight. Then, the old media was replaced with 150 μL of fresh DMEM containing 10% FBS and treated with 50 μL of 5A2-DOT-10 encapsulating Cas9-EGFP/sgLuc RNPs (9 nM of sgRNA per well). At 1 h, 3 h, 6 h, and 24 h after treatment, cells were washed three times with PBS and stained with Hoechst (0.1 mg/mL) for 15 min at 37° C., then imaged by confocal microscopy (Zeiss LSM 700).

To examine the uptake mechanism, assays of specific inhibition on endocytosis pathways were evaluated using Hela-Luc cells. 5A2-DOT10 only treatment was used as a control. HeLa-Luc cells were seeded at a density of $5\times10^5$ cells per well in 12-well plates and incubated in DMEM complete medium for 24 h. The cells were then washed with PBS and followed by pre-incubating at 37° C. for 1 h with one of the following endocytosis inhibitors dissolved in Opti-MEM: 20 μM chlorpromazine (CMZ, an inhibitor of clathrin-mediated endocytosis), 2 mM Amiloride (AMI, an inhibitor of macropinocytosis), 200 μM Genistein (GEN, an inhibitor of caveolae-mediated endocytosis), 5 mM Methyl-β-cyclodextrin (MβCD, an inhibitor of lipid rafts-mediated endocytosis). Next, the medium was removed and replaced with complete DMEM medium containing 5A2-DOT-10 Cas9/sgLuc (24 nM sgLuc) for another 30 min. After that, the medium was removed and the cells were washed three times with PBS. The cells were then collected and analyzed by flow cytometry. All experiments were carried out in triplicate. Here, Cas9-EGFP protein was used to formulate Cas9/sgLuc complex. To evaluate whether it is energy dependent endocytosis, the cells were also pre-incubated under 4° C. for 1 h, and then treated with complete DMEM medium containing 24 nM of 5A2-DOT-10 Cas9/sgLuc (24 nM sgLuc) for another 30 min before analysis by flow cytometry.

VII. T7EI Assay to Detect Genomic Editing.

For in vitro genomic DNA editing analysis, HeLa-Luc cells were seeded into 12-well plates at a cell density of $1.5\times10^5$ cells/well and incubated overnight. Then, different nanoformulations containing 24 nM of sgRNA were added to cells. After 3 days, the cells were collected, washed and re-suspended in 50 μL of 1× passive lysis buffer (Promega) together with 2 μL of proteinase K (Thermofisher). Afterwards, a lysis PCR program (65° C. for 15 min, 95° C. for 10 min) was run to obtain cell lysates. The targeted genomic loci were then amplified using the following PCR amplification program (95° C. for 5 min; (95° C. for 30 sec; 60-64° C. for 30 sec; 72° C. for 1 min) for 40 cycles; 72° C. for 7 min and then keep at 4° C.). Cell lysates were used as DNA templates. The amplicons were then purified using PCR purification kits (Qiagen) and 200 ng of the purified DNA was added to 19 μL of annealing reaction containing 1× NEBuffer 2. Then the PCR products were annealed in a thermocycler using the following conditions (95° C. for 5 min, then the mixture was cooled from 95° C. to 85° C. with Ramp Rate of −2° C./second, following 85° C. to 25° C. with Ramp Rate of −0.1° C./second, then keep at 4° C.) to form heteroduplex DNA. Afterwards, 1 μL of T7EI (NEB) was added and incubated at 37° C. for 15 min. The cleavage reaction was then stopped by adding 1.5 uL of 0.25M EDTA. Next, the digested DNA was analyzed using 2.5% agarose gel electrophoresis. All primers used for T7EI assay are listed in Table 5.

TABLE 5

| sgRNA Sequences | | |
| --- | --- | --- |
| Name | Target Sequences (5' to 3') | PAM (5' to 3') |
| sgLUC | CTTCGAAATGTCCGTTCGGT (SEQ ID NO: 18) | TGG |
| sgGFP | GAAGTTCGAGGGCGACACCC (SEQ ID NO: 19) | TGG |
| sgTOM | AAGTAAAACCTCTACAAATG (SEQ ID NO: 20) | TGG |

TABLE 5-continued sgRNA Sequences

| Name | Target Sequences (5' to 3') | PAM (5' to 3') |
|---|---|---|
| sgPTEN | AGATCGTTAGCAGAAACAAA (SEQ ID NO: 21) | AGG |
| sgP53 | GTGTAATAGCTCCTGCATGG (SEQ ID NO: 22) | GGG |
| sgRB1 | TCTTACCAGGATTCCATCCA (SEQ ID NO: 23) | CGG |
| sgEml4 | CCTGCCCTGAGTAAGCGACA (SEQ ID NO: 24) | CGG |
| sgAlk | TCCTGGCATGTCTATCTGTA (SEQ ID NO: 25) | AGG |

For in vivo genomic DNA editing analysis, genomic DNA was extracted from tissues using PureLink Genomic DNA Mini Kit (Invitrogen) according to manufacturer's instructions. Subsequently, the aforementioned procedures were followed as described above for T7EI detection.

The fragmented PCR products were analyzed and the indels percentages were calculated based on the following formula:

$$\% \text{ gene modification} = 100 \times (1-(1-\text{fraction cleaved})^{1/2})$$

where the fraction cleaved is the sum of the cleavage product peaks divided by the sum of the cleavage product and parent peaks.[5]

VIII. Sanger Sequencing to Detect Genome Editing.

Purified PCR amplicons of the T7EI assay together with their forward primers were sequenced by The McDermott Center Sequencing core facility in UT Southwestern Medical Center. The sequencing data were finally analyzed using online analysis software, ICE Analysis, which is a web tool provided by Synthego.

IX. In Vitro Gene Editing in Hela-GFP Cells.

HeLa-GFP reporter cells were cultured in DMEM containing 10% FBS and 1% penicillin/streptomycin at 37° C./5% $CO_2$. For the experiments, HeLa-GFP cells were seeded into 12-well plates at a cell density of $1.5 \times 10^5$ cells per well and incubated overnight. Then, the medium was replaced with 0.5 mL of fresh complete DMEM and 100 uL of nanoparticle dispersion were added (the final concentration of sgRNA was fixed at 24 nM). Three days after treatment, the cells were analyzed using a fluorescence microscope (Keyence). For the flow cytometry analysis, the cells were collected, washed with PBS, re-suspended in PBS, and analyzed using a BD Analyzers LSRFortessa SORP (BD Biosciences).

X. Stability of 5A2-DOT-10 Cas9/sgGFP.

To measure stability, 5A2-DOT-10 LNPs encapsulating Cas9/sgGFP RNP complexes were prepared and stored them at 4° C. for 2 months. The size and PDI of these nanoparticles were tested after storing for different times and their gene editing efficiency were also evaluated in HeLa-GFP cells by adding nanoparticles (24 nM sgRNA dose) and quantifying gene editing after 3 days. For each time point, an aliquot of stored 5A2-DOT-10 LNPs encapsulating Cas9/sgGFP RNPs was taken and analyzed (size, PDI, efficacy).

XI. Animal Experiments.

All animal experiments were approved by the Institution Animal Care and Use Committees of The University of Texas Southwestern Medical Center and were consistent with local, state and federal regulations as applicable. C57BL/6 mice were obtained from the UTSW Mouse Breeding Core Facility. B6.Cg-Gt(ROSA) 26Sor$^{tm9(CAG-tdTomato)Hze}$/J mice (also known as Ai9 or Ai9 (RCL-tdT) mice) were obtained from The Jackson Laboratory (007909) and bred to maintain homozygous expression of the Cre reporter allele that has a loxP-flanked STOP cassette preventing transcription of a CAG promoter-driven red fluorescent tdTomato protein. Following Cas9/sgRNA RNPs mediated gene editing, Ai9 mice will express tdTomato fluorescence. Ai9 mice are congenic on the C57BL/6J genetic background.

XII. In Vivo Gene Editing.

For gene editing in muscles, Td-Tomato mice were injected with 5A2-DOT-10 LNPs encapsulating Cas9/sgTOM RNP complexes at dose of 1 mg/kg of sgTOM in the left leg by intra-muscle injection. RNAiMAX encapsulating Cas9/sgTOM RNP complexes was used as positive control. After treatment for 7 days, the muscle tissues of all treatment groups were collected and imaged using an IVIS Lumina system (Perkin Elmer). Afterwards, the muscle tissues were embedded in optimal cutting temperature (OCT) compound and cut into 10 μm slices. The sections were fixed with 4% Paraformaldehyde (Thermo Fisher Scientific) for 20 min, washed three times using PBS buffer. Afterwards, one drop of ProLong Gold Mountant with DAPI (Thermo Fisher Scientific) was applied onto each slide. A coverslip was placed, and the slides were imaged by confocal microscopy (Zeiss LSM 700). For gene editing in brain, Td-Tomato mice were injected with 5A2-DOT-10 LNPs encapsulating Cas9/sgTOM RNP complexes at dose of 0.15 mg/kg of sgTOM by intra-brain injection. After treatment for 6 days, the brains were excised and imaged using IVIS Lumina system. Frozen sections of brains were prepared as the protocol mentioned above and imaged by confocal microscopy.

For gene editing by i.v. injection, Td-Tomato mice were treated with 5A2-DOT-X LNPs containing different percentage of DOTAP at dose of 1.5 mg/kg of sgTOM by tail vein injection. After treatment for 7 days, all organs were collected and imaged using IVIS Lumina system. The frozen sections of these tissues were prepared as the protocol mentioned above and imaged by confocal microscopy.

XIII. PCR for Em14-Alk Rearrangements.

The in vivo Em14-Alk rearrangements were tested by nested PCR (Blasco et al., 2014). For the first round PCR, 40 ng of genomic DNA was used as template with PCR program of 95° C. for 5 min; (95° C. for 30 sec; 64° C. for 30 sec; 72° C. for 30 sec) for 18 cycles; 72° C. for 7 min and then keep at 4° C. For the second round PCR, 1 μl of the 1$^{st}$ round PCR product (100 dilutions) was used for PCR reactions (95° C. for 5 min; (95° C. for 30 sec; 68° C. for 30 sec; 72° C. for 30 sec) for 30 cycles; 72° C. for 7 min and then keep at 4° C. Primers used in the PCR reactions are listed in Table 6.

TABLE 6

Listing of Primers

| Name | Forward Primers (5' to 3') | Reverse Primers (5' to 3') |
|---|---|---|
| LUC | ATGGAAGACGCCAAAAACATA AAGAAAGGCCCGGCGCCATTC (SEQ ID NO: 26) | AACACTTAAAATCGCAGTATCCG GAATG (SEQ ID NO: 27) |
| GFP | GTGGTGCCCATCCTGGTCGAG (SEQ ID NO: 28) | CGCTTCTCGTTGGGGTCTTTGC (SEQ ID NO: 29) |
| PTEN | ATCCGTCTTCTCCCCATTCCG (SEQ ID NO: 30) | GACGAGCTCGCTAATCCAGTG (SEQ ID NO: 31) |
| P53 | ATAGAGACGCTGAGTCCGGTTC (SEQ ID NO: 32) | CCTAAGCCCAAGAGGAAACAGA (SEQ ID NO: 33) |
| RB1 | CTGTGCTGGTGTGTGCAAACT ATA (SEQ ID NO: 34) | CTGTCACAGTGAAACTCGTTACT TTGTATATC (SEQ ID NO: 35) |
| Eml4 | ACAAGGCTCTGGCTTCCATTG (SEQ ID NO: 36) | GATCAAAGCAAGGCCTTGTGCAT (SEQ ID NO: 37) |
| Aik | TCTGAGCCCCTTCCATCTGACC (SEQ ID NO: 38) | AGCTCAGCAGAAGCTCAGCAG (SEQ ID NO: 39) |
| Eml4-Alk inversion ($1^{st}$ round) | CCCAGTCATCAGTTGCTATGCA ATT (SEQ ID NO: 40) | GGGTTTCCTTTGGTTCACAGATC CA (SEQ ID NO: 41) |
| Eml4-Alk inversion ($2^{nd}$ round) | CGTTTTTCCACAAGAGCTAAGGCT (SEQ ID NO: 42) | GTGGTTTGGTCACATCTCAGGTG (SEQ ID NO: 43) |

XIV. H&E Staining and Immunohistochemistry (IHC).

Briefly, 10% Formalin solution fixed tissues were embedded in paraffin, sectioned and H&E stained by the Molecular Pathology Core at UTSW. The 4 µm sections were performed in the standard fashion and detected with Elite ABC Kit and DAB Substrate (Vector Laboratories) for IHC.

XV. Statistical Analyses.

Statistical analyses were conducted using two-sided Student's t-test by GraphPad Prism software, version 7.04 (GraphPad Software, USA). No adjustments were made in any statistical test. A P value <0.05 was considered statistically significant.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Amoasii et al., Science, 362:86-91, 2018.
Bailey & Cullis, Biochemistry, 33:12573-12580, 1994.
Blasco et al., Cell Rep., 9:1219-1227, 2014.
Cheng et al., Adv. Mater., 30:e1805308, 2018.
Chew et al., Nature methods, 13:868, 2016.
Cong et al., Science, 339:819-823, 2013.
Doudna & Charpentier, Science, 346:1258096, 2014.
Finn et al., Cell Rep., 22:2227-2235, 2018.
Gustafson et al., Nano Today, 10:487-510, 2015.
Hajj & Whitehead, Nat. Rev. Mater., 2:17056, 2017.
Hao et al., J. Am. Chem. Soc., 137:9206-9209, 2015.
Hendel et al., Nat. Biotechnol., 33:985-989, 2015.
Heyes et al., J. Controlled Release, 107:276-287, 2005.
Jayaraman et al., Angew. Chem. Int. Ed., 51:8529-8533, 2012.
Jinek et al., Science, 337:816-821, 2012.
Kamath et al., J Immunol, 165:6762-6770, 2000.
Kanasty et al., Nat. Mater., 12:967-977, 2013.
Kauffman et al., Nano Lett., 15:7300-7306, 2015.
Love et al., Proc. Natl. Acad. Sci. U.S.A., 107:1864-1869, 2010.
Maddalo et al., Nature, 516:423-427, 2014.
Mali et al., Science, 339:823-826, 2013.
Miller et al., Angew. Chem. Int. Ed., 56:1059-1063, 2017.
McLaughlin & Harary, Biochemistry, 15:1941-1948, 1976.
Nelson et al., ACS Nano, 7:8870-8880, 2013.
Sander & Joung, Nat. Biotechnol., 32:347-355, 2014.
Staahl et al., Nat. Biotechnol., 35:431-434, 2017.
Sun et al., Angew. Chem. Int. Ed., 54:12029-12033, 2015.
Tabebordbar et al., Science, 351:407-411, 2016.
Wang et al., Chem. Rev., 117:9874-9906, 2017.
Wang et al., Nat. Biotechnol., 2018.
Wilhelm et al., Nat. Rev. Mater., 1:16014, 2016.
Wittrup et al., Nat. Biotechnol., 33:870-976, 2015.

Wood, *Nat. Rev. Neurol.*, 14:570, 2018.
Xue et al., *Nature,* 514:380-384, 2014.
Yin et al., *Nat. Biotechnol.*, 34:328-333, 2016.
Yin et al., *Nat. Biotechnol.*, 35:1179, 2017.
Zhang et al., *Gastroenterology,* 154:1421-1434, 2018a.
Zhang et al., *Dev. Cell,* 44:447-459, 2018b.
Zhou, et al., *Proc. Natl. Acad. Sci.,* 113(3):520-525, 2016.
Zuris et al., *Nat. Biotechnol.,* 33:73-80, 2015.

---

What is claimed is:

1. A composition comprising a lipid composition assembled with a therapeutic agent, wherein the lipid composition comprises a cationic selective organ targeting (SORT) lipid in an amount sufficient to yield an apparent pKa of said lipid composition outside a range of about 6 to about 7.

2. The composition of claim 1, further comprising an ionizable cationic lipid.

3. The composition of claim 1, wherein said apparent pKa is about 8 or higher.

4. The composition of claim 1, wherein said apparent pKa is about 6 or lower.

5. The composition of claim 1, wherein said cationic SORT lipid is present in said lipid composition at a molar percentage from about 5% to about 65%, wherein the molar percentage is determined based on total lipids present in the lipid composition.

6. The composition of claim 1, wherein said cationic SORT lipid is a permanently cationic SORT lipid.

7. The composition of claim 6, wherein said permanently cationic SORT lipid comprises a quaternary ammonium ion.

8. The composition of claim 6, wherein said permanently cationic SORT lipid has a structure of Formula (I), Formula (II), or Formula (III), or a pharmaceutically acceptable salt, stereoisomer, or tautomer thereof:

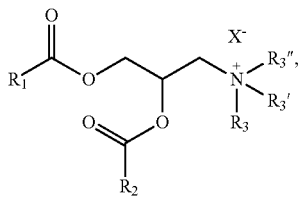

(I)

wherein, in Formula (I):

$R_1$ and $R_2$ are each independently alkyl$_{(C8-C24)}$, alkenyl$_{(C8-C24)}$, or a substituted version of either group;

$R_3$, $R_3'$, and $R_3''$ are each independently alkyl$_{(C\leq 6)}$ or substituted alkyl$_{(C\leq 6)}$; and $X^-$ is a monovalent anion; or

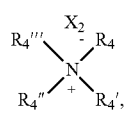

(II)

wherein, in Formula (II):

$R_4$ and $R_4'$ are each independently alkyl$_{(C6-C24)}$, alkenyl$_{(C6-C24)}$, or a substituted version of either group;

$R_4''$ is alkyl$_{(C\leq 24)}$, alkenyl$_{(C\leq 24)}$, or a substituted version of either group;

$R_4'''$ is alkyl$_{(C1-C8)}$, alkenyl$_{(C2-C8)}$, or a substituted version of either group; and $X_2^-$ is a monovalent anion; or

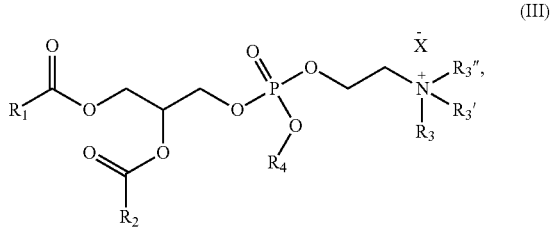

(III)

wherein, in Formula (III):

$R_1$ and $R_2$ are each independently alkyl$_{(C8-C24)}$, alkenyl$_{(C8-C24)}$, or a substituted version of either group;

$R_3$, $R_3'$, and $R_3''$ are each independently alkyl$_{(C\leq 6)}$ or substituted alkyl$_{(C\leq 6)}$;

$R_4$ is alkyl$_{(C\leq 6)}$ or substituted alkyl$_{(C\leq 6)}$; and $X^-$ is a monovalent anion.

9. The composition of claim 1, wherein said cationic SORT lipid is an ionizable cationic SORT lipid.

10. The composition of claim 9, wherein said ionizable cationic SORT lipid is 1,2-dioleoyl-3-dimethylammonium-propane (DODAP).

11. The composition of claim 1, wherein said lipid composition comprises said ionizable cationic lipid at a molar percentage from about 5% to about 30%, wherein the molar percentage is determined based on total lipids present in the lipid composition.

12. The composition of claim 1, wherein said lipid composition further comprises a zwitterionic lipid.

13. The composition of claim 12, wherein said zwitterionic lipid is a zwitterionic phospholipid.

14. The composition of claim 12, wherein said lipid composition comprises said zwitterionic lipid at a molar percentage from about 8% to about 23%, wherein the molar percentage is determined based on total lipids present in the lipid composition.

15. The composition of claim 1, wherein said lipid composition further comprises a polymer-conjugated lipid.

16. The composition of claim 15, wherein said lipid composition comprises said polymer-conjugated lipid at a molar percentage from about 0.5% to about 10%, wherein the molar percentage is determined based on total lipids present in the lipid composition.

17. The composition of claim 16, wherein said polymer-conjugated lipid is a poly(ethylene glycol) (PEG)-conjugated lipid.

18. The composition of claim 1, wherein said lipid composition further comprises a steroid or steroid derivative.

19. The composition of claim 18, wherein said lipid composition comprises said steroid or steroid derivative at a molar percentage from about 15% to about 46%, wherein the molar percentage is determined based on total lipids present in the lipid composition.

20. The composition of claim 1, wherein said therapeutic agent comprises one or more members selected from a small interfering ribonucleic acid (siRNA), a micro-ribonucleic acid (miRNA), a primary micro-ribonucleic acid (pri-miRNA), a messenger ribonucleic acid (mRNA), a clustered regularly interspaced short palindromic repeats (CRISPR) related nucleic acid, a CRISPR-RNA (crRNA), a single guide ribonucleic acid (sgRNA), a trans-activating CRISPR ribonucleic acid (tracrRNA), a plasmid deoxyribonucleic acid (pDNA), a transfer ribonucleic acid (tRNA), an antisense oligonucleotide (ASO), a guide ribonucleic acid, a double stranded deoxyribonucleic acid (dsDNA), a single stranded deoxyribonucleic acid (ssDNA), a single stranded ribonucleic acid (ssRNA), a double stranded ribonucleic acid (dsRNA), a protein, and a CRSIPR-associated (Cas) protein.

21. The composition of claim 1, wherein said therapeutic agent comprises a messenger ribonucleic acid (mRNA).

22. The composition of claim 1, wherein said therapeutic agent comprises an RNA molecule that encodes a Cas protein.

23. The composition of claim 22, wherein said therapeutic agent further comprises a CRISPR-RNA (crRNA), a single guide ribonucleic acid (sgRNA), a trans-activating CRISPR ribonucleic acid (tracrRNA), or a combination thereof.

24. The composition of claim 21, wherein said therapeutic agent further comprises a single guide polynucleotide.

25. The composition of claim 21, wherein said therapeutic agent further comprises a double stranded deoxyribonucleic acid (dsDNA), a single stranded deoxyribonucleic acid (ssDNA), or a combination thereof.

26. The composition of claim 1, wherein said therapeutic agent is present in a ratio of said lipid composition to said therapeutic agent from about 1:1 to about 1:100.

27. The composition of claim 1, wherein said apparent pKa is about 3 to about 6.

28. The composition of claim 1, wherein said apparent pKa is about 8 to about 13.

29. The composition of claim 1, wherein said lipid composition is formulated for delivery of said therapeutic agent to one or more non-liver organs.

30. The composition of claim 29, wherein said one or more non-liver organs comprise a lung, spleen, a bone marrow, a lymph node, or a combination thereof.

* * * * *